US008987248B2

(12) United States Patent
Jeske et al.

(10) Patent No.: US 8,987,248 B2
(45) Date of Patent: Mar. 24, 2015

(54) SUBSTITUTED PIPERIDINES AS PAR-1 ANTAGONISTS

(75) Inventors: Mario Jeske, Solingen (DE); Dirk Heimbach, Düsseldorf (DE); Susanne Röhrig, Hilden (DE); Yolanda Cancho Grande, Leverkusen (DE); Dirk Schneider, Wuppertal (DE); Ulrich Rester, Wuppertal (DE); Eckhard Bender, Langenfeld (DE); Mark Meininghaus, Wuppertal (DE); Katja Zimmermann, Düsseldorf (DE); Dmitry Zubov, Remscheid (DE); Anja Buchmüller, Essen (DE); Georges Von Degenfeld, Leverkusen (DE); Christoph Gerdes, Köln (DE); Michael Gerisch, Wuppertal (DE); Mark Jean Gnoth, Mettmann (DE); Kersten Matthias Gericke, Wuppertal (DE)

(73) Assignee: Bayer Intellectual Property GmbH, Monheim (DE)

( * ) Notice: Subject to any disclaimer, the term of this patent is extended or adjusted under 35 U.S.C. 154(b) by 194 days.

(21) Appl. No.: 13/202,707

(22) PCT Filed: Mar. 12, 2010

(86) PCT No.: PCT/EP2010/001567
§ 371 (c)(1),
(2), (4) Date: Nov. 4, 2011

(87) PCT Pub. No.: WO2010/108608
PCT Pub. Date: Sep. 30, 2010

(65) Prior Publication Data
US 2012/0046268 A1 Feb. 23, 2012

(30) Foreign Application Priority Data
Mar. 23, 2009 (DE) .......................... 10 2009 014 484

(51) Int. Cl.
*A61K 31/5377* (2006.01)
*C07D 413/06* (2006.01)
*C07D 211/60* (2006.01)
*C07D 211/42* (2006.01)
*C07D 211/56* (2006.01)
*C07D 211/62* (2006.01)
*C07D 401/06* (2006.01)
*C07D 405/06* (2006.01)
*C07D 405/12* (2006.01)
*C07D 409/12* (2006.01)
*C07D 413/12* (2006.01)
*C07D 417/06* (2006.01)

(52) U.S. Cl.
CPC ............ *C07D 211/60* (2013.01); *C07D 211/42* (2013.01); *C07D 211/56* (2013.01); *C07D 211/62* (2013.01); *C07D 401/06* (2013.01);
*C07D 405/06* (2013.01); *C07D 405/12* (2013.01); *C07D 409/12* (2013.01); *C07D 413/12* (2013.01); *C07D 417/06* (2013.01)
USPC ................ 514/210.18; 514/227.8; 514/235.5; 514/253.13; 514/318; 514/326; 514/330; 544/58.2; 544/58.4; 544/130; 544/365; 546/194; 546/207; 546/208; 546/209; 546/211; 546/214; 546/226

(58) Field of Classification Search
CPC ............ A61K 31/4523; C07D 401/06; C07D 405/06; C07D 413/06; C07D 417/06
USPC ........... 514/210.2, 227.8, 235.5, 253.13, 318, 514/326, 330, 210.18; 546/194, 207, 208, 546/209, 211, 214, 226; 544/58.2, 58.4, 544/130, 365
See application file for complete search history.

(56) References Cited

U.S. PATENT DOCUMENTS

| 5,767,144 | A | 6/1998 | Winn et al. | |
|---|---|---|---|---|
| 8,071,624 | B2 * | 12/2011 | Yao et al. | 514/330 |
| 8,084,469 | B2 | 12/2011 | Heimbach et al. | |
| 8,119,663 | B2 | 2/2012 | Heimbach et al. | |
| 8,202,862 | B2 | 6/2012 | Heimbach et al. | |
| 2001/0044454 | A1 | 11/2001 | Nantermet et al. | |
| 2005/0004170 | A1 | 1/2005 | Janssens et al. | |
| 2006/0004049 | A1 | 1/2006 | Yao et al. | |
| 2006/0009471 | A1 | 1/2006 | Yao et al. | |
| 2006/0009491 | A1 | 1/2006 | Yao et al. | |
| 2006/0122197 | A1 | 6/2006 | Yao et al. | |
| 2007/0066584 | A1 | 3/2007 | Yao et al. | |
| 2007/0197530 | A1 | 8/2007 | Li et al. | |
| 2007/0213311 | A1 | 9/2007 | Li et al. | |
| 2007/0293529 | A1 | 12/2007 | Li et al. | |
| 2008/0003214 | A1 | 1/2008 | Cezanne et al. | |

(Continued)

FOREIGN PATENT DOCUMENTS

WO 97/36873 A1 10/1997

OTHER PUBLICATIONS

Diaz et al. "Fast and efficient . . . " CA149:448171 (2008).*

(Continued)

*Primary Examiner* — Celia Chang
(74) *Attorney, Agent, or Firm* — Karen B. King

(57) ABSTRACT

The invention relates to novel substituted piperidines, to processes for their preparation, to their use for the treatment and/or prophylaxis of diseases and to their use for preparing medicaments for the treatment and/or prophylaxis of diseases, in particular of cardiovascular disorders and tumor disorders.

9 Claims, No Drawings

(56) References Cited

U.S. PATENT DOCUMENTS

| | | | |
|---|---|---|---|
| 2011/0021489 A1 | 1/2011 | Heimbach et al. | |
| 2012/0129831 A1 | 5/2012 | Heimbach et al. | |
| 2012/0142690 A1* | 6/2012 | Heimbach et al. | 514/237.2 |
| 2012/0149694 A1* | 6/2012 | Heimbach et al. | 514/227.8 |
| 2013/0158020 A1* | 6/2013 | Deng et al. | 514/228.2 |

OTHER PUBLICATIONS

Greene "Protective groups . . . " p. 218-220, 224, 251 (1982).*
Patani et al. "Bioisosterism . . . " Chem. Rev. v.96 p. 3147-3176 (1996).*
Rubini et al. "Synthesis of isosteric . . . " Tetrahedron v.42(21) p. 6039-6045 (1986).*
Improper Markush, Fed. Reg. v.76, p. 7162-7175, slides 1, 64-67 (2011).*
Ahn H-S, et al., "Nonpeptide thrombin receptor antagonists," Drugs of the Future, 2001, 26:1065-1085, at p. 1077.
Angiolillo DJ, et al., "Clinical overview of promising nonthienopyridine antiplatelet agents," Am Heart J, 2008, 156:S23-S28.
Barrow et al.: "Discovery and Initial Structure-Activity Relationships of Trisubstituted Ureas as Thrombin Receptor (PAR-1) Antagonists," Bioorganic & Medicinal Chemistry Letters, Apr. 30, 2001, pp. 2691-2696.
Becker RC, et al., "Safety and tolerability of SCH 530348 in patients undergoing non-urgent percutaneous coronary intervention: a randomised, double-blind, placebo-controlled phase II study," Lancet, 2009, 373: 919-928.
Bhatt et al.: "Scientific and Theraputic Advances in Antiplatelet Therapy," Nat. Rev. Drug Discov., Jan. 2003, 2:15-28.
Chackalamannil: "Thrombin Receptor (Protease Activated Receptor-1) Antagonists as Potent Antithrombotic Agents with Strong Antiplatelet Effects," Journal of Medicinal Chemistry, Sep. 7, 2006, 49(18): 5389-5404.
Chintala M, et al., "Basic and translational research on proteinase-activated receptors: antagonism of the proteinase-activated receptor 1 for thrombin, a novel approach to antiplatelet therapy for atherothrombotic disease," J Pharmacol Sci, 2008, 108: 433-438.
Day JRS, et al., "Clinical inhibition of the seven-transmembrane thrombin receptor (PAR1) by intravenous aprotonin during cardiothoracic surgery," Circulation, 2004, 110:2597-2600.
Dellinger et al.: "Surviving Sepsis Campaign Guidelines for Management of Severe Sepsis and Septic Shock," Crit. Care Med., 2004, 32(3):858-873.
Derian et al.: "Blocade of the Thrombin Receptor Protease-Activated Receptor-1 with a Small-Molecule Antagonist Prevents Thrombus Formation and Vascular Occlusion in Nonhuman Primates," J. Pharmacol. Exp. Ther., 2003, 304 (2):855-861.
Diaz. et al.,: "Fast Efficient Access to a Family of Multifunctional 1,3,5-Trisubstituted Piperidines," Synthetic Communications, 2008, 38:2977-2813.
Gawaz M, et al., "Incomplete inhibition of platelet aggregation and glycoprotein IIb-IIIa receptor blockade by abciximab: importance of internal pool of glycoprotein IIb-IIIa receptors," Thromb Haemost, 2000, 83:915-922.
Golub et al.: Molecular Classification of Cancer: Class Discovery and Class Prediction by Gene Expression Monitoring,: Science, 1999, 286: 531-537.
Howell CD, et al., "Absence of proteinase-activated receptor-1 signaling affords protection from bleomycin-induced lung inflammation and fibrosis," Am J Pathol, 2005, 166:1353-1365.
Kahn et al.: "Protease-Activated Receptors 1 and 4 Mediate Activation of Human Platelets by Thrombin," J. Clin. Invest., 1999, 103: 879-887.
Lala et al.: "Role of Nitric Oxide in Tumor Progression: Lessons from Experimental Tumors," Cancer and Metastasis Reviews, 1998, 17: 91-106.
Landis C, "Pharmacologic strategies for combating the inflammatory response," J Am Soc Extracorporeal Technology, 2007, 39:291-295.
McAtee et al.: "Development of Potent and Selective Small-Molecule Human Urotensin-II Antagonists," Bioorganic and Medicinal Chemistry Letters, 2008, 18: 3500-3503.
Meadows, Telly A et al., "Clinical Aspects of Platelet Inhibitors and Thrombus Formation," Circulation Research, May 11, 2007, pp. 1261-1275.
Mochizuki et al.: "Design, Synthesis, and Biological Activity of Piperdine Diamine Derivatives as Factor Xa Inhibitor," Bioorganic & Medicinal Chemistry Letters 18, 2008, pp. 783-787.
Morissette et al.: "High-throughput Crystallization: Polymorphs, Salts, Co-crystals, and Solvates of Pharmaceutical Solids," Advanced Drug Delivery Reviews, 2004, 56: 275-300.
Mackman, Nigel, "Triggers, targets, and treatments for thrombosis," Nature, Feb. 2008, 451: 914-919.
Stedman's Medical Dictionary, 27th Edition, pub. Lippincott Williams & Wilkins, 2000 copyright, title page, inside cover page, and p. 1458.
TRA-CER executive and steering committees, "The thrombin receptor antagonist for clinical event reduction in acute coronary syndrome (TRA-CER) trial: study design and rationale," Am Heart J, 2009, 158:327-334.
Vippagunta et al.: "Crystalline Solids," Advanced Drug Delivery Reviews, 2001, 48: 3-26.
Vu et al.: "Molecular Cloning of a Functional Thrombin Receptor Reveals a Novel Proteolytic Mechanism of Receptor Activation," Cell, Mar. 22, 1991, 64:1057-1068.
U.S. Appl. No. 13/400,491, filed Feb. 20, 2012.
U.S. Appl. No. 13/321,966, filed Feb. 9, 2012.
U.S. Appl. No. 13/322,593, filed Feb. 17, 2012.

* cited by examiner

SUBSTITUTED PIPERIDINES AS PAR-1 ANTAGONISTS

The invention relates to novel substituted piperidines, to processes for their preparation, to their use for the treatment and/or prophylaxis of diseases and to their use for preparing medicaments for the treatment and/or prophylaxis of diseases, in particular of cardiovascular disorders and tumour disorders.

Thrombocytes (blood platelets) are a significant factor both in physiological haemostasis and in thromboembolic disorders. In particular in the arterial system, platelets are of central importance in the complex interaction between blood components and the wall of the vessel. Unwanted platelet activation may, by formation of platelet-rich thrombi, result in thromboembolic disorders and thrombotic complications with life-threatening states.

One of the most potent platelet activators is the blood coagulation protease thrombin, which is formed at injured blood vessel walls and which, in addition to fibrin formation, leads to the activation of platelets, endothelial cells and mesenchymal cells (Vu T K H, Hung D T, Wheaton V I, Coughlin S R, Cell 1991, 64, 1057-1068). In platelets in vitro and in animal models, thrombin inhibitors inhibit platelet aggregation and the formation of platelet-rich thrombi. In man, arterial thromboses can be prevented or treated successfully with inhibitors of platelet function and thrombin inhibitors (Bhatt D L, Topol E J, Nat. Rev. Drug Discov. 2003, 2, 15-28). Accordingly, there is a high probability that antagonists of thrombin action on platelets reduce the formation of thrombi and the occurrence of clinical sequelae such as myocardial infarction and stroke. Other cellular actions of thrombin, for example on endothelial and smooth-muscle cells of vessels, leukocytes and fibroblasts, are possibly responsible for inflammatory and proliferative disorders.

At least some of the cellular effects of thrombin are mediated via a family of G-protein-coupled receptors (Protease Activated Receptors, PARs), the prototype of which is the PAR-1 receptor. PAR-1 is activated by binding of thrombin and proteolytic cleavage of its extracellular N-terminus. The proteolysis exposes a new N-terminus having the amino acid sequence SFLLRN which, as agonist ("tethered ligand") leads to intramolecular receptor activation and transmission of intracellular signals. Peptides derived from the tethered-ligand sequence can be used as agonists of the receptor and, on platelets, lead to activation and aggregation. Other proteases are likewise capable of activating PAR-1, these proteases include, for example, plasmin, factor VIIa, factor Xa, trypsin, activated protein C (aPC), tryptase, cathepsin G, proteinase 3, granzyme A, elastase and matrix metalloprotease 1 (MMP-1).

In contrast to the inhibition of protease activity of thrombin with direct thrombin inhibitors, blockade of PAR-1 should result in an inhibition of platelet activation without reduction in the coagulability of the blood (anticoagulation).

Antibodies and other selective PAR-1 antagonists inhibit the thrombin-induced aggregation of platelets in vitro at low to medium thrombin concentrations (Kahn M L, Nakanishi-Matsui M, Shapiro M J, Ishihara H, Coughlin S R, J. Clin. Invest. 1999, 103, 879-887). A further thrombin receptor with possible significance for the pathophysiology of thrombotic processes, PAR-4, was identified on human and animal platelets. In experimental thromboses in animals having a PAR expression pattern comparable to humans, PAR-1 antagonists reduce the formation of platelet-rich thrombi (Derian C K, Damiano B P, Addo M F, Darrow A L, D'Andrea M R, Nedelman M, Zhang H-C, Maryanoff B E, Andrade-Gordon P, J. Pharmacol. Exp. Ther. 2003, 304, 855-861).

In the last few years, a large number of substances have been examined for their platelet function-inhibiting action; but only a few platelet function inhibitors have been found to be useful in practice. Accordingly, there is a need for pharmaceuticals which specifically inhibit an increased platelet reaction without significantly increasing the risk of bleeding, thus reducing the risk of thromboembolic complications.

Effects of thrombin which are mediated via the receptor PAR-1 influence the progression of the disease during and after coronary artery bypass graft (CABG) and other surgical interventions and in particular surgical interventions with extracorporeal circulation (for example heart-lung machine). During the course of the operation, there may be bleeding complications owing to pre- or intraoperative medication with coagulation-inhibiting and/or platelet-inhibiting substances. For this reason, for example, medication with clopidogrel has to be interrupted several days prior to a CABG. Moreover, as already mentioned, a disseminated intravascular coagulation or consumption coagulopathy (DIC) may develop (for example owing to the extended contact between blood and synthetic surfaces during extracorporeal circulation or blood transfusions), which in turn can lead to bleeding complications. As the disorder progresses, there is frequently a restenosis of the venous or arterial bypasses grafted (which may even result in occlusion) owing to thrombosis, intimafibrosis, arteriosclerosis, angina pectoris, myocardial infarction, heart failure, arrhythmias, transitory ischaemic attack (TIA) and/or stroke.

In man, the receptor PAR-1 is also expressed in other cells including, for example, endothelial cells, smooth muscle cells and tumour cells. Malignant tumour disorders (cancer) have a high incidence and are generally associated with high mortality. Current therapies achieve full remission in only a fraction of patients and are typically associated with severe side effects. Accordingly, there is a high demand for more effective and safer therapies. The PAR-1 receptor contributes to cancer generation, growth, invasiveness and metastasis. Moreover, PAR-1 expressed on endothelial cells mediates signals resulting in vascular growth ("angiogenesis"), a process which is vital for enabling tumour growth beyond about 1 mm$^3$ Angiogenesis also contributes to the generation or worsening of other disorders including, for example, haematopoetic cancer disorders, macular degeneration, which leads to blindness, and diabetic retinopathy, inflammatory disorders, such as rheumatoid arthritis and colitis.

Sepsis (or septicaemia) is a frequent disorder with high mortality. Initial symptoms of sepsis are typically unspecific (for example fever, reduced general state of health); however, as the disorder progresses there may be a general activation of the coagulation system ("disseminated intravascular coagulation" or "consumption coagulopathy" (DIC)) with the formation of microthrombi in various organs and secondary bleeding complications. DIC may also occur independently of a sepsis, for example during surgical interventions or associated with tumour disorders.

Therapy of sepsis consists, firstly, in the thorough elimination of the infectious cause, for example by operative focal reconstruction and antibiosis. Secondly, it consists in temporary intensive medical support of the affected organ systems. Treatments of the different stages of this disease have been described, for example, in the following publication (Dellinger et al., Crit. Care Med. 2004, 32, 858-873). There are no proven effective treatments for DIC.

Accordingly, it is an object of the present invention to provide novel PAR-1 antagonists for the treatment of disorders such as, for example, cardiovascular disorders and thromboembolic disorders, and also tumour disorders in humans and animals.

WO 2006/012226, WO 2006/020598, WO 2007/038138, WO 2007/130898, WO 2007/101270 and US 2006/0004049 describe structurally similar piperidines as 11-β HSD1 inhibitors for the treatment of, among others, diabetes, thromboembolic disorders and stroke.

The invention provides compounds of the formula

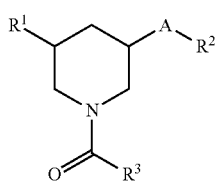

in which
A represents a group of the formula

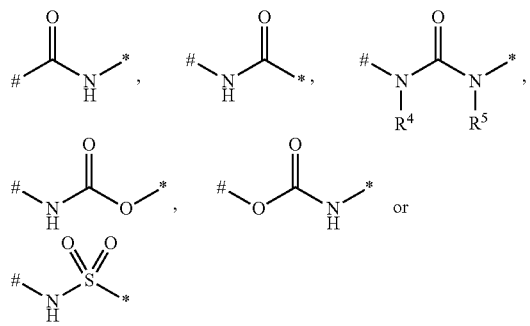

where
# is the point of attachment to the piperidine ring,
* is the point of attachment to $R^2$,
$R^4$ represents hydrogen or $C_1$-$C_3$-alkyl,
and
$R^5$ represents hydrogen or $C_1$-$C_3$-alkyl,
$R^e$ represents phenyl,
where phenyl may be substituted by 1 to 3 substituents independently of one another selected from the group consisting of monofluoromethyl, difluoromethyl, trifluoromethyl, monofluoromethoxy, difluoromethoxy, trifluoromethoxy, monofluoromethylsulphanyl, difluoromethylsulphanyl, trifluoromethylsulphanyl, methylsulphonyl, $C_1$-$C_4$-alkyl, $C_1$-$C_4$-alkoxy and $C_1$-$C_4$-alkoxycarbonyl,
$R^2$ represents $C_1$-$C_6$-alkyl, $C_3$-$C_6$-cycloalkyl, 4- to 6-membered heterocyclyl, phenyl, 2,2-difluoro-1,3-benzodioxolyl or 5- or 6-membered heteroaryl,
where cycloalkyl, heterocyclyl, phenyl and heteroaryl may be substituted by 1 to 3 substituents independently of one another selected from the group consisting of halogen, cyano, hydroxyl, amino, monofluoromethyl, difluoromethyl, trifluoromethyl, monofluoromethoxy, difluoromethoxy, trifluoromethoxy, monofluoromethylsulphanyl, difluoromethylsulphanyl, trifluoromethylsulphanyl, $C_1$-$C_4$-alkyl, $C_1$-$C_4$-alkoxy, $C_1$-$C_6$-alkylamino and phenyl,
where phenyl may be substituted by 1 to 3 substituents independently of one another selected from the group consisting of halogen and trifluoromethyl,
and
where $C_1$-$C_4$-alkyl may be substituted by a substituent selected from the group consisting of $C_3$-$C_6$-cycloalkyl and phenyl,
where cycloalkyl and phenyl may be substituted by 1 to 3 substituents independently of one another selected from the group consisting of halogen, cyano, monofluoromethyl, difluoromethyl, trifluoromethyl, monofluoromethoxy, difluoromethoxy, trifluoromethoxy, $C_1$-$C_4$-alkyl and $C_1$-$C_4$-alkoxy,
$R^3$ represents $C_1$-$C_6$-alkyl, $C_2$-$C_6$-alkenyl, $C_2$-$C_6$-alkynyl, $C_1$-$C_6$-alkoxy, $C_1$-$C_6$-alkylamino, $C_3$-$C_7$-cycloalkyl, 4- to 7-membered heterocyclyl, phenyl, 5- or 6-membered heteroaryl, $C_3$-$C_7$-cycloalkyloxy, $C_3$-$C_7$-cycloalkylamino, 4- to 7-membered heterocyclylamino, phenylamino or 5- or 6-membered heteroarylamino,
where alkyl, $C_2$-$C_6$-alkoxy and alkylamino may be substituted by a substituent selected from the group consisting of halogen, hydroxyl, amino, cyano, $C_1$-$C_4$-alkoxy, $C_1$-$C_4$-alkoxycarbonyl, $C_3$-$C_7$-cycloalkyl, 4- to 6-membered heterocyclyl, phenyl and 5- or 6-membered heteroaryl,
where alkoxy may be substituted by a $C_1$-$C_4$-alkoxy substituent,
and
where cycloalkyl, heterocyclyl, phenyl, heteroaryl, cycloalkyloxy, cycloalkylamino, heterocyclylamino, phenylamino and heteroarylamino may be substituted by 1 to 3 substituents independently of one another selected from the group consisting of halogen, cyano, oxo, hydroxyl, amino, monofluoromethyl, difluoromethyl, trifluoromethyl, monofluoromethoxy, difluoromethoxy, trifluoromethoxy, monofluoromethylsulphanyl, difluoromethylsulphanyl, trifluoromethylsulphanyl, hydroxycarbonyl, aminocarbonyl, $C_1$-$C_4$-alkyl, $C_1$-$C_4$-alkoxy, $C_1$-$C_6$-alkylamino, $C_1$-$C_4$-alkoxycarbonyl, $C_1$-$C_4$-alkylaminocarbonyl and cyclopropyl,
where alkyl may be substituted by a hydroxyl substituent,
and their salts, their solvates and the solvates of their salts.

Compounds according to the invention are the compounds of the formula (I) and their salts, solvates and solvates of the salts, the compounds, comprised by formula (I), of the formulae mentioned below and their salts, solvates and solvates of the salts and the compounds comprised by formula (I), mentioned below as embodiments, and their salts, solvates and solvates of the salts, if the compounds, comprised by formula (I), mentioned below are not already salts, solvates and solvates of the salts.

Depending on their structure, the compounds according to the invention may exist in stereoisomeric forms (enantiomers, diastereomers). The invention therefore encompasses the enantiomers or diastereomers and the respective mixtures thereof. The stereoisomerically homogeneous constituents can be isolated from such mixtures of enantiomers and/or diastereomers in a known manner.

Where the compounds according to the invention can occur in tautomeric forms, the present invention encompasses all the tautomeric forms.

In the context of the present invention, preferred salts are physiologically acceptable salts of the compounds according to the invention. However, the invention also encompasses salts which themselves are unsuitable for pharmaceutical applications but which can be used, for example, for the isolation or purification of the compounds according to the invention.

Physiologically acceptable salts of the compounds according to the invention include acid addition salts of mineral acids, carboxylic acids and sulphonic acids, for example salts of hydrochloric acid, hydrobromic acid, sulphuric acid, phosphoric acid, methanesulphonic acid, ethanesulphonic acid, toluenesulphonic acid, benzenesulphonic acid, naphthalenedisulphonic acid, acetic acid, trifluoroacetic acid, propionic acid, lactic acid, tartaric acid, malic acid, citric acid, fumaric acid, maleic acid and benzoic acid.

Physiologically acceptable salts of the compounds according to the invention also include salts of conventional bases, by way of example and with preference alkali metal salts (e.g. sodium and potassium salts), alkaline earth metal salts (e.g. calcium and magnesium salts) and ammonium salts derived from ammonia or organic amines having 1 to 16 carbon atoms, by way of example and with preference ethylamine, diethylamine, triethylamine, ethyldiisopropylamine, monoethanolamine, diethanolamine, triethanolamine, dicyclohexylamine, dimethylaminoethanol, procaine, dibenzylamine, N-methylmorpholine, arginine, lysine, ethylenediamine, N-methylpiperidine and choline.

In the context of the invention, solvates refer to those forms of the compounds according to the invention which, in the solid or liquid state, form a complex by coordination with solvent molecules. Hydrates are a specific form of the solvates in which the coordination is with water. Moreover, the present invention also encompasses prodrugs of the compounds according to the invention. The term "prodrugs" includes compounds which may themselves be biologically active or inactive but are converted to compounds according to the invention while resident in the body (for example metabolically or hydrolytically).

In the context of the present invention, unless specified otherwise, the substituents are defined as follows:

Alkyl per se and "Alk" and "alkyl" in alkoxy, alkylamino, alkoxycarbonyl and alkylaminocarbonyl represent a straight-chain or branched alkyl radical having 1 to 6 carbon atoms, by way of example and by way of preference methyl, ethyl, n-propyl, isopropyl, n-butyl, tert-butyl, n-pentyl and n-hexyl.

Alkenyl represents a straight-chain or branched alkenyl radical having 2 to 6 carbon atoms. Preference is given to a straight-chain or branched alkenyl radical having 2 to 4, particularly preferably 2 or 3, carbon atoms. The following radicals may be mentioned by way of example and by way of preference: vinyl, allyl, n-prop-1-en-1-yl and n-but-2-en-1-yl.

Alkynyl represents a straight-chain or branched alkynyl radical having 2 to 6 carbon atoms. Preference is given to a straight-chain or branched alkynyl radical having 2 to 4, particularly preferably 2 or 3, carbon atoms. The following radicals may be mentioned by way of example and by way of preference: ethynyl, n-prop-2-yn-1-yl and n-but-3-yn-1-yl.

By way of example and by way of preference, alkoxy represents methoxy, ethoxy, n-propoxy, isopropoxy, n-butoxy, tert-butoxy, n-pentoxy and n-hexoxy.

Alkylamino represents an alkylamino radical having one or two alkyl substituents (selected independently of one another), by way of example and by way of preference methylamino, ethylamino, n-propylamino, isopropylamino, tert-butylamino, N,N-dimethylamino, N,N-diethylamino, N-ethyl-N-methylamino, N-methyl-N-n-propylamino, N-isopropyl-N-n-propylamino and N-tert-butyl-N-methylamino. $C_1$-$C_4$-Alkylamino represents, for example, a monoalkylamino radical having 1 to 4 carbon atoms or a dialkylamino radical having in each case 1 to 4 carbon atoms per alkyl substituent.

By way of example and by way of preference, alkoxycarbonyl represents methoxycarbonyl, ethoxycarbonyl, n-propoxycarbonyl, isopropoxycarbonyl, n-butoxycarbonyl, tert-butoxycarbonyl, n-pentoxycarbonyl and n-hexoxycarbonyl.

Alkylaminocarbonyl represents an alkylaminocarbonyl radical having one or two alkyl substituents (selected independently of one another), by way of example and by way of preference methylaminocarbonyl, ethylaminocarbonyl, n-propylaminocarbonyl, isopropylaminocarbonyl, tert-butylaminocarbonyl, N,N-dimethylaminocarbonyl, N,N-diethylaminocarbonyl, N-ethyl-N-methylaminocarbonyl, N-methyl-N-n-propylaminocarbonyl, N-isopropyl-N-n-propylaminocarbonyl and N-tert-butyl-N-methylaminocarbonyl. $C_1$-$C_4$-Alkylaminocarbonyl represents, for example, a monoalkylaminocarbonyl radical having 1 to 4 carbon atoms or a dialkylaminocarbonyl radical having in each case 1 to 4 carbon atoms per alkyl substituent.

Cycloalkyl represents a monocyclic cycloalkyl group having generally 3 to 7, preferably 5 or 6, carbon atoms; cycloalkyl groups which may be mentioned by way of example and by way of preference are cyclopropyl, cyclobutyl, cyclopentyl, cyclohexyl and cycloheptyl.

Cycloalkyloxy represents a monocyclic cycloalkyloxy group having generally 3 to 7, preferably 5 or 6, carbon atoms; cycloalkyloxy groups which may be mentioned by way of example and by way of preference are cyclopropyloxy, cyclobutyloxy, cyclopentyloxy and cyclohexyloxy.

Cycloalkylamino represents a monocyclic cycloalkylamino group having generally 3 to 7, preferably 3 or 4, carbon atoms; cycloalkylamino groups which may be mentioned by way of example and by way of preference are cyclopropylamino, cyclobutylamino, cyclopentylamino and cyclohexylamino.

Heterocyclyl represents a monocyclic or bicyclic heterocyclic radical having 4 to 7 ring atoms and up to 3, preferably up to 2, heteroatoms and/or hetero groups from the group of N, O, S, SO, $SO_2$, where a nitrogen atom may also form an N-oxide. The heterocyclyl radicals can be saturated or partially unsaturated. Preference is given to 5- or 6-membered monocyclic saturated heterocyclyl radicals having up to two heteroatoms from the group consisting of O, N and S, by way of example and by way of preference oxetanyl, azetidinyl, pyrrolidin-2-yl, pyrrolidin-3-yl, pyrrolinyl, tetrahydrofuranyl, tetrahydrothienyl, pyranyl, piperidin-1-yl, piperidin-2-yl, piperidin-3-yl, piperidin-4-yl, 1,2,5,6-tetrahydropyridin-3-yl, 1,2,5,6-tetrahydropyridin-4-yl, thiopyranyl, morpholin-1-yl, morpholin-2-yl, morpholin-3-yl, piperazin-1-yl, piperazin-2-yl.

Heterocyclylamino represents a monocyclic or bicyclic heterocyclic heterocyclylamino radical having 4 to 7 ring atoms and up to 3, preferably up to 2, heteroatoms and/or hetero groups from the group of N, O, S, SO, $SO_2$, where a nitrogen atom may also form an N-oxide. The heterocyclyl radicals can be saturated or partially unsaturated. Preference is given to 5- or 6-membered monocyclic saturated heterocyclyl radicals having up to two heteroatoms from the group consisting of O, N and S, by way of example and by way of preference oxetanylamino, azetidinylamino, pyrrolidin-2-ylamino, pyrrolidin-3-ylamino, tetrahydrofuranylamino, tetrahydrothienylamino, pyranylamino, piperidin-2-ylamino, piperidin-3-ylamino, piperidin-4-ylamino, 1,2,5,6-tetrahydropyridin-3-ylamino, 1,2,5,6-tetrahydropyridin-4-ylamino, thiopyranylamino, morpholin-2-ylamino, morpholin-3-ylamino, piperazin-2-ylamino.

Heteroaryl represents an aromatic monocyclic radical having generally 5 or 6 ring atoms and up to 4 heteroatoms from the group consisting of S, O and N, where a nitrogen atom may also form an N-oxide, by way of example and by way of preference thienyl, furyl, pyrrolyl, thiazolyl, oxazolyl, isoxazolyl, oxadiazolyl, pyrazolyl, imidazolyl, triazolyl, pyridyl, pyrimidyl, pyridazinyl, pyrazinyl.

Heteroarylamino represents an aromatic monocyclic heteroarylamino radical having generally 5 or 6 ring atoms and up to 4 heteroatoms from the group consisting of S, O and N, where a nitrogen atom may also form an N-oxide, by way of example and by way of preference thienylamino, furylamino, pyrrolylamino, thiazolylamino, oxazolylamino, isoxazolylamino, oxadiazolylamino, pyrazolylamino, imidazolylamino, pyridylamino, pyrimidylamino, pyridazinylamino, pyrazinylamino.

Halogen represents fluorine, chlorine, bromine and iodine, preferably fluorine and chlorine.

In the formula of the group which may represent A, the end point of the line marked by # or * does not represent a carbon atom or a $CH_2$ group, but is part of the bond to the atom to which A is attached.

Preference is given to compounds of the formula (I) in which
A represents a group of the formula where
# is the point of attachment to the piperidine ring,
* is the point of attachment to $R^2$,
$R^4$ represents hydrogen or $C_1$-$C_3$-alkyl,
and
$R^5$ represents hydrogen or $C_1$-$C_3$-alkyl,
$R^1$ represents phenyl,
where phenyl is substituted by 1 to 3 substituents independently of one another selected from the group consisting of trifluoromethyl, trifluoromethoxy, $C_1$-$C_4$-alkyl, $C_1$-$C_4$-alkoxy and $C_1$-$C_4$-alkoxycarbonyl,
$R^2$ represents $C_1$-$C_6$-alkyl, $C_3$-$C_6$-cycloalkyl, 4- to 6-membered heterocyclyl, phenyl, 2,2-difluoro-1,3-benzodioxolyl or 5- or 6-membered heteroaryl,
where cycloalkyl, heterocyclyl, phenyl and heteroaryl may be substituted by 1 to 3 substituents independently of one another selected from the group consisting of halogen, cyano, hydroxyl, amino, trifluoromethyl, difluoromethoxy, trifluoromethoxy, methyl, ethyl, methoxy, ethoxy and phenyl,
where phenyl may be substituted by 1 to 3 substituents independently of one another selected from the group consisting of halogen and trifluoromethyl,
and
where $C_1$-$C_2$-alkyl may be substituted by a phenyl substituent,
where phenyl may be substituted by 1 to 3 substituents independently of one another selected from the group consisting of halogen, cyano, trifluoromethyl, trifluoromethoxy, methyl, ethyl, methoxy and ethoxy,
$R^3$ represents $C_1$-$C_6$-alkyl, $C_2$-$C_6$-alkenyl, $C_2$-$C_6$-alkynyl, $C_1$-$C_6$-alkoxy, $C_1$-$C_6$-alkylamino, $C_3$-$C_7$-cycloalkyl, 4- to 7-membered heterocyclyl, phenyl, 5- or 6-membered heteroaryl, $C_3$-$C_7$-cycloalkyloxy, $C_3$-$C_7$-cycloalkylamino, 4- to 7-membered heterocyclylamino, phenylamino or 5- or 6-membered heteroarylamino,
where alkyl, $C_2$-$C_6$-alkoxy and alkylamino may be substituted by a substituent selected from the group consisting of halogen, hydroxyl, amino, cyano, $C_1$-$C_4$-alkoxy, $C_1$-$C_4$-alkoxycarbonyl, $C_3$-$C_7$-cycloalkyl, 4- to 6-membered heterocyclyl, phenyl and 5- or 6-membered heteroaryl,
where alkoxy may be substituted by a $C_1$-$C_4$-alkoxy substituent,
and
where cycloalkyl, heterocyclyl, phenyl, heteroaryl, cycloalkyloxy, cycloalkylamino, heterocyclylamino, phenylamino and heteroarylamino may be substituted by 1 to 3 substituents independently of one another selected from the group consisting of halogen, cyano, oxo, hydroxyl, amino, trifluoromethyl, difluoromethoxy, trifluoromethoxy, hydroxycarbonyl, aminocarbonyl, methyl, ethyl, methoxy, ethoxy, dimethylamino, methoxycarbonyl, ethoxycarbonyl, dimethylaminocarbonyl and cyclopropyl,
in which methyl and ethyl may be substituted by a hydroxyl substituent,
and their salts, their solvates and the solvates of their salts.

Preference is also given to compounds of the formula (I) in which
A represents a group of the formula where
# is the point of attachment to the piperidine ring,
* is the point of attachment to $R^2$,
$R^4$ represents hydrogen or methyl,
and
$R^5$ represents hydrogen or methyl,
$R^1$ represents phenyl,
where phenyl is substituted by 1 or 2 substituents independently of one another selected from the group consisting of trifluoromethyl, trifluoromethoxy, methyl, ethyl, isopropyl, methoxy and ethoxycarbonyl,
$R^2$ represents methyl, ethyl, isopropyl, tert-butyl, cyclopropyl, cyclopentyl, pyrrolidinyl, piperazinyl, phenyl, 2,2-difluoro-1,3-benzodioxolyl, thienyl, thiazolyl or pyridyl,
where cyclopentyl, piperazinyl, phenyl, thienyl, thiazolyl and pyridyl may be substituted by 1 or 2 substituents independently of one another selected from the group consisting of halogen, cyano, hydroxyl, trifluoromethyl, difluoromethoxy, trifluoromethoxy, methyl, ethyl, methoxy, ethoxy and phenyl,
where phenyl may be substituted by 1 or 2 substituents independently of one another selected from the group consisting of halogen and trifluoromethyl,
and
where methyl may be substituted by a phenyl substituent,
$R^3$ represents methyl, ethyl, isopropyl, tert-butyl, ethoxy, ethylamino, tert-butylamino, N-methyl-N-ethylamino, diethylamino, cyclopropyl, cyclobutyl, cyclopentyl, cyclohexyl, tetrahydrofuranyl, tetrahydropyranyl, morpholin-4-yl, thiomorpholin-4-yl, 1,1-dioxidothiomorpholin-4-yl, azetidin-1-yl, pyrrolidin-1-yl, piperidin-1-yl, piperazin-1-yl, phenyl, pyrrolyl, furyl, thiazolyl, pyrazolyl, pyridyl, cyclopentyloxy, cyclohexylamino, phenylamino or pyridylamino,
where methyl, ethyl, isopropyl, tert-butyl, ethoxy and ethylamino may be substituted by a substituent selected from the group consisting of halogen, hydroxyl, methoxy, cyclopropyl, phenyl, furyl, thienyl and pyrazolyl,
and
where cyclopropyl, cyclobutyl, cyclohexyl, tetrahydrofuranyl, morpholin-4-yl, azetidin-1-yl, pyrrolidin-1-yl, piperidin-1-yl, piperazin-1-yl, phenyl, furyl, thiazolyl, pyrazolyl, pyridyl, cyclohexylamino and phenylamino may be substituted by 1 or 2 substituents independently of one another selected from the group consisting of halogen, cyano, oxo, hydroxyl, amino, trifluoromethyl, difluoromethoxy, trifluoromethoxy, hydroxycarbonyl, aminocarbonyl, methyl, ethyl, methoxy, ethoxy, dimethylamino, methoxycarbonyl, ethoxycarbonyl, dimethylaminocarbonyl and cyclopropyl,
in which methyl and ethyl may be substituted by a hydroxyl substituent, and their salts, their solvates and the solvates of their salts.

Preference is also given to compounds of the formula (I) in which
A represents a group of the formula

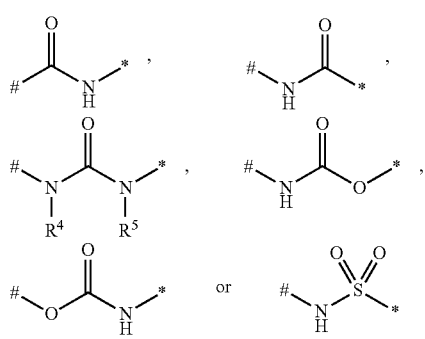

where
# is the point of attachment to the piperidine ring,
* is the point of attachment to $R^2$,
$R^4$ represents hydrogen or methyl,
and
$R^5$ represents hydrogen or methyl,
$R^1$ represents phenyl,
where phenyl is substituted by 1 or 2 substituents independently of one another selected from the group consisting of trifluoromethyl, trifluoromethoxy, methyl and ethyl,
$R^2$ represents methyl, ethyl, isopropyl, tert-butyl, cyclopropyl, cyclopentyl, phenyl, thienyl or pyridyl,
where cyclopentyl, phenyl, thienyl and pyridyl may be substituted by 1 or 2 substituents independently of one another selected from the group consisting of halogen, cyano, trifluoromethyl, trifluoromethoxy, methyl, methoxy and phenyl,
where phenyl may be substituted by 1 or 2 substituents independently of one another selected from the group consisting of chlorine, fluorine and trifluoromethyl,
and
where methyl may be substituted by a phenyl substituent,
$R^3$ represents morpholin-4-yl, 1,1-dioxidothiomorpholin-4-yl, 3-hydroxyazetidiny-1-yl, 3-hydroxypyrrolidin-1-yl, 4-cyanopiperidin-1-yl or 4-hydroxypiperidin-1-yl,
and their salts, their solvates and the solvates of their salts.

Preference is also given to compounds of the formula (I) in which
A represents a group of the formula

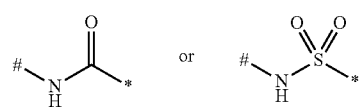

where
# is the point of attachment to the piperidine ring,
* is the point of attachment to $R^2$,
$R^1$ represents phenyl,
where phenyl is substituted by 1 or 2 substituents independently of one another selected from the group consisting of trifluoromethyl, trifluoromethoxy, methyl and ethyl,
$R^2$ represents methyl, ethyl, isopropyl, tert-butyl, cyclopropyl, cyclopentyl, phenyl, thienyl or pyridyl,
where cyclopentyl, phenyl, thienyl and pyridyl may be substituted by 1 or 2 substituents independently of one another selected from the group consisting of halogen, cyano, trifluoromethyl, trifluoromethoxy, methyl, methoxy and phenyl,
where phenyl may be substituted by 1 or 2 substituents independently of one another selected from the group consisting of chlorine, fluorine and trifluoromethyl,
and
where methyl may be substituted by a phenyl substituent,
$R^3$ represents morpholin-4-yl, 1,1-dioxidothiomorpholin-4-yl, 3-hydroxyazetidiny-1-yl, 3-hydroxypyrrolidin-1-yl, 4-cyanopiperidin-1-yl or 4-hydroxypiperidin-1-yl,
and their salts, their solvates and the solvates of their salts.

Preference is also given to compounds of the formula (I) in which the substituents —$R^1$ and -A-$R^2$ are in the cis-position to one another.

Preference is also given to compounds of the formula (I) in which
A represents a group of the formula

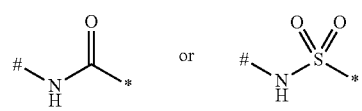

where
# is the point of attachment to the piperidine ring,
* is the point of attachment to $R^2$.

Preference is also given to compounds of the formula (I) in which
A represents a group of the formula

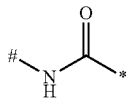

where
# is the point of attachment to the piperidine ring,
* is the point of attachment to R².
Preference is also given to compounds of the formula (I) in which
A represents a group of the formula

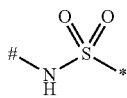

where
# is the point of attachment to the piperidine ring,
* is the point of attachment to R².
Preference is also given to compounds of the formula (I) in which
A represents a group of the formula

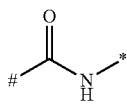

where
# is the point of attachment to the piperidine ring,
* is the point of attachment to R².
Preference is also given to compounds of the formula (I) in which
A represents a group of the formula

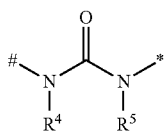

where
# is the point of attachment to the piperidine ring,
* is the point of attachment to R².
R⁴ represents hydrogen or methyl,
and
R⁵ represents hydrogen or methyl.
Preference is also given to compounds of the formula (I) in which
A represents a group of the formula

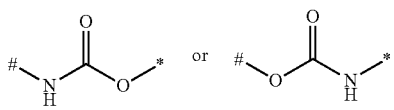

where
# is the point of attachment to the piperidine ring,
* is the point of attachment to R².
Preference is also given to compounds of the formula (I) in which R¹ represents phenyl, where phenyl is substituted in the para-position to the point of attachment to the piperidine ring by a substituent selected from the group consisting of trifluoromethyl, trifluoromethoxy and ethyl.
Preference is also given to compounds of the formula (I) in which R¹ is phenyl, where phenyl is substituted in the para-position to the point of attachment to the piperidine ring by an ethyl substituent.
Preference is also given to compounds of the formula (I) in which
R² represents methyl, ethyl, isopropyl, tert-butyl, cyclopropyl, cyclopentyl, phenyl, thienyl or pyridyl,
where cyclopentyl, phenyl, thienyl and pyridyl may be substituted by 1 or 2 substituents independently of one another selected from the group consisting of halogen, cyano, trifluoromethyl, trifluoromethoxy, methyl, methoxy and phenyl,
where phenyl may be substituted by 1 or 2 substituents independently of one another selected from the group consisting of chlorine, fluorine and trifluoromethyl,
and
where methyl may be substituted by a phenyl substituent.
Preference is also given to compounds of the formula (I) in which R² represents phenyl.
Preference is also given to compounds of the formula (I) in which R³ represents morpholin-4-yl, 1,1-dioxidothiomorpholin-4-yl, 3-hydroxyazetidin-1-yl, 3-hydroxypyrrolidin-1-yl, 4-cyanopiperidin-1-yl or 4-hydroxypiperidin-1-yl.
Preference is also given to compounds of the formula (I) in which R³ represents morpholin-4-yl.
Preference is also given to compounds of the formula (I) in which R³ represents 4-hydroxypiperidin-1-yl.
The individual radical definitions specified in the respective combinations or preferred combinations of radicals are, independently of the respective combinations of the radicals specified, also replaced as desired by radical definitions of other combinations.
Very particular preference is given to combinations of two or more of the preferred ranges mentioned above.
The invention further provides a process for preparing the compounds of the formula (I), or the salts thereof, solvates thereof and the solvates of the salts thereof, wherein either
[A] compounds of the formula

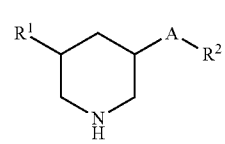

(II)

in which
A, R¹ and R² have the meaning given above,
are reacted with compounds of the formula

(III)

in which
R³ has the meaning given above and
X¹ represents halogen, preferably bromine or chlorine, or hydroxyl,
or
[B] compounds of the formula (II) are reacted with compounds of the formula

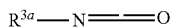  (IV)

in which
R³ᵃ represents $C_1$-$C_6$-alkyl, $C_3$-$C_7$-cycloalkyl, 4- to 7-membered heterocyclyl, phenyl or 5- or 6-membered heteroaryl,
  where alkyl may be substituted by a substituent selected from the group consisting of halogen, hydroxyl, amino, cyano, $C_1$-$C_4$-alkoxy, $C_1$-$C_4$-alkoxycarbonyl, $C_3$-$C_7$-cycloalkyl, 4- to 6-membered heterocyclyl, phenyl and 5- or 6-membered heteroaryl,
    where alkoxy may be substituted by a $C_1$-$C_4$-alkoxy substituent,
  and
  where cycloalkyl, heterocyclyl, phenyl and heteroaryl may be substituted by 1 to 3 substituents independently of one another selected from the group consisting of halogen, cyano, oxo, hydroxyl, amino, monofluoromethyl, difluoromethyl, trifluoromethyl, monofluoromethoxy, difluoromethoxy, trifluoromethoxy, monofluoromethylsulphanyl, difluoromethylsulphanyl, trifluoromethylsulphanyl, hydroxycarbonyl, aminocarbonyl, $C_1$-$C_4$-alkyl, $C_1$-$C_4$-alkoxy, $C_1$-$C_6$-alkylamino, $C_1$-$C_4$-alkoxycarbonyl, $C_1$-$C_4$-alkylaminocarbonyl and cyclopropyl,
    where alkyl may be substituted by a hydroxyl substituent,
to give compounds of the formula

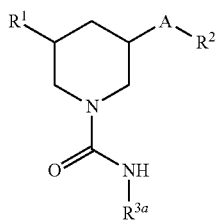  (Ia)

in which
A, R¹, R² and R³ᵃ have the meaning given above,
or
[C] compounds of the formula

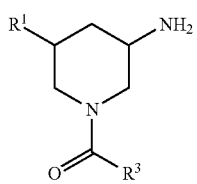  (V)

in which
R¹ and R³ have the meaning given above,
are reacted with compounds of the formula

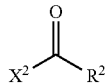  (VI)

in which
R² has the meaning given above and
X² represents halogen, preferably bromine or chlorine, or hydroxyl,
to give compounds of the formula

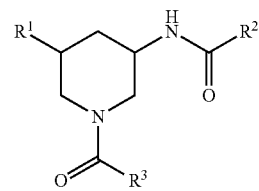  (Ib)

in which
R¹, R² and R³ have the meaning given above,
or
[D] compounds of the formula (V) are reacted with compounds of the formula

  (VII)

in which
R² has the meaning given above,
to give compounds of the formula

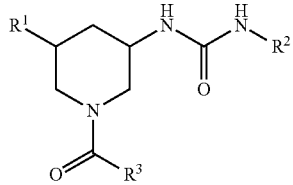  (Ic)

in which
R¹, R² and R³ have the meaning given above,
or
[E] compounds of the formula (V) are reacted with compounds of the formula

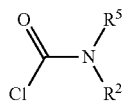  (VIII)

in which
R² and R⁵ have the meaning given above,
to give compounds of the formula

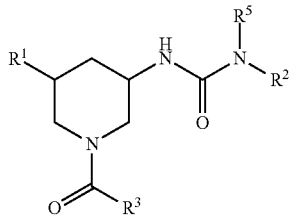
(Id)

in which
R¹, R², R³ and R⁵ have the meaning given above,
or
[F] compounds of the formula (Id) are reacted with compounds of the formula

 R⁴—X³ (IX)

in which
R⁴ has the meaning given above and
X³ represents halogen, preferably iodine, bromine or chlorine,
to give compounds of the formula

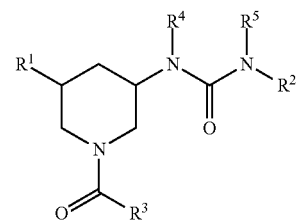
(Ie)

in which
R¹, R², R³, R⁴ and R⁵ have the meaning given above,
or
[G] compounds of the formula (V) are reacted with compounds of the formula

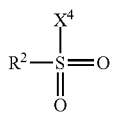
(X)

in which
R² has the meaning given above and
X⁴ represents chlorine or hydroxyl,
to give compounds of the formula

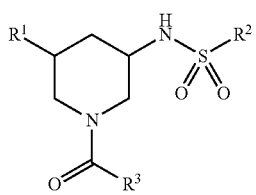
(If)

in which
R¹, R² and R³ have the meaning given above,
or
[H] compounds of the formula

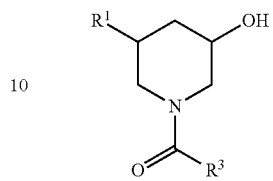
(XI)

in which
R¹ and R³ have the meaning given above,
are reacted initially with disuccinimidyl carbonate and then with compounds of the formula

 H₂N—R² (XII)

in which
R² has the meaning given above,
to give compounds of the formula

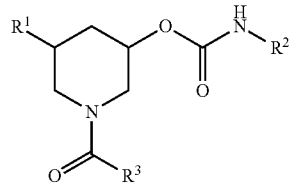
(Ig)

in which
R¹, R² and R³ have the meaning given above.

When X² represents halogen, the reaction according to process [A] is generally carried out in inert solvents, if appropriate in the presence of a base, preferably in a temperature range of from −30° C. to 50° C. at atmospheric pressure.

Inert solvents are, for example, tetrahydrofuran, methylene chloride, pyridine, dioxane or dimethylformamide; preference is given to tetrahydrofuran.

Bases are, for example, triethylamine, diisopropylethylamine or N-methylmorpholine; preference is given to triethylamine or diisopropylethylamine.

When X² represents hydroxyl, the reaction according to process [A] is generally carried out in inert solvents in the presence of a dehydrating agent, if appropriate in the presence of a base, preferably in a temperature range of from −30° C. to 50° C. at atmospheric pressure.

Inert solvents are, for example, halogenated hydrocarbons, such as dichloromethane or trichloromethane, hydrocarbons, such as benzene, nitromethane, dioxane, dimethylformamide or acetonitrile. It is equally possible to use mixtures of the solvents. Particular preference is given to dichloromethane or dimethylformamide.

Suitable dehydrating agents are, for example, carbodiimides such as, for example, N,N'-diethyl-, N,N,'-dipropyl-, N,N'-diisopropyl-, N,N'-dicyclohexylcarbodiimide, N-(3-dimethylaminoisopropyl)-N'-ethylcarbodiimide hydrochloride (EDC), N-cyclohexylcarbodiimide N'-propyloxymethyl-polystyrene (PS-carbodiimide) or carbonyl compounds such as carbonyl diimidazole, or 1,2-oxazolium compounds such as 2-ethyl-5-phenyl-1,2-oxazolium 3-sulphate or 2-tert-butyl-5-methylisoxazolium perchlorate, or acylamino compounds such as 2-ethoxy-1-ethoxycarbonyl-1,2-dihydroquinoline, or propanephosphonic anhydride, or isobutyl chloroformate, or bis-(2-oxo-3-oxazolidinyl)phosphoryl chloride or benzotriazolyloxytri(dimethylamino)phosphonium hexafluorophosphate, or O-(benzotriazol-1-yl)-N,N,N', N'-tetramethyluronium hexafluorophosphate (HBTU), 2-(2-oxo-1-(2H)-pyridyl)-1,1,3,3-tetramethyluronium tetrafluoroborate (TPTU) or O-(7-azabenzotriazol-1-yl)-N,N,N',N'-tetramethyluronium hexafluorophosphate (HATU), or 1-hydroxybenzotriazole (HOBt), or benzotriazol-1-yloxytris(dimethylamino)phosphonium hexafluorophosphate (BOP), or N-hydroxysuccinimide, or mixtures of these, with bases.

Bases are, for example, alkali metal carbonates such as, for example, sodium carbonate or potassium carbonate, or sodium bicarbonate or potassium bicarbonate, or organic bases such as trialkylamines, for example triethylamine, N-methylmorpholine, N-methylpiperidine, 4-dimethylaminopyridine or diisopropylethylamine.

Preferably, the condensation is carried out with HATU or with EDC in the presence of HOBt.

The compounds of the formula (III) are known or can be synthesized by known processes from the appropriate starting materials.

The reaction according to process [B] is generally carried out in inert solvents, if appropriate in the presence of a base, preferably in a temperature range of from 0° C. to 50° C. at atmospheric pressure. Inert solvents are, for example, tetrahydrofuran, methylene chloride, dioxane or dimethylformamide; preference is given to tetrahydrofuran.

Bases are, for example, triethylamine, diisopropylethylamine or N-methylmorpholine; preference is given to triethylamine or diisopropylethylamine.

The compounds of the formula (IV) are known or can be synthesized by known processes from the appropriate starting materials.

The reaction according to process [C] is carried out as described for process [A].

The compounds of the formula (VI) are known or can be synthesized by known processes from the appropriate starting materials.

The reaction according to process [D] is carried out as described for process [B].

The compounds of the formula (VII) are known or can be synthesized by known processes from the appropriate starting materials.

The reaction according to process [E] is carried out as described for process [B].

The compounds of the formula (VIII) are known or can be synthesized by known processes from the appropriate starting materials.

The reaction according to process [F] is generally carried out in inert solvents, in the presence of a base, if appropriate in the presence of a potassium iodide, preferably in a temperature range from room temperature up to reflux of the solvents at atmospheric pressure.

Inert solvents are, for example, halogenated hydrocarbons such as methylene chloride, trichloromethane or 1,2-dichloroethane, ethers such as dioxane, tetrahydrofuran or 1,2-dimethoxyethane, or other solvents such as acetone, dimethylformamide, dimethylacetamide, 2-butanone or acetonitrile; preference is given to dimethylformamide.

Bases are, for example, alkali metal carbonates such as caesium carbonate, sodium carbonate or potassium carbonate, or sodium methoxide or potassium methoxide, or sodium ethoxide or potassium ethoxide or potassium tert-butoxide, or amides such as sodium amide, lithium bis(trimethylsilyl)amide or lithium diisopropylamide, or organometallic compounds such as butyllithium or phenyllithium, or other bases such as sodium hydride, DBU; preference is given to sodium hydride.

The compounds of the formula (IX) are known or can be synthesized by known processes from the appropriate starting materials.

When $X^2$ represents halogen, the reaction according to process [G] is generally carried out in inert solvents, if appropriate in the presence of a base, preferably in a temperature range of from 0° C. to 50° C. at atmospheric pressure.

Inert solvents are, for example, tetrahydrofuran, methylene chloride, pyridine, dioxane or dimethylformamide; preference is given to methylene chloride.

Bases are, for example, triethylamine, diisopropylethylamine or N-methylmorpholine; preference is given to triethylamine or diisopropylethylamine.

When $X^2$ represents hydroxyl, the reaction according to process [G] is generally carried out in inert solvents in the presence of 4-dimethylaminopyridine, if appropriate in the presence of a base, preferably in a temperature range of from 0° C. to 50° C. at atmospheric pressure.

Inert solvents are, for example, halogenated hydrocarbons, such as dichloromethane or trichloromethane, hydrocarbons, such as benzene, nitromethane, dioxane, dimethylformamide or acetonitrile. It is equally possible to use mixtures of the solvents. Particular preference is given to dichloromethane or dimethylformamide.

Bases are, for example, organic bases such as trialkylamines, for example triethylamine, N-methylmorpholine, N-methylpiperidine, 4-dimethylaminopyridine or diisopropylethylamine; preference is given to diisopropylethylamine.

The compounds of the formula (X) are known or can be synthesized by known processes from the appropriate starting materials.

The reaction according to process [H] is generally carried out in inert solvents, if appropriate in the presence of a base, preferably in a temperature range of from 0° C. to 50° C. at atmospheric pressure.

Bases are, for example, organic bases such as trialkylamines, for example triethylamine, N-methylmorpholine, N-methylpiperidine, 4-dimethylaminopyridine or diisopropylethylamine; preference is given to diisopropylethylamine.

The compounds of the formula (XII) are known or can be synthesized by known processes from the appropriate starting materials.

The compounds of the formula (II) are known or can be prepared by hydrogenating compounds of the formula

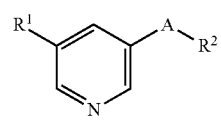

(XIII)

in which
A, $R^1$ and $R^2$ have the meaning given above.

The hydrogenation is generally carried out using a reducing agent in inert solvents, if appropriate with addition of acid such as mineral acids and carboxylic acids, preferably acetic acid, preferably in a temperature range of from room temperature to reflux of the solvents and in a pressure range of from atmospheric pressure to 100 bar, preferably at 50-80 bar.

Preferred reducing agents are hydrogen with palladium on activated carbon, with rhodium on activated carbon, with ruthenium on activated carbon or mixed catalysts thereof, or hydrogen with palladium on alumina or with rhodium on alumina; preference is given to hydrogen with palladium on activated carbon or with rhodium on activated carbon.

Inert solvents are, for example, alcohols such as methanol, ethanol, n-propanol, isopropanol, n-butanol or tert-butanol; preference is given to methanol or ethanol.

The compounds of the formula (XIII) are known or can be prepared by reacting compounds of the formula

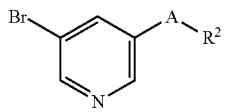

(XIV)

in which
A and R² have the meaning given above,
with compounds of the formula

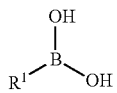

(XV)

in which
R¹ has the meaning given above.

The reaction is generally carried out in inert solvents, in the presence of a catalyst, if appropriate in the presence of an additive, preferably in a temperature range of from room temperature to reflux of the solvent at atmospheric pressure.

Inert solvents are, for example, ethers, such as dioxane, tetrahydrofuran or 1,2-dimethoxyethane, hydrocarbons, such as benzene, xylene or toluene, or other solvents, such as nitrobenzene, dimethylformamide, dimethylacetamide, dimethyl sulphoxide or N-methylpyrrolidone, if appropriate, some water is added to these solvents. Preference is given to toluene with water or to a mixture of 1,2-dimethoxyethane, dimethylformamide and water.

Catalysts are, for example, palladium catalysts customary for Suzuki reaction conditions; preference is given to catalysts such as, for example, dichlorobis(triphenylphosphine) palladium, tetrakistriphenylphosphinepalladium(0), palladium(II) acetate or bis(diphenylphosphaneferrocenyl) palladium(II) chloride.

Additives are, for example, potassium acetate, caesium carbonate, potassium carbonate or sodium carbonate, barium hydroxide, potassium tert-butoxide, caesium fluoride, potassium fluoride or potassium phosphate; preference is given to potassium fluoride or sodium carbonate.

The compounds of the formulae (XIV) and (XV) are known or can be synthesized by known processes from the appropriate starting materials.

The compounds of the formula

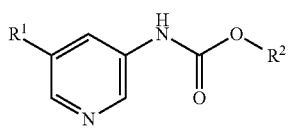

(XIIIa)

in which
R¹ and R² have the meaning given above,
are known or can be prepared by reacting compounds of the formula

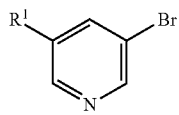

(XVI)

in which
R¹ has the meaning given above,
with compounds of the formula

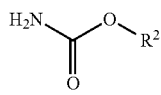

(XVII)

in which
R² has the meaning given above.

The reaction is generally carried out in inert solvents, in the presence of a catalyst, in the presence of a ligand, if appropriate in the presence of an additive, preferably in a temperature range of from room temperature to reflux of the solvent at atmospheric pressure.

Inert solvents are, for example, ethers, such as dioxane, tetrahydrofuran or 1,2-dimethoxyethane, hydrocarbons, such as benzene, xylene or toluene, or other solvents, such as nitrobenzene, dimethylformamide, dimethylacetamide, dimethyl sulphoxide or N-methylpyrrolidone, if appropriate, some water is added to these solvents. Preference is given to dioxane.

Catalysts are, for example, palladium catalysts customary for Buchwald-Hartwig crosscouplings; preference is given to catalysts such as, for example, dichlorobis(triphenylphosphine)palladium, tetrakistriphenylphosphinepalladium(0), tris(dibenzylideneacetone)dipalladium, palladium(II) acetate or bis(diphenylphosphaneferrocenyl)palladium(II) chloride; preference is given to tris(dibenzylideneacetone) dipalladium.

Ligands are, for example, 4,5-bis(diphenylphosphino)-9, 9'-dimethylxanthene, 1,2-bis(diphenylphosphino)ethane, 2,2'-bis(diphenylphosphino)-1,1'-binaphthyl (BINAP) and 1,1'-bis(diphenylphosphanyl)ferrocene; preference is given to 4,5-bis(diphenylphosphino)-9,9'-dimethylxanthene.

Additives are, for example, potassium acetate, caesium carbonate, potassium carbonate or sodium carbonate, barium hydroxide, potassium tert-butoxide, caesium fluoride, potassium fluoride or potassium phosphate; preference is given to caesium carbonate.

The compounds of the formula (XVI) are known or can be synthesized by known processes from the appropriate starting materials. The compounds of the formula (XVI) can also be synthesized from the appropriate starting materials using the process described for the reaction of compounds of the formula (XIV) with compounds of the formula (XV).

The compounds of the formula (XVII) are known or can be synthesized by known processes from the appropriate starting materials.

The compounds of the formula (V) are known or can be prepared by reacting compounds of the formula

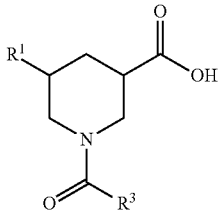

(XVIII)

in which
$R^1$ and $R^3$ have the meaning given above,
with diphenyl phosphorazidate and then working up the reaction, if appropriate with addition of acid.

The reaction is generally carried out in solvents, in the presence of a base, if appropriate in the presence of di-tert-butyl dicarbonate, if appropriate in the presence of molecular sieves, preferably in a temperature range of from room temperature to reflux of the solvent at atmospheric pressure.

Solvents are, for example, alcohols such as methanol, ethanol, n-propanol, isopropanol, n-butanol or tert-butanol, or mixtures of these alcohols with hydrocarbons such as benzene, xylene or toluene; preference is given to a mixture of tert-butanol and toluene.

Bases are, for example, organic bases such as trialkylamines, for example triethylamine, N-methylmorpholine, N-methylpiperidine, 4-dimethylaminopyridine or diisopropylethylamine; preference is given to triethylamine.

Acids are, for example, trifluoroacetic acid, trifluoroacetic acid in dichloromethane or concentrated hydrochloric acid.

The compounds of the formula (XVIII) are known or can be prepared by reacting compounds of the formula

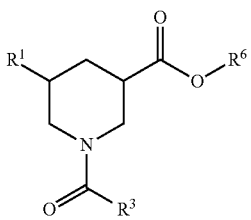

(XIX)

in which
$R^1$ and $R^3$ have the meaning given above and
$R^6$ represents methyl or ethyl,
with a base.

The reaction is generally carried out in inert solvents, in the presence of a base, preferably in a temperature range of from room temperature to reflux of the solvents at atmospheric pressure.

Inert solvents are, for example, halogenated hydrocarbons, such as methylene chloride, trichloromethane, carbon tetrachloride or 1,2-dichloroethane, ethers, such as diethyl ether, methyl tert-butyl ether, 1,2-dimethoxyethane, dioxane or tetrahydrofuran, or other solvents, such as dimethylformamide, dimethylacetamide, acetonitrile or pyridine, or mixtures of solvents, or mixtures of solvent with water; preference is given to a mixture of tetrahydrofuran and water.

Bases are, for example, alkali metal hydroxides such as sodium hydroxide, lithium hydroxide or potassium hydroxide, or alkali metal carbonates such as caesium carbonate, sodium carbonate or potassium carbonate; preference is given to lithium hydroxide.

The compounds of the formula (XIX) are known or can be prepared by reacting compounds of the formula

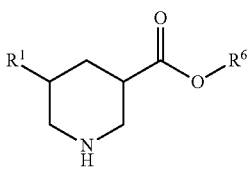

(XX)

in which
$R^1$ and $R^6$ have the meaning given above,
with compounds of the formula (III).
The reaction is carried out as described for process [A].

The compounds of the formula (XX) are known or can be prepared by hydrogenating compounds of the formula

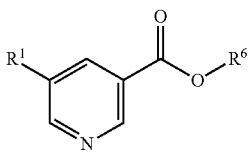

(XXI)

in which
$R^1$ and $R^6$ have the meaning given above.

The hydrogenation is carried out under the reaction conditions given for the hydrogenation of compounds of the formula (XIII).

The compounds of the formula (XXI) are known or can be prepared by reacting compounds of the formula

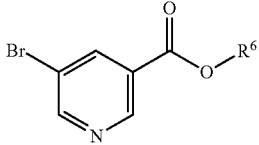

(XXII)

with compounds of the formula (XV).

The reaction is carried out under the reaction conditions given for the reaction of compounds of the formula (XIV) with compounds of the formula (XV).

The compounds of the formula (XXII) are known or can be synthesized by known processes from the appropriate starting materials.

The compounds of the formula (XI) are known or can be prepared by reacting compounds of the formula

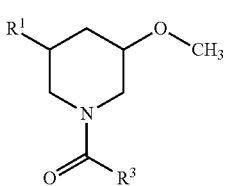

(XXIII)

in which
R[1] and R[3] have the meaning given above,
with boron tribromide.

The reaction is generally carried out in inert solvents, preferably in a temperature range of from −20° C. to room temperature at atmospheric pressure.

Inert solvents are, for example, halogenated hydrocarbons such as methylene chloride, trichloromethane, carbon tetrachloride or 1,2-dichloroethane; preference is given to methylene chloride.

The compounds of the formula (XXIII) are known or can be prepared by reacting compounds of the formula

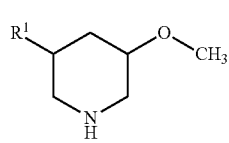
(XXIV)

in which
R[1] has the meaning given above,
with compounds of the formula (III).

The reaction is carried out as described for process [A].

The compounds of the formula (XXIV) are known or can be prepared by hydrogenating compounds of the formula

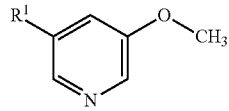
(XXV)

in which
R[1] has the meaning given above.

The hydrogenation is carried out under the reaction conditions given for the hydrogenation of compounds of the formula (XIII).

The compounds of the formula (XXV) are known or can be prepared by reacting compounds of the formula

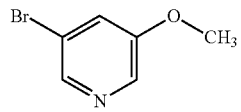
(XXVI)

with compounds of the formula (XV).

The reaction is carried out under the reaction conditions given for the reaction of compounds of the formula (XIV) with compounds of the formula (XV).

The compound of the formula (XXVI) is known or can be synthesized by known processes from the appropriate starting materials.

Free amino groups in the compounds of the processes mentioned above are optionally protected during the reaction by protective groups known to the person skilled in the art; preference is given to a tert-butoxycarbonyl protective group. After the reaction, these protective groups are removed using reactions known to the person skilled in the art; preference is given to reaction with trifluoroacetic acid or concentrated hydrochloric acid.

The preparation of the compounds of the formula (I) can be illustrated by the synthesis schemes below.

Scheme 1

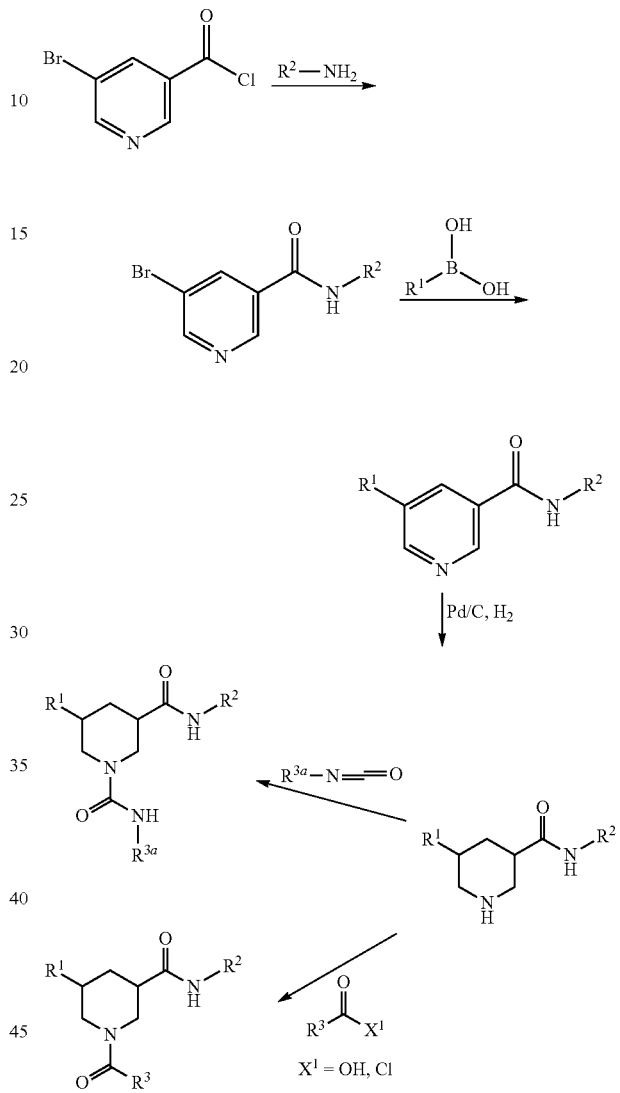

Scheme 2

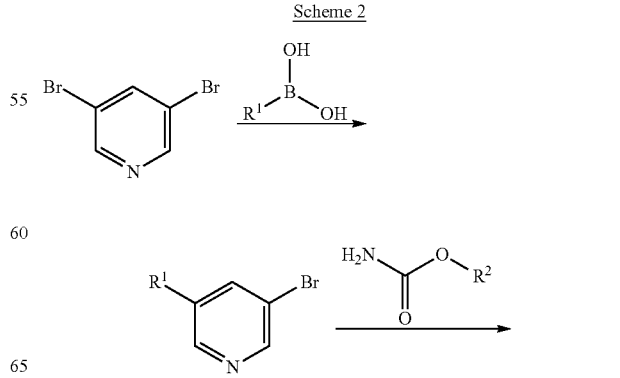

25 -continued
26 -continued
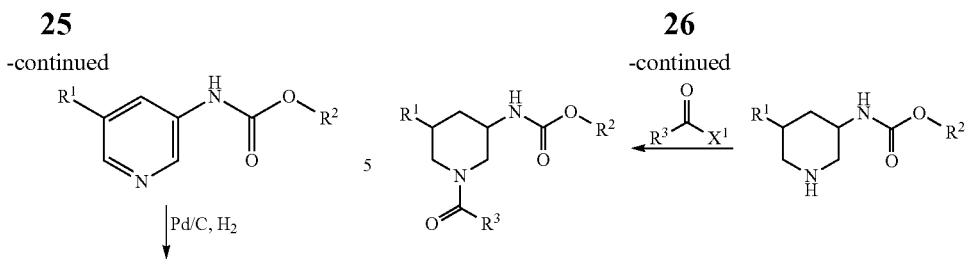
Scheme 3
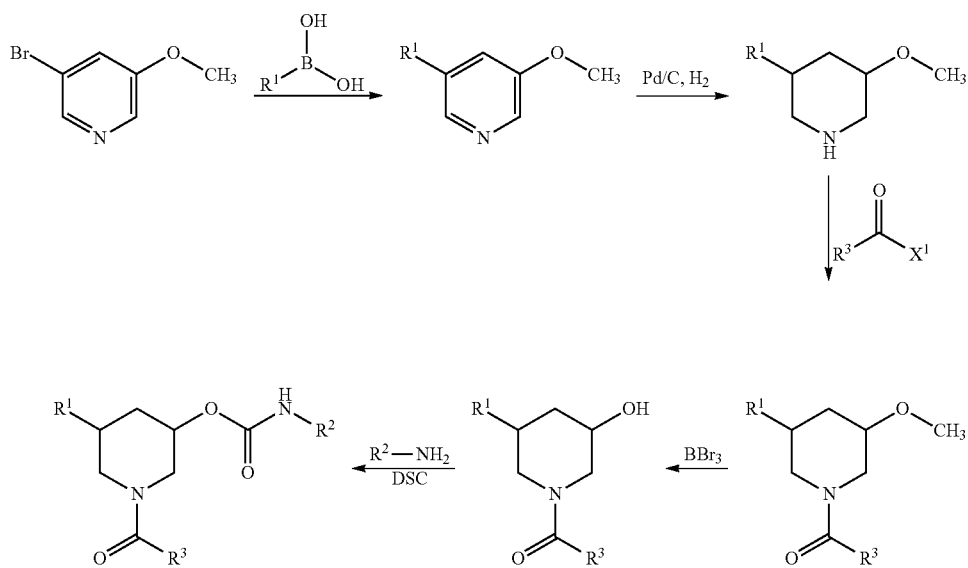
Scheme 4
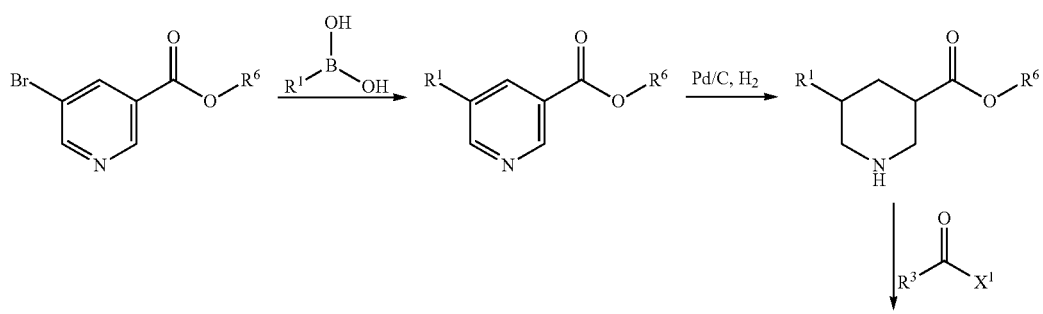
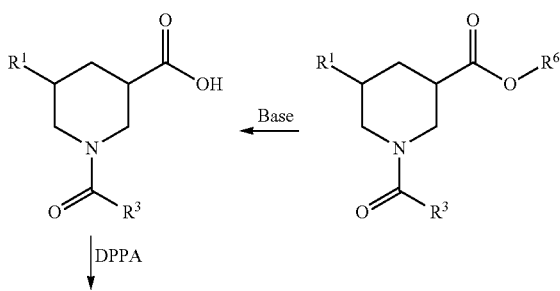

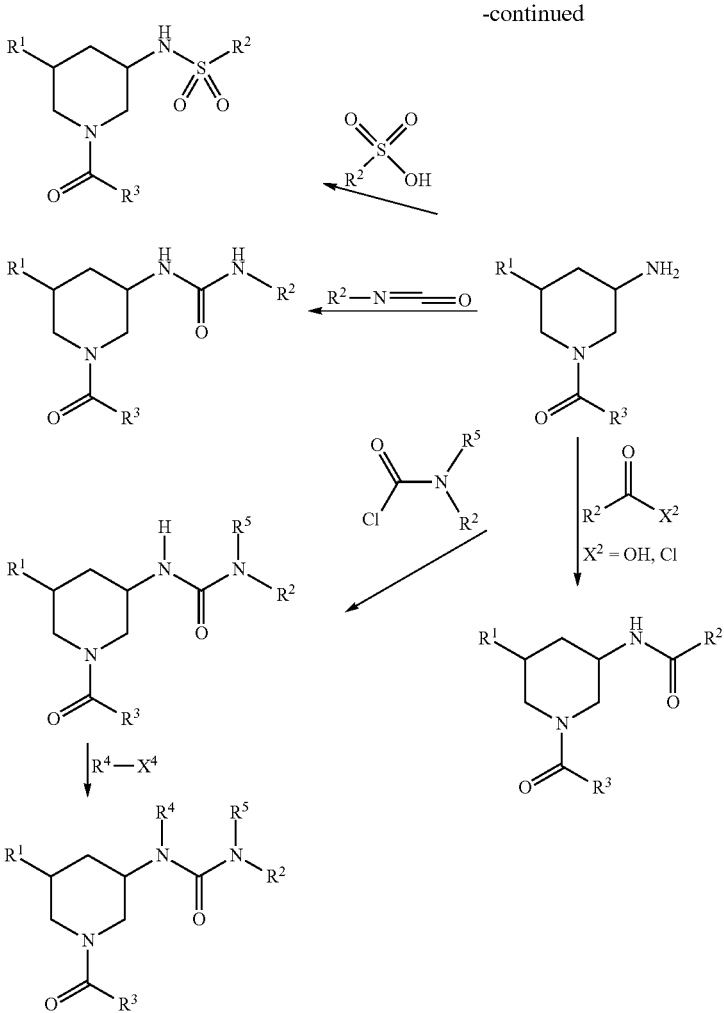

The compounds according to the invention have an unforeseeable useful spectrum of pharmacological and pharmacokinetic activity. They are selective antagonists of the PAR-1 receptor acting in particular as platelet aggregation inhibitors, as inhibitors of endothelium proliferation and as inhibitors of tumour growth.

They are therefore suitable for use as medicaments for the treatment and/or prophylaxis of diseases in humans and animals.

The present invention furthermore provides the use of the compounds according to the invention for the treatment and/or prophylaxis of disorders, preferably of thromboembolic disorders and/or thromboembolic complications.

"Thromboembolic disorders" in the sence of the present invention include in particular disorders such as ST-segment elevation myocardial infarction (STEMI) and non-ST-segment elevation myocardial infarction (non-STEMI), stabile angina pectoris, unstable angina pectoris, reocclusions and restenoses after coronary interventions such as angioplasty, stent implantations or aortocoronary bypass, peripheral arterial occlusion diseases, pulmonary embolisms, deep venous thromboses and renal vein thromboses, transitory ischaemic attacks and also thrombotic and thromboembolic stroke.

Accordingly, the substances are also suitable for the prevention and treatment of cardiogenic thromboembolisms, such as, for example, brain ischaemias, stroke and systemic thromboembolisms and ischaemias, in patients with acute, intermittent or persistent cardiac arrhythmias, such as, for example, atrial fibrillation, and those undergoing cardioversion, furthermore in patients with heart valve disorders or with intravasal objects, such as, for example, artificial heart valves, catheters, intraaortic balloon counterpulsation and pacemaker probes.

Thromboembolic complications are furthermore encountered in connection with microangiopathic haemolytic anaemias, extracorporeal circulation, such as, for example, haemodialysis, haemofiltration, ventricular assist devices and artificial hearts, and also heart valve prostheses.

Moreover, the compounds according to the invention are also used for influencing wound healing, for the prophylaxis and/or treatment of atherosclerotic vascular disorders and inflammatory disorders, such as rheumatic disorders of the locomotive system, coronary heart diseases, of heart failure, of hypertension, of inflammatory disorders, such as, for example, asthma, COPD, inflammatory pulmonary disorders, glomerulonephritis and inflammatory intestinal disorders, and additionally also for the prophylaxis and/or treatment of Alzheimer's disease, autoimmune disorders, Crohn's disease and ulcerative colitis.

Moreover, the compounds according to the invention can be used for inhibiting tumour growth and the formation of metastases, for microangiopathies, age-related macular degeneration, diabetic retinopathy, diabetic nephropathy and other microvascular disorders, and also for the prevention and treatment of thromboembolic complications, such as, for example, venous thromboembolisms, for tumour patients, in particular those undergoing major surgical interventions or chemo- or radiotherapy.

The compounds according to the invention are additionally suitable for the treatment of cancer. Cancers include: carcinomas (including breast cancer, hepatocellular carcinomas, lung cancer, colorectal cancer, cancer of the colon and melanomas), lymphomas (for example non-Hodgkin's lymphomas and mycosis fungoides), leukaemias, sarcomas, mesotheliomas, brain cancer (for example gliomas), germinomas (for example testicular cancer and ovarian cancer), choriocarcinomas, renal cancer, cancer of the pancreas, thyroid cancer, head and neck cancer, endometrial cancer, cancer of the cervix, cancer of the bladder, stomach cancer and multiple myeloma.

Moreover, PAR-1 expressed on endothelial cells mediates signals resulting in vascular growth ("angiogenesis"), a process which is vital for enabling tumour growth beyond about 1 mm$^3$ Induction of angiogenesis is also relevant for other disorders; these include disorders of the rheumatic type (for example rheumatoid arthritis), pulmonary disorders (for example pulmonary fibrosis, pulmonary hypertension, in particular pulmonary arterial hypertension, disorders characterized by pulmonary occlusion), arteriosclerosis, plaque rupture, diabetic retinopathy and wet macular degeneration.

In addition, the compounds according to the invention are suitable for treatment of sepsis. Sepsis (or septicaemia) is a frequent disorder with high mortality. Initial symptoms of sepsis are typically unspecific (for example fever, reduced general state of health); however, as the disease progresses there may be a general activation of the coagulation system ("disseminated intravascular coagulation" or "consumption coagulopathy"; hereinbelow referred to as "DIC") with the formation of microthrombi in various organs and secondary bleeding complications. Moreover, there may be endothelial damage with increased permeability of the vessels and diffusion of fluid and proteins into the extravasal space. As the disorder worsens, there may be organ dysfunction or organ failure (for example kidney failure, liver failure, respiratory failure, deficits of the central nervous system and heart/circulatory failure) and even multi-organ failure. In principle, this may affect any organ; the most frequently encountered organ dysfunctions and organ failures are those of the lung, the kidney, the cardiovascular system, the coagulation system, the central nervous system, the endocrine glands and the liver. Sepsis may be associated with an "acute respiratory distress syndrome" (referred to hereinafter as ARDS). ARDS may also occur independently of sepsis. "Septic shock" is the occurrence of treatment-requiring hypotension which facilitates further organ damage and is associated with a worsening of the prognosis.

Pathogens can be bacteria (gram-negative and gram-positive), fungi, viruses and/or eukaryotes. The site of entry or primary infection may be pneumonia, an infection of the urinary tract or peritonitis, for example. The infection may, but need not necessarily, be associated with bacteriaemia.

Sepsis is defined as the presence of an infection and a "systemic inflammatory response syndrome" (hereinbelow referred to as "SIRS"). SIRS occurs during infections, but also during other states such as injuries, burns, shock, surgical interventions, ischaemia, pancreatitis, reanimation or tumours. The definition of the ACCP/SCCM Consensus Conference Committee of 1992 (*Crit. Care Med.* 1992, 20, 864-874) describes the symptoms required for the diagnosis "SIRS" and measurement parameters (inter alia a change in body temperature, increased heart rate, breathing difficulties and changes in the blood picture). The later (2001) SCCM/ESICM/ACCP/ATS/SIS International Sepsis Definitions Conference essentially maintained the criteria, but fine-tuned details (Levy et al., *Crit. Care Med.* 2003, 31, 1250-1256).

DIC and SIRS may occur during sepsis, but also as a result of surgical interventions, tumour disorders, burns or other injuries. In the case of DIC, there is a massive activation of the coagulation system at the surface of damaged endothelial cells, the surfaces of foreign bodies or injured extravascular tissue. As a consequence, there is coagulation in small vessels of various organs with hypoxia and subsequent organ dysfunction. A secondary effect is the consumption of coagulation factors (for example factor X, prothrombin, fibrinogen) and platelets, which reduces the coagulability of the blood and may result in heavy bleeding.

In addition, the compounds according to the invention can also be used for preventing coagulation ex vivo, for example for preserving blood and plasma products, for cleaning/pretreating catheters and other medical auxiliaries and instruments, including extracorporeal circulation, for coating synthetic surfaces of medical auxiliaries and instruments used in vivo or ex vivo or for platelet-containing biological samples.

The present invention furthermore provides the use of the compounds according to the invention for coating medical instruments and implants, for example catheters, prostheses, stents or artificial heart valves. Here, the compounds according to the invention can be firmly attached to the surface or, for local action, be released over a certain period of time from a carrier coating into the immediate surroundings.

The present invention further provides for the use of the compounds according to the invention for the treatment and/or prophylaxis of disorders, in particular the disorders mentioned above.

The present invention further provides for the use of the compounds according to the invention for producing a medicament for the treatment and/or prophylaxis of disorders, in particular the disorders mentioned above.

The present invention further provides a method for the treatment and/or prophylaxis of disorders, especially the disorders mentioned above, using a therapeutically effective amount of a compound according to the invention.

The present invention further provides medicaments comprising a compound according to the invention and one or more further active compounds, especially for the treatment and/or prophylaxis of the disorders mentioned above. Preferred examples of suitable active compound combinations include:

calcium channel blockers, for example amlodipine besilate (for example Norvasc™), felodipine, diltiazem, verapamil, nifedipine, nicardipine, nisoldipine and bepridil;

iomerizine;

statins, for example atorvastatin, fluvastatin, lovastatin, pitavastatin, pravastatin, rosuvastatin and simvastatin;

cholesterol resorption inhibitors, for example ezetimibe and AZD4121;

cholesteryl ester transfer protein ("CETP") inhibitors, for example torcetrapib;

low-molecular weight heparins, for example dalteparin sodium, ardeparin, certoparin, enoxaparin, parnaparin, tinzaparin, reviparin and nadroparin;

further anticoagulants, for example warfarin, marcumar, fondaparinux;

antiarrhythmics, for example dofetilide, ibutilide, metoprolol, metoprolol tartrate, propranolol, atenolol, ajmaline, disopyramide, prajmaline, procainamide, quinidine, sparteine, aprindine, lidocaine, mexiletine, tocamide, encamide, flecamide, lorcamide, moricizine, propafenone, acebutolol, pindolol, amiodarone, bretylium tosylate, bunaftine, sotalol, adenosine, atropine and digoxin;

alpha-adrenergic agonists, for example doxazosin mesylate, terazoson and prazosin;

beta-adrenergic blockers, for example carvedilol, propranolol, timolol, nadolol, atenolol, metoprolol, bisoprolol, nebivolol, betaxolol, acebutolol and bisoprolol;

aldosterone antagonists, for example eplerenone and spironolactone;

angiotensin-converting enzyme inhibitors ("ACE inhibitors"), for example moexipril, quinapril hydrochloride, ramipril, lisinopril, benazepril hydrochloride, enalapril, captopril, spirapril, perindopril, fosinopril and trandolapril;

angiotensin II receptor blockers ("ARBs"), for example olmesartan-medoxomil, candesartan, valsartan, telmisartan, irbesartan, losartan and eprosartan;

endothelin antagonists, for example tezosentan, bosentan and sitaxsentan-sodium;

inhibitors of neutral endopeptidase, for example candoxatril and ecadotril;

phosphodiesterase inhibitors, for example milrinone, theophylline, vinpocetine, EHNA (erythro-9-(2-hydroxy-3-nonyl)adenine), sildenafil, vardenafil and tadalafil;

fibrinolytics, for example reteplase, alteplase and tenecteplase;

GP IIb/IIIa antagonists, for example integrillin, abciximab and tirofiban;

direct thrombin inhibitors, for example AZD0837, argatroban, bivalirudin and dabigatran;

indirect thrombin inhibitors, for example odiparcil;

direct and indirect factor Xa inhibitors, for example fondaparinux-sodium, apixaban, razaxaban, rivaroxaban (BAY 59-7939), KFA-1982, DX-9065a, AVE3247, otamixaban (XRP0673), AVE6324, SAR377142, idraparinux, SSR126517, DB-772d, DT-831j, YM-150, 813893, LY517717 and DU-1766;

direct and indirect factor Xa/IIa inhibitors, for example enoxaparin-sodium, AVE5026, SSR128428, SSR128429 and BIBT-986 (Tanogitran);

lipoprotein-associated phospholipase A2 ("LpPLA2") modulators;

diuretics, for example chlorthalidone, ethacrynic acid, furosemide, amiloride, chlorothiazide, hydrochlorothiazide, methylclothiazide and benzthiazide;

nitrates, for example isosorbide 5-mononitrate;

thromboxane antagonists, for example seratrodast, picotamide and ramatroban;

platelet aggregation inhibitors, for example clopidogrel, tiklopidin, cilostazol, aspirin, abciximab, limaprost, eptifibatide and CT-50547;

cyclooxygenase inhibitors, for example meloxicam, rofecoxib and celecoxib;

B-type natriuretic peptides, for example nesiritide and ularitide;

NV1FGF modulators, for example XRP0038;

HT1B/5-HT2A antagonists, for example SL65.0472;

guanylate cyclase activators, for example ataciguat (HMR1766) and HMR1069;

e-NOS transcription enhancers, for example AVE9488 and AVE3085;

antiatherogenic substances, for example AGI-1067:

CPU inhibitors, for example AZD9684;

renin inhibitors, for example aliskirin and VNP489;

inhibitors of adenosine diphosphate-induced platelet aggregation, for example clopidogrel, tiklopidin, prasugrel and AZD6140;

NHE-1 inhibitors, for example AVE4454 and AVE4890.

Antibiotic therapy: various antibiotics or antifungal medicament combinations are suitable, either as calculated therapy (before a microbial assessment has been made) or as specific therapy; fluid therapy, for example crystalloid or colloidal fluids; vasopressors, for example norepinephrine, dopamine or vasopressin; inotropic therapy, for example dobutamine; corticosteroids, for example hydrocortisone, or fludrocortisone; recombinant human activated protein C, Xigris; blood products, for example erythrocyte concentrates, platelet concentrates, erythropoietin or fresh frozen plasma; assisted ventilation in sepsis-induced acute lung injury (ALI) or acute respiratory distress syndrome (ARDS), for example permissive hypercapnia, low tidal volumes; sedation: for example diazepam, lorazepam, midazolam or propofol. Opioids: for example fentanyl, hydromorphone, morphine, meperidine or remifentanil. NSAIDs: for example ketorolac, ibuprofen or acetaminophen. Neuromuscular blockade: for example pancuronium; glucose control, for example insulin, glucose; renal replacement therapies, for example continuous veno-venous haemofiltration or intermittent haemodialysis. Low-dose dopamine for renal protection; anticoagulants, for example for thrombosis prophylaxis or for renal replacement therapies, for example unfractionated heparins, low-molecular weight heparins, heparinoids, hirudin, bivalirudin or argatroban; bicarbonate therapy; stress ulcer prophylaxis, for example H2 receptor inhibitors, antacids.

Medicaments for proliferative disorders: uracil, chlormethine, cyclophosphamide, ifosfamide, melphalan, chlorambucil, pipobroman, triethylenemelamine, triethylenethiophosphoramine, busulfan, carmustine, lomustine, streptozocin, dacarbazine, methotrexate, 5-fluorouracil, floxuridine, cytarabine, 6-mercaptopurine, 6-thioguanine, fludarabine phosphate, pentostatin, vinblastine, vincristine, vindesine, bleomycin, dactinomycin, daunorubicin, doxorubicin, epirubicin, idarubicin, paclitaxel, mithramycin, deoxycoformycin, mitomycin-C, L-asparaginase, interferons, etoposide, teniposide, 17.alpha.-ethynylestradiol, diethylstilbestrol, testosterone, prednisone, fluoxymesterone, dromostanolone propionate, testolactone, megestrol acetate, tamoxifen, methylprednisolone, methyltestosterone, prednisolone, triamcinolone, chlorotrianisene, hydroxyprogesterone, aminoglutethimide, estranrustine, medroxyprogesterone acetate, leuprolide, flutamide, toremifene, goserelin, cisplatin, carboplatin, hydroxyurea, amsacrine, procarbazine, mitotane, mitoxantrone, levamisole, navelbene, anastrazole, letrazole, capecitabine, reloxafine, droloxafine, hexamethylmelamine, oxaliplatin (Eloxatin®), Iressa (gefmitib, Zd1839), XELODA® (capecitabine), Tarceva® (erlotinib), Azacitidine (5-azacytidine; 5-AzaC), temozolomide (Temodar®), gemcitabine (e.g. GEMZAR® (gemcitabine HCl)), vasostatin or a combination of two or more of the above.

The present invention furthermore provides a method for preventing the coagulation of blood in vitro, in particular in banked blood or biological samples containing platelets, which method is characterized in that an anticoagulatory effective amount of the compound according to the invention is added.

The compounds according to the invention may act systemically and/or locally. For this purpose, they can be administered in a suitable manner, for example by the oral, parenteral, pulmonal, nasal, sublingual, lingual, buccal, rectal, dermal, transdermal, conjunctival, otic route, or as an implant or stent.

The compounds according to the invention can be administered in administration forms suitable for these administration routes.

Suitable administration forms for oral administration are those which function according to the prior art and deliver the compounds according to the invention rapidly and/or in modified fashion, and which contain the compounds according to the invention in crystalline and/or amorphized and/or dissolved form, for example tablets (uncoated or coated tablets, for example having enteric coatings or coatings which are insoluble or dissolve with a delay and control the release of the compound according to the invention), tablets which disintegrate rapidly in the mouth, or films/wafers, films/lyophilizates, capsules (for example hard or soft gelatin capsules), sugar-coated tablets, granules, pellets, powders, emulsions, suspensions, aerosols or solutions.

Parenteral administration can bypass an absorption step (e.g. intravenously, intraarterially, intracardially, intraspinally or intralumbally) or include an absorption (e.g. intramuscularly, subcutaneously, intracutaneously, percutaneously or intraperitoneally). Administration forms suitable for parenteral administration include preparations for injection and infusion in the form of solutions, suspensions, emulsions, lyophilizates or sterile powders.

Oral administration is preferred.

Suitable administration forms for the other administration routes are, for example, pharmaceutical forms for inhalation (including powder inhalers, nebulizers), nasal drops, solutions or sprays; tablets for lingual, sublingual or buccal administration, films/wafers or capsules, suppositories, preparations for the ears or eyes, vaginal capsules, aqueous suspensions (lotions, shaking mixtures), lipophilic suspensions, ointments, creams, transdermal therapeutic systems (for example patches), milk, pastes, foams, dusting powders, implants or stents.

The compounds according to the invention can be converted to the administration forms mentioned. This can be done in a manner known per se, by mixing with inert, non-toxic, pharmaceutically suitable excipients. These excipients include carriers (for example microcrystalline cellulose, lactose, mannitol), solvents (e.g. liquid polyethylene glycols), emulsifiers and dispersing or wetting agents (for example sodium dodecylsulphate, polyoxysorbitan oleate), binders (for example polyvinylpyrrolidone), synthetic and natural polymers (for example albumin), stabilizers (e.g. antioxidants, for example ascorbic acid), dyes (e.g. inorganic pigments, for example iron oxides) and flavour and/or odour correctants.

The present invention further provides medicaments comprising at least one compound according to the invention, preferably together with one or more inert nontoxic pharmaceutically suitable excipients, and the use thereof for the purposes mentioned above.

In the case of parenteral administration, it has generally been found to be advantageous to administer amounts of about 5 to 250 mg every 24 hours to achieve effective results. In the case of oral administration, the amount is about 5 to 100 mg every 24 hours.

It may nevertheless be necessary where appropriate to deviate from the stated amounts, specifically as a function of the body weight, route of administration, individual response to the active ingredient, nature of the preparation and time or interval over which administration takes place.

The percentages in the tests and examples which follow are, unless indicated otherwise, percentages by weight; parts are parts by weight. Solvent ratios, dilution ratios and concentration data for liquid/liquid solutions are based in each case on volume. "w/v" means "weight/volume". For example, "10% w/v" means: 100 ml of solution or suspension comprise 10 g of substance.

A) EXAMPLES

Abbreviations approx. approximately
CDI carbonyldiimidazole
d day(s), doublet (in NMR)
TLC thin-layer chromatography
DCI direct chemical ionization (in MS)
dd doublet of doublets (in NMR)
DMAP 4-dimethylaminopyridine
DMF N,N-dimethylformamide
DMSO dimethyl sulphoxide
DPPA diphenyl phosphorazidate
DSC disuccinimidyl carbonate
eq. equivalent(s)
ESI electrospray ionization (in MS)
h hour(s)
HATU O-(7-azabenzotriazol-1-yl)-N,N,N',N'-tetramethyluronium hexafluorophosphate
HPLC high-pressure high-performance liquid chromatography
LC-MS liquid chromatography-coupled mass spectroscopy
LDA lithium diisopropylamide
m multiplet (in NMR)
min minute(s)
MS mass spectroscopy
NMR nuclear magnetic resonance spectroscopy
PYBOP benzotriazol-1-yloxytris(pyrrolidino)phosphonium hexafluorophosphate
q quartet (in NMR)
RP reversed phase (in HPLC)
RT room temperature
$R_t$, retention time (in HPLC)
s singlet (in NMR)
t triplet (in NMR)
THF tetrahydrofuran HPLC Methods Method 1A:

Instrument: HP 1100 with DAD detection; column: Kromasil 100 RP-18, 60 mm×2.1 mm, 3.5 µm; mobile phase A: 5 ml of perchloric acid (70% strength)/1 of water, mobile phase B: acetonitrile; gradient: 0 min 2% B→0.5 min 2% B→4.5 min 90% B 6.5 min 90% B→6.7 min 2% B→7.5 min 2% B; flow rate: 0.75 ml/min; column temperature: 30° C.; UV detection: 210 nm.

Method 2A:

Instrument: HP 1100 with DAD detection; column: Kromasil 100 RP-18, 60 mm×2.1 mm, 3.5 µm; eluent A: 5 ml of perchloric acid (70% strength)/1 of water, mobile phase B: acetonitrile; gradient: 0 min 2% B→0.5 min 2% B→4.5 min 90% B→9 min 0% B→9.2 min 2% B→10 min 2% B; flow rate: 0.75 ml/min; column temperature: 30° C.; UV detection: 210 nm.

Method 3A:

Phase: Kromasil 100, C18, 5 µm, 250 mm×4 mm; mobile phase: water/acetonitrile 50:50; flow rate: 1 ml/min; T: 40° C.; UV: 210 nm.

LC-MS Methods:

Method 1B:

MS instrument type: Micromass ZQ; apparatus type HPLC: HP 1100 series; UV DAD; column: Phenomenex Gemini 3µ, 30 mm×3.0 mm; mobile phase A: 1 l of water+0.5 ml of 50% strength formic acid, mobile phase B: 1 l of acetonitrile+0.5 ml of 50% strength formic acid; gradient: 0.0 min 90% A→2.5 min 30% A→3.0 min 5% A→4.5 min 5% A; flow rate 0.0 min 1 ml/min, 2.5 min/3.0 min/4.5 min 2 ml/min; oven: 50° C.; UV detection: 210 nm.

Method 2B:
Instrument: Micromass QuattroPremier with Waters HPLC Acquity; column: Thermo Hypersil GOLD 1.9µ 50 mm×1 mm; mobile phase A: 1 l of water+0.5 ml of 50% strength formic acid, mobile phase B: 1 l of acetonitrile+0.5 ml of 50% strength formic acid; gradient: 0.0 min 90% A→0.1 min 90% A→1.5 min 10% A→2.2 min 10% A; oven: 50° C.; flow rate: 0.33 ml/min; UV detection: 210 nm.

Method 3B:
MS instrument type: Micromass ZQ; apparatus type HPLC: Waters Alliance 2795; column: Phenomenex Synergi 2.5µ MAX-RP 100A Mercury 20 mm×4 mm; mobile phase A: 1 l of water+0.5 ml of 50% strength formic acid, mobile phase B: 1 l of acetonitrile+0.5 ml of 50% strength formic acid; gradient: 0.0 min 90% A→0.1 min 90% A→3.0 min 5% A→4.0 min 5% A→4.01 min 90% A; flow rate: 2 ml/min; oven: 50° C.; UV detection: 210 nm.

Method 4B:
MS instrument type: Waters ZQ; HPLC instrument type: Waters Alliance 2795; column: Phenomenex Onyx Monolithic C18, 100 mm×3 mm; mobile phase A: 1 l of water+0.5 ml of 50% strength formic acid, mobile phase B: 1 l of acetonitrile+0.5 ml of 50% strength formic acid; gradient: 0.0 min 90% A→2 min 65% A→4.5 min 5% A→6 min 5% A; flow rate: 2 ml/min; oven: 40° C.; UV detection: 210 nm.

Method 5B:
Instrument: Micromass Quattro Micro MS with HPLC Agilent Series 1100; column: Thermo Hypersil GOLD 3µ 20 mm×4 mm; mobile phase A: 1 l of water+0.5 ml of 50% strength formic acid, mobile phase B: 1 l of acetonitrile+0.5 ml of 50% strength formic acid; gradient: 0.0 min 100% A→3.0 min 10% A→4.0 min 10% A→4.01 min 100% A→5.00 min 100% A; oven 50° C.; flow rate: 2 ml/min; UV detection: 210 nm.

Method 6B:
Instrument: Micromass Quattro LCZ with HPLC Agilent Series 1100; column: Phenomenex Synergi 2.5 µLE MAX-RP 100A Mercury 20 mm×4 mm; mobile phase A: 1 l of water+0.5 ml of 50% strength formic acid, mobile phase B: 1 l of acetonitrile+0.5 ml of 50% strength formic acid; gradient: 0.0 min 90% A→0.1 min 90% A→3.0 min 5% A→4.0 min 5% A→4.1 min 90% A; flow rate: 2 ml/min; oven: 50° C.; UV detection: 208-400 nm.

Method 7B:
Instrument: Micromass Quattro LCZ with HPLC Agilent Series 1100; column: Phenomenex Onyx Monolithic C18, 100 mm×3 mm; mobile phase A: 1 l of water+0.5 ml of 50% strength formic acid, mobile phase B: 1 l of acetonitrile+0.5 ml of 50% strength formic acid; gradient: 0.0 min 90% A→2 min 65% A→4.5 min 5% A→6 min 5% A; flow rate: 2 ml/min; oven: 40° C.; UV detection: 208-400 nm.

Method 8B:
Instrument: Micromass Platform LCZ with HPLC Agilent Series 1100; column: Thermo HyPURITY Aquastar 3µ 50 mm×2.1 mm; mobile phase 1 l of water+0.5 ml of 50% strength formic acid, mobile phase B: 1 l of acetonitrile+0.5 ml of 50% strength formic acid; gradient: 0.0 min 100% A→0.2 min 100% A→2.9 min 30% A→3.1 min 10% A→5.5 min 10% A; oven: 50° C.; flow rate: 0.8 ml/min; UV detection: 210 nm.

Method 9B:
MS instrument: Waters ZQ 2000; HPLC instrument: Agilent 1100, 2-column system, autosampler: HTC PAL; column: YMC-ODS-AQ, 50 mm×4.6 mm, 3.0 µm; mobile phase A: water+0.1% formic acid, mobile phase B: acetonitrile+0.1% formic acid; gradient 0.0 min 100% A→0.2 min 95% A→1.8 min 25% A→1.9 min 10% A→2.0 min 5% A→3.2 min 5% A→3.21 min 100% A→3.35 min 100% A; oven: 40° C.; flow rate: 3.0 ml/min; UV detection: 210 nm.

Method 10B:
MS instrument type: Waters ZQ; HPLC instrument type: Agilent 1100 Series; UV DAD; column: Thermo Hypersil GOLD 3µ, 20 mm×4 mm; eluent A: 1 l of water+0.5 ml of 50% strength formic acid, mobile phase B: 1 l of acetonitrile+0.5 ml of 50% strength formic acid; gradient: 0.0 min 100% A→3.0 min 10% A→4.0 min 10% A→4.1 min 100% (flow rate: 2.5 ml/min); oven: 55° C.; flow rate: 2 ml/min; UV detection: 210 nm.

Method 11B:
Instrument: Waters ACQUITY SQD HPLC System; column: Waters Acquity HPLC HSS T3 1.8µ 50 mm×1 mm; mobile phase A: 1 l of water+0.25 ml of 99% strength formic acid, mobile phase B: 1 l of acetonitrile+0.25 ml of 99% strength formic acid; gradient: 0.0 min 90% A→1.2 min 5% A→2.0 min 5% A; oven: 50° C.; flow rate: 0.40 ml/min; UV detection: 210-400 nm.

Preparative Separation of Diastereomers:
Method 1C:
Phase: Kromasil 100, C18, 5 µm, 250 mm×20 mm; mobile phase: 0.2% strength aqueous trifluoroacetic acid/acetonitrile 47:53; flow rate: 25 ml/min, temperature: 23° C.; UV detection: 210 nm.

Method 2C:
Phase: Sunfire C18, 5 µm 150 mm×19 mm, mobile phase: water/acetonitrile 50:50; flow rate: 25 ml/min, temperature: 24° C.; UV detection: 225 nm.

Method 3C:
Phase: Kromasil 100, C18, 5 µm, 250 mm×20 mm; mobile phase: water/acetonitrile 50:50; flow rate: 25 ml/min, temperature: 40° C.; UV detection: 210 nm.

Method 4C:
Phase: Kromasil 100, C18, 5 µm, 250 mm×20 mm; mobile phase: water/acetonitrile 35:65; flow rate: 25 ml/min, temperature: 30° C.; UV detection: 210 nm.

Method 5C:
Phase: Sunfire C18, 5 µm 150 mm×30 mm, mobile phase: water/acetonitrile 50:50; flow rate: 56 ml/min, temperature: 30° C.; UV detection: 210 nm.

Method 6C:
Phase: Xbrdge C18, 5 µm OBD 150 mm×19 mm, mobile phase: 0.1% strength diethylamine solution/acetonitrile 30:70; flow rate: 25 ml/min, temperature: 24° C.; UV detection: 254 nm.

Method 7C:
Phase: Sunfire C18, 5 µm 250 mm×20 mm, mobile phase: water/acetonitrile 55:45; flow rate: 25 ml/min, temperature: 30° C.; UV detection: 210 nm.

Method 8C:
Phase: Sunfire C18, 5 µm 150 mm×19 mm, mobile phase: water/acetonitrile 62:38; flow rate: 25 ml/min, temperature: 40° C.; UV detection: 210 nm.

Method 9C:
Phase: Kromasil 100, C18, 5 µm, 150 mm×19 mm; mobile phase: 0.2% strength aqueous trifluoroacetic acid/acetonitrile 50:50; flow rate: 25 ml/min, temperature: 40° C.; UV detection: 210 nm.

Method 10C:
Phase: Xbrdge C18, 5 µm OBD 19 mm×150 mm, mobile phase: 0.1% strength aqueous ammonia solution/acetonitrile 50:50; flow rate: 25 ml/min, temperature: 30° C.; UV detection: 210 nm.

Method 11C:
Phase: XBridge C18, 5 µm OBD, 19 mm×150 mm, mobile phase: aqueous ammonia solution/acetonitrile 70:30; flow rate: 25 ml/min, temperature: 40° C.; UV detection: 210 nm.

Method 12C:
Phase: XBridge C18, 5 µm OBD, 19 mm×150 mm, mobile phase: aqueous ammonia solution/acetonitrile 65:35; flow rate: 25 ml/min, temperature: 40° C.; UV detection: 210 nm.

Method 13C:
Phase: Daisogel SP120-, 10 µm ODS Bio, 250 mm×20 mm, mobile phase: 0.1% strength diethylamine solution/acetonitrile 50:50; flow rate: 25 ml/min, temperature: 30° C.; UV detection: 240 nm.

Method 14C:
Phase: Xbrdge C18, 5 µm OBD 19 mm×150 mm, mobile phase: 0.1% strength diethylamine solution/acetonitrile 55:45; flow rate: 25 ml/min, temperature: 20° C. (RT); UV detection: 254 nm.

Method 15C:
Phase: Xbrdge C18, 5 µm OBD 19 mm×150 mm, mobile phase: 0.2% strength diethylamine solution/acetonitrile 63:37; flow rate: 25 ml/min, temperature: 20° C. (RT); UV detection: 235 nm.

Preparative Separation of Enantiomers:

Method 1D:
Phase: chiral silica gel phase based on the selector poly(N-methacryloyl-L-leucine-1-menthylamide, 250 mm×20 mm, mobile phase: isohexane/ethyl acetate 70:30; flow rate: 25 ml/min, temperature: 24° C.; UV detection: 260 nm.

Method 2D:
Phase: Daicel Chiralpak AD-H, 5 µm 250 mm×20 mm, mobile phase: isopropanol/isohexane 30:70; flow rate: 20 ml/min, temperature: 25° C.; UV detection: 260 nm.

Method 3D:
Phase: Daicel Chiralpak AD-H, 5 µm 250 mm×20 mm, mobile phase: isopropanol/isohexane 50:50; flow rate: 18 ml/min, temperature: 25° C.; UV detection: 260 nm.

Method 4D:
Phase: chiral silica gel phase based on the selector poly(N-methacryloyl-L-leucine-1-menthylamide, 670 mm×40 mm, mobile phase: isohexane/ethyl acetate 50:50; flow rate: 80 ml/min, temperature: 24° C.; UV detection: 260 nm.

Method 5D:
Phase: Daicel Chiralcel OD-H, 5 µm, 250 mm×20 mm; mobile phase: isopropanol/isohexane 40:60; flow rate: 15 ml/min, temperature: 24° C.; UV detection: 230 nm.

Method 6D:
Phase: Daicel Chiralpak AD-H, 5 µm 250 mm×20 mm, mobile phase: isopropanol/isohexane 40:60; flow rate: 20 ml/min, temperature: 24° C.; UV detection: 260 nm.

Method 7D:
Phase: Daicel Chiralcel OD-H, 5 µm 250 mm×20 mm, mobile phase: isohexane/ethanol 90:10; flow rate: 15 ml/min, temperature: 30° C.; UV detection: 220 nm.

Method 8D:
Phase: Daicel Chiralcel AD-H, 5 µm 250 mm×20 mm, mobile phase: isohexane/ethanol 55:45; flow rate: 15 ml/min, temperature: 40° C.; UV detection: 220 nm.

Method 9D:
Phase: Daicel Chiralcel AS-H, 5 µm 250 mm×20 mm, mobile phase: isohexane/2-propanol 75:25; flow rate: 15 ml/min, temperature: 40° C.; UV detection: 220 nm.

Method 10D:
Phase: Daicel Chiralcel AD-H, 5 µm 250 mm×20 mm, mobile phase: isohexane/ethanol 50:50; flow rate: 15 ml/min, temperature: 40° C.; UV detection: 220 nm.

Method 11D:
Phase: Daicel Chiralpak AD-H, 5 µm 250 mm×20 mm, mobile phase: isopropanol/isohexane 30:70; flow rate: 20 ml/min, temperature: 20° C. (RT); UV detection: 230 nm.

Method 12D:
Phase: Daicel Chiralpak AD-H, 5 µm 250 mm×20 mm, mobile phase: isohexane/ethanol 50:50; flow rate: 15 ml/min, temperature: 40° C.; UV detection: 220 nm.

Method 13D:
Phase: Waters Sunfire C18, 5 µm, 250 mm×20 mm, mobile phase A: water, mobile phase B: acetonitrile; gradient: 0.0 min 70% A→15 min 10% A→15.1 min 70% A→20 min 70% A; flow rate: 25 ml/min, temperature: 30° C.; UV detection: 210 nm.

Method 14D:
Phase: Kromasil 100, C18, 5 µm, 250 mm×20 mm; mobile phase: water/acetonitrile 62:38; flow rate: 25 ml/min, temperature: 40° C.; UV detection: 210 nm.

Method 15D:
Phase: Daicel Chiralcel OD-H, 5 µm, 250 mm×20 mm; mobile phase: isohexane/ethanol 70:30; flow rate: 15 ml/min, temperature: 40° C.; UV detection: 220 nm.

Method 16D:
Phase: Daicel Chiralpak AD-H, 5 µm 250 mm×20 mm, mobile phase: isohexane/ethanol 75:25; flow rate: 15 ml/min, temperature: 25° C.; UV detection: 220 nm.

Method 17D:
Phase: Daicel Chiralpak AD-H, 5 µm 250 mm×20 mm, mobile phase: isohexane/ethanol 80:20; flow rate: 15 ml/min, temperature: 38° C.; UV detection: 220 nm.

Analytical Separation of Enantiomers:

Method 1E:
Phase: chiral silica gel phase based on the selector poly(N-methacryloyl-L-leucine-1-menthylamide, 250 mm×4.6 mm, mobile phase: isohexane/ethyl acetate 50:50; flow rate: 1 ml/min, temperature: 20° C.; UV detection: 265 nm.

Method 2E:
Phase: Daicel Chiralpak AD-H, 5 µm 250 mm×4 mm, mobile phase: isopropanol/isohexane: 50:50; flow rate: 1 ml/min; UV detection: 230 nm.

Method 3E:
Phase: chiral silica gel phase based on the selector poly(N-methacryloyl-L-leucine-1-menthylamide, 250 mm×4.6 mm, mobile phase: isohexane/ethyl acetate 50:50; flow rate: 2 ml/min, temperature: 20° C.; UV detection: 265 nm.

Method 4E:
Phase: Daicel Chiralcel OD-H, 5 µm, 250 mm×4 mm; mobile phase: isopropanol/isohexane 50:50; flow rate: 1 ml/min, temperature: 20° C.; UV detection: 230 nm.

Method 5E:
Phase: Daicel Chiralcel OD-H, 5 µm 250 mm×4.6 mm, mobile phase: isohexane/ethanol 85:15; flow rate: 1 ml/min, temperature: 40° C.; UV detection: 220 nm.

Method 6E:
Phase: Daicel Chiralcel AD-H, 5 µm 250 mm×4.6 mm, mobile phase: isohexane/ethanol 50:50; flow rate: 1 ml/min, temperature: 40° C.; UV detection: 220 nm.

Method 7E:
Phase: Daicel Chiralcel AS-H, 5 µm 250 mm×20 mm, mobile phase: isohexane/2-propanol 75:25; flow rate: 1 ml/min, temperature: 40° C.; UV detection: 220 nm.

Method 8E:

Phase: Daicel Chiralcel AD-H, 5 μm 250 mm×4.6 mm, mobile phase: isohexane/ethanol 70:30+0.2% trifluoroacetic acid+1% water; flow rate: 1 ml/min, temperature: 40° C.; UV detection: 220 nm.

The microwave reactor used was a single-mode instrument of the Emrys™ Optimizer type.

Starting Materials

General Method 1A: Suzuki Coupling

A mixture of the appropriate bromopyridine in toluene (1.8 ml/mmol) is admixed under argon and at RT with tetrakis(triphenylphosphine)palladium (0.02 eq.), with a solution of the appropriate arylboronic acid (1.2 eq.) in ethanol (0.5 ml/mmol) and with a solution of potassium fluoride (2.0 eq.) in water (0.2 ml/mmol). The reaction mixture is stirred under reflux for a number of hours until the conversion is substantially complete. After addition of ethyl acetate and phase separation, the organic phase is washed once with water and once with saturated aqueous sodium chloride solution, dried (magnesium sulphate), filtered and concentrated under reduced pressure. The crude product is purified by flash chromatography (silica gel 60, mobile phase: dichloromethane/methanol mixtures).

General Method 2A: Hydrogenation of the Pyridine

A solution of the pyridine in ethanol (9 ml/mmol) is admixed under argon with palladium on activated carbon (moistened with approx. 50% water, 0.3 g/mmol), and the mixture is hydrogenated at 60° C. in a 50 bar hydrogen atmosphere overnight. The catalyst is then filtered off over a filter layer and washed repeatedly with ethanol. The combined filtrates are concentrated under reduced pressure.

General Method 3A: Reaction with Carbamoyl Chlorides or Carbonyl Chlorides

Under argon and at 0° C., N,N-diisopropylethylamine (1.2 eq.) and the appropriate carbamoyl chloride or carbonyl chloride (1.2 eq.) are added dropwise to a solution of the piperidine in dichloromethane (2.5 ml/mmol). The reaction mixture is stirred at RT. After addition of water and phase separation, the organic phase is washed three times with water and once with saturated aqueous sodium chloride solution, dried (sodium sulphate), filtered and concentrated under reduced pressure.

General Method 4A: Hydrolysis

At RT, lithium hydroxide (2 eq.) is added to a solution of the appropriate ester in a mixture of tetrahydrofuran/water (3:1, 12.5 ml/mmol). The reaction mixture is stirred at 60° C. and then adjusted to pH 1 using aqueous 1 N hydrochloric acid solution. After addition of water/ethyl acetate, the aqueous phase is extracted three times with ethyl acetate. The combined organic phases are dried (sodium sulphate), filtered and concentrated under reduced pressure.

General Method 5A: Curtius Degradation

Under argon and at RT, triethylamine (1.7 eq.), diphenyl phosphorazidate (1.1 eq.) and di-tert-butyl dicarbonate (1.1 eq.) are added to a solution of the appropriate carboxylic acid in tert-butanol/toluene (1:1, 8 ml/mmol). The reaction mixture is stirred at 65° C. for 30 min and then overnight at 95° C. After addition of water and phase separation, the organic phase is washed with water and with saturated aqueous sodium chloride solution, dried (sodium sulphate), filtered and concentrated under reduced pressure. The crude product is then purified by flash chromatography (silica gel-60, mobile phase: dichloromethane/methanol mixtures). Subsequently, under argon and at RT, trifluoroacetic acid (10 eq.) is added to a solution of this boc-protected amine in dichloromethane (10 ml/mmol). The reaction mixture is stirred at RT and then concentrated under reduced pressure. The residue is coevaporated three times with toluene and dichloromethane and used without further purification for the next step.

General Method 6A: Hydrogenation of the Pyridine Using a Flow Hydrogenation Apparatus A solution of the pyridine in concentrated acetic acid (about 35 ml/mmol) is hydrogenated in a flow hydrogenation apparatus ("H-Cube" from ThalesNano, Budapest, Hungary) (conditions: 10% Pd/C catalyst, "controlled" mode, 60 bar, 0.5 ml/min, 85° C.). Removal of the solvent on a rotary evaporator gives the corresponding crude product which is optionally purified by means of preparative HPLC.

General Method 7A: Methyl Ester Hydrolysis/Epimerization

At RT, potassium tert-butoxide (10 eq.) is added to a solution of the appropriate methyl ester (1.0 eq.) in methanol (35-40 ml/mmol). The mixture is stirred at 60° C. overnight. If the conversion is incomplete, water (1.0 eq.) is added and the mixture is stirred at 60° C. until the conversion is complete. For workup, the methanol is removed under reduced pressure, the residue is admixed with water and the mixture is acidified (pH 1) with aqueous 1 N hydrochloric acid solution. The mixture is extracted with ethyl acetate and the organic phase is dried with magnesium sulphate, filtered and concentrated under reduced pressure.

General Method 8A: Urea Formation

A solution of the nitrophenyl carbamate (1.0 eq.) in dimethylformamide (10 ml/mmol) is admixed at RT with the appropriate amine (2.0-3.0 eq.) and potassium carbonate (1.0 eq.), and the mixture is stirred in 15 ml portions in a single-mode microwave (Emrys Optimizer) at 150° C. for 0.5-1 h. The reaction solution is filtered and the filtrate is purified by means of preparative HPLC.

General Method 9A: Methyl Ester Hydrolysis/Epimerization

At RT, potassium tert-butoxide (10 eq.) is added to a solution of the appropriate methyl ester (1.0 eq.) in methanol (35-40 ml/mmol). The mixture is stirred at 60° C. overnight. If the conversion is incomplete, water (1.0 eq.) is added and the mixture is stirred at 60° C. until the conversion is complete. For workup, the methanol is removed under reduced pressure, the residue is admixed with water and the mixture is acidified to pH=1 with 1N hydrochloric acid. The mixture is extracted with ethyl acetate and the organic phase is dried over magnesium sulphate, filtered and concentrated under reduced pressure.

Example 1A

Methyl 5-(4-ethylphenyl)pyridine-3-carboxylate

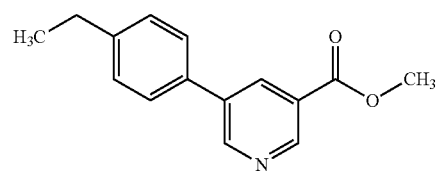 [SMILES: CCc1ccc(-c2cncc(C(=O)OC)c2)cc1]

32 g (148 mmol) of methyl 5-bromonicotinate and 27 g (178 mmol, 1.2 eq.) of 4-ethylphenylboronic acid were reacted according to General Method 1A. Yield: 24 g (64% of theory)

LC-MS (Method 3B): $R_t$=2.03 min; MS (ESIpos): m/z=242 $[M+H]^+$.

Example 2A

Methyl 5-(4-ethylphenyl)piperidine-3-carboxylate [racemic cis/trans isomer mixture]

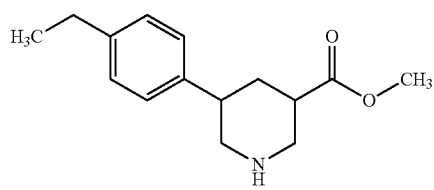 [SMILES: CCc1ccc(C2CNCC(C(=O)OC)C2)cc1]

24 g (94 mmol) of methyl 5-(4-ethylphenyl)pyridine-3-carboxylate were hydrogenated according to General Method 2A. Yield: 20 g (77% of theory)

LC-MS (Method 5B): $R_t$=1.43 min; MS (ESIpos): m/z=248 (M+H)$^+$.

Example 3A

Ethyl 5-(4-ethylphenyl)pyridine-3-carboxylate

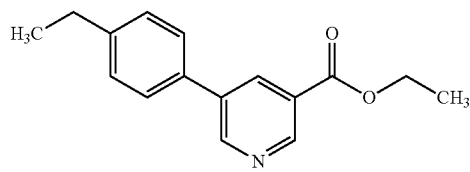 [SMILES: CCOC(=O)c1cncc(-c2ccc(CC)cc2)c1]

29 g (126 mmol) of ethyl 5-bromonicotinate and 23 g (152 mmol, 1.2 eq.) of 4-ethylphenylboronic acid were reacted according to General Method 1A. Yield: 32 g (82% of theory)

LC-MS (Method 4B): $R_t$=3.80 min; MS (ESIpos): m/z=256 (M+H)$^+$.

Example 4A

Ethyl 5-(4-ethylphenyl)piperidine-3-carboxylate [racemic cis/trans isomer mixture]

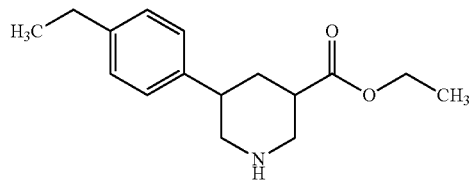 [SMILES: CCOC(=O)C1CNCC(c2ccc(CC)cc2)C1]

24 g (71 mmol) of ethyl 5-(4-ethylphenyl)pyridine-3-carboxylate were hydrogenated according to General Method 2A. Yield: 15 g (81% of theory)

LC-MS (Method 5B): $R_t$=1.78 min and 1.91 min (cis/trans isomers); MS (ESIpos): m/z=262 [M+H]$^+$.

Example 5A

Ethyl 1-(cyclopentylcarbonyl)-5-(4-ethylphenyl)piperidine-3-carboxylate [racemic cis/trans isomer mixture]

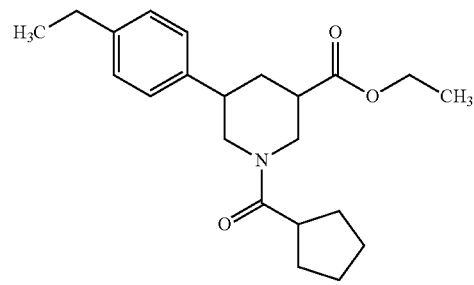 [SMILES: CCOC(=O)C1CC(c2ccc(CC)cc2)CN(C(=O)C2CCCC2)C1]

5.2 g (14.0 mmol) of ethyl 5-(4-ethylphenyl)piperidine-3-carboxylate and 2.1 g (2.1 mmol, 1.2 eq.) of cyclopentanecarbonyl chloride were reacted according to General Method 3A. Yield: 4.8 g (96% of theory)

LC-MS (Method 4B): $R_t$=4.04 min and 4.14 min (cis/trans isomers); MS (ESIpos): m/z=358 [M+H]$^+$.

Example 6A 1-(Cyclopentylcarbonyl)-5-(4-ethylphenyl)piperidine-3-carboxylic acid [racemic cis/trans isomer mixture]

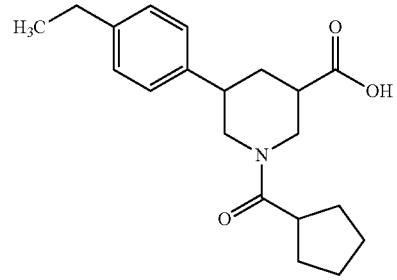

13.8 g (38.6 mmol) of ethyl 1-(cyclopentylcarbonyl)-5-(4-ethylphenyl)piperidine-3-carboxylate were hydrolysed according to General Method 4A. Yield: 11.5 g (87% of theory)

LC-MS (Method 1B): $R_t$=2.50 min and 2.57 min (cis/trans isomers); MS (ESIpos): m/z=330 [M+H]$^+$.

Example 7A 1-(Cyclopentylcarbonyl)-5-(4-ethylphenyl)piperidine-3-carboxylic acid [racemic cis isomer]

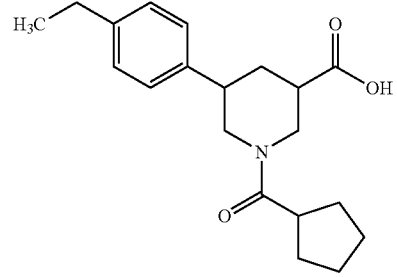 [SMILES: CCc1ccc(C2CC(C(=O)O)CN(C(=O)C3CCCC3)C2)cc1]

Diastereomer separation of 11.5 g of the cis/trans isomer mixture of Example 6A according to Method 1C gave 4.1 g of the title compound 7A (cis isomer) and 4.1 g of the trans isomer.

LC-MS (Method 1B): $R_t$=2.57 min; MS (ESIpos): m/z=330 (M+H)$^+$.

Example 8A 1-(Cyclopentylcarbonyl)-5-(4-ethylphenyl)piperidine-3-amine trifluoroacetate [racemic cis isomer]

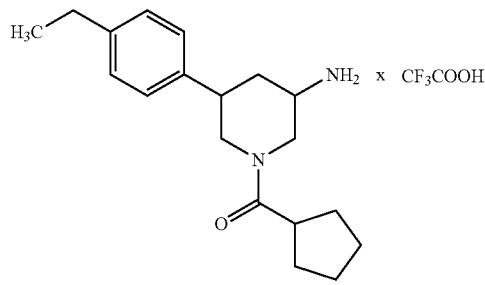 [SMILES: CCc1ccc(C2CC(N)CN(C(=O)C3CCCC3)C2)cc1 ; "CF3COOH"]

816 mg (2.48 mmol) of 1-(cyclopentylcarbonyl)-5-(4-ethylphenyl)piperidine-3-carboxylic acid were subjected to a Curtius degradation according to General Method 5A. Yield: 730 mg (71% of theory)

LC-MS (Method 5B): $R_t$=1.68 min; MS (ESIpos): m/z=301 (M+H)$^+$ (free base).

Example 9A

Methyl 5-(4-ethylphenyl)-1-(pyrrolidin-1-ylcarbonyl)piperidine-3-carboxylate [racemic cis/trans isomer mixture]

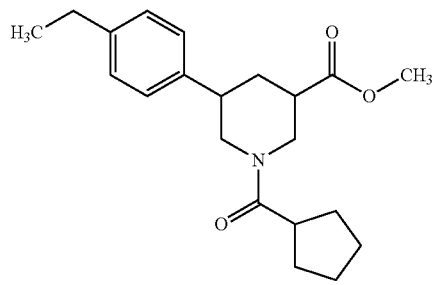

6.7 g (24.1 mmol) of methyl 5-(4-ethylphenyl)piperidine-3-carboxylate and 4.2 g (31.4 mmol, 1.3 eq.) of pyrrolidine-1-carbonyl chloride were reacted according to General Method 3A. Yield: 7.6 g (91% of theory)

LC-MS (Method 3B): $R_t$=2.08 min and 2.16 min (cis/trans isomers); MS (ESIpos): m/z=345 [M+H]$^+$.

Example 10A

Methyl 5-(4-ethylphenyl)-1-(pyrrolidin-1-ylcarbonyl)piperidine-3-carboxylate [racemic cis isomer]

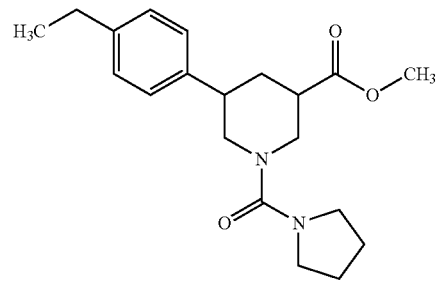 [SMILES: CCc1ccc(C2CC(C(=O)OC)CN(C(=O)N3CCCC3)C2)cc1]

Diastereomer separation of 7.6 g of the cis/trans isomer mixture of Example 9A according to Method 4C gave 1.6 g of Example 10A (cis isomer) and 4.1 g of the trans isomer.

LC-MS (Method 1B): $R_t$=2.55 min; MS (ESIpos): m/z=345 (M+H)$^+$.

Example 11A 5-(4-Ethylphenyl)-1-(pyrrolidin-1-ylcarbonyl)piperidine-3-carboxylic acid [racemic cis isomer]

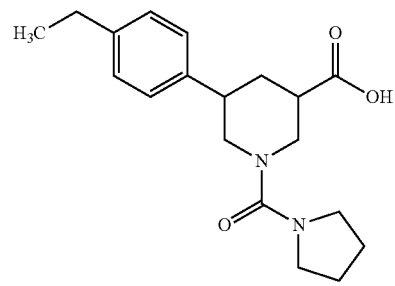

1.4 g (3.9 mmol) of methyl 5-(4-ethylphenyl)-1-(pyrrolidin-1-ylcarbonyl)piperidine-3-carboxylate were hydrolysed according to General Method 4A. Yield: 1.2 g (92% of theory)

LC-MS (Method 2B): $R_t$=1.18 min; MS (ESIpos): m/z=331 (M+H)$^+$.

Example 12A 5-(4-Ethylphenyl)-1-(pyrrolidin-1-ylcarbonyl)piperidine-3-amine trifluoroacetate [racemic cis isomer]

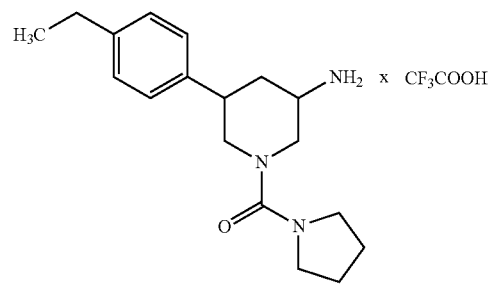 [SMILES: CCc1ccc(C2CC(N)CN(C(=O)N3CCCC3)C2)cc1 ; "CF3COOH"]

1.2 g (3.6 mmol) of 5-(4-ethylphenyl)-1-(pyrrolidin-1-yl-carbonyl)piperidine-3-carboxylic acid were subjected to a Curtius degradation according to General Method 5A. Yield: 1.2 g (78% of theory)

LC-MS (Method 5B): $R_t$=1.61 min; MS (ESIpos): m/z=302 (M+H)$^+$ (free base).

Example 13A

Methyl 5-[4-(trifluoromethoxy)phenyl]pyridine-3-carboxylate

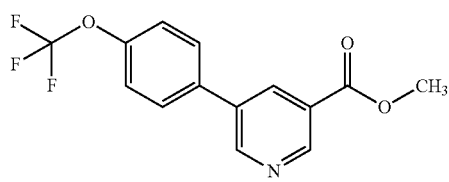 [SMILES: COC(=O)c1cncc(-c2ccc(OC(F)(F)F)cc2)c1]

23 g (105 mmol) of methyl 5-bromonicotinate and 26 g (126 mmol, 1.2 eq.) of 4-trifluoromethoxyphenylboronic acid were reacted according to General Method 1A. Yield: 14 g (41% of theory)

LC-MS (Method 1B): $R_t$=2.44 min; MS (ESIpos): m/z=298 (M+H)$^+$.

Example 14A

5-Bromo-N-phenylpyridine-3-carboxamide

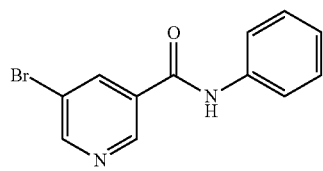 [SMILES: O=C(Nc1ccccc1)c1cncc(Br)c1]

Under argon and at RT, 32.4 ml (400 mmol, 2 eq.) of pyridine, 2.4 g (20 mmol, 0.1 eq.) of 4-dimethylaminopyridine and, dropwise, a solution of 44.1 g (200 mmol, 1.0 eq.) of 5-bromopyridine-3-carbonyl chloride in 200 ml of DMF were added to a solution of 18.6 g (200 mmol) of aniline in 500 ml of tetrahydrofuran. After 3 h, the reaction mixture was concentrated under reduced pressure. The residue was suspended in water/dichloromethane and the solid was stirred well, washed repeatedly with water and dichloromethane and dried under reduced pressure. Yield: 35.7 g (52% of theory) After phase separation of the mother liquor, the organic phase was extracted twice with dichloromethane. The combined organic phases were dried (sodium sulphate), filtered and concentrated under reduced pressure. The residue was purified by flash chromatography (silica gel, dichloromethane/methanol 100:1), which gave 11.7 g (18% of theory) of Example 14A.

LC-MS (Method 6B): $R_t$=1.77 min; MS (ESIpos): m/z=277 (M+H)$^+$.

Example 15A 5-(4-Ethylphenyl)-N-phenylpyridine-3-carboxamide

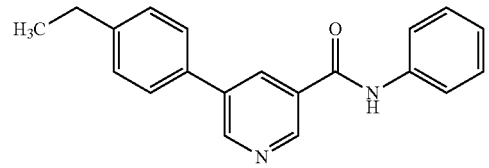 [SMILES: CCc1ccc(-c2cncc(C(=O)Nc3ccccc3)c2)cc1]

74 g (222 mmol) of 5-bromo-N-phenylpyridine-3-carboxamide and 40 g (266 mmol, 1.2 eq.) of 4-ethylphenylboronic acid were reacted according to General Method 1A. Yield: 68 g (87% of theory)

LC-MS (Method 6B): $R_t$=2.26 min; MS (ESIpos): m/z=303 (M+H)$^+$.

Example 16A 5-(4-Ethylphenyl)-N-phenylpiperidine-3-carboxamide [racemic cis/trans isomer mixture]

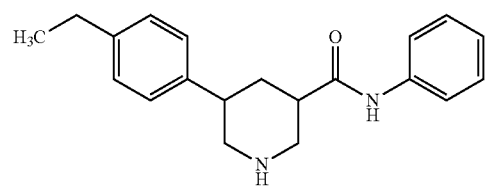 [SMILES: CCc1ccc(C2CNCC(C(=O)Nc3ccccc3)C2)cc1]

67 g (218 mmol) of 5-(4-ethylphenyl)-N-phenylpyridine-3-carboxamide were hydrogenated according to General Method 2A. Yield: 63 g (88% of theory)

Example 17A 5-(4-Ethylphenyl)-N-phenylpiperidine-3-carboxamide [racemic cis isomer]

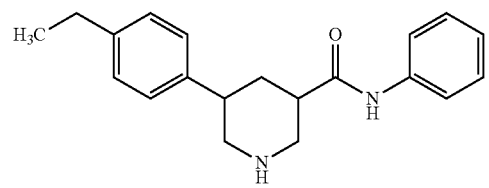 [SMILES: CCc1ccc(C2CNCC(C(=O)Nc3ccccc3)C2)cc1]

Diastereomer separation of 63 g of the cis/trans isomer mixture (Example 16A) according to Method 4C gave 25.9 g of Example 17A (cis isomer) and 15.4 g of the trans isomer.

LC-MS (Method 6B): $R_t$=1.35 min; MS (ESIpos): m/z=309 (M+H)$^+$.

Example 18A

Methyl 1-[(4-cyanopiperidin-1-yl)carbonyl]-5-(4-ethylphenyl)piperidine-3-carboxylate [racemic cis/trans isomer mixture]

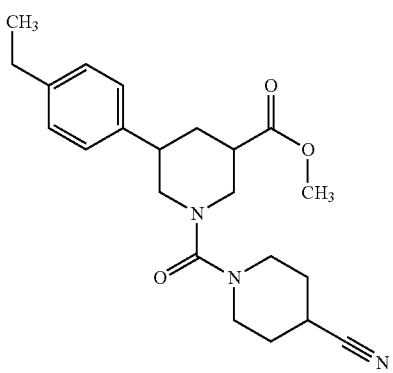 [SMILES: CCc1ccc(C2CC(C(=O)OC)CN(C(=O)N3CCC(C#N)CC3)C2)cc1]

3.0 g (6.1 mmol) of the compound from Example 65A were reacted according to General Method 8A. Yield: 2.1 g (83% of theory)

LC-MS (Method 11B): $R_t$=1.12 min and 1.14 min (cis/trans isomers); MS (ESIpos): m/z=384 [M+H]$^+$.

Example 19A

3-Bromo-5-(4-ethylphenyl)pyridine

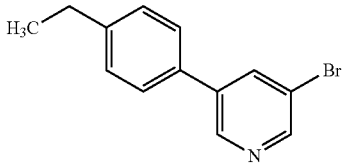

23 g (97 mmol) of methyl 3,5-dibromopyridine and 18 g (117 mmol, 1.2 eq.) of 4-ethylphenylboronic acid were reacted according to General Method 1A. Yield: 17 g (66% of theory)

LC-MS (Method 3B): $R_t$=2.35 min; MS (ESIpos): m/z=262 (M+H)$^+$.

Example 20A

Methyl [5-(4-ethylphenyl)pyridin-3-yl]carbamate

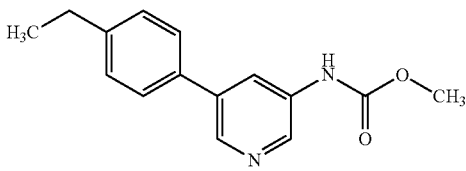 [SMILES: CCc1ccc(-c2cncc(NC(=O)OC)c2)cc1]

Under argon and at RT, a solution of 16.8 g (64 mmol) of 3-bromo-5-(4-ethylphenyl)pyridine in 70 ml of dioxane was added to a suspension of 555 mg (0.96 mmol, 0.015 eq.) of Xantphos (4,5-bis(diphenylphosphino)-9,9'-dimethylxanthene), 293 mg (0.32 mmol, 0.005 eq.) of tris(dibenzylideneacetone)dipalladium, 29.1 g (89 mmol, 1.4 eq.) of caesium carbonate and 5.8 g (77 mmol, 1.2 eq.) of methyl carbamate in 100 ml of dioxane. The reaction mixture was stirred at 90° C. for 20 h. Since the progress of the reaction was slow, a little at a time, three times in total, 555 mg (0.96 mmol, 0.015 eq.) of Xantphos and 293 mg (0.32 mmol, 0.005 eq.) of tris(dibenzylideneacetone)dipalladium were added to the reaction mixture, and in each case the mixture was stirred at 90° C. overnight. After addition of dichloromethane, the reaction mixture was filtered through Celite and the filtrate was concentrated under reduced pressure. The crude product was stirred with acetonitrile and the residue that remained was repeatedly washed with cold acetonitrile and dried under reduced pressure. Yield: 15 g (90% of theory)

LC-MS (Method 5B): $R_t$=1.84 min; MS (ESIpos): m/z=257 (M+H)$^+$.

Example 21A

Methyl [5-(4-ethylphenyl)piperidin-3-yl]carbamate [racemic cis/trans isomer mixture]

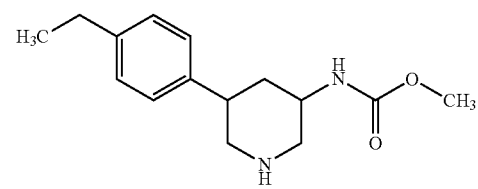 [SMILES: CCc1ccc(C2CNCC(NC(=O)OC)C2)cc1]

A solution of 1.0 g (3.7 mmol) of methyl [5-(4-ethylphenyl)pyridin-3-yl]carbamate in 100 ml of ethanol and 100 ml of acetic acid was reacted according to General Method 5A. The solution was concentrated under reduced pressure. The crude product was purified by flash chromatography (silica gel, dichloromethane/methanol 4:1). Yield: 171 mg (16% of theory)

LC-MS (Method 2B): $R_t$=0.81 min; MS (ESIpos): m/z=263 (M+H)$^+$.

Example 22A 3-(4-Ethylphenyl)-5-methoxypyridine

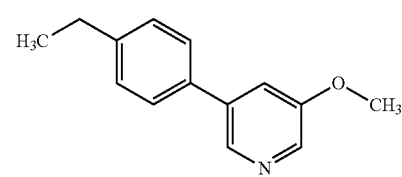 [SMILES: CCc1ccc(-c2cncc(OC)c2)cc1]

5.0 g (27 mmol) of 3-bromo-5-methoxypyridine and 4.8 g (32 mmol, 1.2 eq.) of 4-ethylphenylboronic acid were reacted according to General Method 1A. Yield: 3.0 g (53% of theory)

LC-MS (Method 1B): $R_t$=2.10 min; MS (ESIpos): m/z=214 (M+H)$^+$.

Example 23A 3-(4-Ethylphenyl)-5-methoxypiperidine [racemic cis/trans isomer mixture]

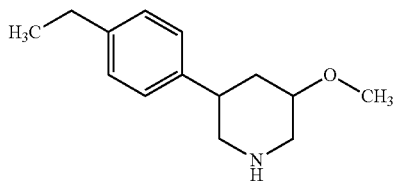 [SMILES: CCc1ccc(C2CNCC(OC)C2)cc1]

A solution of 1.0 g (4.7 mmol) of 3-(4-ethylphenyl)-5-methoxypyridine in 120 ml of acetic acid was reacted according to General Method 5A. The solution was concentrated under reduced pressure. The crude product was purified by flash chromatography (silica gel, dichloromethane/methanol gradient). Yield: 880 mg (86% of theory)

LC-MS (Method 1B): $R_t$=1.10 min; MS (ESIpos): m/z=220 (M+H)$^+$.

Example 24A

4-{[3-(4-Ethylphenyl)-5-methoxypiperidin-1-yl]carbonyl}morpholine [racemic cis/trans isomer mixture]

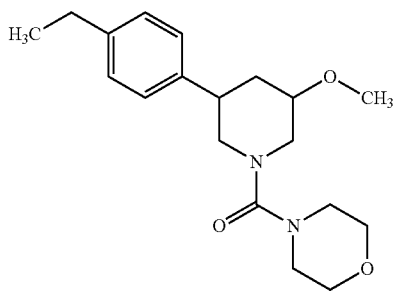 [SMILES: CCc1ccc(C2CC(OC)CN(C(=O)N3CCOCC3)C2)cc1]

880 mg (4.0 mmol) of 3-(4-ethylphenyl)-5-methoxypiperidine and 780 mg (5.2 mmol, 1.3 eq.) of morpholine-4-carbonyl chloride were reacted according to General Method 3A. Yield: 896 mg (58% of theory)

LC-MS (Method 3B): $R_t$=1.81 min and 1.84 min (cis/trans isomers); MS (ESIpos): m/z=333 [M+H]$^+$.

Example 25A 5-(4-Ethylphenyl)-1-(morpholin-4-ylcarbonyl)piperidin-3-ol [racemic cis/trans isomer mixture]

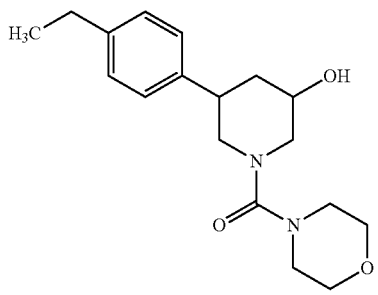 [SMILES: CCc1ccc(C2CC(O)CN(C(=O)N3CCOCC3)C2)cc1]

Under argon and at 0° C., 4.6 ml of a boron tribromide solution (1 molar in dichloromethane, 4.6 mmol, 2 eq.) were added to a solution of 890 mg (2.3 mmol) of 4-{[3-(4-ethylphenyl)-5-methoxypiperidin-1-yl]carbonyl}morpholine in 22 ml of dichloromethane. The reaction mixture was stirred at RT for 2 h, then poured onto ice, neutralized with solid sodium bicarbonate and, after addition of water and phase separation, extracted three times with dichloromethane. The combined organic phases were dried over sodium sulphate, filtered and concentrated under reduced pressure. The crude product was then purified by preparative HPLC (Reprosil C18, water with 0.1% trifluoroacetic acid/acetonitrile gradient). Yield: 314 mg (43% of theory)

LC-MS (Method 3B): $R_t$=1.50 min; MS (ESIpos): m/z=319 (M+H)$^+$.

Example 26A

N-{5-[4-(Trifluoromethoxy)phenyl]pyridin-3-yl}benzenecarboxamide

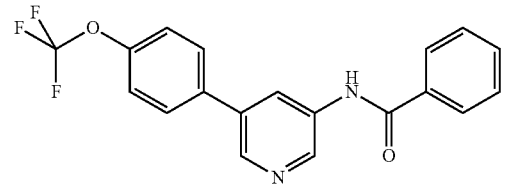 [SMILES: O=C(Nc1cncc(-c2ccc(OC(F)(F)F)cc2)c1)c1ccccc1]

At 50° C., 11.8 g (41.4 mmol) of N-(5-bromopyridin-3-yl)benzamide, 12.8 g (62.1 mmol) of [4-(trifluoromethoxy)phenyl]boronic acid and 11.4 g (82.7 mmol) of potassium carbonate were dissolved in 70 ml of 1,2-dimethoxyethane, 21 ml of water and 156 ml of DMF. The mixture was flushed with argon, 0.24 g (0.2 mmol) of tetrakis(triphenylphosphine)palladium(0) was added and the mixture was stirred at 85° C. for 12 h. The reaction mixture was concentrated slightly on a rotary evaporator, diluted with water and extracted with dichloromethane. The organic phase was concentrated under reduced pressure and the residue was triturated with methyl tert-butyl ether. The solid was filtered off and the filtrate was purified by column chromatography on silica gel (cyclohexane/ethyl acetate 2:1=>1:5). The separated solid and the appropriate fraction from the chromatography were combined. Yield: 6.7 g (45% of theory)

LC-MS (Method 1B): $R_t$=2.47 min; m/z=359 [M+H]$^+$.

Example 27A

N-{5-[4-(Trifluoromethoxy)phenyl]piperidin-3-yl}benzenecarboxamide [racemic cis/trans isomer mixture]

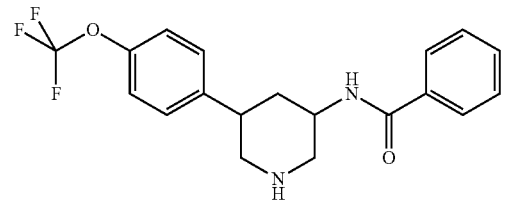 [SMILES: O=C(NC1CNCC(c2ccc(OC(F)(F)F)cc2)C1)c1ccccc1]

10.4 g (29.0 mmol) of the compound from Example 26A were reacted according to General Method 2A. The reaction mixture was purified by column chromatography on silica gel (dichloromethane/methanol 10:1). Yield: 4.1 g (29% of theory)

LC-MS (Method 1B): $R_t$=1.50 min; m/z=365 [M+H]$^+$.

Example 28A

N-{5-[4-(Trifluoromethoxy)phenyl]piperidin-3-yl}benzenecarboxamide [racemic cis isomer]

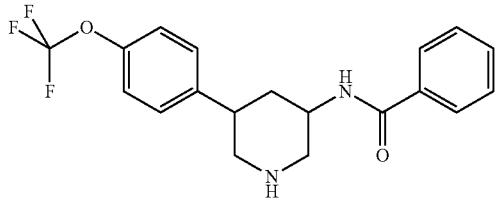 [SMILES: O=C(NC1CNCC(c2ccc(OC(F)(F)F)cc2)C1)c1ccccc1]

Diastereomer separation of 4.1 g of the cis/trans isomer mixture (Example 27A) according to Method 10C gave 1.1 g of Example 28A (cis isomer).

LC-MS (Method 1B): $R_t$=1.56 min; m/z=365 [M+H]$^+$.

Example 29A

4-Nitrophenyl 3-[(phenylcarbonyl)amino]-5-[4-(trifluoromethoxy)phenyl]piperidine-1-carboxylate [racemic cis isomer]

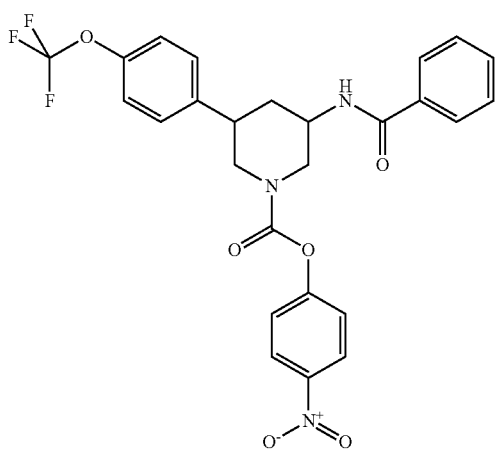 [SMILES: O=C(NC1CC(c2ccc(OC(F)(F)F)cc2)CN(C(=O)Oc2ccc([N+](=O)[O-])cc2)C1)c1ccccc1]

At 0° C., 200 mg (0.55 mmol) of N-{5-[4-(trifluoromethoxy)phenyl]piperidin-3-yl}benzamide and 153 μl (1 1 mmol) of triethylamine were initially charged in 17 ml of dichloromethane, and 111 mg (0.55 mmol) of 4-nitrophenyl chlorocarbonate were added slowly. The mixture was stirred at 0° C. for 2 h and then warmed to RT. Water and saturated aqueous sodium bicarbonate solution were added, and the reaction mixture was extracted. The organic phase was dried over sodium sulphate and concentrated under reduced pressure. The crude product was then purified by preparative HPLC (Reprosil C18, water/acetonitrile gradient). Yield: 254 mg (87% of theory)

LC-MS (Method 1B): $R_t$=2.88 min; m/z=530 [M+H]$^+$.

Example 30A

1-[(4-Cyanopiperidin-1-yl)carbonyl]-5-(4-ethylphenyl)piperidine-3-carboxylic acid [racemic cis isomer]

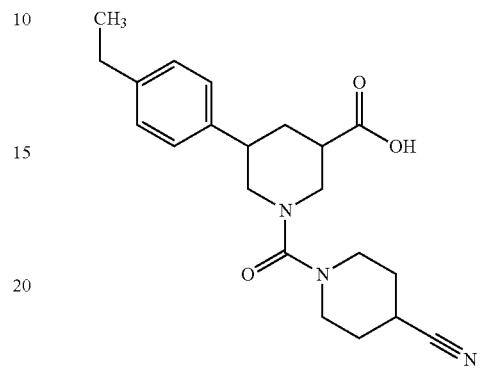

2.0 g (5.2 mmol) of the compound from Example 18A were reacted according to General Method 7A. Yield: 1.8 g (91% of theory)

LC-MS (Method 2B): $R_t$=1.13 min; MS (ESIpos): m/z=370 (M+H)$^+$.

Example 31A

N-[5-(3,4-Dimethylphenyl)pyridin-3-yl]benzenecarboxamide

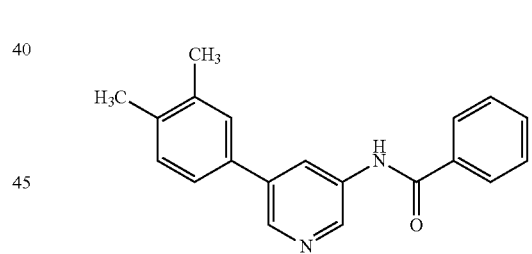

At 50° C., 4.5 g (16.2 mmol) of N-(5-bromopyridin-3-yl)benzamide, 3.0 g (19.5 mmol) of (3,4-dimethylphenyl)boronic acid and 4.5 g (32.5 mmol) of potassium carbonate were dissolved in 59 ml of 1,2-dimethoxyethane, 19 ml of water and 117 ml of DMF. The mixture was flushed with argon, 0.1 g (0.08 mmol) of tetrakis(triphenylphosphine)palladium(0) was added and the mixture was stirred at 85° C. for 12 h. The reaction mixture was concentrated slightly on a rotary evaporator, diluted with water and extracted with dichloromethane. The organic phase was concentrated and purified by column chromatography on silica gel (dichloromethane/methanol 100:1→100:4).

Yield: 3.4 g (68% of theory)

LC-MS (Method 2B): $R_t$=1.17 min; m/z=303 [M+H]$^+$.

Example 32A

N-[5-(3,4-Dimethylphenyl)piperidin-3-yl]benzenecarboxamide [racemic cis/trans isomer mixture]

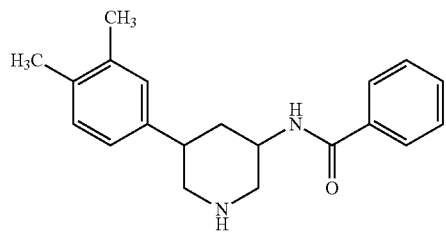

A solution of 1.0 g (3.7 mmol) of N-[5-(3,4-dimethylphenyl)pyridin-3-yl]benzamide in 120 ml of acetic acid was reacted according to General Method 6A. The solution was concentrated under reduced pressure. Yield: 1.85 g LC-MS (Method 2B): $R_t$=0.93 min; MS (ESIpos): m/z=309 (M+H)$^+$.

Example 33A

N-[5-(3,4-Dimethylphenyl)piperidin-3-yl]benzenecarboxamide [racemic cis isomer]

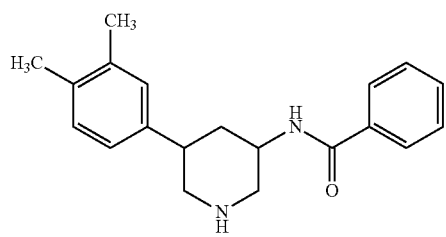 [SMILES: Cc1ccc(C2CNCC(NC(=O)c3ccccc3)C2)cc1C]

Diastereomer separation of 3.7 g of the cis/trans isomer mixture (Example 32A) according to Method 11C gave 0.8 g of Example 33A (cis isomer).

LC-MS (Method 2B): $R_t$=0.93 min; m/z=309 [M+H]$^+$.

Example 34A tert-Butyl [4-({3-(3,4-dimethylphenyl)-5-[(phenylcarbonyl)amino]piperidin-1-yl}carbonyl)tetrahydro-2H-pyran-4-yl]carbamate [racemic cis isomer]

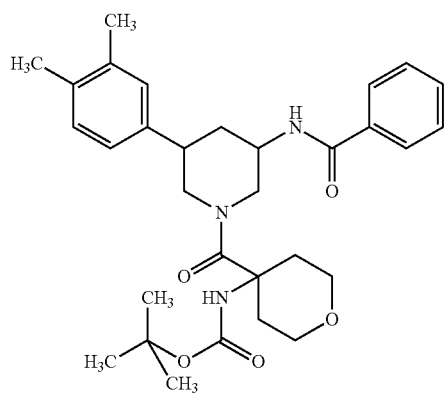 [SMILES: Cc1ccc(C2CC(NC(=O)c3ccccc3)CN(C(=O)C3(NC(=O)OC(C)(C)C)CCOCC3)C2)cc1C]

75 mg (0.3 mmol) of 4-[(tert-butoxycarbonyl)amino]tetrahydro-2H-pyran-4-carboxylic acid together with 110 mg (0.3 mmol) of HATU and 47 mg (0.4 mmol) of 4-dimethylaminopyridine were initially charged in 2 ml of DMF, and 60 mg (0.2 mmol) of N-[5-(3,4-dimethylphenyl)piperidin-3-yl] benzamide were added. The reaction mixture was stirred overnight at RT and then purified by preparative HPLC (Reprosil C18, water/acetonitrile gradient). Yield: 46 mg (44% of theory)

LC-MS (Method 1B): $R_t$=2.45 min; m/z=536 [M+H]$^+$.

Example 35A tert-Butyl [1-({3-(3,4-dimethylphenyl)-5-[(phenylcarbonyl)amino]piperidin-1-yl}carbonyl)cyclobutyl]carbamate [racemic cis isomer]

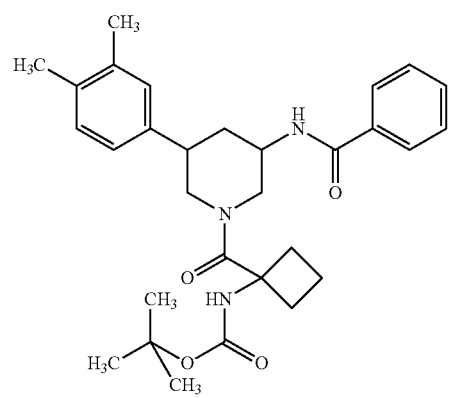 [SMILES: Cc1ccc(C2CC(NC(=O)c3ccccc3)CN(C(=O)C3(NC(=O)OC(C)(C)C)CCC3)C2)cc1C]

62 mg (0.3 mmol) of 1-[(tert-butoxycarbonyl)amino]cyclobutanecarboxylic acid together with 110 mg (0.3 mmol) of HATU and 47 mg (0.4 mmol) of 4-dimethylaminopyridine were initially charged in 2 ml of DMF, and 60 mg (0.2 mmol) of N-[-5-(3,4-dimethylphenyl)piperidin-3-yl]benzamide were added. The reaction mixture was stirred overnight and then purified by preparative HPLC (Reprosil C18, water/acetonitrile gradient). Yield: 54 mg (55% of theory)

LC-MS (Method 1B): $R_t$=2.61 min; m/z=505 [M+H]$^+$.

Example 36A

N-{5-[3-(Propan-2-yl)phenyl]pyridin-3-yl}benzenecarboxamide

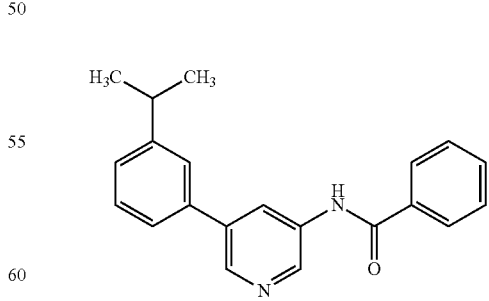

At 50° C., 1.4 g (4.9 mmol) of N-(5-bromopyridin-3-yl)benzamide, 1.0 g (5.9 mmol) of [3-(1-methylethyl)phenyl]boronic acid and 1.4 g (9.9 mmol) of potassium carbonate were dissolved in 15 ml of 1,2-dimethoxyethane, 5 ml of water and 30 ml of DMF. The mixture was flushed with argon, 29 mg (0.03 mmol) of tetrakis(triphenylphosphine)palladium (0) were added and the mixture was stirred at 85° C. for 12 h. The reaction mixture was concentrated slightly on a rotary evaporator, diluted with water and extracted with dichloromethane. The organic phase was concentrated and then purified by preparative HPLC (Reprosil C18, water/acetonitrile gradient). Yield: 1.4 g (92% of theory)

LC-MS (Method 2B): $R_t$=1.27 min; m/z=317 [M+H]$^+$.

Example 37A

N-{5-[3-(Propan-2-yl)phenyl]piperidin-3-yl}benzenecarboxamide [racemic cis/trans isomer mixture] trifluoroacetic acid

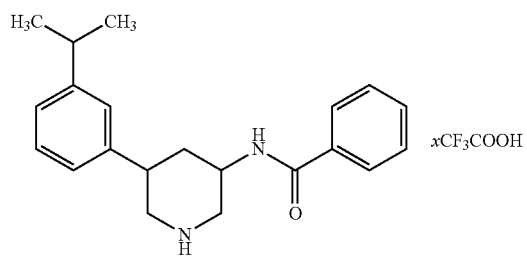 [SMILES: CC(C)c1cccc(C2CNCC(NC(=O)c3ccccc3)C2)c1]

A solution of 1.43 g (4.52 mmol) of N-{5-[3-(1-methylethyl)phenyl]pyridin-3-yl}benzamide in 130 ml of ethanol and 30 ml of acetic acid was reacted according to General Method 2A. The solution was filtered through Celite and the filtrate was concentrated under reduced pressure. The product was purified chromatographically. Yield: 0.18 g (8.8% of theory)

LC-MS (Method 3B): $R_t$=1.20 min; MS (ESIpos): m/z=323 (M+H)$^+$.

Example 38A

N-[5-(2,3-Dimethylphenyl)pyridin-3-yl]benzenecarboxamide

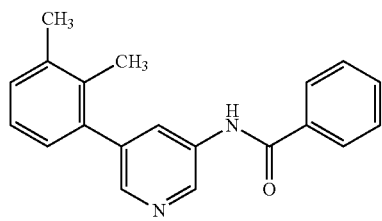 [SMILES: Cc1cccc(-c2cncc(NC(=O)c3ccccc3)c2)c1C]

At 50° C., 3.93 g (13.9 mmol) of N-(5-bromopyridin-3-yl)benzamide, 2.50 g (16.7 mmol) of (2,3-dimethylphenyl)boronic acid and 3.84 g (27.8 mmol) of potassium carbonate were dissolved in 50 ml of 1,2-dimethoxyethane, 17 ml of water and 100 ml of DMF. The mixture was flushed with argon, 81 mg (0.07 mmol) of tetrakis(triphenylphosphine)palladium(0) were added and the mixture was stirred at 85° C. for 12 h. The reaction mixture was concentrated slightly on a rotary evaporator, diluted with water and extracted with dichloromethane. The organic phase was concentrated under reduced pressure and the residue was triturated with methyl tert-butyl ether, the solid was filtered off and the filtrate was purified by column chromatography on silica gel (cyclohexane/ethyl acetate 2:1→1:1). The separated solid and the appropriate fraction from the chromatography were combined. Yield: 4.2 g (96% of theory)

LC-MS (Method 1B): $R_t$=2.24 min; m/z=303 [M+H]$^+$.

Example 39A

N-[5-(2,3-Dimethylphenyl)piperidin-3-yl]benzenecarboxamide [racemic cis/trans isomer mixture]

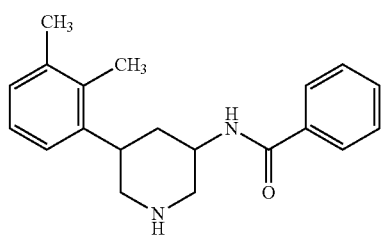 [SMILES: Cc1cccc(C2CNCC(NC(=O)c3ccccc3)C2)c1C]

A solution of 550 mg (1.82 mmol) of N-[5-(2,3-dimethylphenyl)pyridin-3-yl]benzamide in 150 ml of ethanol was reacted according to General Method 5A. The solution was concentrated under reduced pressure. The product was purified by preparative HPLC (Reprosil C18, water/acetonitrile gradient). Yield: 760 mg (77% of theory, purity 57%)

LC-MS (Method 3B): $R_t$=1.26 min; MS (ESIpos): m/z=309 (M+H)$^+$.

Example 40A

N-[5-(2,3-Dimethylphenyl)piperidin-3-yl]benzenecarboxamide [racemic cis isomer]

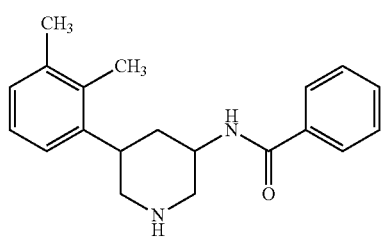 [SMILES: Cc1cccc(C2CNCC(NC(=O)c3ccccc3)C2)c1C]

Diastereomer separation of 720 mg of the cis/trans isomer mixture (Example 39A) according to Method 12C gave 95 mg of Example 40A (cis isomer).

LC-MS (Method 1B): $R_t$=1.41 min; m/z=309 [M+H]$^+$.

Example 41A

Ethyl 4-{5-[(phenylcarbonyl)amino]pyridin-3-yl}benzenecarboxylate

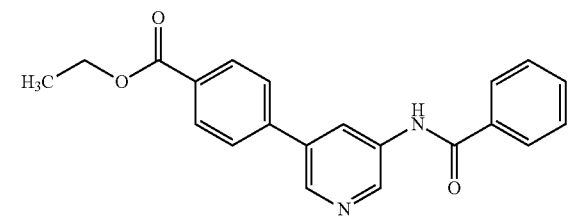 [SMILES: CCOC(=O)c1ccc(-c2cncc(NC(=O)c3ccccc3)c2)cc1]

At 50° C., 5.14 g (18.2 mmol) of N-(5-bromopyridin-3-yl)benzamide, 5.40 g (27.8 mmol) of 4-ethoxycarbonylphenylboronic acid and 5.03 g (36.4 mmol) of potassium carbonate were dissolved in 30 ml of 1,2-dimethoxyethane, 9 ml of water and 65 ml of DMF. The mixture was flushed with argon, 105 mg (0.09 mmol) of tetrakis(triphenylphosphine)palladium(0) were added and the mixture was stirred at 85° C. for 12 h. The reaction mixture was concentrated slightly on a rotary evaporator, diluted with water and extracted with dichloromethane. The organic phase was concentrated under reduced pressure and the residue was triturated with methyl tert-butyl ether, the solid was filtered off and the filtrate was purified by column chromatography (cyclohexane/ethyl acetate 2:1→1:1). The separated solid and the appropriate fraction from the chromatography were combined. Yield: 4.6 g (60% of theory)

LC-MS (Method 1B): $R_t$=2.36 min; m/z=347 $[M+H]^+$.

Example 42A

Ethyl 4-{5-[(phenylcarbonyl)amino]piperidin-3-yl}benzenecarboxylate [racemic cis/trans isomer mixture]

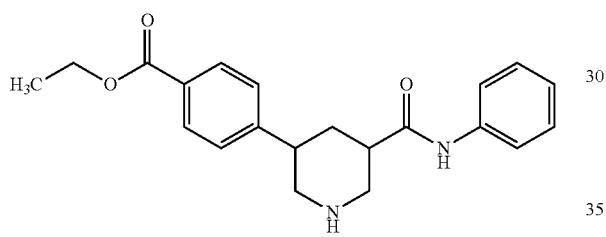

17.45 g (50.37 mmol) of ethyl 4-{5-[(phenylcarbonyl)amino]pyridin-3-yl}benzoate were reacted according to General Method 2A. The reaction mixture was purified by column chromatography (dichloromethane/methanol 10:1). Yield: 10.4 g (about 75% pure).

LC-MS (Method 2B): $R_t$=0.85 min; m/z=353 $[M+H]^+$.

Example 43A

Ethyl 4-{5-[(phenylcarbonyl)amino]piperidin-3-yl}benzenecarboxylate [racemic cis isomer]

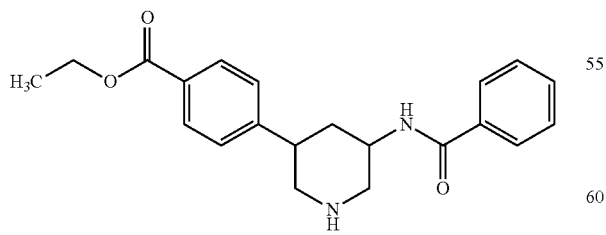

Diastereomer separation of 10.3 g of the cis/trans isomer mixture (Example 42A) according to Method 13C gave 4.2 g of Example 43A (cis isomer).

LC-MS (Method 2B): $R_t$=0.87 min; m/z=353 $[M+H]^+$.

Example 44A

N-{5-[3-(Trifluoromethyl)phenyl]pyridin-3-yl}benzenecarboxamide

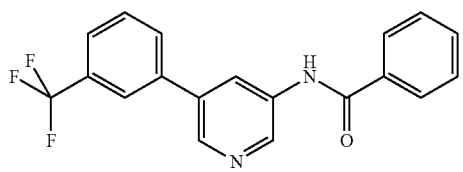 [SMILES: O=C(Nc1cncc(-c2cccc(C(F)(F)F)c2)c1)c1ccccc1]

At 50° C., 1.95 g (7.02 mmol) of N-(5-bromopyridin-3-yl)benzamide, 2.00 g (10.5 mmol) of [3-(trifluoromethyl)phenyl]boronic acid and 1.49 g (14.04 mmol) of sodium carbonate were dissolved in 12 ml of 1,2-dimethoxyethane, 3.5 ml of water and 261 ml of DMF. The mixture was flushed with argon, 41 mg (0.04 mmol) of tetrakis(triphenylphosphine)palladium(0) were added and the mixture was stirred at 85° C. for 12 h. The reaction mixture was concentrated slightly on a rotary evaporator, diluted with water and extracted with dichloromethane. The organic phase was concentrated under reduced pressure and the residue was purified by column chromatography (cyclohexane/ethyl acetate 2:1). Yield: 860 mg (35% of theory)

LC-MS (Method 5B): $R_t$=2.26 min; m/z=343 $[M+H]^+$.

Example 45A

N-{5-[3-(Trifluoromethyl)phenyl]piperidin-3-yl}benzenecarboxamide [racemic cis/trans isomer mixture]

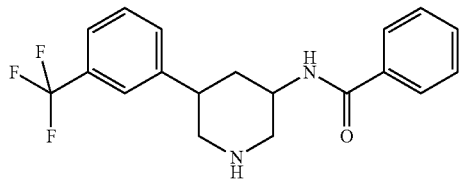 [SMILES: O=C(NC1CNCC(c2cccc(C(F)(F)F)c2)C1)c1ccccc1]

A solution of 840 mg (1.82 mmol) of N-{5-[3-(trifluoromethyl)phenyl]pyridin-3-yl}benzamide in 100 ml of glacial acetic acid was reacted according to General Method 6A. The solution was concentrated under reduced pressure. The product was purified by preparative HPLC (Reprosil C18, water/acetonitrile gradient). Yield: 700 mg LC-MS (Method 5B): $R_t$=1.55 min; m/z=349 $[M+H]^+$.

Example 46A

N-{5-[3-(Trifluoromethyl)phenyl]piperidin-3-yl}benzenecarboxamide [racemic cis isomer]

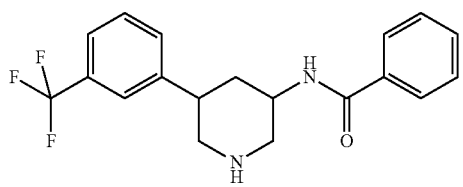 [SMILES: O=C(NC1CNCC(c2cccc(C(F)(F)F)c2)C1)c1ccccc1]

Diastereomer separation of 840 mg of the cis/trans isomer mixture (Example 45A) according to Method 14C gave 176 mg of Example 46A (cis isomer).

$^1$H-NMR (400 MHz, DMSO-$d_6$): δ=8.22 (d, 1H), 7.85 (d, 2H), 7.39-7.63 (m, 7H), 3.88-4.06 (m, 1H), 3.09 (dd, 1H), 2.99 (d, 1H), 2.85-2.95 (m, 1H), 2.37-2.47 (m, 2H), 2.02-2.14 (m, 1H), 1.74 (q, 1H).

Example 47A

N-{5-[4-(Trifluoromethyl)phenyl]pyridin-3-yl}benzenecarboxamide

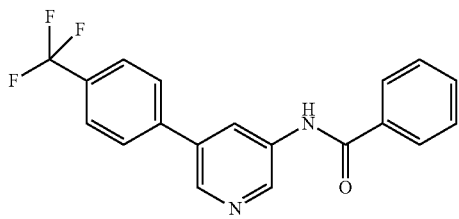 [SMILES: O=C(Nc1cncc(-c2ccc(C(F)(F)F)cc2)c1)c1ccccc1]

At 50° C., 11.35 g (40.96 mmol) of N-(5-bromopyridin-3-yl)benzamide, 11.67 g (61.43 mmol) of [4-(trifluoromethyl)phenyl]boronic acid and 8.68 g (81.91 mmol) of sodium carbonate were dissolved in 68 ml of 1,2-dimethoxyethane, 21 ml of water and 151 ml of DMF. The mixture was flushed with argon, 237 mg (0.21 mmol) of tetrakis(triphenylphosphine)palladium(0) were added and the mixture was stirred at 85° C. for 12 h. The reaction mixture was concentrated slightly on a rotary evaporator, diluted with water and extracted with dichloromethane. The organic phase was concentrated under reduced pressure and the residue was purified by column chromatography (cyclohexane/ethyl acetate 1:1). Yield: 10.6 g (76% of theory)

LC-MS (Method 5B): $R_t$=2.31 min; m/z=343 [M+H]$^+$.

Example 48A

N-{5-[4-(Trifluoromethyl)phenyl]piperidin-3-yl}benzenecarboxamide [racemic cis/trans isomer mixture]

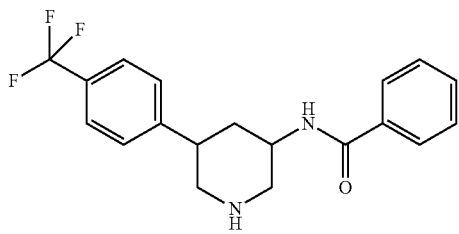 [SMILES: O=C(NC1CNCC(c2ccc(C(F)(F)F)cc2)C1)c1ccccc1]

A solution of 1.0 g (2.9 mmol) of N-{5-[4-(trifluoromethyl)phenyl]pyridin-3-yl]benzamide in 120 ml of glacial acetic acid was reacted according to General Method 6A. The solution was concentrated under reduced pressure. The product was purified by preparative HPLC (Reprosil C18, water/acetonitrile gradient). Yield: 657 mg (50% pure).

LC-MS (Method 5B): $R_t$=1.69 min; m/z=349 [M+H]$^+$.

Example 49A

N-{5-[4-(Trifluoromethyl)phenyl]piperidin-3-yl}benzenecarboxamide [racemic cis isomer]

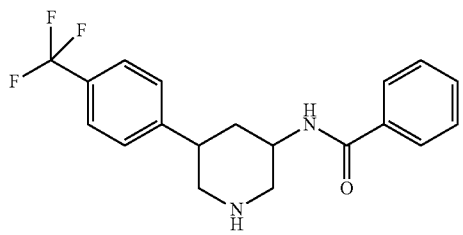 [SMILES: O=C(NC1CNCC(c2ccc(C(F)(F)F)cc2)C1)c1ccccc1]

Diastereomer separation of 2.0 g of the cis/trans isomer mixture (Example 48A) according to Method 15C gave 708 mg of Example 49A (cis isomer).

$^1$H NMR (400 MHz, DMSO-$d_6$): δ=8.24 (d, 1H), 7.84 (d, 2H), 7.68 (d, 2H), 7.40-7.56 (m, 5H), 3.93-4.06 (m, 1H), 3.09 (dd, 1H), 2.99 (d, 1H), 2.83-2.94 (m, 1H), 2.37-2.47 (m, 2H), 2.08 (d, 1H), 1.72 (q, 1H).

Example 50A

4-Nitrophenyl 3-[(phenylcarbonyl)amino]-5-[4-(trifluoromethyl)phenyl]piperidine-1-carboxylate [racemic cis isomer]

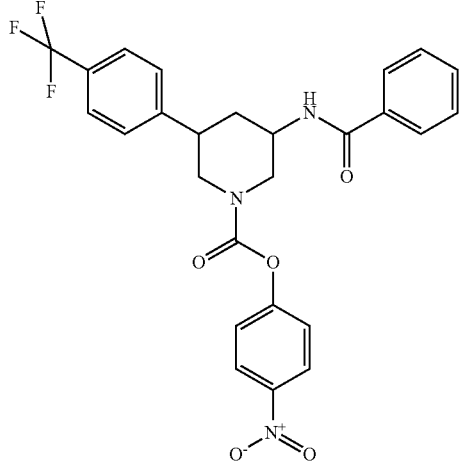 [SMILES: O=C(NC1CC(c2ccc(C(F)(F)F)cc2)CN(C(=O)Oc2ccc([N+](=O)[O-])cc2)C1)c1ccccc1]

At 0° C., 1.5 g (4.3 mmol) of N-{5-[4-(trifluoromethyl)phenyl]piperidin-3-yl}benzamide and 1.2 ml (1.1 mmol) of triethylamine were initially charged in 131 ml of dichloromethane, and 868 mg (4.3 mmol) of 4-nitrophenyl chlorocarbonate were added slowly. The mixture was stirred at 0° C. for 2 h and then warmed to RT. Water and saturated aqueous sodium bicarbonate solution were added, and the reaction mixture was extracted. The organic phase was concentrated under reduced pressure and purified by column chromatography (cyclohexane/ethyl acetate 1:2). Yield: 1.95 g (88% of theory)

LC-MS (Method 1B): $R_t$=2.82 min; m/z=514 [M+H]$^+$.

Example 51A tert-Butyl [1-({3-[(phenylcarbonyl)amino]-5-[4-(trifluoromethyl)phenyl]piperidin-1-yl}carbonyl)cyclopropyl]carbamate [racemic cis isomer]

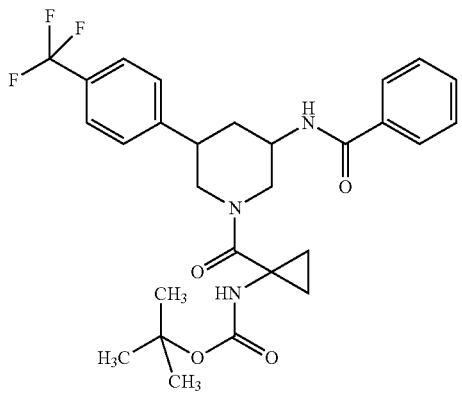 [SMILES: CC(C)(C)OC(=O)NC1(C(=O)N2CC(NC(=O)c3ccccc3)CC(c3ccc(C(F)(F)F)cc3)C2)CC1]

125 mg (0.62 mmol) of 1-[(tert-butoxycarbonyl)amino]cyclopropanecarboxylic acid together with 295 mg (0.78 mmol) of HATU and 127 mg (1.03 mmol) of 4-dimethylaminopyridine were initially charged in 8 ml of DMF, and 180 mg (0.52 mmol) of N-{5-[4-(trifluoromethyl)phenyl]piperidin-3-yl}benzamide were added. The reaction mixture was stirred overnight at RT and then purified by preparative HPLC (Reprosil C18, water/acetonitrile gradient). Yield: 179 mg (65% of theory)

Example 52A

Methyl 5-[4-(trifluoromethyl)phenyl]pyridine-3-carboxylate

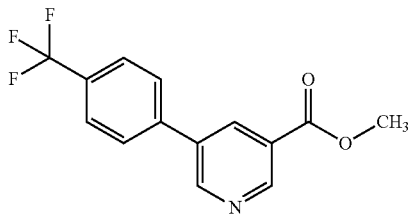 [SMILES: COC(=O)c1cncc(-c2ccc(C(F)(F)F)cc2)c1]

28 g (132 mmol) of methyl 5-bromonicotinate and 30 g (158 mmol, 1.2 eq.) of 4-trifluoromethylphenylboronic acid were reacted according to General Method 1A. Yield: 32 g (85% of theory)

LC-MS (Method 8B): $R_t$=2.27 min; MS (ESIpos): m/z=282 (M+H)$^+$.

Example 53A

Methyl 5-[4-(trifluoromethyl)phenyl]piperidine-3-carboxylate [racemic cis/trans isomer mixture]

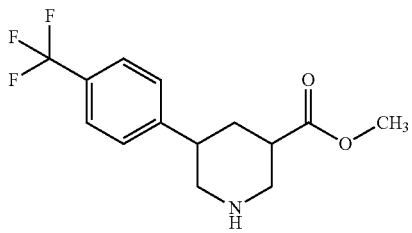 [SMILES: COC(=O)C1CNCC(c2ccc(C(F)(F)F)cc2)C1]

32 g (112 mmol) of methyl 5-[4-(trifluoromethyl)phenyl]pyridine-3-carboxylate (Example 52A) were hydrogenated according to the General Method 2A. Yield: 26 g (82% of theory)

LC-MS (Method 1B): $R_t$=1.35 min and 1.41 min (cis/trans isomers); MS (ESIpos): m/z=288 [M+H]$^+$.

Example 54A

Methyl 1-(morpholin-4-ylcarbonyl)-5-[4-(trifluoromethyl)phenyl]piperidine-3-carboxylate [racemic cis/trans isomer mixture]

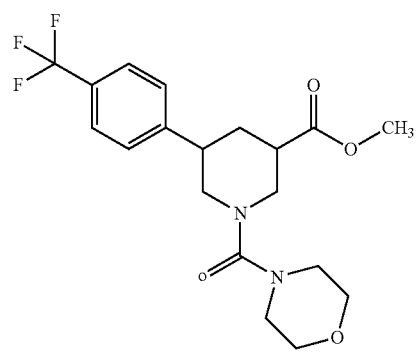

According to General Method 3A, 9.25 g (32.2 mmol) of methyl 5-[4-(trifluoromethyl)phenyl]piperidine-3-carboxylate and 9.63 g (64.7 mmol) of morpholine-4-carbonyl chloride were reacted. This gave 16.3 g of crude product in 76% purity (LC-MS), which was converted without any further purifying operations.

LC-MS (Method 10B): $R_t$=1.19 min and 1.22 min (cis/trans isomers); MS (ESIpos): m/z=401 [M+H]$^+$.

Example 55A 1-(Morpholin-4-ylcarbonyl)-5-[4-(trifluoromethyl)phenyl]piperidine-3-carboxylic acid [racemic cis isomer]

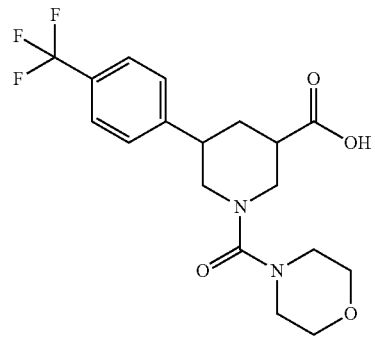 [SMILES: O=C(O)C1CC(c2ccc(C(F)(F)F)cc2)CN(C(=O)N2CCOCC2)C1]

22.19 g (39.90 mmol) of the compound from Example 54A and 44.78 g (399.0 mmol) of potassium tert-butoxide were reacted according to the General Method 7A. Yield: 18.29 g (100% of theory)

LC-MS (Method 5B): $R_t$=1.95 min; MS (ESIpos): m/z=387 (M+H)$^+$.

Example 56A

1-{[3-Amino-5-(4-ethylphenyl)piperidin-1-yl]carbonyl}piperidine-4-carbonitrile [racemic cis isomer]

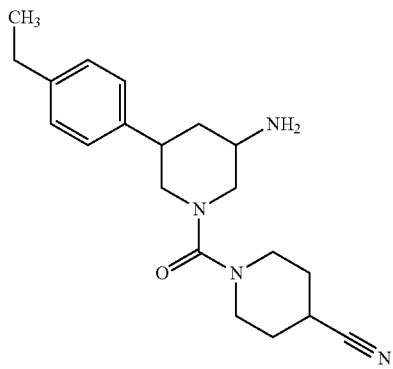 [SMILES: CCc1ccc(C2CC(N)CN(C(=O)N3CCC(C#N)CC3)C2)cc1]

1.9 g (5.2 mmol) of the compound from Example 30A were reacted according to General Method 5A. Yield: 0.9 g (49% of theory)

LC-MS (Method 11B): $R_t$=0.72 min; MS (ESIpos): m/z=341 (M+H)$^+$.

Example 57A

{3-Amino-5-[4-(trifluoromethyl)phenyl]piperidin-1-yl}(morpholin-4-yl)methanone hydrochloride [racemic cis isomer]

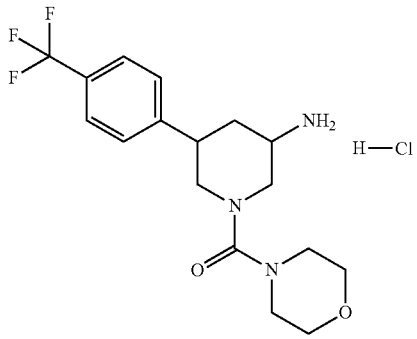

101 ml of a 4 N solution of hydrogen chloride in dioxane were added to the carbamate from Example 172 (9.50 g, 20.1 mmol), and the mixture was then stirred at RT for 1 h. The reaction solution was concentrated under reduced pressure and the residue was taken up in 1 N aqueous hydrogen chloride solution. After washing of the aqueous phase with diethyl ether, the aqueous phase was concentrated under reduced pressure. The crude product obtained in this manner was used further without further purification. Yield: 5.27 g (65% of theory)

LC-MS (Method 11B): $R_t$=0.71 min; MS (ESIpos): m/z=358 (M+H)$^+$.

Example 58A

3-Methyl 1-(4-nitrophenyl) 5-[4-(trifluoromethyl)phenyl]piperidine-1,3-dicarboxylate [racemic cis/trans isomer mixture]

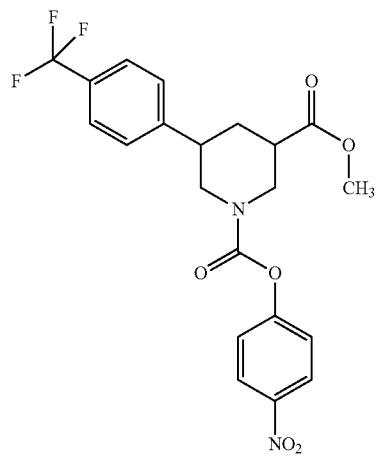 [SMILES: COC(=O)C1CC(c2ccc(C(F)(F)F)cc2)CN(C(=O)Oc2ccc([N+](=O)[O-])cc2)C1]

20.0 g (69.6 mmol) of the compound from Example 53A were dissolved in 1.0 l of dichloromethane, and 14.1 g (139 mmol) of triethylamine were added at 0° C. 14.0 g (69.6 mmol) of 4-nitrophenyl chlorocarbonate were then added dropwise. The reaction mixture was stirred at 0° C. for 2 h and then at RT for 16 h. For workup, the mixture was washed with saturated aqueous sodium bicarbonate solution. The organic phase was dried over magnesium sulphate, filtered and concentrated under reduced pressure. This gave 31.3 g of crude product, which was reacted without any further purification steps.

LC-MS (Method 1B): $R_t$=2.44 min and 2.48 min (cis/trans isomers); MS (ESIpos): m/z=453 [M+H]$^+$.

Example 59A

Methyl 1-(1,4-dioxa-8-azaspiro[4.5]dec-8-ylcarbonyl)-5-[4-(trifluoromethyl)phenyl]piperidine-3-carboxylate [racemic cis/trans isomer mixture]

6.00 g (13.3 mmol) of the compound from Example 58A, 4.75 g (33.2 mmol) of 8-aza-1,4-dioxa-spiro[4.5]decane and 1.83 g (13.3 mmol) of potassium carbonate were reacted according to General Method 8A. Yield: 5.15 g (81% of theory)

LC-MS (Method 11B): R$_t$=1.19 min and 1.14 min (cis/trans isomers); MS (ESIpos): m/z=457 [M+H]$^+$.

Example 60A 1-(1,4-Dioxa-8-azaspiro[4.5]dec-8-ylcarbonyl)-5-[4-(trifluoromethyl)phenyl]piperidine-3-carboxylic acid [racemic cis isomer]

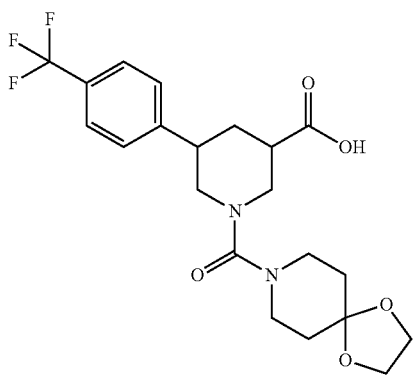 [SMILES: O=C(O)C1CC(c2ccc(C(F)(F)F)cc2)CN(C(=O)N2CCC3(CC2)OCCO3)C1]

5.15 g (11.3 mmol) of the compound from Example 59A and 12.7 g (113 mmol) of potassium tert-butoxide were reacted according to the General Method 7A. Yield: 5.00 g (99% of theory)

LC-MS (Method 11B): R$_t$=0.99 min; MS (ESIpos): m/z=443 (M+H)$^+$.

Example 61A tert-Butyl {1-(1,4-dioxa-8-azaspiro[4.5]dec-8-ylcarbonyl)-5-[4-(trifluoromethyl)phenyl]piperidin-3-yl}carbamate [racemic cis isomer]

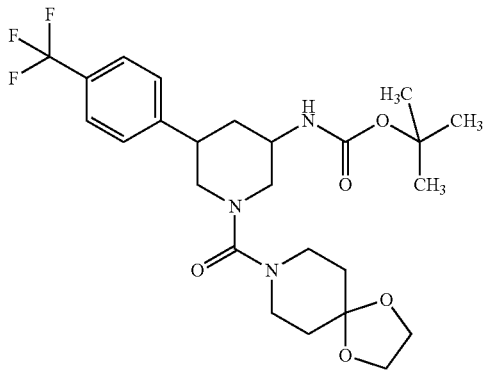 [SMILES: CC(C)(C)OC(=O)NC1CC(c2ccc(C(F)(F)F)cc2)CN(C(=O)N2CCC3(CC2)OCCO3)C1]

Activated molecular sieves 4 Å (about 8.4 g), 1.74 ml of triethylamine (12.5 mmol) and 3.15 g (11.4 mmol) of diphenyl phosphorazidate were added to the carboxylic acid from Example 60A (5.00 g, 10.4 mmol) in tert-butanol (189 ml), and the mixture was stirred under reflux overnight. The reaction solution was cooled, and the molecular sieves was then filtered off and thoroughly washed with ethyl acetate. The solvent was removed under reduced pressure and the residue was taken up in ethyl acetate. After washing with 2 N aqueous hydrogen chloride solution, saturated aqueous sodium bicarbonate solution and water, the organic phase was dried over magnesium sulphate, filtered and concentrated under reduced pressure. The crude product was used for the next step without further purification. Yield: 5.32 g (70% of theory, purity 71%)

LC-MS (Method 11B): R$_t$=1.21 min; MS (ESIpos): m/z=514 (M+H)$^+$.

Example 62A

{3-Amino-5-[4-(trifluoromethyl)phenyl]piperidin-1-yl}(1,4-dioxa-8-azaspiro[4.5]dec-8-yl)methanone hydrochloride [racemic cis isomer]

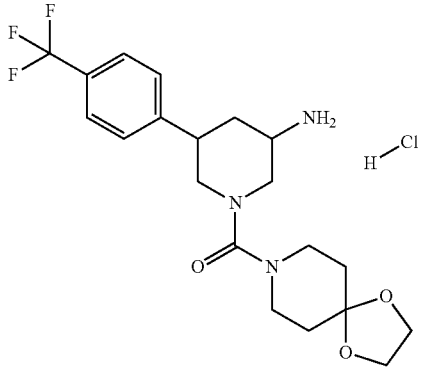 [SMILES: NC1CC(c2ccc(C(F)(F)F)cc2)CN(C(=O)N2CCC3(CC2)OCCO3)C1 ; Cl]

37 ml of a 4 N solution of hydrochloric acid in dioxane were added to the carbamate from Example 61A (5.30 g, 7.33 mmol), and the mixture was then stirred at RT for 1 h. Another 37 ml of a 4 N hydrochloric acid solution in dioxane were added, and the mixture was stirred at 60° C. for 3 h. The reaction solution was concentrated under reduced pressure and the residue was taken up in 1 N aqueous hydrogen chloride solution. After washing of the aqueous phase with diethyl ether, the aqueous phase was concentrated under reduced pressure. The crude product obtained in this manner was used further without further purification. Yield: 3.20 g (92% of theory)

LC-MS (Method 5B): R$_t$=1.57 min; MS (ESIpos): m/z=414 (M+H)$^+$.

Example 63A

N-{1-(1,4-Dioxa-8-azaspiro[4.5]dec-8-ylcarbonyl)-5-[4-(trifluoromethyl)phenyl]piperidin-3-yl}-cyclopentanecarboxamide [racemic cis isomer]

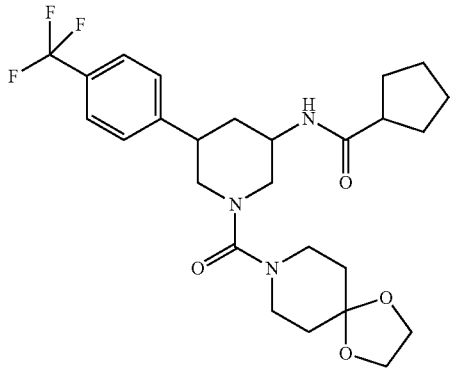 [SMILES: O=C(NC1CC(c2ccc(C(F)(F)F)cc2)CN(C(=O)N2CCC3(CC2)OCCO3)C1)C1CCCC1]

177 μl of triethylamine (1.27 mmol) and 15.5 mg of DMAP (0.127 mmol) were added to a solution of the amine hydrochloride from Example 62A (200 mg, 0.422 mmol) in dichloromethane (10 ml), and 84 mg of cyclopentanecarbonyl chloride (0.633 mmol) were then added at 0° C. The reaction mixture was warmed to RT and stirred overnight. The reaction solution was washed with aqueous 1 N hydrogen chloride solution and the organic phase was dried over magnesium sulphate, filtered and concentrated under reduced pressure. The crude product was purified by preparative HPLC (RP18 column; acetonitrile/water gradient). Yield: 112 mg (52% of theory)

LC-MS (Method 2B): $R_t$=1.28 min; MS (ESIpos): m/z=510 (M+H)$^+$.

Example 64A

3-Chloro-N-{1-(1,4-dioxa-8-azaspiro[4.5]dec-8-ylcarbonyl)-5-[4-(trifluoromethyl)phenyl]piperidin-3-yl}benzenecarboxamide [racemic cis isomer]

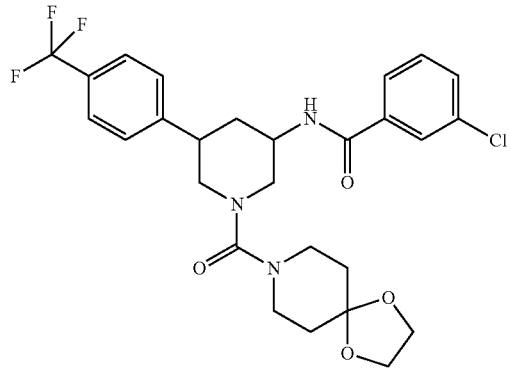 [SMILES: O=C(NC1CC(c2ccc(C(F)(F)F)cc2)CN(C(=O)N2CCC3(CC2)OCCO3)C1)c1cccc(Cl)c1]

0.59 ml (3.38 mmol) of N,N'-diisopropylethylamine and 248 mg (1.58 mmol) of 3-chlorobenzoic acid were added to a solution of the compound from Example 62A (500 mg, 1.06 mmol) in N,N'-dimethylformamide (18 ml). After addition of 522 mg (1.37 mmol) of HATU, the mixture was stirred at RT overnight. The reaction mixture was purified directly by preparative HPLC(RP18 column; acetonitrile/water gradient). Yield: 414 mg (67% of theory)

LC-MS (Method 2B): $R_t$=1.36 min; MS (ESIpos): m/z=552 (M+H)$^+$.

Example 65A

3-Methyl 1-(4-nitrophenyl) 5-(4-ethylphenyl)piperidine-1,3-dicarboxylate [racemic cis/trans isomer mixture]

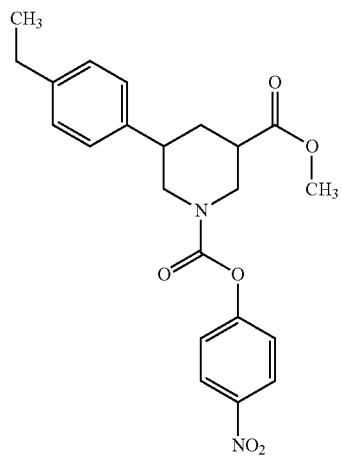 [SMILES: CCc1ccc(C2CC(C(=O)OC)CN(C(=O)Oc3ccc([N+](=O)[O-])cc3)C2)cc1]

10.0 g (40.4 mmol) of the compound from Example 2A were initially charged in 135 ml of dichloromethane and cooled to 0° C., and 11.2 ml (8.2 g, 80.9 mmol) of triethylamine and 8.5 g (40.4 mmol) of 4-nitrophenyl chloroformate were added. The reaction mixture was allowed to warm to room temperature over a period of 2 h. For work-up, the mixture was twice washed with water, and the organic phase was dried over sodium sulphate. The solvent was removed under reduced pressure and the residue was dried under high vacuum. Yield: 16.5 g (83% of theory)

LC-MS (Method 11B): $R_t$=1.31 min and 1.33 min (cis/trans isomers); MS (ESIpos): m/z=413 [M+H]$^+$.

Example 66A

Methyl 1-[(4-cyanopiperidin-1-yl)carbonyl]-5-[4-(trifluoromethyl)phenyl]piperidine-3-carboxylate [racemic cis/trans isomer mixture]

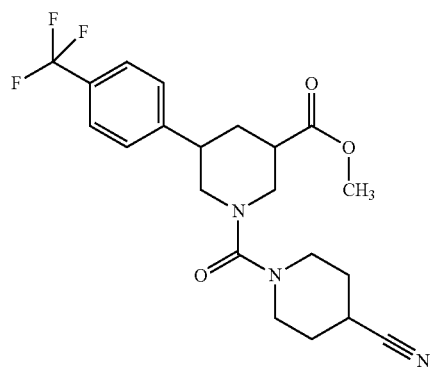 [SMILES: COC(=O)C1CC(c2ccc(C(F)(F)F)cc2)CN(C(=O)N2CCC(C#N)CC2)C1]

4.00 g (8.84 mmol) of 3-methyl 1-(4-nitrophenyl) 5-[4-(trifluoromethyl)phenyl]piperidine-1,3-dicarboxylate (Example 58A) and 2.92 g (26.5 mmol) of piperidine-4-carbonitrile were reacted according to the General Method 8A. Yield: 3.15 g (77% of theory)

LC-MS (Method 1B): $R_t$=2.35 min and 2.41 min (cis/trans isomers); MS (ESIpos): m/z=424 [M+H]$^+$.

Example 67A

1-[(4-Cyanopiperidin-1-yl)carbonyl]-5-[4-(trifluoromethyl)phenyl]piperidine-3-carboxylic acid [racemic cis isomer]

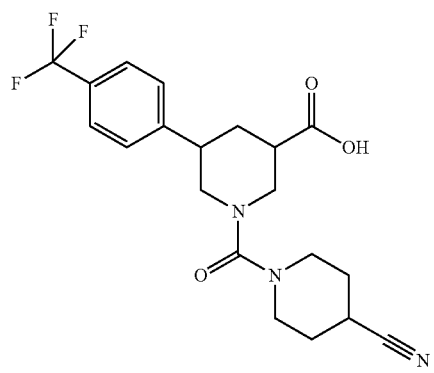 [SMILES: N#CC1CCN(C(=O)N2CC(C(=O)O)CC(c3ccc(C(F)(F)F)cc3)C2)CC1]

2.90 g (6.85 mmol) of methyl 1-[(4-cyanopiperidin-1-yl) carbonyl]-5-[4-(trifluoromethyl)phenyl]piperidine-3-carboxylate (Example 66A) were reacted according to General Method 9A (reaction time 2 h). Yield: 2.86 g (98% of theory)

LC-MS (Method 1B): $R_t$=2.15 min; MS (ESIpos): m/z=410 (M+H)$^+$.

Example 68A tert-Butyl {1-[(4-cyanopiperidin-1-yl)carbonyl]-5-[4-(trifluoromethyl)phenyl]piperidin-3-yl}carbamate [racemic cis/trans isomer mixture]

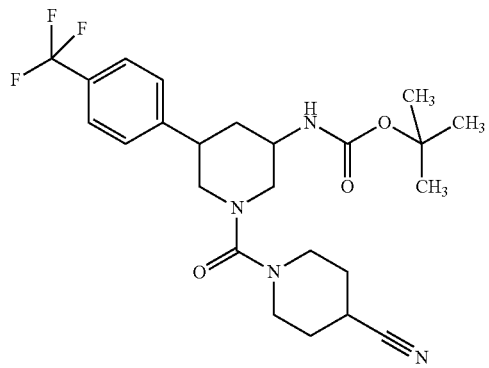 [SMILES: CC(C)(C)OC(=O)NC1CC(c2ccc(C(F)(F)F)cc2)CN(C(=O)N2CCC(C#N)CC2)C1]

18 g of molecular sieves 4 Å, 3.2 ml (2.3 g, 23 mmol) of triethylamine and 4.6 ml (5.8 g, 21 mmol) of diphenyl phosphorazidate were added to a solution of 7.90 g (19.3 mmol) of the carboxylic acid from Example 67A in 350 ml of tert-butanol, and the mixture was stirred under reflux overnight. The molecular sieves were then filtered off and washed repeatedly with ethyl acetate, and the filtrate was concentrated under reduced pressure. The residue was taken up in ethyl acetate and then washed with 2N hydrochloric acid, saturated aqueous sodium bicarbonate solution and water. The organic phase was dried over magnesium sulphate, filtered and concentrated under reduced pressure. Yield: 8.34 g with a purity of 91% (82% of theory)

LC-MS (Method 11B): $R_t$=1.16 min and 1.19 min (cis/trans isomers); MS (ESIpos): m/z=481 [M+H]$^+$.

Example 69A 1-({3-Amino-5-[4-(trifluoromethyl)phenyl]piperidin-1-yl}carbonyl)piperidine-4-carbonitrile hydrochloride [racemic cis isomer]

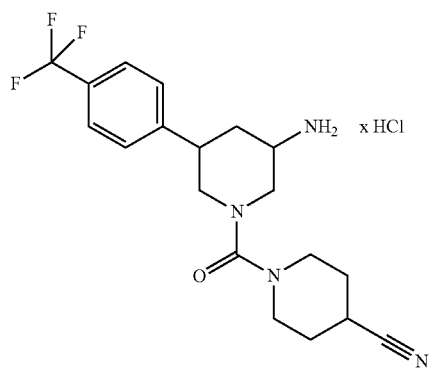 [SMILES: N#CC1CCN(C(=O)N2CC(N)CC(c3ccc(C(F)(F)F)cc3)C2)CC1]

78 ml of a 4N solution of hydrochloric acid in dioxane were added to 8.30 g (15.7 mmol) of the carbamate from Example 68A having a purity of 91%, and the mixture was stirred at room temperature for 1 h. The reaction solution was concentrated under reduced pressure and the residue was taken up in 1 N hydrochloric acid. After washing with diethyl ether, the organic phase was concentrated under reduced pressure and the residue was taken up in dichloromethane and extracted repeatedly with 1N hydrochloric acid. The combined aqueous phases were concentrated under reduced pressure, and the residue was dried under high vacuum. Yield: 4.93 g (71% of theory)

LC-MS (Method 2B): $R_t$=0.82 min; MS (ESIpos): m/z=381 [M+H—HCl]$^+$.

WORKING EXAMPLES

General Method 1

Amide Coupling with Carboxylic Acids

Under argon and at RT, HATU (1.2 eq.) and N,N-diisopropylethylamine (3.2 eq.) are added to a solution of the appropriate carboxylic acid (1.1 eq.) in dimethylformamide (10 ml/mmol). The reaction mixture is stirred at RT for 30 min, and the amine (1.0 eq.) is added. The reaction mixture is stirred at RT. After addition of water and phase separation, the organic phase is washed with water and with saturated aqueous sodium chloride solution, dried (sodium sulphate), filtered and concentrated under reduced pressure. The crude product is then purified by preparative HPLC (Reprosil C18, water/acetonitrile gradient).

General Method 2

Amide Coupling with Carbonyl Chlorides

Under argon and at RT, the appropriate carbonyl chloride (1.1 eq.) and N,N-diisopropylethylamine (3.2 eq.) are added dropwise to a solution of the amine (1.0 eq.) in tetrahydrofuran (10 ml/mmol). The reaction mixture is stirred at RT. After addition of water and phase separation, the organic phase is washed with water and with saturated aqueous sodium chloride solution, dried (sodium sulphate), filtered and concentrated under reduced pressure. The crude product is then purified by preparative HPLC (Reprosil C18, water/acetonitrile gradient).

General Method 3

Reaction with Carbamoyl Chlorides

Under argon and at RT, N,N-diisopropylethylamine (2.5 eq.) and the appropriate carbamoyl chloride (1.3 eq.) are added dropwise to a solution of the amine (1.0 eq.) in tetrahydrofuran (1.25 ml/mmol). The reaction mixture is stirred at RT. After addition of water and phase separation, the organic phase is washed with water and with saturated aqueous sodium chloride solution, dried (sodium sulphate), filtered and concentrated under reduced pressure. The crude product is then purified by preparative HPLC (Reprosil C18, water/acetonitrile gradient).

General Method 4

Urea Formation with Isocyanate

Under argon and at RT, N,N-diisopropylethylamine (3.2 eq.) and the appropriate isocyanate (1.1 eq.) are added dropwise to a solution of the amine (1.0 eq.) in tetrahydrofuran (10 ml/mmol). The reaction mixture is stirred at RT. After addition of water and phase separation, the organic phase is washed with water and with saturated aqueous sodium chloride solution, dried (sodium sulphate), filtered and concentrated under reduced pressure. The crude product is then purified by preparative HPLC (Reprosil C18, water/acetonitrile gradient).

General Method 5

Reaction with Chloroformates

Under argon and at RT, N,N-diisopropylethylamine (3 eq.) and the appropriate chloroformate (1.3 eq.) are added dropwise to a solution of the amine (1.0 eq.) in tetrahydrofuran (1.25 ml/mmol). The reaction mixture is stirred at RT. After addition of water and phase separation, the organic phase is washed with water and with saturated aqueous sodium chloride solution, dried (sodium sulphate), filtered and concentrated under reduced pressure. The crude product is then purified by preparative HPLC (Reprosil C18, water/acetonitrile gradient).

General Method 6

Sulphonamide Formation

At RT, N,N'-diisopropylethylamine (2.5 eq.) and the appropriate sulphonyl chloride (1.5 eq.) are added to a solution of the appropriate amine (1 eq) in dichloromethane (21 ml/mmol). The reaction mixture is stirred at room temperature overnight. For work-up, the dichloromethane is removed under reduced pressure and the residue is purified by means of preparative HPLC.

General Method 7

Suzuki Reaction

Under argon and at RT, tetrakis(triphenylphosphine)palladium (0.02 eq.), a solution of the boronic acid (1.2 eq.) in ethanol (1 ml/mmol) and a solution of potassium fluoride (2.0 eq.) in water (1 ml/mmol) are added to a solution of the bromide (1.0 eq.) in toluene (5 ml/mmol). The reaction mixture is stirred at reflux. After addition of ethyl acetate and phase separation, the organic phase is washed with water, dried (magnesium sulphate), filtered and concentrated under reduced pressure. The crude product is then purified by preparative HPLC (Reprosil C18, water/acetonitrile gradient).

General Method 8

Amide Formation

At RT, HATU (1.3 eq.) and N,N'-diisopropylethylamine (3.2 eq.) are added to a solution of 1.0 equivalent of the appropriate amine hydrochloride in N,N'-dimethylformamide. 1.5 equivalents of the appropriate carboxylic acid are then added. The reaction mixture is stirred at RT for 16 h and then purified by preparative HPLC.

Example 1

1-(Cyclopropylcarbonyl)-5-(4-ethylphenyl)-N-phenylpiperidine-3-carboxamide [racemic cis isomer]

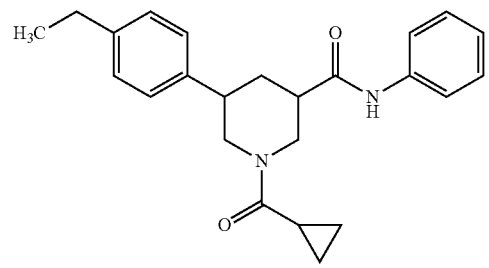 [SMILES: CCc1ccc(C2CC(C(=O)Nc3ccccc3)CN(C(=O)C3CC3)C2)cc1]

68 mg (0.20 mmol) of 5-(4-ethylphenyl)-N-phenylpiperidine-3-carboxamide (Example 17A) and 19 mg (0.22 mmol, 1.1 eq.) of cyclopropanecarboxylic acid were reacted according to General Method 1. Yield: 38 mg (50% of theory)

HPLC (Method 1A): $R_t$=4.81 min; MS (ESIpos): m/z=377 [M+H]$^+$;

$^1$H-NMR (400 MHz, DMSO-$d_6$): δ=10.04 (s, 1H), 7.59 (d, 2H), 7.33-7.12 (m, 6H), 7.04 (t, 1H), 4.61 (br d, 0.5H), 4.52-4.41 (m, 1H), 4.28 (br d, 0.5H), 3.28-3.13 (m, 2H), 2.80-2.69 (m, 1H), 2.65-2.53 (m, 3H), 2.20-1.89 (m, 3H), 1.17 (t, 3H), 0.88-0.65 (m, 4H).

Example 2

1-(2,2-Dimethylpropanoyl)-5-(4-ethylphenyl)-N-phenylpiperidine-3-carboxamide [racemic cis isomer]

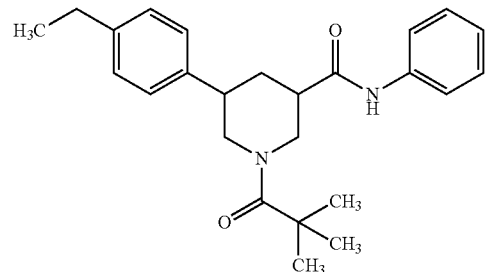

68 mg (0.20 mmol) of 5-(4-ethylphenyl)-N-phenylpiperidine-3-carboxamide (Example 17A) and 22 mg (0.22 mmol, 1.1 eq.) of pivalic acid were reacted according to General Method 1. Yield: 37 mg (34% of theory)

HPLC (Method 2A): $R_t$=5.08 min; MS (ESIpos): m/z=393 [M+H]$^+$;

$^1$H-NMR (400 MHz, DMSO-$d_6$): δ=10.03 (s, 1H), 7.59 (d, 2H), 7.29 (t, 2H), 7.23 (d, 2H), 7.18 (d, 2H), 7.04 (t, 1H), 4.51

(br d, 1H), 4.25 (br d, 1H), 3.03-2.88 (m, 2H), 2.71-2.58 (m, 2H), 2.58 (q, 2H), 2.13 (br d, 1H), 1.97 (q, 1H), 1.22 (s, 9H), 1.17 (t, 3H).

Example 3

1-(2,2-Dimethylpropanoyl)-5-(4-ethylphenyl)-N-phenylpiperidine-3-carboxamide [enantiomerically pure cis isomer]

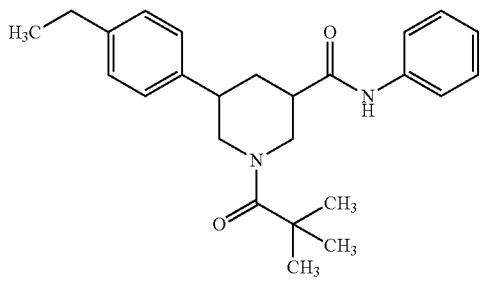 [SMILES: CCc1ccc(C2CC(C(=O)Nc3ccccc3)CN(C(=O)C(C)(C)C)C2)cc1]

The enantiomer separation of 13 mg of the racemate from Example 2 according to Method 1D gave 5.9 mg of the compound from Example 3 (enantiomer 1) and 5.3 mg of the compound from Example 4 (enantiomer 2).

LC-MS (Method 1E): $R_t$=3.17 min; MS (ESIpos): m/z=393 [M+H]$^+$.

Example 4

1-(2,2-Dimethylpropanoyl)-5-(4-ethylphenyl)-N-phenylpiperidine-3-carboxamide [enantiomerically pure cis isomer]

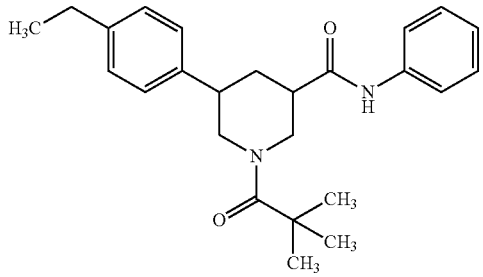 [SMILES: CCc1ccc(C2CC(C(=O)Nc3ccccc3)CN(C(=O)C(C)(C)C)C2)cc1]

The enantiomer separation of 13 mg of the racemate from Example 2 according to Method 1D gave 5.9 mg of the compound from Example 3 (enantiomer 1) and 5.3 mg of the compound from Example 4 (enantiomer 2).

LC-MS (Method 1E): $R_t$=4.65 min; MS (ESIpos): m/z=393 [M+H]$^+$.

Example 5

1-(Cyclopropylacetyl)-5-(4-ethylphenyl)-N-phenylpiperidine-3-carboxamide [racemic cis isomer]

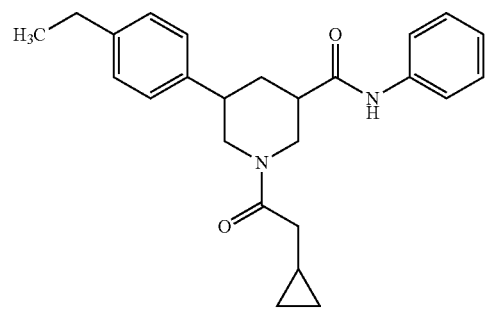 [SMILES: CCc1ccc(C2CC(C(=O)Nc3ccccc3)CN(C(=O)CC3CC3)C2)cc1]

68 mg (0.20 mmol) of 5-(4-ethylphenyl)-N-phenylpiperidine-3-carboxamide (Example 17A) and 22 mg (0.22 mmol, 1.1 eq.) of cyclopropylacetic acid were reacted according to General Method 1.

Yield: 65 mg (79% of theory)

HPLC (Method 1A): $R_t$=4.83 min; MS (ESIpos): m/z=391 [M+H]$^+$;

$^1$H-NMR (500 MHz, DMSO-d$_6$): δ=10.02 (s, 0.5H), 9.95 (s, 0.5H), 7.59 (d, 2H), 7.29 (t, 2H), 7.25 (d, 1H), 7.22 (d, 1H), 7.17 (d, 2H), 7.04 (t, 1H), 4.65 (br d, 0.5H), 4.49 (br d, 0.5H), 4.03 (br d, 0.5H), 3.84 (br d, 0.5H), 3.19 (t, 0.5H), 3.10 (t, 0.5H), 2.75-2.53 (m, 3H), 2.58 (q, 2H), 2.40-2.35 (m, 1H), 2.36 (dd, 0.5H), 2.28 (dd, 0.5H), 2.18-2.05 (m, 1H), 2.00-1.86 (m, 1H), 1.17 (t, 3H), 1.03-0.93 (m, 1H), 0.51-0.43 (m, 2H), 0.17-0.09 (m, 2H).

Example 6

1-(Cyclopropylacetyl)-5-(4-ethylphenyl)-N-phenylpiperidine-3-carboxamide [enantiomerically pure cis isomer]

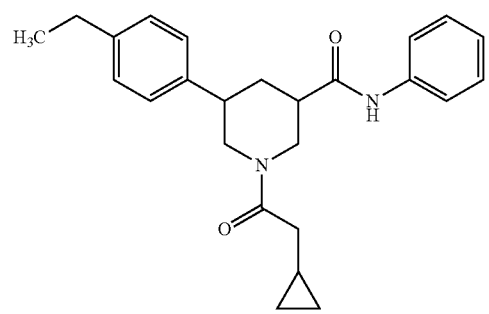 [SMILES: CCc1ccc(C2CC(C(=O)Nc3ccccc3)CN(C(=O)CC3CC3)C2)cc1]

The enantiomer separation of 50 mg of the racemate from Example 5 according to Method 2D gave 18 mg of the compound from Example 6 (enantiomer 1) and 18 mg of the compound from Example 7 (enantiomer 2).

LC-MS (Method 2E): $R_t$=6.40 min; MS (ESIpos): m/z=391 [M+H]$^+$.

Example 7

5-(4-Ethylphenyl)-1-(3-fluoro-2,2-dimethylpropanoyl)-N-phenylpiperidine-3-carboxamide [racemic cis isomer]

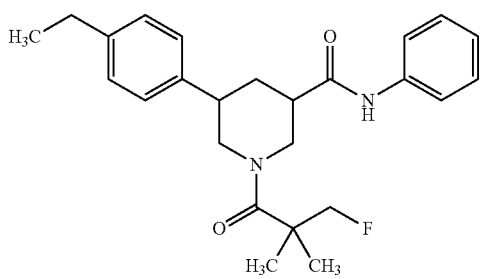 [SMILES: CCc1ccc(C2CC(C(=O)Nc3ccccc3)CN(C(=O)C(C)(C)CF)C2)cc1]

62 mg (0.20 mmol) of 5-(4-ethylphenyl)-N-phenylpiperidine-3-carboxamide (Example 17A) and 42 mg (0.3 mmol, 1.5 eq.) of 3-fluoro-2,2-dimethylpropanoyl chloride were reacted according to General Method 2. Yield: 68 mg (83% of theory)

HPLC (Method 1A): $R_t$=4.97 min; MS (ESIpos): m/z=411 [M+H]$^+$;

$^1$H-NMR (400 MHz, DMSO-d$_6$): δ=10.03 (s, 1H), 7.60 (d, 2H), 7.29 (t, 2H), 7.24 (d, 2H), 7.19 (d, 2H), 7.04 (t, 1H), 4.54-4.43 (m, 2H), 4.40-4.31 (m, 1H), 4.23 (br d, 1H), 3.06-2.90 (m, 2H), 2.73-2.59 (m, 2H), 2.58 (q, 2H), 2.14 (br d, 1H), 1.98 (q, 1H), 1.28 (d, 3H), 1.26 (d, 3H), 1.17 (t, 3H).

Example 8

5-(4-Ethylphenyl)-1-(3-methoxypropanoyl)-N-phenylpiperidine-3-carboxamide [racemic cis isomer]

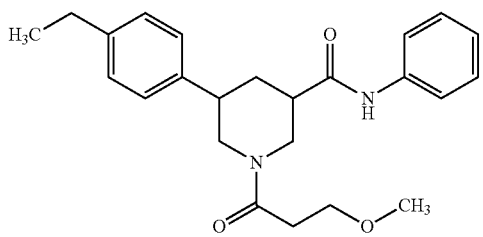 [SMILES: CCc1ccc(C2CC(C(=O)Nc3ccccc3)CN(C(=O)CCOC)C2)cc1]

62 mg (0.18 mmol) of 5-(4-ethylphenyl)-N-phenylpiperidine-3-carboxamide (Example 17A) and 33 mg (0.27 mmol, 1.5 eq.) of methoxypropionyl chloride were reacted according to General Method 2. Yield: 65 mg (91% of theory)

HPLC (Method 1A): $R_t$=4.64 min; MS (ESIpos): m/z=395 [M+H]$^+$;

$^1$H-NMR (400 MHz, DMSO-d$_6$): δ=10.04 (s, 0.5H), 10.00 (s, 0.5H), 7.59 (d, 2H), 7.35-7.12 (m, 6H), 7.04 (t, 1H), 4.64 (br d, 0.5H), 4.47 (br d, 0.5H), 4.10 (br d, 0.5H), 3.89 (br d, 0.5H), 3.65-3.50 (m, 2H), 3.27 (s, 3H), 3.18 (t, 0.5H), 3.09 (t, 0.5H), 2.80-2.60 (m, 3H), 2.60-2.50 (m, 3H), 2.19-2.02 (m, 1H), 2.01-1.85 (m, 1H), 1.17 (t, 3H).

Example 9

5-(4-Ethylphenyl)-N-phenyl-1-(tetrahydro-2H-pyran-4-ylcarbonyl)piperidine-3-carboxamide [racemic cis isomer]

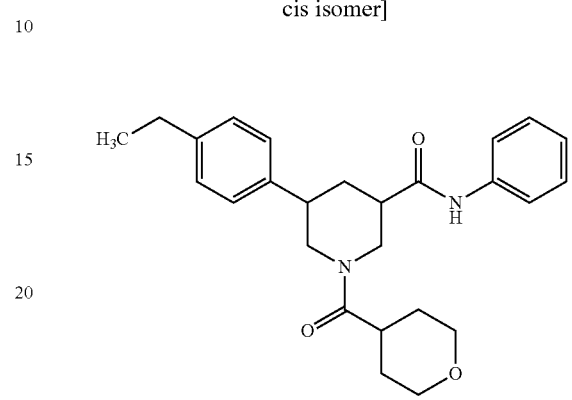

62 mg (0.18 mmol) of 5-(4-ethylphenyl)-N-phenylpiperidine-3-carboxamide (Example 17A) and 41 mg (0.27 mmol, 1.5 eq.) of tetrahydro-2H-pyran-4-carbonyl chloride were reacted according to General Method 2. Yield: 67 mg (88% of theory)

HPLC (Method 1A): $R_t$=4.64 min; MS (ESIpos): m/z=421 [M+H]$^+$;

$^1$H-NMR (400 MHz, DMSO-d$_6$): δ=10.05 (s, 0.5H), 10.01 (s, 0.5H), 7.65-7.55 (m, 2H), 7.32-7.23 (m, 3H), 7.23-7.13 (m, 3H), 7.04 (t, 1H), 4.66 (br d, 0.5H), 4.49 (br d, 0.5H), 4.20 (br d, 0.5H), 3.99 (br d, 0.5H), 3.91-3.77 (m, 2H), 3.49-3.33 (m, 2H), 3.24 (t, 0.5H), 3.16 (t, 0.5H), 3.10-2.92 (m, 1H), 2.75-2.53 (m, 5H), 2.20-2.03 (m, 1H), 2.01-1.83 (m, 1H), 1.75-1.45 (m, 4H), 1.17 (t, 3H).

Example 10

1-[(1-Aminocyclopropyl)carbonyl]-5-(4-ethylphenyl)-N-phenylpiperidine-3-carboxamide [racemic cis isomer]

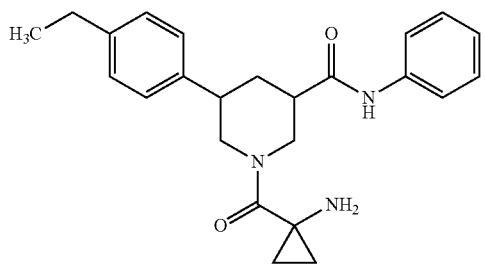 [SMILES: CCc1ccc(C2CC(C(=O)Nc3ccccc3)CN(C(=O)C3(N)CC3)C2)cc1]

Step a): tert-Butyl (1-{[3-(4-ethylphenyl)-5-(phenyl-carbamoyl)piperidin-1-yl]carbonyl}cyclopropyl) carbamate [racemic cis isomer]

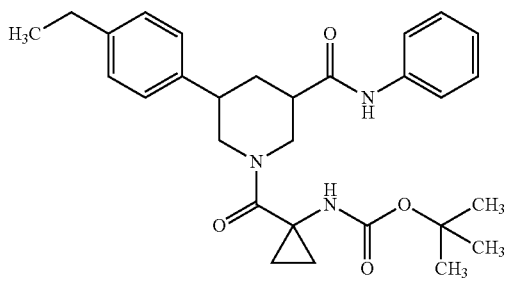 [SMILES: CCc1ccc(C2CC(C(=O)Nc3ccccc3)CN(C(=O)C3(NC(=O)OC(C)(C)C)CC3)C2)cc1]

169 mg (0.50 mmol) of 5-(4-ethylphenyl)-N-phenylpiperidine-3-carboxamide (Example 17A) and 111 mg (0.55 mmol, 1.1 eq.) of 1-[(tert-butoxycarbonyl)amino]cyclopropanecarboxylic acid were reacted according to General Method 1. Yield: 119 mg (48% of theory)

HPLC (Method 2A): $R_t$=4.90 min; MS (ESIpos): m/z=492 [M+H]$^+$.

Step b): 1-[(1-Aminocyclopropyl)carbonyl]-5-(4-ethylphenyl)-N-phenylpiperidine-3-carboxamide [racemic cis isomer]

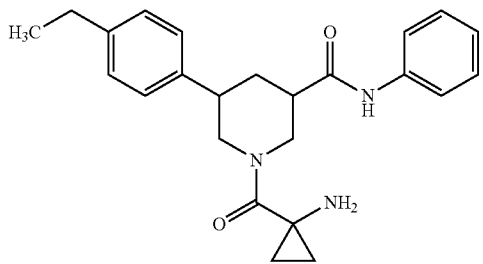

Under argon and at RT, 190 μl (2.5 mmol, 15 eq.) of trifluoroacetic acid were added to a solution of 81 mg (0.16 mmol) of tert-butyl (1-{[3-(4-ethylphenyl)-5-(phenylcarbamoyl)piperidin-1-yl]carbonyl}cyclopropyl)carbamate in 2 ml of dichloromethane. The reaction mixture was stirred at RT for 20 h, then concentrated under reduced pressure and repeatedly coevaporated with toluene. The crude product was purified by preparative HPLC (Reprosil C18, water/acetonitrile gradient). Yield: 29 mg (45% of theory)

HPLC (Method 1A): $R_t$=4.20 min; MS (ESIpos): m/z=392 [M+H]$^+$;

$^1$H-NMR (500 MHz, DMSO-d$_6$): δ=9.99 (s, 1H), 7.60 (d, 2H), 7.29 (t, 2H), 7.24 (d, 2H), 7.18 (d, 2H), 7.04 (t, 1H), 4.54 (br d, 1H), 4.42 (br d, 1H), 3.09-2.79 (m, 2H), 2.80-2.61 (m, 2H), 2.57 (q, 2H), 2.33-2.20 (m, 2H), 2.13 (br d, 1H), 1.94 (q, 1H), 1.17 (t, 3H), 0.94-0.82 (m, 2H), 0.72-0.61 (m, 2H).

Example 11

5-(4-Ethylphenyl)-N-phenyl-1-(tetrahydrofuran-2-ylcarbonyl)piperidine-3-carboxamide [racemic cis isomer]

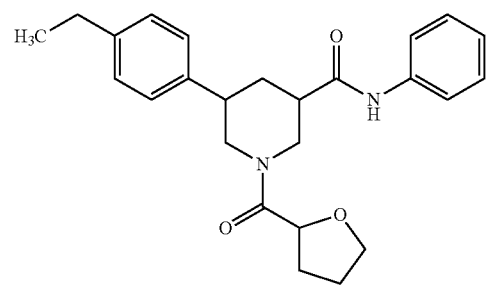 [SMILES: CCc1ccc(C2CC(C(=O)Nc3ccccc3)CN(C(=O)C3CCCC3)C2)cc1]

68 mg (0.20 mmol) of 5-(4-ethylphenyl)-N-phenylpiperidine-3-carboxamide (Example 17A) and 26 mg (0.22 mmol, 1.1 eq.) of tetrahydrofuran-2-carboxylic acid were reacted according to General Method 1. Yield: 67 mg (81% of theory)

HPLC (Method 1A): $R_t$=4.66 min; MS (ESIpos): m/z=407 [M+H]$^+$;

$^1$H-NMR (400 MHz, DMSO-d$_6$): δ=10.06-9.06 (m, 1H), 7.59 (d, 2H), 7.29 (t, 2H), 7.26-7.20 (m, 2H), 7.20-7.13 (m, 2H), 7.04 (t, 1H), 4.85-4.77 (m, 0.5H), 4.77-4.69 (m, 0.5H), 4.62-4.54 (m, 0.5H), 4.42 (br d, 0.5H), 4.29-4.12 (m, 0.5H), 4.09-3.96 (m, 0.5H), 3.86-3.69 (m, 2H), 3.21 (t, 0.5H), 3.07 (t, 0.5H), 2.82-2.53 (m, 5H), 2.20-1.78 (m, 6H), 1.17 (t, 3H).

The following examples [racemic cis isomers] were prepared in an analogous manner:

| Example | Structure | LC-MS Method | $R_t$ [min] | MS (ESIpos) m/z |
|---|---|---|---|---|
| 12 | 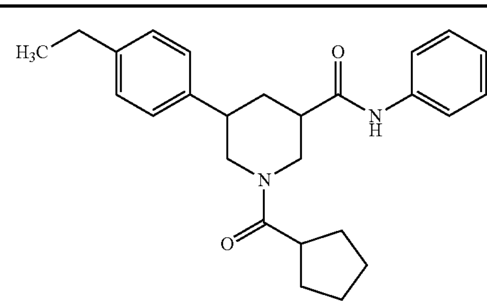 | 1B | 2.98 | 405 |

-continued

| Example | Structure | LC-MS Method | R_t [min] | MS (ESIpos) m/z |
|---|---|---|---|---|
| 13 | 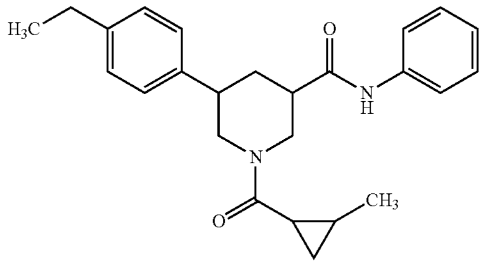 [SMILES: CCc1ccc(C2CC(C(=O)Nc3ccccc3)CN(C(=O)C3CC3C)C2)cc1] | 2B | 1.41 | 391 |
| 14 | 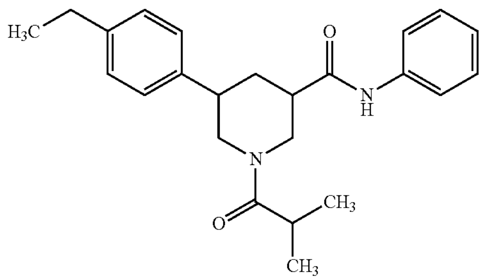 [SMILES: CCc1ccc(C2CC(C(=O)Nc3ccccc3)CN(C(=O)C(C)C)C2)cc1] | 2B | 1.36 | 379 |
| 15 | 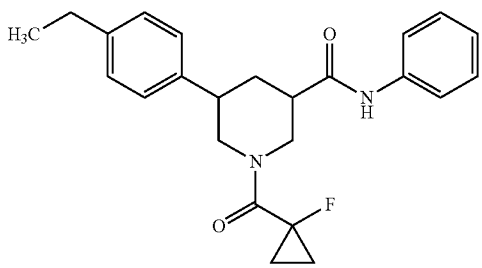 [SMILES: CCc1ccc(C2CC(C(=O)Nc3ccccc3)CN(C(=O)C3(F)CC3)C2)cc1] | 1B | 2.86 | 395 |
| 16 | 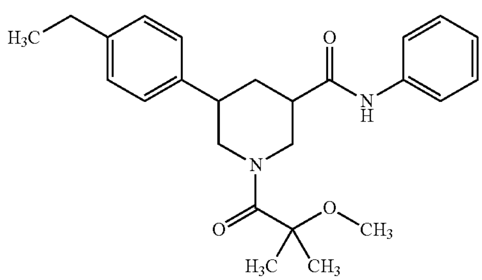 [SMILES: CCc1ccc(C2CC(C(=O)Nc3ccccc3)CN(C(=O)C(C)(C)OC)C2)cc1] | 1B | 2.87 | 409 |
| 17 | 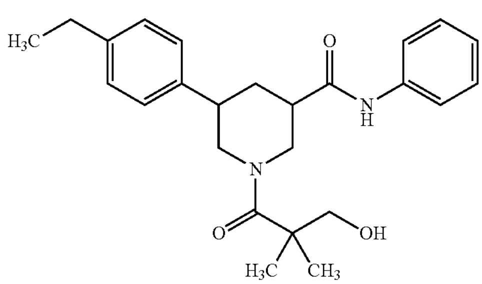 | 1B | 2.09 | 409 |

-continued
| Example | Structure | LC-MS Method | R_t [min] | MS (ESIpos) m/z |
|---|---|---|---|---|
| 18 | 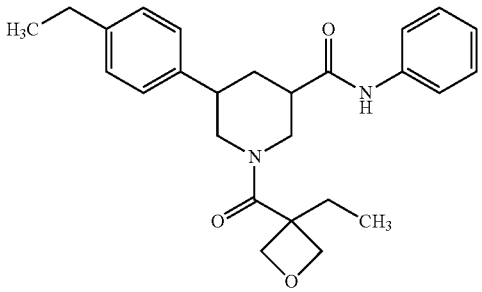 [SMILES: CCc1ccc(C2CC(C(=O)Nc3ccccc3)CN(C(=O)C3(CC)COC3)C2)cc1] | 3B | 2.13 | 421 |
| 19 | 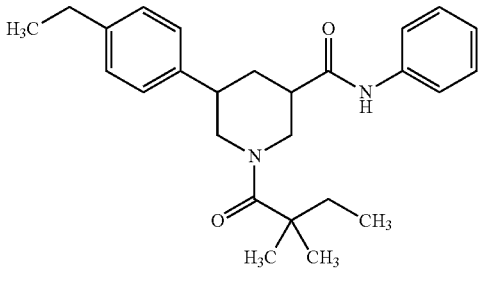 | 2B | 1.49 | 407 |
| 20 | 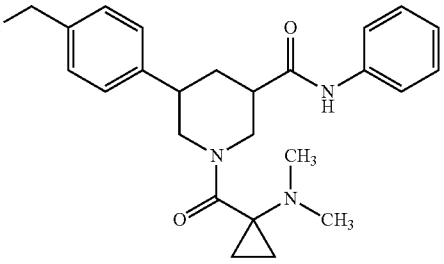 | 5B | 1.93 | 420 |
| 21 | 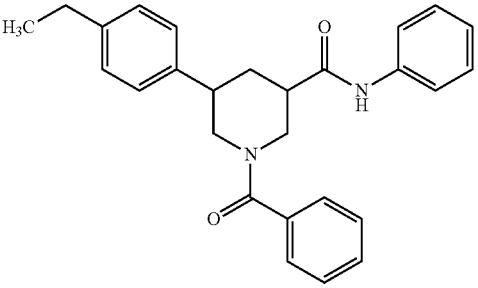 [SMILES: CCc1ccc(C2CC(C(=O)Nc3ccccc3)CN(C(=O)c3ccccc3)C2)cc1] | 1B | 2.86 | 413 |
| 22 | 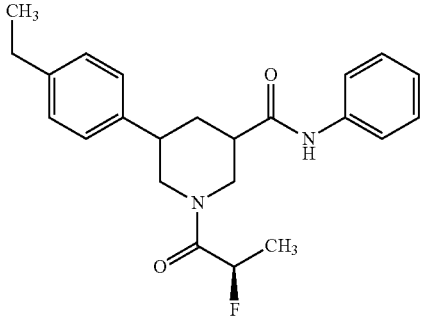 [SMILES: CCc1ccc(C2CC(C(=O)Nc3ccccc3)CN(C(=O)[C@@H](C)F)C2)cc1] | 9B | 2.27 | 383 |

-continued

| Example | Structure | LC-MS Method | R$_t$ [min] | MS (ESIpos) m/z |
|---|---|---|---|---|
| 23 | 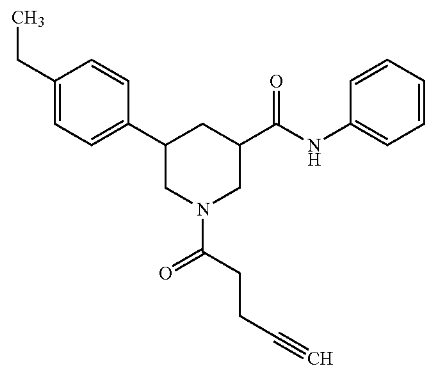 [SMILES: C#CCCC(=O)N1CC(C(=O)Nc2ccccc2)CC(c2ccc(CC)cc2)C1] | 9B | 2.29 | 389 |
| 24 | 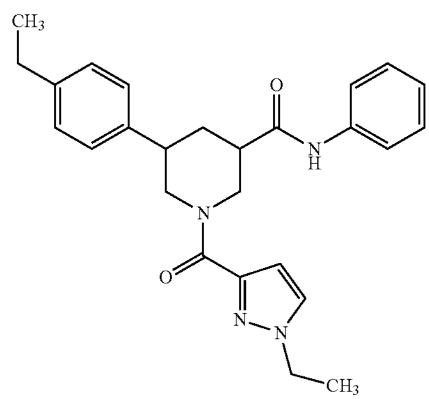 [SMILES: CCc1ccc(C2CC(C(=O)Nc3ccccc3)CN(C(=O)c3ccn(CC)n3)C2)cc1] | 9B | 2.29 | 431 |
| 25 | 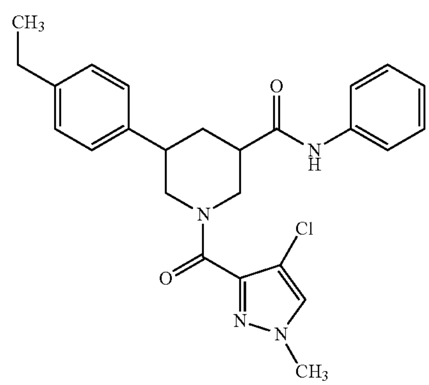 [SMILES: CCc1ccc(C2CC(C(=O)Nc3ccccc3)CN(C(=O)c3nn(C)cc3Cl)C2)cc1] | 9B | 2.31 | 451 |
| 26 | 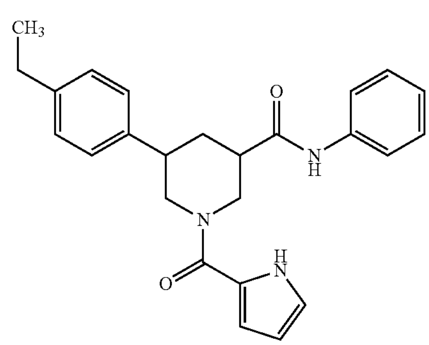 [SMILES: CCc1ccc(C2CC(C(=O)Nc3ccccc3)CN(C(=O)c3ccc[nH]3)C2)cc1] | 9B | 2.31 | 402 |

-continued

| Example | Structure | LC-MS Method | R$_t$ [min] | MS (ESIpos) m/z |
|---|---|---|---|---|
| 27 | 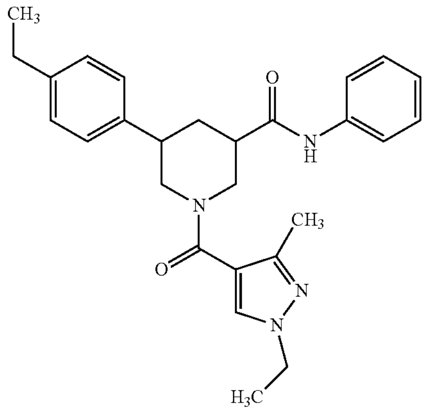 [SMILES: CCc1ccc(C2CC(C(=O)Nc3ccccc3)CN(C(=O)c3cn(CC)nc3C)C2)cc1] | 9B | 2.26 | 445 |
| 28 | 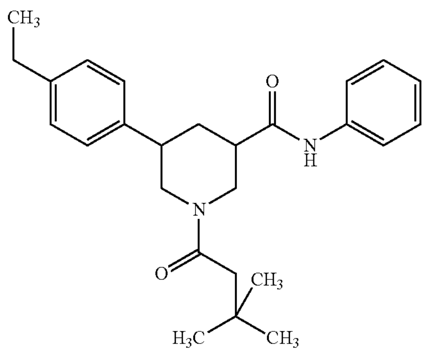 [SMILES: CCc1ccc(C2CC(C(=O)Nc3ccccc3)CN(C(=O)CC(C)(C)C)C2)cc1] | 9B | 2.42 | 407 |
| 29 | 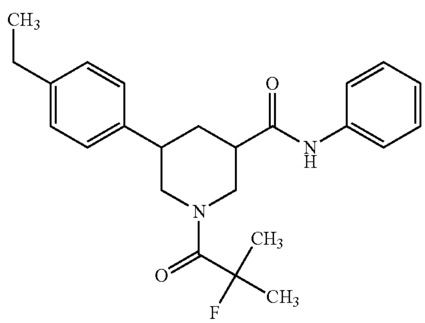 [SMILES: CCc1ccc(C2CC(C(=O)Nc3ccccc3)CN(C(=O)C(C)(C)F)C2)cc1] | 9B | 2.36 | 397 |
| 30 | 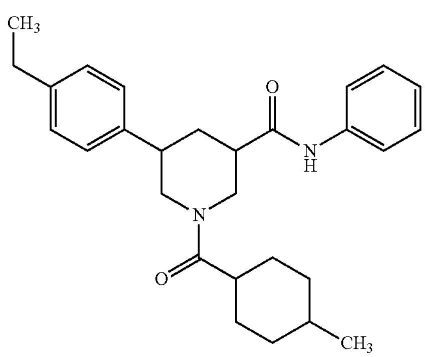 [SMILES: CCc1ccc(C2CC(C(=O)Nc3ccccc3)CN(C(=O)C3CCC(C)CC3)C2)cc1] | 9B | 2.48 | 433 |

| Example | Structure | LC-MS Method | R$_t$ [min] | MS (ESIpos) m/z |
|---|---|---|---|---|
| 31 | 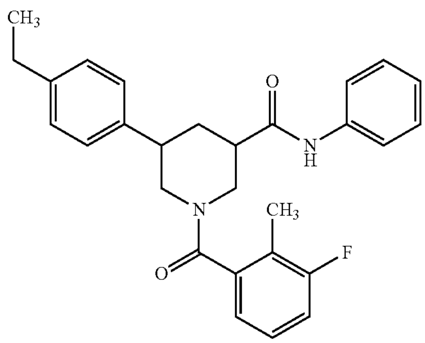 [SMILES: CCc1ccc(C2CC(C(=O)Nc3ccccc3)CN(C(=O)c3cccc(F)c3C)C2)cc1] | 9B | 2.4 | 445 |
| 32 | 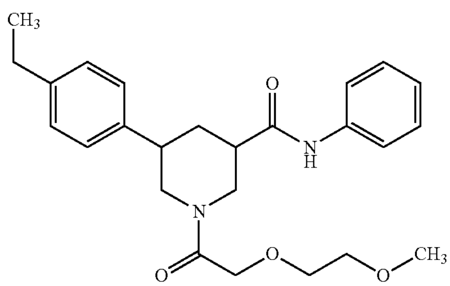 [SMILES: CCc1ccc(C2CC(C(=O)Nc3ccccc3)CN(C(=O)COCCOC)C2)cc1] | 9B | 2.23 | 425 |
| 33 | 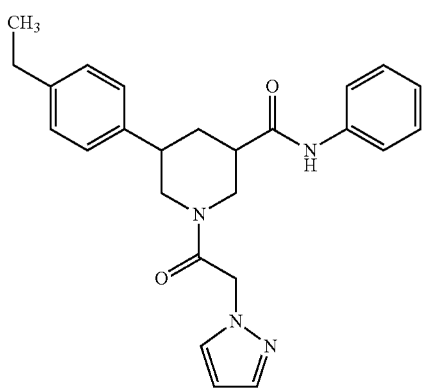 [SMILES: CCc1ccc(C2CC(C(=O)Nc3ccccc3)CN(C(=O)Cn3cccn3)C2)cc1] | 9B | 2.2 | 417 |
| 34 | 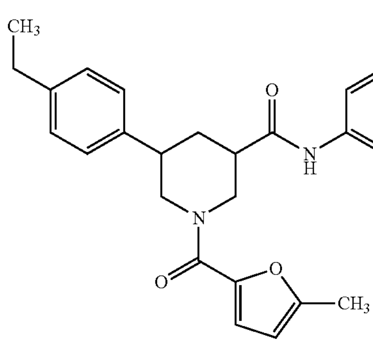 | 9B | 2.36 | 417 |

| Example | Structure | LC-MS Method | R$_t$ [min] | MS (ESIpos) m/z |
|---|---|---|---|---|
| 35 | 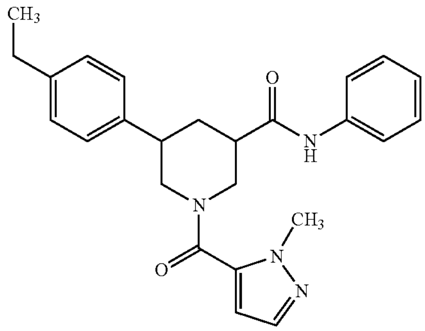 [SMILES: CCc1ccc(C2CC(C(=O)Nc3ccccc3)CN(C(=O)c3ccnn3C)C2)cc1] | 9B | 2.26 | 417 |
| 36 | 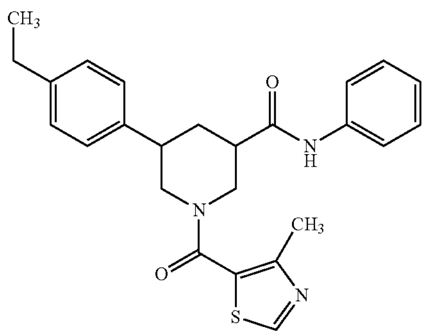 [SMILES: CCc1ccc(C2CC(C(=O)Nc3ccccc3)CN(C(=O)c3scnc3C)C2)cc1] | 9B | 2.25 | 434 |
| 37 | 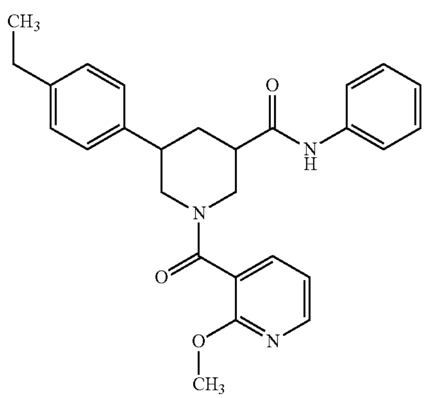 [SMILES: CCc1ccc(C2CC(C(=O)Nc3ccccc3)CN(C(=O)c3cccnc3OC)C2)cc1] | 9B | 2.31 | 444 |

Example 38

N$^1$-Cyclopentyl-5-(4-ethylphenyl)-N$^3$-phenylpiperidine-1,3-dicarboxamide [racemic cis isomer]

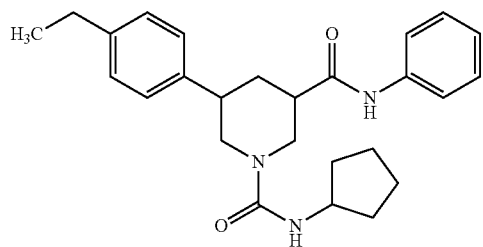 [SMILES: CCc1ccc(C2CC(C(=O)Nc3ccccc3)CN(C(=O)NC3CCCC3)C2)cc1]

62 mg (0.20 mmol) of 5-(4-ethylphenyl)-N-phenylpiperidine-3-carboxamide (Example 17A) and 22 mg (0.20 mmol, 1.0 eq.) of cyclopentyl isocyanate were reacted according to General Method 4. Yield: 70 mg (83% of theory)

HPLC (Method 1A): R$_t$=4.94 min; MS (ESIpos): m/z=420 [M+H]$^+$;

$^1$H-NMR (400 MHz, DMSO-d$_6$): δ=10.00 (s, 1H), 7.59 (d, 2H), 7.29 (t, 2H), 7.21 (d, 2H), 7.16 (d, 2H), 7.03 (t, 1H), 6.36 (d, 1H), 4.22 (br d, 1H), 4.08 (br d, 1H), 3.99-3.88 (m, 1H), 2.80 (t, 1H), 2.67 (q, 1H), 2.64-2.58 (m, 2H), 2.57 (q, 2H), 2.07 (br d, 1H), 1.88-1.72 (m, 3H), 1.68-1.55 (m, 2H), 1.52-1.33 (m, 4H), 1.16 (t, 3H).

Example 39

N[1]-Cyclopropyl-5-(4-ethylphenyl)-N[3]-phenylpiperidine-1,3-dicarboxamide [racemic cis isomer]

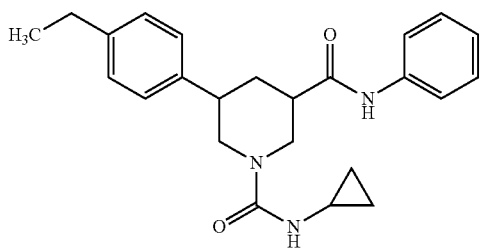 [SMILES: CCc1ccc(C2CC(C(=O)Nc3ccccc3)CN(C(=O)NC3CC3)C2)cc1]

62 mg (0.20 mmol) of 5-(4-ethylphenyl)-N-phenylpiperidine-3-carboxamide (Example 17A) and 17 mg (0.20 mmol, 1.0 eq.) of cyclopropyl isocyanate were reacted according to General Method 4. Yield: 63 mg (80% of theory)

HPLC (Method 1A): $R_t$=4.63 min; MS (ESIpos): m/z=392 [M+H]$^+$;

$^1$H-NMR (400 MHz, DMSO-$d_6$): δ=10.00 (s, 1H), 7.59 (d, 2H), 7.29 (t, 2H), 7.21 (d, 2H), 7.16 (d, 2H), 7.03 (t, 1H), 6.68 (d, 1H), 4.16 (br d, 1H), 4.02 (br d, 1H), 2.81 (t, 1H), 2.69 (q, 1H), 2.64-2.52 (m, 3H), 2.57 (q, 2H), 2.07 (br d, 1H), 1.83 (q, 1H), 1.16 (t, 3H), 0.57-0.52 (m, 2H), 0.42-0.35 (m, 2H).

Example 40

N[1]-tert-Butyl-5-(4-ethylphenyl)-N[3]-phenylpiperidine-1,3-dicarboxamide [racemic cis isomer]

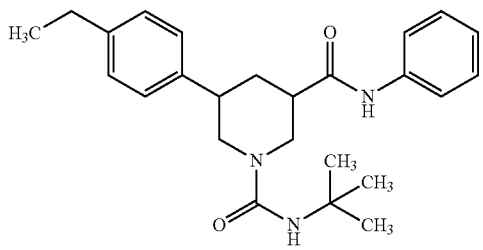 [SMILES: CCc1ccc(C2CC(C(=O)Nc3ccccc3)CN(C(=O)NC(C)(C)C)C2)cc1]

62 mg (0.20 mmol) of 5-(4-ethylphenyl)-N-phenylpiperidine-3-carboxamide (Example 17A) and 20 mg (0.20 mmol, 1.0 eq.) of tert-butyl isocyanate were reacted according to General Method 4.

Yield: 34 mg (42% of theory)

HPLC (Method 1A): $R_t$=4.95 min; MS (ESIpos): m/z=408 [M+H]$^+$;

$^1$H-NMR (400 MHz, DMSO-$d_6$): δ=10.00 (s, 1H), 7.60 (d, 2H), 7.29 (t, 2H), 7.21 (d, 2H), 7.16 (d, 2H), 7.03 (t, 1H), 5.93 (s, 1H), 4.19 (br d, 1H), 4.05 (br d, 1H), 2.77 (t, 1H), 2.70-2.53 (m, 3H), 2.57 (q, 2H), 2.06 (br d, 1H), 1.81 (q, 1H), 1.27 (s, 9H), 1.16 (t, 3H).

Example 41

5-(4-Ethylphenyl)-N-phenyl-1-(pyrrolidin-1-ylcarbonyl)piperidine-3-carboxamide [racemic cis isomer]

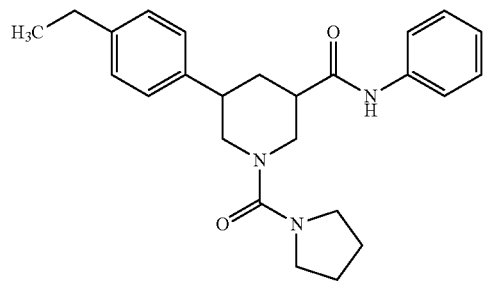

33 mg (0.10 mmol) of 5-(4-ethylphenyl)-1-(pyrrolidin-1-ylcarbonyl)piperidine-3-carboxylic acid (Example 11A) and 10 mg (0.11 mmol, 1.1 eq.) of aniline were reacted according to General Method 1. Yield: 26 mg (64% of theory)

HPLC (Method 1A): $R_t$=4.89 min; MS (ESIpos): m/z=406 [M+H]$^+$;

$^1$H-NMR (400 MHz, DMSO-$d_6$): δ=10.00 (s, 1H), 7.59 (d, 2H), 7.29 (t, 2H), 7.21 (d, 2H), 7.16 (d, 2H), 7.03 (t, 1H), 3.87 (br d, 1H), 3.68 (br d, 1H), 3.31-3.22 (m, 4H), 2.88 (t, 1H), 2.81-2.65 (m, 3H), 2.57 (q, 2H), 2.10 (br d, 1H), 1.87 (q, 1H), 1.81-1.68 (m, 4H), 1.16 (t, 3H).

Example 42

5-(4-Ethylphenyl)-1-(morpholin-4-ylcarbonyl)-N-phenylpiperidine-3-carboxamide [racemic cis isomer]

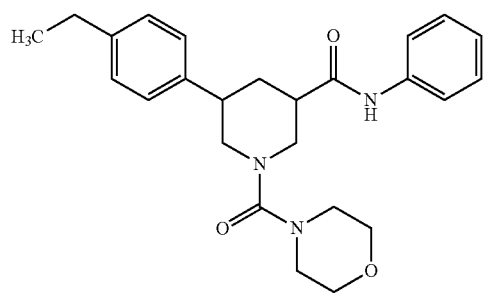 [SMILES: CCc1ccc(C2CC(C(=O)Nc3ccccc3)CN(C(=O)N3CCOCC3)C2)cc1]

250 mg (0.74 mmol) of 5-(4-ethylphenyl)-N-phenylpiperidine-3-carboxamide (Example 17A) and 143 mg (0.96 mmol, 1.3 eq.) of morpholine-4-carbonyl chloride were reacted according to General Method 3. Yield: 276 mg (88% of theory)

HPLC (Method 1A): $R_t$=4.55 min; MS (ESIpos): m/z=422 [M+H]$^+$;

$^1$H-NMR (400 MHz, DMSO-$d_6$): δ=10.00 (s, 1H), 7.59 (d, 2H), 7.29 (t, 2H), 7.21 (d, 2H), 7.16 (d, 2H), 7.03 (t, 1H), 3.80 (br d, 1H), 3.61 (br d, 1H), 3.60-3.51 (m, 4H), 3.22-3.12 (m,

4H), 2.94 (t, 1H), 2.84 (q, 1H), 2.80-2.66 (m, 2H), 2.57 (q, 2H), 2.10 (br d, 1H), 1.87 (q, 1H), 1.17 (t, 3H).

Example 43

5-(4-Ethylphenyl)-1-(morpholin-4-ylcarbonyl)-N-phenylpiperidine-3-carboxamide [enantiomerically pure cis isomer]

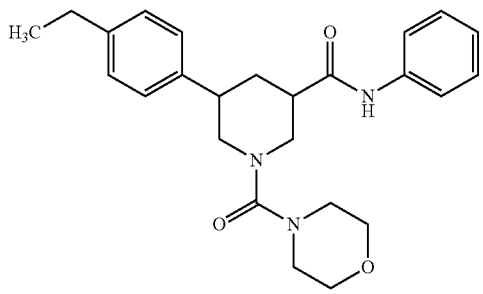

The enantiomer separation of 280 mg of the racemate from Example 42 according to Method 3D gave 131 mg of the compound from Example 43 (enantiomer 1) and 145 mg of the compound from Example 44 (enantiomer 2).

LC-MS (Method 2E): $R_t$=4.67 min; MS (ESIpos): m/z=422 [M+H]$^+$.

Example 44

5-(4-Ethylphenyl)-1-(morpholin-4-ylcarbonyl)-N-phenylpiperidine-3-carboxamide [enantiomerically pure cis isomer]

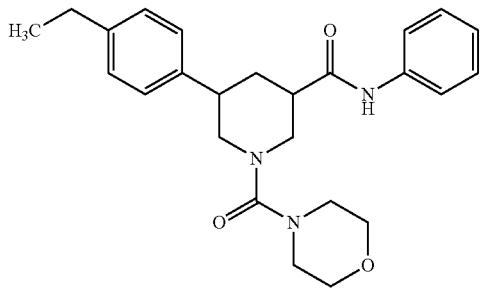

The enantiomer separation of 280 mg of the racemate from Example 42 according to Method 3D gave 131 mg of the compound from Example 43 (enantiomer 1) and 145 mg of the compound from Example 44 (enantiomer 2).

LC-MS (Method 2E): $R_t$=6.54 min; MS (ESIpos): m/z=422 [M+H]$^+$.

Example 45

$N^1$-Ethyl-5-(4-ethylphenyl)-$N^1$-methyl-$N^3$-phenylpiperidine-1,3-dicarboxamide [racemic cis isomer]

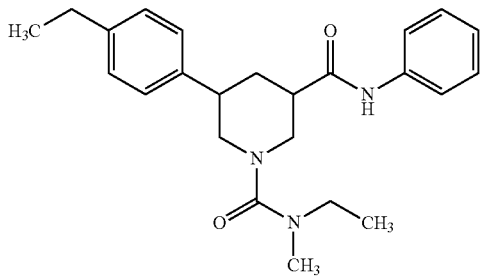 [SMILES: CCc1ccc(C2CC(C(=O)Nc3ccccc3)CN(C(=O)N(C)CC)C2)cc1]

250 mg (0.74 mmol) of 5-(4-ethylphenyl)-N-phenylpiperidine-3-carboxamide (Example 17A) and 117 mg (0.96 mmol, 1.3 eq.) of ethyl(methyl)carbamoyl chloride were reacted according to General Method 3. Yield: 215 mg (74% of theory)

HPLC (Method 1A): $R_t$=4.74 min; MS (ESIpos): m/z=394 [M+H]$^+$;

$^1$H-NMR (400 MHz, DMSO-d$_6$): δ=10.00 (s, 1H), 7.59 (d, 2H), 7.29 (t, 2H), 7.21 (d, 2H), 7.16 (d, 2H), 7.03 (t, 1H), 3.72 (br d, 1H), 3.53 (br d, 1H), 3.21-3.05 (m, 2H), 2.88 (t, 1H), 2.82-2.66 (m, 6H), 2.57 (q, 2H), 2.09 (br d, 1H), 1.86 (q, 1H), 1.16 (t, 3H), 1.06 (t, 3H).

Example 46

5-(4-Ethylphenyl)-1-[(4-methylpiperazin-1-yl)carbonyl]-N-phenylpiperidine-3-carboxamide [racemic cis isomer]

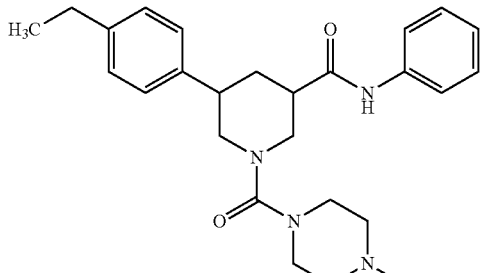

250 mg (0.74 mmol) of 5-(4-ethylphenyl)-N-phenylpiperidine-3-carboxamide (Example 17A) and 156 mg (0.96 mmol, 1.3 eq.) of 4-methylpiperazine-1-carbonyl chloride were reacted according to General Method 3. Yield: 213 mg (66% of theory)

HPLC (Method 1A): $R_t$=3.45 min; MS (ESIpos): m/z=435 [M+H]$^+$;

$^1$H-NMR (400 MHz, DMSO-d$_6$): δ=10.00 (s, 1H), 7.59 (d, 2H), 7.29 (t, 2H), 7.21 (d, 2H), 7.16 (d, 2H), 7.03 (t, 1H), 3.77

(br d, 1H), 3.58 (br d, 1H), 3.23-3.10 (m, 4H), 2.92 (t, 1H), 2.81 (q, 1H), 2.79-2.66 (m, 2H), 2.57 (q, 2H), 2.09 (br d, 1H), 1.86 (q, 1H), 1.17 (t, 3H).

Example 47

5-(4-Ethylphenyl)-N-phenyl-1-(piperazin-1-ylcarbonyl)piperidine-3-carboxamide [racemic cis isomer]

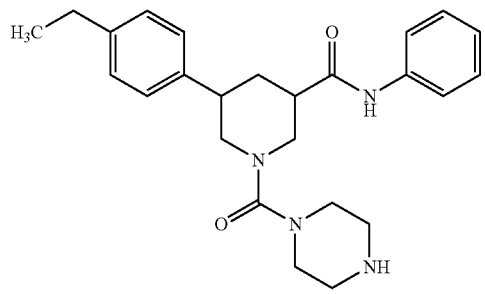

At RT, 13.4 ml (53.5 mmol, 8 eq.) of a 4-molar solution of hydrogen chloride in dioxane were added dropwise to a solution of 3.5 g (6.7 mmol) of tert-butyl 4-{[3-(4-ethylphenyl)-5-(phenylcarbamoyl)piperidin-1-yl]carbonyl}piperazine-1-carboxylate (Example 50) in 60 ml of dioxane. The reaction mixture was stirred at RT for 20 h and then concentrated under reduced pressure and coevaporated twice with dioxane, which gave 3.37 g of the compound from Example 47 as the hydrochloride. Using preparative HPLC (Reprosil C18, water/acetonitrile gradient with 0.1% triethylamine), 180 mg of the crude product were purified further to afford the free base (136 mg).

HPLC (Method 1A): $R_t$=4.18 min; MS (ESIpos): m/z=421 [M+H]$^+$;

$^1$H-NMR (400 MHz, DMSO-$d_6$): δ=10.00 (s, 1H), 7.60 (d, 2H), 7.29 (t, 2H), 7.21 (d, 2H), 7.17 (d, 2H), 7.03 (t, 1H), 3.77 (br d, 1H), 3.57 (br d, 1H), 3.16-3.03 (m, 4H), 2.90 (t, 1H), 2.85-2.69 (m, 3H), 2.69-2.60 (m, 4H), 2.57 (q, 2H), 2.40-2.30 (m, 1H), 2.10 (br d, 1H), 1.86 (q, 1H), 1.17 (t, 3H).

Example 48

1-[(4-Cyclopropylpiperazin-1-yl)carbonyl]-5-(4-ethylphenyl)-N-phenylpiperidine-3-carboxamide [racemic cis isomer]

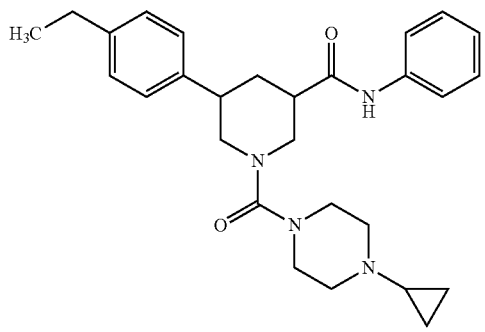 [SMILES: CCc1ccc(C2CC(C(=O)Nc3ccccc3)CN(C(=O)N3CCN(C4CC4)CC3)C2)cc1]

At RT, 898 µl of a 1-molar solution of sodium cyanoborohydride in tetrahydrofuran were added to a solution of 94 mg (0.20 mmol) of 5-(4-ethylphenyl)-N-phenyl-1-(piperazin-1-ylcarbonyl)piperidine-3-carboxamide, 241 µl (1.20 mmol, 6 eq.) of [(1-ethoxycyclopropyl)oxy](trimethyl)silane, 35 µl (0.62 mmol, 3.1 eq.) of acetic acid and 115 mg of molecular sieves (4 Å) in 1 ml of methanol. The reaction mixture was stirred under reflux for 5 h and then filtered and adjusted to pH 8 using a 0.2-molar sodium hydroxide solution. After addition of water/dichloromethane and phase separation, the aqueous phase was extracted twice with dichloromethane. The combined organic phases were dried (sodium sulphate), filtered and concentrated under reduced pressure. The crude product was purified by preparative HPLC (Reprosil C18, water/acetonitrile gradient). Yield: 60 mg (65% of theory)

HPLC (Method 2A): $R_t$=4.30 min; MS (ESIpos): m/z=461 [M+H]$^+$;

$^1$H-NMR (400 MHz, DMSO-$d_6$): δ=10.01 (s, 1H), 7.59 (d, 2H), 7.29 (t, 2H), 7.21 (d, 2H), 7.16 (d, 2H), 7.03 (t, 1H), 3.77 (br d, 1H), 3.58 (br d, 1H), 3.19-3.07 (m, 4H), 2.92 (t, 1H), 2.81 (q, 1H), 2.78-2.65 (m, 2H), 2.57 (q, 2H), 2.09 (br d, 1H), 1.87 (q, 1H), 1.66-1.58 (m, 1H), 1.17 (t, 3H), 0.44-0.38 (m, 2H), 0.33-0.27 (m, 2H).

The following example [racemic cis isomer] was prepared in an analogous manner by reductive amination:

| Example | Structure | LC-MS Method | $R_t$ [min] | MS (ESIpos) m/z |
|---|---|---|---|---|
| 49 | ![structure] | 1B | 1.61 | 465 |

Example 50 tert-Butyl 4-{[3-(4-ethylphenyl)-5-(phenylcarbamoyl)piperidin-1-yl]carbonyl}piperazine-1-carboxylate [racemic cis isomer]

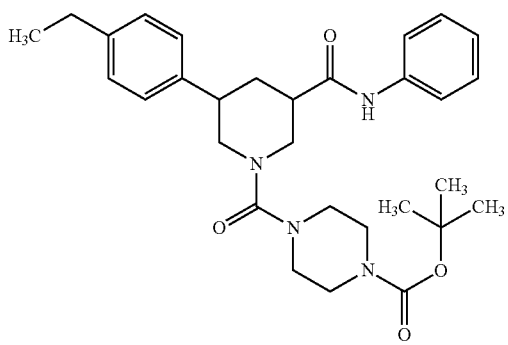 [SMILES: CCc1ccc(C2CC(C(=O)Nc3ccccc3)CN(C(=O)N3CCN(C(=O)OC(C)(C)C)CC3)C2)cc1]

Under argon and at RT, 1.9 g (7.7 mmol) of tert-butyl 4-(chlorocarbonyl)piperazine-1-carboxylate were added to a solution of 2.0 g (5.9 mmol) of 5-(4-ethylphenyl)-N-phenylpiperidine-3-carboxamide, 144 mg (1.2 mmol, 0.2 eq.) of 4-dimethylaminopyridine and 2.1 ml (14.6 mmol, 2.5 eq.) of triethylamine in 64 ml of tetrahydrofuran. The reaction mixture was stirred at RT for 17 h, and water and dichloromethane were then added. After phase separation, the aqueous phase was extracted twice with dichloromethane. The combined organic phases were dried (sodium sulphate), filtered and concentrated under reduced pressure. The crude product was purified by flash chromatography (silica gel 60, dichloromethane/methanol 300:1→100:1), which gave 3.5 g of Example 50.

LC-MS (Method 1B): $R_t$=2.94 min; MS (ESIpos): m/z=521 [M+H]$^+$.

The following examples [racemic cis isomers] were prepared by General Method 3:

| Example | Structure | LC-MS Method | $R_t$ [min] | MS (ESIpos) m/z |
|---------|-----------|--------------|-------------|-----------------|
| 51 | 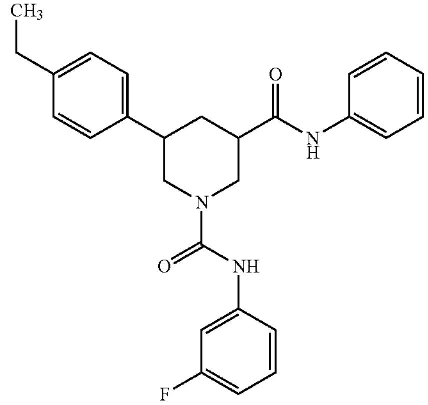 [SMILES: CCc1ccc(C2CC(C(=O)Nc3ccccc3)CN(C(=O)Nc3cccc(F)c3)C2)cc1] | 9B | 2.4 | 446 |
| 52 | 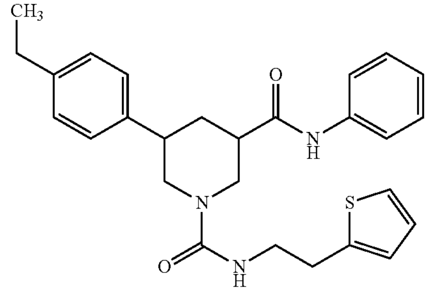 [SMILES: CCc1ccc(C2CC(C(=O)Nc3ccccc3)CN(C(=O)NCCc3cccs3)C2)cc1] | 9B | 2.36 | 462 |

| Example | Structure | LC-MS Method | R$_t$ [min] | MS (ESIpos) m/z |
|---------|-----------|--------------|-------------|-----------------|
| 53 | 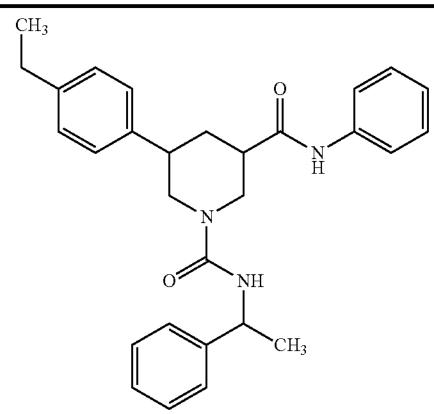 | 9B | 2.38 | 456 |
| 54 | 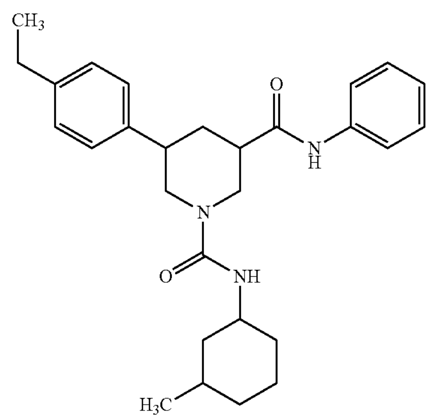 [SMILES: CCc1ccc(C2CC(C(=O)Nc3ccccc3)CN(C(=O)NC3CCCC(C)C3)C2)cc1] | 9B | 2.43 | 448 |
| 55 | 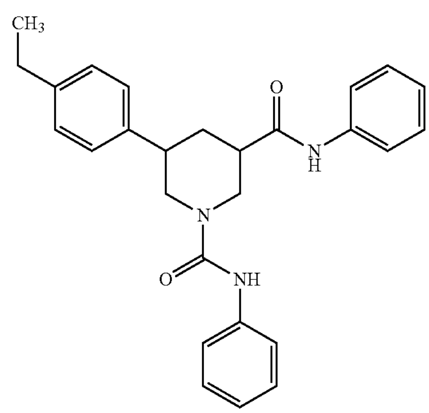 [SMILES: CCc1ccc(C2CC(C(=O)Nc3ccccc3)CN(C(=O)Nc3ccccc3)C2)cc1] | 9B | 2.35 | 428 |
| 56 | 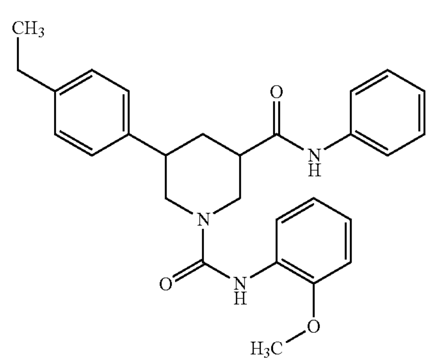 [SMILES: CCc1ccc(C2CC(C(=O)Nc3ccccc3)CN(C(=O)Nc3ccccc3OC)C2)cc1] | 9B | 2.39 | 458 |

-continued

| Example | Structure | LC-MS Method | R$_t$ [min] | MS (ESIpos) m/z |
|---|---|---|---|---|
| 57 | 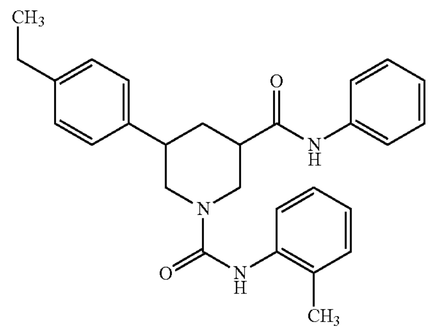 [SMILES: CCc1ccc(C2CC(C(=O)Nc3ccccc3)CN(C(=O)Nc3ccccc3C)C2)cc1] | 9B | 2.36 | 442 |
| 58 | 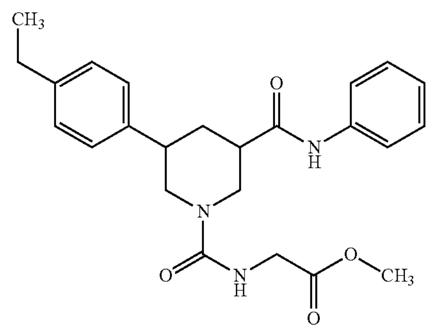 [SMILES: CCc1ccc(C2CC(C(=O)Nc3ccccc3)CN(C(=O)NCC(=O)OC)C2)cc1] | 9B | 2.2 | 424 |
| 59 | 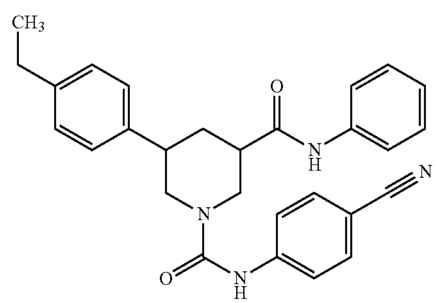 [SMILES: CCc1ccc(C2CC(C(=O)Nc3ccccc3)CN(C(=O)Nc3ccc(C#N)cc3)C2)cc1] | 9B | 2.36 | 453 |
| 60 | 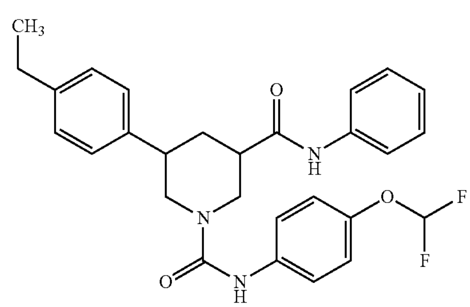 [SMILES: CCc1ccc(C2CC(C(=O)Nc3ccccc3)CN(C(=O)Nc3ccc(OC(F)F)cc3)C2)cc1] | 9B | 2.38 | 494 |

-continued

| Example | Structure | LC-MS Method | R_t [min] | MS (ESIpos) m/z |
|---------|-----------|--------------|-----------|-----------------|
| 61 | 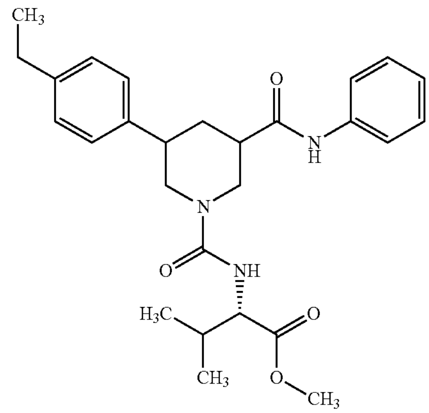 [SMILES: CCc1ccc(C2CC(C(=O)Nc3ccccc3)CN(C(=O)N[C@H](C(=O)OC)C(C)C)C2)cc1] | 9B | 2.35 | 466 |
| 62 | 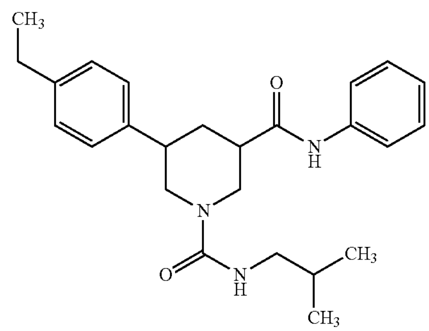 [SMILES: CCc1ccc(C2CC(C(=O)Nc3ccccc3)CN(C(=O)NCC(C)C)C2)cc1] | 9B | 2.35 | 408 |
| 63 | 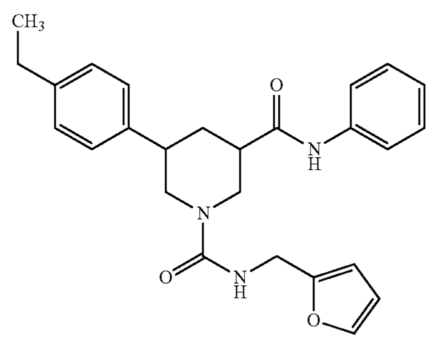 [SMILES: CCc1ccc(C2CC(C(=O)Nc3ccccc3)CN(C(=O)NCc3ccco3)C2)cc1] | 9B | 2.30 | 432 |
| 64 | 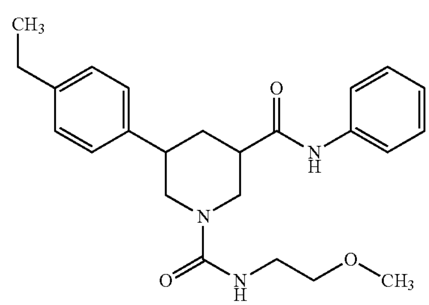 [SMILES: CCc1ccc(C2CC(C(=O)Nc3ccccc3)CN(C(=O)NCCOC)C2)cc1] | 9B | 2.29 | 410 |

-continued

| Example | Structure | LC-MS Method | R$_t$ [min] | MS (ESIpos) m/z |
|---|---|---|---|---|
| 65 | 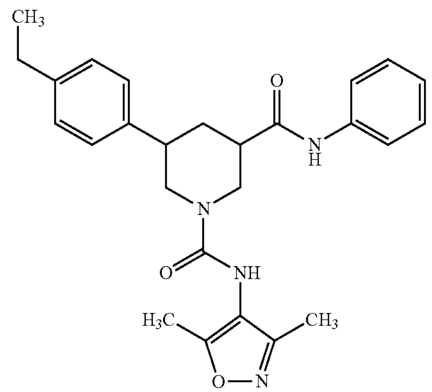 [SMILES: CCc1ccc(C2CC(C(=O)Nc3ccccc3)CN(C(=O)Nc3c(C)noc3C)C2)cc1] | 9B | 2.24 | 447 |
| 66 | 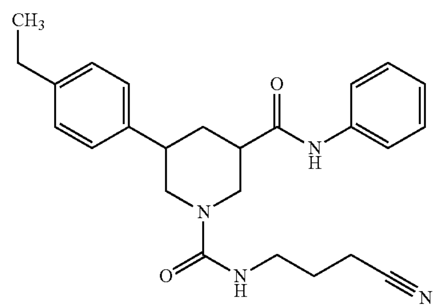 [SMILES: CCc1ccc(C2CC(C(=O)Nc3ccccc3)CN(C(=O)NCCCC#N)C2)cc1] | 9B | 2.22 | 419 |
| 67 | 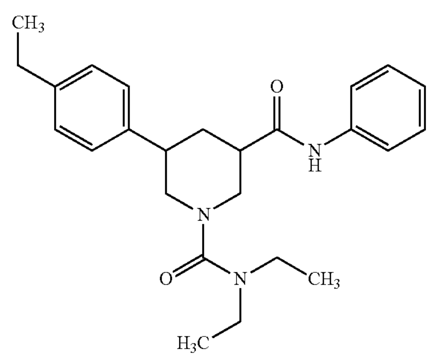 [SMILES: CCc1ccc(C2CC(C(=O)Nc3ccccc3)CN(C(=O)N(CC)CC)C2)cc1] | 9B | 2.42 | 408 |
| 68 | 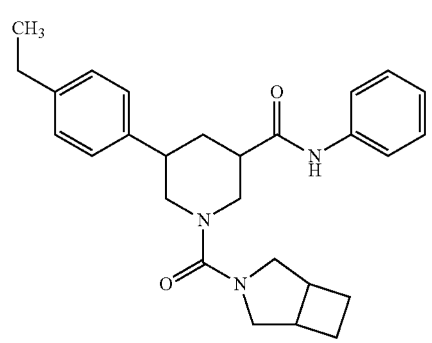 [SMILES: CCc1ccc(C2CC(C(=O)Nc3ccccc3)CN(C(=O)N3CC4CCC4C3)C2)cc1] | 9B | 2.43 | 432 |

Example 69 tert-Butyl 4-({3-[(phenylcarbonyl)amino]-5-[4-(trifluoromethoxy)phenyl]piperidin-1-yl}carbonyl)piperazine-1-carboxylate [racemic cis isomer]

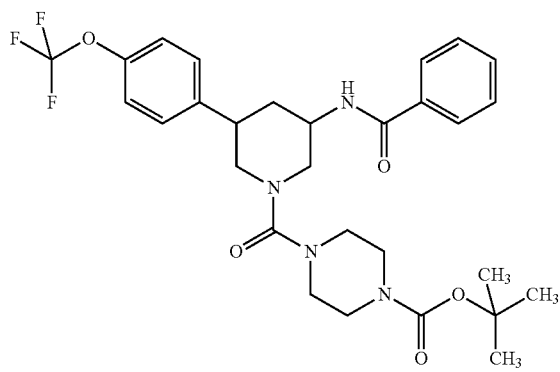 [SMILES: CC(C)(C)OC(=O)N1CCN(C(=O)N2CC(NC(=O)c3ccccc3)CC(c3ccc(OC(F)(F)F)cc3)C2)CC1]

At 0° C., 220 mg (0.55 mmol) of N-{5-[4-(trifluoromethoxy)phenyl]piperidin-3-yl}benzamide were initially charged in 3 ml of dichloromethane, and 273 mg (1.10 mmol) of tert-butyl 4-(chlorocarbonyl)piperazine-1-carboxylate and 116 µl (0.82 mmol) of triethylamine were added. The mixture was slowly warmed to RT overnight. Water was added, and the reaction mixture was extracted. The organic phase was dried over magnesium sulphate and concentrated under reduced pressure. The residue was then purified by preparative HPLC (Reprosil C18, water/acetonitrile gradient). Yield: 88 mg (28% of theory)

LC-MS (Method 1B): $R_t$=2.75 min; m/z=577 [M+H]$^+$.

Example 70

2-Methoxyethyl 3-(4-ethylphenyl)-5-(phenylcarbamoyl)piperidine-1-carboxylate [racemic cis isomer]

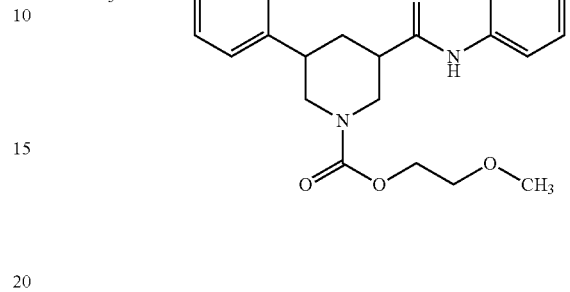

68 mg (0.20 mmol) of 5-(4-ethylphenyl)-N-phenylpiperidine-3-carboxamide (Example 17A) and 38 mg (0.22 mmol, 1.1 eq.) of 2-methoxyethyl chloroformate were reacted according to General Method 5. Yield: 73 mg (89% of theory)

HPLC (Method 2A): $R_t$=4.67 min; MS (ESIpos): m/z=411 [M+H]$^+$;

$^1$H-NMR (400 MHz, DMSO-d$_6$): δ=10.04 (s, 1H), 7.59 (d, 2H), 7.29 (t, 2H), 7.22 (d, 2H), 7.17 (d, 2H), 7.04 (t, 1H); 4.27-4.09 (m, 3H), 4.09-3.95 (m, 1H), 3.58-3.49 (m, 2H), 3.27 (s, 3H), 3.05-2.80 (m, 2H), 2.72-2.60 (m, 2H), 2.58 (q, 2H), 2.18-2.06 (m, 1H), 1.88 (q, 1H), 1.17 (t, 3H).

The following examples [racemic cis isomers] were prepared in an analogous manner:

| Example | Structure | LC-MS Method | $R_t$ [min] | MS (ESIpos) m/z |
|---|---|---|---|---|
| 71 | ![structure] | 2B | 1.41 | 381 |
| 72 | ![structure] | 2B | 1.54 | 421 |

Example 73

1-(Cyclopentylcarbonyl)-5-(4-ethylphenyl)-N-(3-fluorophenyl)piperidine-3-carboxamide [racemic cis isomer]

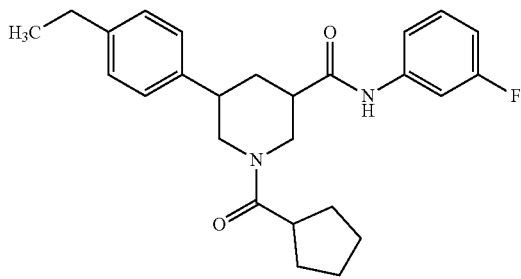 [SMILES: CCc1ccc(C2CC(C(=O)Nc3cccc(F)c3)CN(C(=O)C3CCCC3)C2)cc1]

66 mg (0.20 mmol) of 1-(cyclopentylcarbonyl)-5-(4-ethylphenyl)piperidine-3-carboxylic acid (Example 7A) and 24 mg (0.22 mmol, 1.1 eq.) of 3-fluoroaniline were reacted according to General Method 1. Yield: 38 mg (45% of theory)

HPLC (Method 1A): $R_t$=5.31 min; MS (ESIpos): m/z=423 [M+H]$^+$;

$^1$H-NMR (500 MHz, DMSO-$d_6$): δ=10.23 (s, 0.5H), 10.19 (s, 0.5H), 7.60 (d, 1H), 7.37-7.28 (m, 2H), 7.25 (d, 1H), 7.24-7.14 (m, 3H), 6.91-6.83 (m, 1H), 4.66 (br d, 0.5H), 4.50 (br d, 0.5H), 4.19 (br d, 0.5H), 3.97 (br d, 0.5H), 3.18-3.00 (m, 1.5H), 2.72-2.53 (m, 3H), 2.57 (q, 2H), 2.19-2.08 (m, 1H), 2.02-1.86 (m, 1H), 1.85-1.46 (m, 8H), 1.17 (t, 3H).

Example 74

1-(Cyclopentylcarbonyl)-5-(4-ethylphenyl)-N-(3-fluorophenyl)piperidine-3-carboxamide [enantiomerically pure cis isomer]

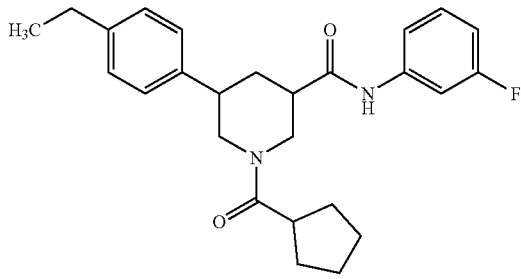 [SMILES: CCc1ccc(C2CC(C(=O)Nc3cccc(F)c3)CN(C(=O)C3CCCC3)C2)cc1]

The enantiomer separation of 36 mg of the racemate from Example 73 according to Method 4D gave 14 mg of the compound from Example 74 (enantiomer 1) and 13 mg of enantiomer 2.

HPLC (Method 3E): $R_t$=2.26 min; MS (ESIpos): m/z=423 [M+H]$^+$.

Example 75

1-(Cyclopentylcarbonyl)-5-(4-ethylphenyl)-N-(3-methoxyphenyl)piperidine-3-carboxamide [racemic cis isomer]

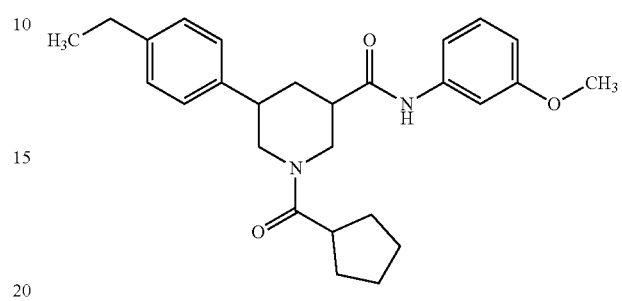

66 mg (0.20 mmol) of 1-(cyclopentylcarbonyl)-5-(4-ethylphenyl)piperidine-3-carboxylic acid (Example 7A) and 27 mg (0.22 mmol, 1.1 eq.) of 3-methoxyaniline were reacted according to General Method 1. Yield: 52 mg (60% of theory)

HPLC (Method 1A): $R_t$=5.19 min; MS (ESIpos): m/z=435 [M+H]$^+$;

$^1$H-NMR (500 MHz, DMSO-$d_6$): δ=10.00 (s, 0.5H), 9.96 (s, 0.5H), 7.31 (s, 1H), 7.28-7.11 (m, 6H), 6.62 (d, 1H), 4.65 (br d, 0.5H), 4.50 (br d, 0.5H), 4.17 (br d, 0.5H), 3.97 (br d, 0.5H), 3.21 (t, 0.5H), 3.15-3.00 (m, 1.5H), 2.72-2.53 (m, 3H), 2.57 (q, 2H), 2.17-2.06 (m, 1H), 2.01-1.86 (m, 1H), 1.86-1.46 (m, 8H), 1.17 (t, 3H).

Example 76

N-[1-(Cyclopentylcarbonyl)-5-(4-ethylphenyl)piperidin-3-yl]benzamide [racemic cis isomer]

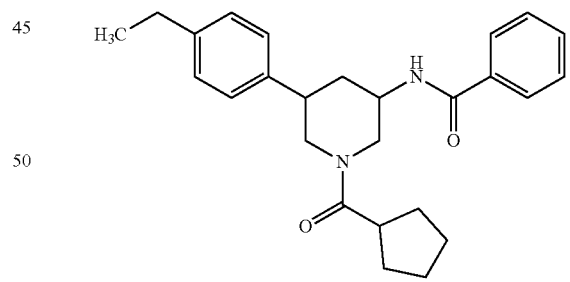

170 mg (0.41 mmol) of 1-(cyclopentylcarbonyl)-5-(4-ethylphenyl)piperidine-3-amine trifluoroacetate (Example 8A) and 50 mg (0.41 mmol, 1.0 eq.) of benzoic acid were reacted according to General Method 1. Yield: 58 mg (35% of theory)

HPLC (Method 1A): $R_t$=4.89 min; MS (ESIpos): m/z=405 [M+H]$^+$;

$^1$H-NMR (500 MHz, DMSO-$d_6$): δ=8.40 (d, 0.6H), 8.36 (d, 0.4H), 7.86 (dd, 2H), 7.53 (t, 1H), 7.47 (t, 2H), 7.27-7.16 (m, 4H), 4.67 (br d, 0.4H), 4.50 (br d, 0.6H), 4.23 (br d, 0.6H), 3.98 (br d, 0.4H), 3.97-3.83 (m, 1H), 3.08-2.99 (m, 1.4H), 2.89 (t, 0.6H), 2.83-2.75 (m, 0.4H), 2.72-2.63 (m, 0.6H), 2.58 (q, 2H), 2.12-2.01 (m, 1.6H), 1.95-1.78 (m, 1.4H), 1.78-1.46 (m, 8H), 1.17 (t, 3H).

Example 77

N-[5-(4-Ethylphenyl)-1-(pyrrolidin-1-ylcarbonyl)piperidin-3-yl]benzamide [racemic cis isomer]

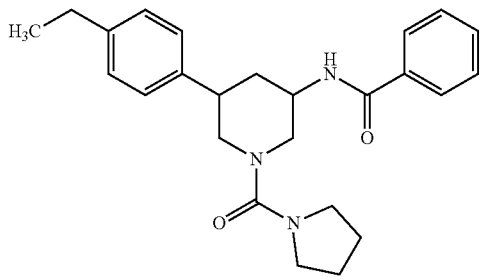 [SMILES: CCc1ccc(C2CC(NC(=O)c3ccccc3)CN(C(=O)N3CCCC3)C2)cc1]

125 mg (50% pure, 0.15 mmol) of 5-(4-ethylphenyl)-1-(pyrrolidin-1-ylcarbonyl)piperidine-3-amine trifluoroacetate (Example 12A) and 20 mg (0.17 mmol, 1.1 eq.) of benzoic acid were reacted according to General Method 1. Yield: 35 mg (56% of theory)

HPLC (Method 1A): $R_t$=4.72 min; MS (ESIpos): m/z=406 [M+H]$^+$;

$^1$H-NMR (400 MHz, DMSO-d$_6$): δ=8.35 (d, 1H), 7.85 (d, 2H), 7.53 (t, 1H), 7.46 (t, 2H), 7.24-7.14 (m, 4H), 4.07-3.95 (m, 1H), 3.91 (br d, 1H), 3.71 (br d, 1H), 3.33-2.24 (m, 4H), 2.90-2.80 (m, 1H), 2.75-2.60 (m, 2H), 2.57 (q, 2H), 2.08 (br d, 1H), 1.85-1.72 (m, 5H), 1.17 (t, 3H).

Example 78

N-[5-(4-Ethylphenyl)-1-(pyrrolidin-1-ylcarbonyl)piperidin-3-yl]-3-fluorobenzamide [racemic cis isomer]

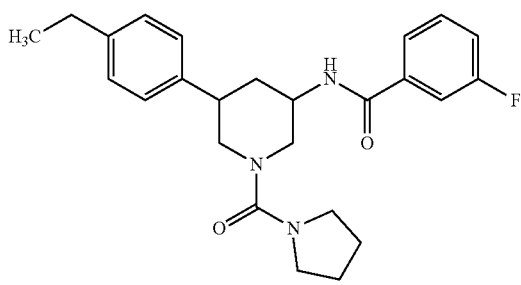 [SMILES: CCc1ccc(C2CC(NC(=O)c3cccc(F)c3)CN(C(=O)N3CCCC3)C2)cc1]

83 mg (75% pure, 0.15 mmol) of 5-(4-ethylphenyl)-1-(pyrrolidin-1-ylcarbonyl)piperidine-3-amine trifluoroacetate (Example 12A) and 23 mg (0.17 mmol, 1.1 eq.) of 3-fluorobenzoic acid were reacted according to General Method 1. Yield: 41 mg (65% of theory)

HPLC (Method 1A): $R_t$=4.79 min; MS (ESIpos): m/z=424 [M+H]$^+$;

$^1$H-NMR (400 MHz, DMSO-d$_6$): δ=8.45 (d, 1H), 7.71 (d, 1H), 7.66 (dd, 1H), 7.52 (dt, 1H), 7.38 (dt, 1H), 7.23-7.14 (m, 4H), 4.06-3.94 (m, 1H), 3.91 (br d, 1H), 3.70 (br d, 1H), 3.32-2.25 (m, 4H), 2.90-2.80 (m, 1H), 2.73-2.60 (m, 2H), 2.57 (q, 2H), 2.08 (br d, 1H), 1.84-1.71 (m, 5H), 1.17 (t, 3H).

Example 79

N-[5-(4-Ethylphenyl)-1-(pyrrolidin-1-ylcarbonyl)piperidin-3-yl]-3-methoxybenzamide [racemic cis isomer]

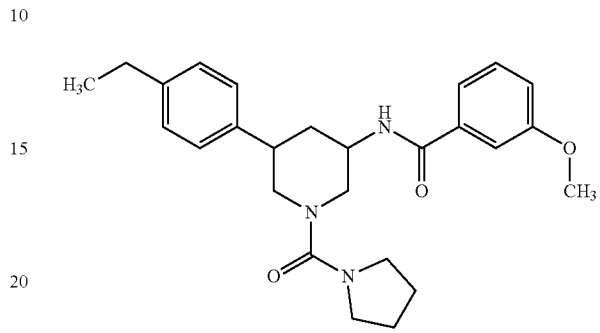

83 mg (75% pure, 0.15 mmol) of 5-(4-ethylphenyl)-1-(pyrrolidin-1-ylcarbonyl)piperidine-3-amine trifluoroacetate (Example 12A) and 25 mg (0.17 mmol, 1.1 eq.) of 3-methoxybenzoic acid were reacted according to General Method 1. Yield: 47 mg (72% of theory)

HPLC (Method 2A): $R_t$=4.75 min; MS (ESIpos): m/z=436 [M+H]$^+$;

$^1$H-NMR (400 MHz, DMSO-d$_6$): δ=8.33 (d, 1H), 7.47-7.34 (m, 3H), 7.23-7.14 (m, 4H), 7.09 (dd, 1H), 4.07-3.94 (m, 1H), 3.91 (br d, 1H), 3.80 (s, 3H), 3.71 (br d, 1H), 3.36-2.26 (m, 4H), 2.91-2.80 (m, 1H), 2.65 (t, 2H), 2.57 (q, 2H), 2.09 (br d, 1H), 1.86-1.70 (m, 5H), 1.17 (t, 3H).

Example 80

N-[5-(4-Ethylphenyl)-1-(pyrrolidin-1-ylcarbonyl)piperidin-3-yl]-4-fluorobenzamide [racemic cis isomer]

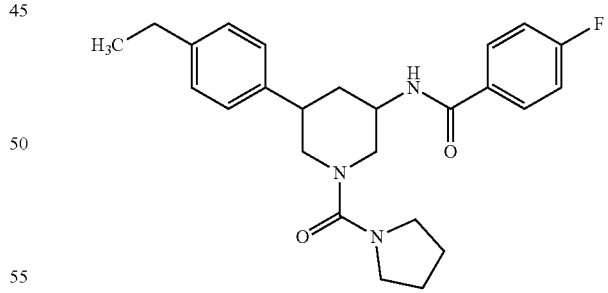

125 mg (50% pure, 0.15 mmol) of 5-(4-ethylphenyl)-1-(pyrrolidin-1-ylcarbonyl)piperidine-3-amine trifluoroacetate (Example 12A) and 23 mg (0.17 mmol, 1.1 eq.) of 4-fluorobenzoic acid were reacted according to General Method 1. Yield: 53 mg (83% of theory)

HPLC (Method 1A): $R_t$=4.78 min; MS (ESIpos): m/z=424 [M+H]$^+$;

$^1$H-NMR (400 MHz, DMSO-d$_6$): δ=8.37 (d, 1H), 7.93 (dd, 2H), 7.30 (dd, 2H), 7.24-7.14 (m, 4H), 4.06-3.93 (m, 1H), 3.90 (br d, 1H), 3.70 (br d, 1H), 3.32-2.22 (m, 4H), 2.90-2.80

(m, 1H), 2.73-2.60 (m, 2H), 2.57 (q, 2H), 2.08 (br d, 1H), 1.84-1.71 (m, 5H), 1.17 (t, 3H).

Example 81

5-Chloro-N-[1-(cyclopentylcarbonyl)-5-(4-ethylphenyl)piperidin-3-yl]pyridine-3-carboxamide [racemic cis isomer]

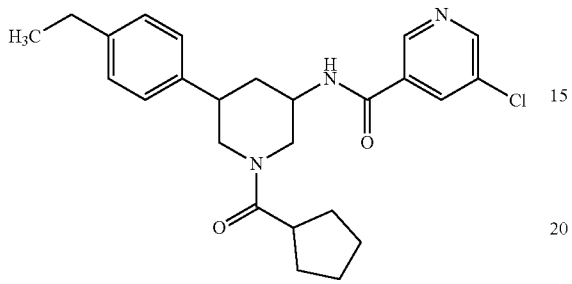

65 mg (0.15 mmol) of 1-(cyclopentylcarbonyl)-5-(4-ethylphenyl)piperidine-3-amine trifluoroacetate (Example 8A) and 21 mg (0.13 mmol, 0.9 eq.) of 5-chloropyridine-3-carboxylic acid were reacted according to General Method 1. Yield: 39 mg (62% of theory)

HPLC (Method 1A): $R_t$=4.72 min; MS (ESIpos): m/z=440 [M+H]$^+$;

$^1$H-NMR (400 MHz, DMSO-d$_6$): δ=8.96 (d, 1H), 8.79 (s, 1H), 8.74 (d, 0.5H), 8.70 (d, 0.5H), 8.33 (d, 1H), 7.27-7.13 (m, 4H), 4.69 (br d, 0.5H), 4.49 (br d, 0.5H), 4.26 (br d, 0.5H), 3.97 (br d, 0.5H), 3.95-3.81 (m, 1H), 3.10-2.97 (m, 1.5H), 2.90 (t, 0.5H), 2.85-2.75 (m, 0.5H), 2.73-2.62 (m, 0.5H), 2.58 (q, 2H), 2.16-1.98 (m, 1.5H), 1.92-1.45 (m, 9.5H), 1.17 (t, 3H).

Example 82

5-Bromo-N-[1-(cyclopentylcarbonyl)-5-(4-ethylphenyl)piperidin-3-yl]pyridine-2-carboxamide [racemic cis isomer]

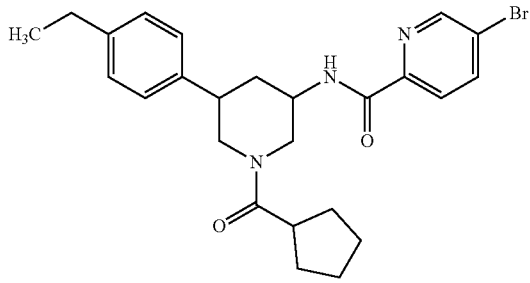 [SMILES: CCc1ccc(C2CC(NC(=O)c3ccc(Br)cn3)CN(C(=O)C3CCCC3)C2)cc1]

139 mg (0.34 mmol) of 1-(cyclopentylcarbonyl)-5-(4-ethylphenyl)piperidine-3-amine trifluoroacetate (Example 8A) and 68 mg (0.34 mmol, 1.0 eq.) of 5-bromopyridine-2-carboxylic acid were reacted according to General Method 1. Yield: 75 mg (44% of theory)

HPLC (Method 2A): $R_t$=5.06 min; MS (ESIpos): m/z=484 [M+H]$^+$;

$^1$H-NMR (400 MHz, DMSO-d$_6$): δ=8.83-8.75 (m, 2H), 8.34-8.23 (m, 1H), 8.02-7.96 (m, 1H), 7.26-7.15 (m, 4H), 4.58 (br d, 0.5H), 4.48 (br d, 0.5H), 4.14 (br d, 0.5H), 4.02-3.85 (m, 1.5H), 3.08-2.93 (m, 2H), 2.84-2.73 (m, 0.5H), 2.71-2.62 (m, 0.5H), 2.57 (q, 2H), 2.13-1.98 (m, 2.5H), 1.87-1.46 (m, 8.5H), 1.17 (t, 3H).

Example 83

N-[1-(Cyclopentylcarbonyl)-5-(4-ethylphenyl)piperidin-3-yl]-5-[3-(trifluoromethyl)phenyl]pyridine-2-carboxamide [racemic cis isomer]

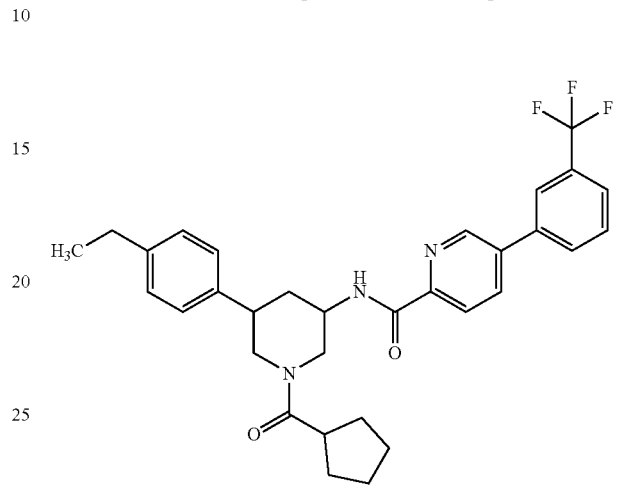

59 mg (0.12 mmol) of 5-bromo-N-[1-(cyclopentylcarbonyl)-5-(4-ethylphenyl)piperidin-3-yl]pyridine-2-carboxamide (Example 82) and 27 mg (0.14 mmol, 1.2 eq.) of [3-(trifluoromethyl)phenyl]boronic acid were reacted according to General Method 7. Yield: 46 mg (71% of theory)

HPLC (Method 2A): $R_t$=5.40 min; MS (ESIpos): m/z=550 [M+H]$^+$;

$^1$H-NMR (400 MHz, DMSO-d$_6$): δ=9.05-9.00 (m, 1H), 8.80 (t, 1H), 8.44-8.37 (m, 1H), 8.19-8.10 (m, 3H), 7.85 (d, 1H), 7.79 (t, 1H), 7.24 (t, 1H), 7.22-7.15 (m, 3H), 4.61 (br d, 0.5H), 4.49 (br d, 0.5H), 4.18 (br d, 0.5H), 4.07-3.91 (m, 1.5H), 3.12-2.96 (m, 2H), 2.87-2.77 (m, 0.5H), 2.72-2.63 (m, 1H), 2.58 (q, 2H), 2.18-2.01 (m, 2.5H), 1.87-1.47 (m, 8H), 1.17 (t, 3H).

Example 84

N-[1-(Cyclopentylcarbonyl)-5-(4-ethylphenyl)piperidin-3-yl]-5-[3-(trifluoromethyl)phenyl]pyridine-2-carboxamide [enantiomerically pure cis isomer]

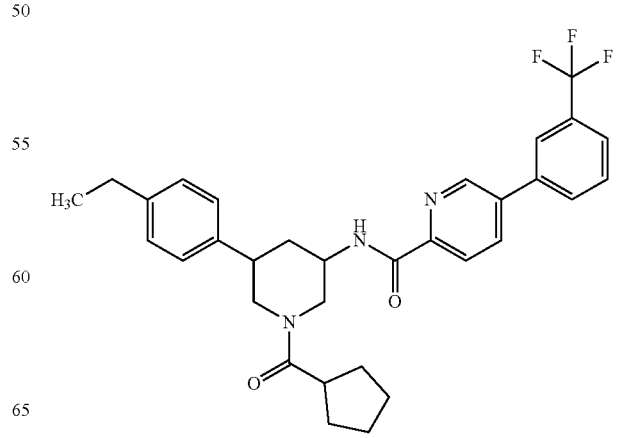

The enantiomer separation of 36 mg of the racemate from Example 83 according to Method 6D gave 17 mg of the compound from Example 84 (enantiomer 1) and 15 mg of the compound from Example 85 (enantiomer 2).

HPLC (Method 2E): $R_t$=6.39 min; MS (ESIpos): m/z=550 [M+H]$^+$.

Example 85

N-[1-(Cyclopentylcarbonyl)-5-(4-ethylphenyl)piperidin-3-yl]-5-[3-(trifluoromethyl)phenyl]pyridine-2-carboxamide [enantiomerically pure cis isomer]

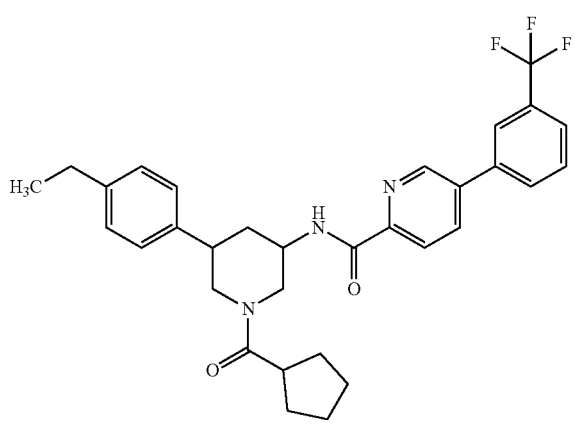 [SMILES: CCc1ccc(C2CC(NC(=O)c3ccc(-c4cccc(C(F)(F)F)c4)cn3)CN(C(=O)C3CCCC3)C2)cc1]

The enantiomer separation of 36 mg of the racemate from Example 83 according to Method 6D gave 17 mg of the compound from Example 84 (enantiomer 1) and 15 mg of the compound from Example 85 (enantiomer 2).

HPLC (Method 2E): $R_t$=7.07 min; MS (ESIpos): m/z=550 [M+H]$^+$.

Example 86

N-[5-(4-Ethylphenyl)-1-(pyrrolidin-1-ylcarbonyl)piperidin-3-yl]-5-(3-fluorophenyl)pyridine-2-carboxamide [racemic cis isomer]

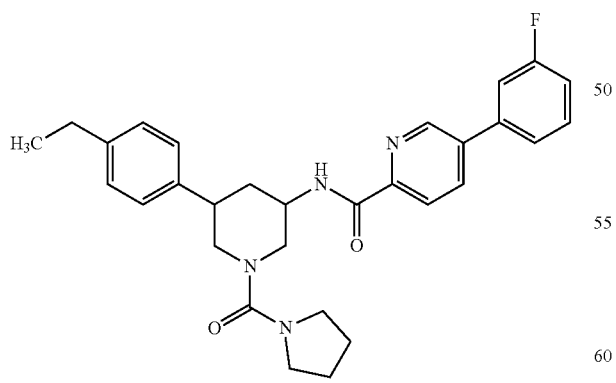

62 mg (0.11 mmol) of 5-(4-ethylphenyl)-1-(pyrrolidin-1-ylcarbonyl)piperidine-3-amine trifluoroacetate (Example 12A) and 27 mg (0.12 mmol, 1.1 eq.) of 5-(3-fluorophenyl)pyridine-2-carboxylic acid were reacted according to General Method 1. Yield: 31 mg (56% of theory)

HPLC (Method 2A): $R_t$=5.18 min; MS (ESIpos): m/z=501 [M+H]$^+$;

$^1$H-NMR (400 MHz, DMSO-d$_6$): δ=8.98 (d, 1H), 8.73 (d, 1H), 8.34 (dd, 1H), 8.12 (d, 1H), 7.76-7.65 (m, 2H), 7.63-7.55 (m, 1H), 7.37-7.28 (m, 1H), 7.21 (d, 2H), 7.17 (d, 2H), 4.13-4.02 (br m, 1H), 3.85 (br d, 1H), 3.70 (br d, 1H), 3.32-3.25 (m, 4H), 2.91-2.81 (m, 1H), 2.77 (t, 1H), 2.72-2.63 (m, 1H), 2.57 (q, 2H), 2.10-1.93 (m, 2H), 1.83-1.71 (m, 4H), 1.17 (t, 3H).

Example 87

5-Chloro-N-[1-(cyclopentylcarbonyl)-5-(4-ethylphenyl)piperidin-3-yl]thiophene-2-carboxamide [racemic cis isomer]

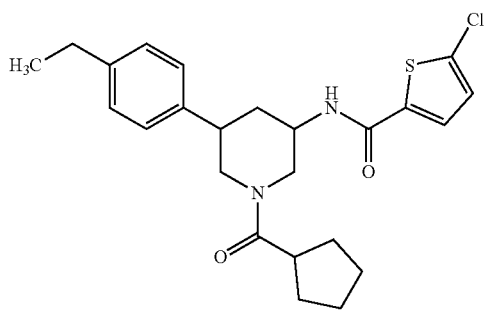 [SMILES: CCc1ccc(C2CC(NC(=O)c3ccc(Cl)s3)CN(C(=O)C3CCCC3)C2)cc1]

65 mg (0.15 mmol) of 1-(cyclopentylcarbonyl)-5-(4-ethylphenyl)piperidine-3-amine trifluoroacetate (Example 8A) and 22 mg (0.13 mmol, 0.9 eq.) of 5-chlorothiophene-2-carboxylic acid were reacted according to General Method 1. Yield: 43 mg (72% of theory)

HPLC (Method 2A): $R_t$=5.02 min; MS (ESIpos): m/z=445 [M+H]$^+$;

$^1$H-NMR (400 MHz, DMSO-d$_6$): δ=8.55 (d, 0.6H), 8.50 (d, 0.4H), 7.71 (d, 0.6H), 7.68 (d, 0.4H), 7.26-7.13 (m, 5H), 4.64 (br d, 0.4H), 4.47 (br d, 0.6H), 4.21 (br d, 0.6H), 3.96 (br d, 0.4H), 3.90-3.73 (m, 1H), 3.07-2.97 (m, 1.4H), 2.87 (t, 0.6H), 2.82-2.73 (m, 0.4H), 2.71-2.61 (m, 0.6H), 2.58 (q, 2H), 2.43 (t, 0.6H), 2.11-1.96 (m, 1.4H), 1.91-1.44 (m, 9H), 1.17 (t, 3H).

Example 88

N-[1-(Cyclopentylcarbonyl)-5-(4-ethylphenyl)piperidin-3-yl]-2,4-dimethyl-1,3-thiazole-5-carboxamide [racemic cis isomer]

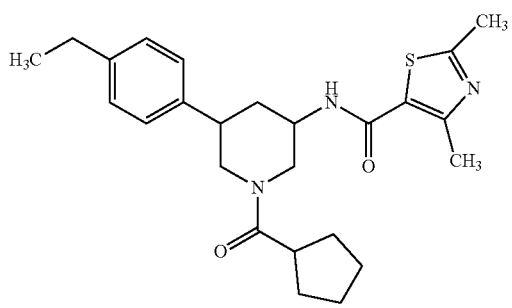 [SMILES: CCc1ccc(C2CC(NC(=O)c3sc(C)nc3C)CN(C(=O)C3CCCC3)C2)cc1]

65 mg (0.15 mmol) of 1-(cyclopentylcarbonyl)-5-(4-ethylphenyl)piperidine-3-amine trifluoroacetate (Example 8A) and 21 mg (0.13 mmol, 0.9 eq.) of 2,4-dimethyl-1,3-thiazole-5-carboxylic acid were reacted according to General Method 1. Yield: 43 mg (73% of theory)

HPLC (Method 1A): $R_t$=4.50 min; MS (ESIpos): m/z=440 [M+H]$^+$;

$^1$H-NMR (400 MHz, DMSO-d$_6$): δ=8.10 (t, 1H), 7.24-7.13 (m, 4H), 4.62 (br d, 0.4H), 4.47 (br d, 0.6H), 4.18 (br d, 0.6H), 3.96 (br d, 0.4H), 3.90-3.74 (m, 1H), 3.08-2.96 (m, 1.4H), 2.89 (t, 0.6H), 2.82-2.73 (m, 0.4H), 2.71-2.62 (m, 0.6H), 2.61 (s, 3H), 2.57 (q, 2H), 2.54 (s, 3H), 2.44 (t, 0.6H), 2.08-1.98 (m, 1.4H), 1.90-1.46 (m, 9H), 1.17 (t, 3H).

Example 89

N-[1-(Cyclopentylcarbonyl)-5-(4-ethylphenyl)piperidin-3-yl]-2-phenylacetamide [racemic cis isomer]

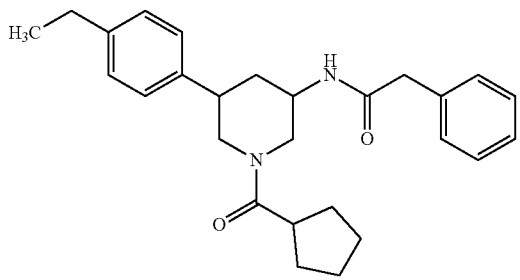 [SMILES: CCc1ccc(C2CC(NC(=O)Cc3ccccc3)CN(C(=O)C3CCCC3)C2)cc1]

57 mg (0.12 mmol) of 1-(cyclopentylcarbonyl)-5-(4-ethylphenyl)piperidine-3-amine trifluoroacetate (Example 8A) and 16 mg (0.12 mmol, 1.0 eq.) of phenylacetic acid were reacted according to General Method 1. Yield: 28 mg (58% of theory)

HPLC (Method 2A): $R_t$=4.79 min; MS (ESIpos): m/z=419 [M+H]$^+$;

$^1$H-NMR (400 MHz, DMSO-d$_6$): δ=8.19 (d, 0.6H), 8.12 (d, 0.4H), 7.32-7.12 (m, 9H), 4.56 (br d, 0.5H), 4.44 (br d, 0.5H), 4.15 (br d, 0.5H), 3.92 (br d, 0.5H), 3.68-3.53 (m, 1H), 3.42 (s, 1.2H), 3.40 (s, 0.8H), 3.07-2.88 (m, 2H), 2.75 (t, 1H), 2.57 (q, 2H), 2.32 (t, 0.6H), 2.08-1.96 (m, 1.4H), 1.86-1.44 (m, 8H), 1.17 (t, 3H).

Example 90

N-[1-(Cyclopentylcarbonyl)-5-(4-ethylphenyl)piperidin-3-yl]-2,2-dimethylpropanamide [racemic cis isomer]

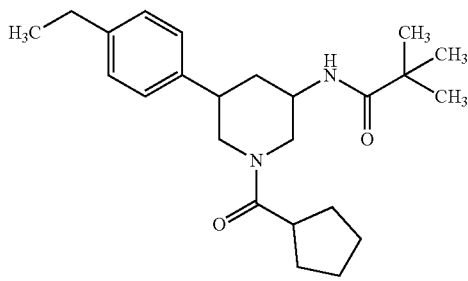 [SMILES: CCc1ccc(C2CC(NC(=O)C(C)(C)C)CN(C(=O)C3CCCC3)C2)cc1]

99 mg (0.20 mmol) of 1-(cyclopentylcarbonyl)-5-(4-ethylphenyl)piperidine-3-amine trifluoroacetate (Example 8A) and 20 mg (0.20 mmol, 1.0 eq.) of pivalic acid were reacted according to General Method 1. Yield: 56 mg (73% of theory)

HPLC (Method 1A): $R_t$=4.81 min; MS (ESIpos): m/z=385 [M+H]$^+$;

$^1$H-NMR (400 MHz, DMSO-d$_6$): δ=7.33 (t, 1H), 7.23-7.14 (m, 4H), 4.52-4.42 (m, 1H), 4.06 (br d, 0.6H), 3.93 (br d, 0.4H), 3.72-3.60 (m, 1H), 3.05-2.92 (m, 1.4H), 2.77 (t, 0.6H), 2.74-2.65 (m, 0.4H), 2.63-2.53 (m, 2.6H), 2.37 (t, 0.6H), 2.08-1.97 (m, 0.4H), 1.96-1.88 (m, 1H), 1.87-1.45 (m, 9H), 1.16 (t, 3H), 1.10 (s, 5.4H), 1.09 (3.6H).

Example 91

N-[5-(4-Ethylphenyl)-1-(pyrrolidin-1-ylcarbonyl)piperidin-3-yl]-3-phenylurea [racemic cis isomer]

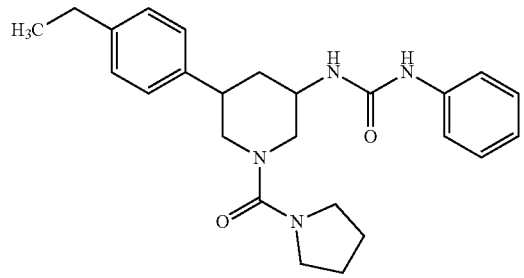 [SMILES: CCc1ccc(C2CC(NC(=O)Nc3ccccc3)CN(C(=O)N3CCCC3)C2)cc1]

125 mg (50% pure, 0.15 mmol) of 5-(4-ethylphenyl)-1-(pyrrolidin-1-ylcarbonyl)piperidine-3-amine trifluoroacetate (Example 12A) and 21 mg (0.18 mmol, 1.2 eq.) of phenyl isocyanate were reacted according to General Method 4. Yield: 58 mg (92% of theory)

HPLC (Method 1A): $R_t$=4.72 min; MS (ESIpos): m/z=421 [M+H]$^+$;

$^1$H-NMR (400 MHz, DMSO-d$_6$): δ=8.39 (s, 1H), 7.37 (d, 2H), 7.26-7.13 (m, 6H), 6.89 (t, 1H), 6.17 (d, 1H), 3.92 (br d, 1H), 3.72-3.60 (m, 2H), 3.30-3.23 (m, 4H), 2.88-2.77 (m, 1H), 2.66 (q, 1H), 2.57 (q, 2H), 2.52-2.40 (m, 1H), 2.06 (br d, 1H), 1.82-1.70 (m, 4H), 1.56 (q, 1H), 1.17 (t, 3H).

Example 92

1-[5-(4-Ethylphenyl)-1-(pyrrolidin-1-ylcarbonyl)piperidin-3-yl]-3-(3-methoxyphenyl)urea [racemic cis isomer]

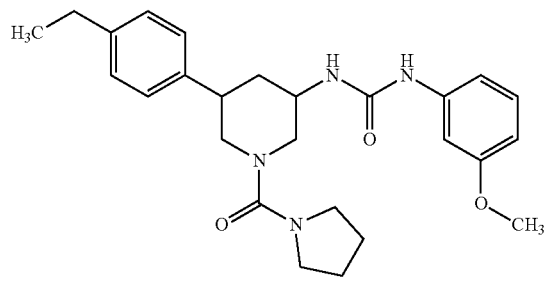 [SMILES: CCc1ccc(C2CC(NC(=O)Nc3cccc(OC)c3)CN(C(=O)N3CCCC3)C2)cc1]

83 mg (50% pure, 0.15 mmol) of 5-(4-ethylphenyl)-1-(pyrrolidin-1-ylcarbonyl)piperidine-3-amine trifluoroacetate (Example 12A) and 25 mg (0.17 mmol, 1.1 eq.) of 3-methoxyphenyl isocyanate were reacted according to General Method 4. Yield: 46 mg (67% of theory)

HPLC (Method 2A): $R_t$=4.71 min; MS (ESIpos): m/z=451 [M+H]$^+$;

$^1$H-NMR (400 MHz, DMSO-d$_6$): δ=8.41 (s, 1H), 7.20 (d, 2H), 7.16 (d, 2H), 7.14-7.08 (m, 2H), 6.85 (d, 1H), 6.48 (dd, 1H), 6.16 (d, 1H), 3.91 (br d, 1H), 3.70 (s, 3H), 3.70-3.60 (m, 2H), 3.32-3.25 (m, 4H), 2.87-2.77 (m, 1H), 2.65 (t, 1H), 2.58 (q, 2H), 2.50-2.44 (m, 1H), 2.05 (br d, 1H), 1.80-1.70 (m, 4H), 1.56 (q, 1H), 1.17 (t, 3H).

Example 93

1-[5-(4-Ethylphenyl)-1-(pyrrolidin-1-ylcarbonyl)piperidin-3-yl]-3-(4-fluorophenyl)urea [racemic cis isomer]

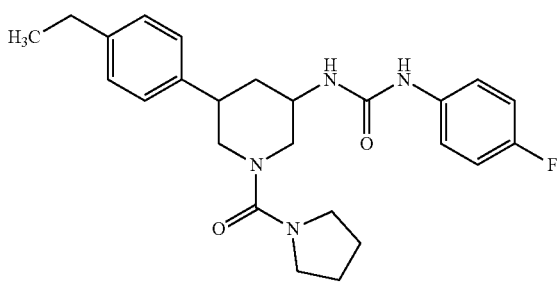 [SMILES: CCc1ccc(C2CC(NC(=O)Nc3ccc(F)cc3)CN(C(=O)N3CCCC3)C2)cc1]

83 mg (50% pure, 0.15 mmol) of 5-(4-ethylphenyl)-1-(pyrrolidin-1-ylcarbonyl)piperidine-3-amine trifluoroacetate (Example 12A) and 23 mg (0.17 mmol, 1.2 eq.) of 4-fluorophenyl isocyanate were reacted according to General Method 4. Yield: 44 mg (67% of theory)

HPLC (Method 2A): $R_t$=4.73 min; MS (ESIpos): m/z=439 [M+H]$^+$;

$^1$H-NMR (400 MHz, DMSO-d$_6$): δ=8.43 (s, 1H), 7.42-7.34 (m, 2H), 7.20 (d, 2H), 7.16 (d, 2H), 7.06 (t, 2H), 6.16 (d, 1H), 3.91 (br d, 1H), 3.71-3.60 (m, 2H), 3.32-3.25 (m, 4H), 2.83-2.76 (m, 1H), 2.66 (t, 1H), 2.58 (q, 2H), 2.46 (t, 1H), 2.05 (br d, 1H), 1.81-1.70 (m, 4H), 1.57 (q, 1H), 1.17 (t, 3H).

The following compound [racemic cis isomer] was prepared in an analogous manner:

Example 95

3-[1-(Cyclopentylcarbonyl)-5-(4-ethylphenyl)piperidin-3-yl]-1-methyl-1-phenylurea [racemic cis isomer]

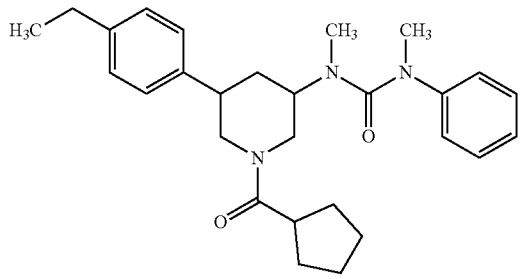 [SMILES: CCc1ccc(C2CC(N(C)C(=O)N(C)c3ccccc3)CN(C(=O)C3CCCC3)C2)cc1]

60 mg (0.14 mmol) of 1-(cyclopentylcarbonyl)-5-(4-ethylphenyl)piperidine-3-amine trifluoroacetate (Example 8A) and 22 mg (0.14 mmol, 1.0 eq.) of methyl(phenyl)carbamoyl chloride were reacted according to General Method 3. Yield: 37 mg (69% of theory)

HPLC (Method 1A): $R_t$=4.87 min; MS (ESIpos): m/z=434 [M+H]$^+$;

$^1$H-NMR (400 MHz, DMSO-d$_6$): δ=7.38 (t, 2H), 7.30-7.24 (m, 2H), 7.21 (t, 1H), 7.18-7.12 (m, 4H), 5.89 (d, 0.5H), 5.85 (d, 0.5H), 4.54 (br d, 0.5H), 4.42 (br d, 0.5H), 4.11 (br d, 0.5H), 3.89 (br d, 0.5H), 3.68-3.53 (m, 1H), 3.16 (s, 1.5H), 3.15 (s, 1.5H), 3.04-2.94 (m, 1H), 2.90 (t, 0.5H), 2.77 (t, 0.5H), 2.73-2.64 (m, 0.5H), 2.56 (q, 2H), 2.43 (t, 0.5H), 2.33 (t, 0.5H), 2.06-1.88 (m, 1.5H), 1.83-1.44 (m, 9H), 1.16 (t, 3H).

Example 96

1-[1-(Cyclopentylcarbonyl)-5-(4-ethylphenyl)piperidin-3-yl]-1,3-dimethyl-3-phenylurea [racemic cis isomer]

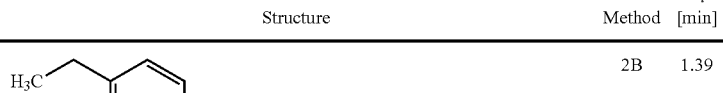

| Example | Structure | LC-MS Method | $R_t$ [min] | MS (ESIpos) m/z |
|---|---|---|---|---|
| 94 | 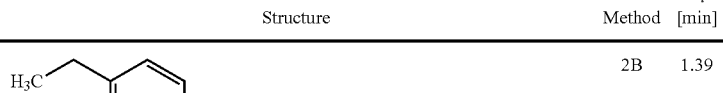 | 2B | 1.39 | 449 |

Under argon and at RT, 8 mg of sodium hydride (60% in mineral oil, 0.19 mmol, 2 eq.) were added to a solution of 40 mg (0.10 mmol) of 1-[1-(cyclopentylcarbonyl)-5-(4-ethylphenyl)piperidin-3-yl]-3-phenylurea (Example 171) in 1 ml of dimethylformamide, and the mixture was stirred at RT for 30 min. 13 µl (0.21 mmol, 2.2 eq.) of iodomethane were added, and the reaction mixture was stirred at RT for a further 1.5 h. After addition of water/dichloromethane and phase separation, the aqueous phase was extracted three times with dichloromethane. The combined organic phases were dried (sodium sulphate), filtered and concentrated under reduced pressure. The crude product was purified by preparative HPLC (Reprosil C18, water/acetonitrile gradient). Yield: 26 mg (61% of theory)

HPLC (Method 2A): $R_t$=5.03 min; MS (ESIpos): m/z=448 [M+H]$^+$;

$^1$H-NMR (400 MHz, DMSO-d$_6$): δ=7.34 (d, 2H), 7.28-7.13 (m, 7H), 4.46-4.33 (m, 1H), 3.91-3.78 (m, 2H), 3.16 (t, 1H), 3.08 (s, 3H), 3.05-2.95 (m, 1H), 2.80-2.70 (m, 1H), 2.58 (q, 2H), 1.98-1.84 (m, 2H), 1.83-1.44 (m, 9H), 1.17 (t, 3H).

Example 97

1-tert-Butyl-3-[1-(cyclopentylcarbonyl)-5-(4-ethylphenyl)piperidin-3-yl]urea [racemic cis isomer]

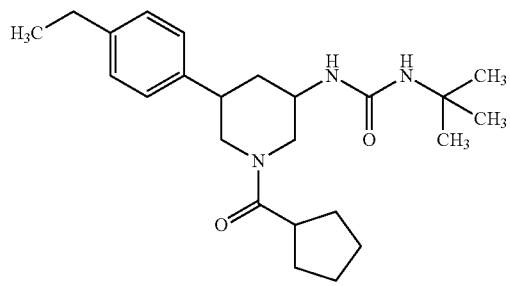 [SMILES: CCc1ccc(C2CC(NC(=O)NC(C)(C)C)CN(C(=O)C3CCCC3)C2)cc1]

108 mg (0.22 mmol) of 1-(cyclopentylcarbonyl)-5-(4-ethylphenyl)piperidine-3-amine trifluoroacetate (Example 7A) and 26 mg (0.26 mmol, 1.2 eq.) of tert-butyl isocyanate were reacted according to General Method 4. Yield: 69 mg (78% of theory)

HPLC (Method 2A): $R_t$=4.74 min; MS (ESIpos): m/z=400 [M+H]$^+$;

$^1$H-NMR (400 MHz, DMSO-d$_6$): δ=7.24-7.14 (m, 4H), 5.73 (d, 0.5H), 5.67 (d, 0.5H), 5.66 (s, 0.5H), 5.61 (s, 0.5H), 4.57 (br d, 0.5H), 4.42 (br d, 0.5H), 4.14 (br d, 0.5H), 3.89 (br d, 0.5H), 3.50-3.36 (m, 1H), 3.05-2.94 (m, 1.5H), 2.73-2.61 (m, 1.5H), 2.57 (q, 2H), 2.18 (t, 0.5H), 2.07-1.92 (m, 1.5H), 1.83-1.43 (m, 9H), 1.22 (s, 4.5H), 1.21 (s, 4.5H), 1.16 (t, 3H).

Example 98

1-[1-(Cyclopentylcarbonyl)-5-(4-ethylphenyl)piperidin-3-yl]-3-cyclopropylurea [racemic cis isomer]

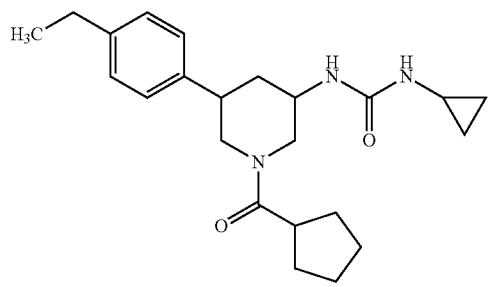 [SMILES: CCc1ccc(C2CC(NC(=O)NC3CC3)CN(C(=O)C3CCCC3)C2)cc1]

108 mg (0.22 mmol) of 1-(cyclopentylcarbonyl)-5-(4-ethylphenyl)piperidine-3-amine trifluoroacetate (Example 7A) and 22 mg (0.26 mmol, 1.2 eq.) of cyclopropyl isocyanate were reacted according to General Method 4. Yield: 64 mg (76% of theory)

HPLC (Method 2A): $R_t$=4.50 min; MS (ESIpos): m/z=384 [M+H]$^+$;

$^1$H-NMR (400 MHz, DMSO-d$_6$): δ=7.24-7.14 (m, 4H), 6.14 (s, 0.6H), 6.12 (s, 0.4H), 5.86 (d, 0.6H), 5.81 (d, 0.4H), 4.56 (br d, 0.4H), 4.42 (br d, 0.6H), 4.15 (br d, 0.6H), 3.90 (br d, 0.4H), 3.56-3.41 (m, 1H), 3.04-2.92 (m, 1.4H), 2.77-2.65 (m, 1H), 2.64-2.52 (m, 0.6H and q, 2H), 2.45-2.35 (m, 1H), 2.26 (t, 0.4H), 2.08-1.91 (m, 1.6H), 1.83-1.43 (m, 9H), 1.16 (t, 3H), 0.60-0.52 (m, 2H), 0.36-0.28 (m, 2H).

Example 99

N-[1-(Cyclopentylcarbonyl)-5-(4-ethylphenyl)piperidin-3-yl]pyrrolidine-1-carboxamide [racemic cis isomer]

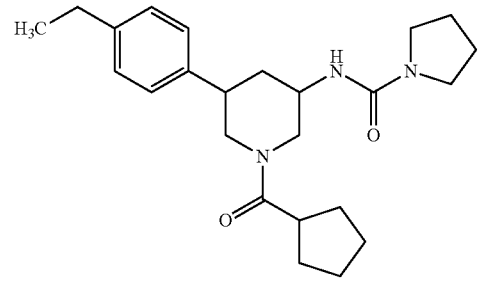 [SMILES: CCc1ccc(C2CC(NC(=O)N3CCCC3)CN(C(=O)C3CCCC3)C2)cc1]

57 mg (0.12 mmol) of 1-(cyclopentylcarbonyl)-5-(4-ethylphenyl)piperidine-3-amine trifluoroacetate (Example 7A) and 20 mg (0.15 mmol, 1.3 eq.) of pyrrolidine-N-carbonyl chloride were reacted according to General Method 3. Yield: 24 mg (52% of theory)

HPLC (Method 2A): $R_t$=4.60 min; MS (ESIpos): m/z=398 [M+H]$^+$;

$^1$H-NMR (400 MHz, DMSO-d$_6$): δ=7.23-7.11 (m, 4H), 5.95 (d, 0.6H), 5.91 (d, 0.4H), 4.55 (br d, 0.4H), 4.45 (br d, 0.6H), 4.13 (br d, 0.6H), 3.92 (br d, 0.4H), 3.62-3.49 (m, 1H), 3.26-3.14 (m, 4H), 3.04-2.88 (m, 1.4H), 2.79-2.63 (m, 1H), 2.57 (q, 2H), 2.49-2.40 (m, 0.6H), 2.36-2.28 (m, 0.4H), 2.05-1.92 (m, 1.6H), 1.85-1.73 (m, 5H), 1.73-1.43 (m, 8H), 1.17 (t, 3H).

Example 100

N-Benzyl-N'-[1-(cyclopentylcarbonyl)-5-(4-ethylphenyl)piperidin-3-yl]urea [racemic cis isomer]

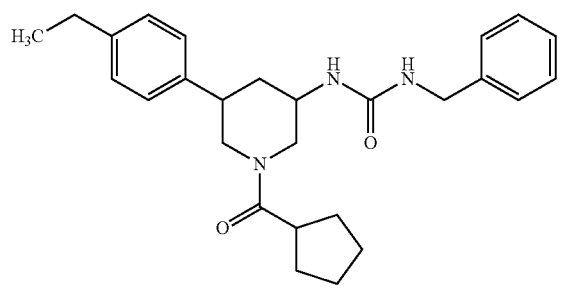 [SMILES: CCc1ccc(C2CC(NC(=O)NCc3ccccc3)CN(C(=O)C3CCCC3)C2)cc1]

108 mg (0.22 mmol) of 1-(cyclopentylcarbonyl)-5-(4-ethylphenyl)piperidine-3-amine trifluoroacetate (Example 7A) and 35 mg (0.26 mmol, 1.2 eq.) of benzyl isocyanate were reacted according to General Method 4. Yield: 74 mg (77% of theory)

HPLC (Method 1A): $R_t$=4.74 min; MS (ESIpos): m/z=434 [M+H]$^+$;

$^1$H-NMR (400 MHz, DMSO-d$_6$): δ=7.35-7.28 (m, 2H), 7.27-7.19 (m, 3H), 7.19-7.14 (m, 4H), 6.34 (t, 0.6H), 6.29 (t, 0.4H), 6.04 (d, 0.6H), 5.98 (d, 0.4H), 4.60 (br d, 0.4H), 4.43 (br d, 0.6H), 4.26 (dd, 0.6H), 4.23-4.14 (m, 2H), 3.90 (br d, 0.4H), 3.56-3.43 (m, 1H), 3.03-2.94 (m, 1.4H), 2.71 (t, 1H), 2.62-2.55 (m, 0.6H and q, 2H), 2.26 (t, 0.4H), 2.06-1.96 (m, 1.6H), 1.83-1.45 (m, 9H), 1.17 (t, 3H).

Example 101

N-[5-(4-Ethylphenyl)-1-(pyrrolidin-1-ylcarbonyl)piperidin-3-yl]-4-phenylpiperazine-1-carboxamide [racemic cis isomer]

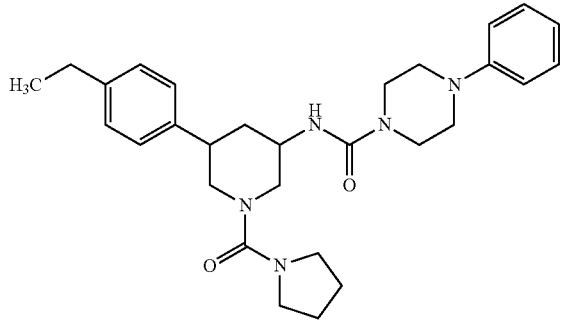 [SMILES: CCc1ccc(C2CC(NC(=O)N3CCN(c4ccccc4)CC3)CN(C(=O)N3CCCC3)C2)cc1]

125 mg (50% pure, 0.15 mmol) of 5-(4-ethylphenyl)-1-(pyrrolidin-1-ylcarbonyl)piperidine-3-amine trifluoroacetate (Example 12A) and 40 mg (0.18 mmol, 1.2 eq.) of 4-phenylpiperazine-1-carbonyl chloride were reacted according to General Method 3. Yield: 13 mg (18% of theory)

HPLC (Method 2A): $R_t$=4.37 min; MS (ESIpos): m/z=490 [M+H]$^+$;

$^1$H-NMR (400 MHz, DMSO-d$_6$): δ=7.22 (t, 2H), 7.19-7.13 (m, 4H), 6.96 (d, 2H), 6.79 (t, 1H), 6.45 (d, 1H), 3.84 (br d, 1H), 3.73-3.61 (m, 2H), 3.48-3.41 (m, 4H), 3.30-3.23 (m, 4H), 3.12-3.04 (m, 4H), 2.83-2.73 (m, 1H), 2.57 (q, 2H), 2.48-2.40 (m, 2H), 1.99 (br d, 1H), 1.80-1.70 (m, 4H), 1.66 (q, 1H), 1.16 (t, 3H).

Example 102

Methyl [5-(4-ethylphenyl)-1-(morpholin-4-ylcarbonyl)piperidin-3-yl]carbamate [racemic cis isomer]

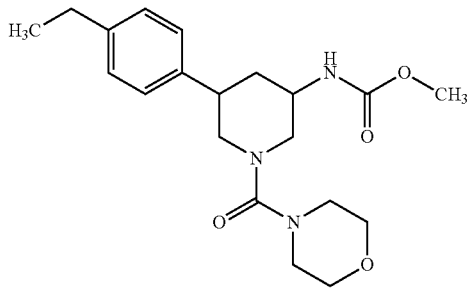 [SMILES: CCc1ccc(C2CC(NC(=O)OC)CN(C(=O)N3CCOCC3)C2)cc1]

170 mg (0.58 mmol) of methyl [5-(4-ethylphenyl)piperidin-3-yl]carbamate (Example 21A) and 113 mg (0.76 mmol, 1.3 eq.) of morpholine-4-carbonyl chloride were reacted according to General Method 3. Diastereomer separation of the cis/trans isomer mixture according to Method 7C gave 70 mg of the compound from Example 102.

LC-MS (Method 1B): $R_t$=2.13 min; MS (ESIpos): m/z=376 [M+H]$^+$;

$^1$H-NMR (400 MHz, DMSO-d$_6$): δ=7.27 (d, 1H), 7.16 (s, 4H), 3.77 (br d, 1H), 3.62-3.51 (br d, 1H and s, 3H and m, 4H), 3.53-3.22 (m, 1H), 3.19-3.11 (m, 4H), 2.83-2.73 (m, 1H), 2.68 (t, 1H), 2.57 (q, 2H), 2.48 (t, 1H), 1.99 (br d, 1H), 1.54 (q, 1H), 1.16 (t, 3H).

Example 103

Phenyl [5-(4-ethylphenyl)-1-(pyrrolidin-1-ylcarbonyl)piperidin-3-yl]carbamate [racemic cis isomer]

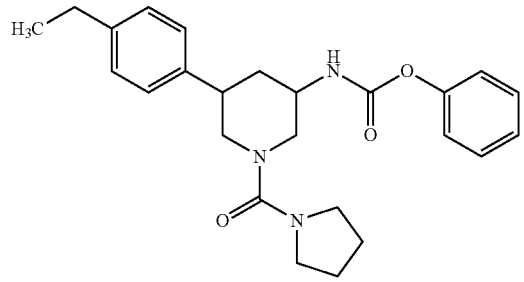 [SMILES: CCc1ccc(C2CC(NC(=O)Oc3ccccc3)CN(C(=O)N3CCCC3)C2)cc1]

83 mg (0.15 mmol) of 5-(4-ethylphenyl)-1-(pyrrolidin-1-ylcarbonyl)piperidine-3-amine trifluoroacetate (Example 12A) and 26 mg (0.17 mmol, 1.1 eq.) of phenyl chloroformate were reacted according to General Method 5. Yield: 25 mg (39% of theory)

HPLC (Method 2A): $R_t$=4.90 min; MS (ESIpos): m/z=422 [M+H]$^+$;

$^1$H-NMR (400 MHz, DMSO-d$_6$): δ=7.90 (d, 1H), 7.38 (d, 2H), 7.24-7.14 (m, 5H), 7.11 (d, 2H), 3.92 (br d, 1H), 3.67 (br d, 1H), 3.62-3.32 (m, 1H), 3.30-3.21 (m, 4H), 2.87-2.77 (m, 1H), 2.72-2.61 (m, 2H), 2.57 (q, 2H), 2.09 (br d, 1H), 1.80-1.70 (m, 4H), 1.63 (q, 1H), 1.17 (t, 3H).

Example 104

N-[1-(Cyclopentylcarbonyl)-5-(4-ethylphenyl)piperidin-3-yl]-1-phenylmethanesulphonamide [racemic cis isomer]

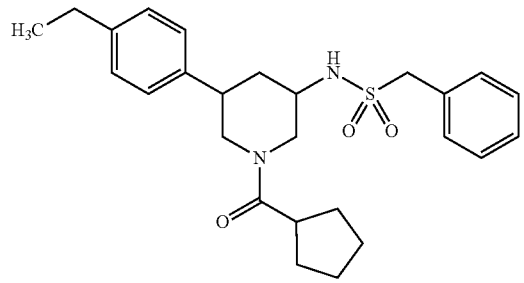 [SMILES: CCc1ccc(C2CC(NS(=O)(=O)Cc3ccccc3)CN(C(=O)C3CCCC3)C2)cc1]

55 mg (0.12 mmol) of 1-(cyclopentylcarbonyl)-5-(4-ethylphenyl)piperidine-3-amine trifluoroacetate (Example 7A) and 21 mg (0.11 mmol, 0.9 eq.) of phenylmethanesulphonic acid were reacted according to General Method 6. Yield: 14 mg (24% of theory)

HPLC (Method 2A): R$_t$=4.81 min; MS (ESIpos): m/z=455 [M+H]$^+$;

$^1$H-NMR (400 MHz, DMSO-d$_6$): δ=7.43-7.33 (m, 5H), 7.21-7.12 (m, 4H), 4.68 (br d, 0.5H), 4.43-4.32 (br d, 0.5H and d, 2H), 4.03 (br d, 0.5H), 3.88 (br d, 0.5H), 3.20-3.02 (m, 1H), 3.01-2.87 (m, 1.5H), 2.76 (t, 0.5H), 2.58 (q, 2H), 2.11-1.99 (m, 1.5H), 1.92-1.82 (m, 0.5H), 1.77-1.47 (m, 9H), 1.17 (t, 3H).

Example 105

Phenyl 5-(4-ethylphenyl)-1-(morpholin-4-ylcarbonyl)piperidin-3-ylcarbamate [racemic cis isomer]

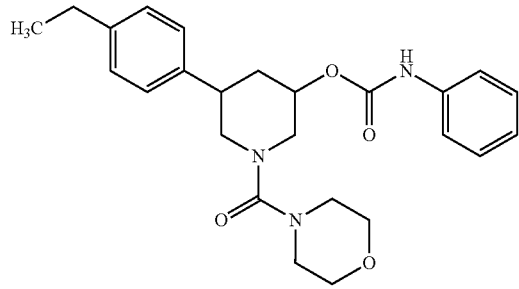 [SMILES: CCc1ccc(C2CC(OC(=O)Nc3ccccc3)CN(C(=O)N3CCOCC3)C2)cc1]

Under argon and at RT, 184 µl (1.06 mmol, 3 eq.) of N,N-diisopropylethylamine and 135 mg (0.53 mmol, 1.5 eq.) of N,N'-disuccinimidyl carbonate were added to a solution of 112 mg (0.35 mmol) of 5-(4-ethylphenyl)-1-(morpholin-4-ylcarbonyl)piperidin-3-ol (Example 25A) in 1.7 ml of acetonitrile. The reaction mixture was stirred at RT for 3 h, then 96 µl (1.06 mmol, 3 eq.) of aniline and 61 µl (0.35 mmol, 1.0 eq.) of N,N-diisopropylethylamine were added at RT and the mixture was stirred at RT for 1 h. The crude product was then purified by preparative HPLC (Reprosil C18, water/acetonitrile gradient). Yield: 18 mg (12% of theory)

HPLC (Method 2A): R$_t$=4.75 min; MS (ESIpos): m/z=438 [M+H]$^+$;

$^1$H-NMR (400 MHz, DMSO-d$_6$): δ=9.71 (s, 1H), 7.47 (d, 2H), 7.28 (t, 2H), 7.23 (d, 2H), 7.17 (d, 2H), 6.99 (t, 1H), 4.78-4.68 (m, 1H), 3.94 (br d, 1H), 3.62-3.53 (m, 5H), 3.23-3.15 (m, 4H), 2.94-2.83 (m, 1H), 2.83-2.70 (m, 2H), 2.58 (q, 2H), 2.25 (br d, 1H), 1.77 (q, 1H), 1.17 (t, 3H).

Example 106

N-{1-[(4-Cyanopiperidin-1-yl)carbonyl]-5-[4-(trifluoromethoxy)phenyl]piperidin-3-yl}benzenecarboxamide [racemic cis isomer]

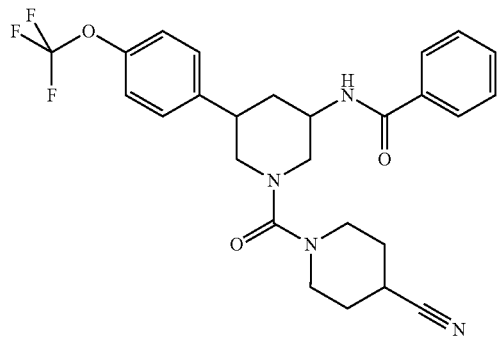 [SMILES: N#CC1CCN(C(=O)N2CC(NC(=O)c3ccccc3)CC(c3ccc(OC(F)(F)F)cc3)C2)CC1]

115 mg (0.22 mmol) of 4-nitrophenyl 3-[(phenylcarbonyl)amino]-5-[4-(trifluoromethoxy)phenyl]piperidine-1-carboxylate were initially charged in 3 ml of DMF, and 72 mg (0.65 mmol) of piperidine-4-carbonitrile and 30 mg (0.22 mmol) of potassium carbonate were added. The mixture was reacted in a microwave (Emrys Optimizer) at 150° C. for 30 min. The crude product was then purified by preparative HPLC (Reprosil C18, water/acetonitrile gradient). Yield: 53 mg (48% of theory)

LC-MS (Method 1B): R$_t$=2.43 min; m/z=501 [M+H]$^+$;

$^1$H-NMR (400 MHz, DMSO-d$_6$): δ=8.39 (d, 1H), 7.89-7.83 (m, 2H), 7.50-7.55 (m, 1H), 7.49-7.41 (m, 4H), 7.35 (d, 2H), 4.07-3.96 (m, 1H), 3.81 (dd, 1H), 3.64 (d, 1H), 3.43-3.35 (m, 2H), 3.13-2.94 (m, 4H), 2.80-2.61 (m, 2H), 2.12 (d, 1H), 1.93-1.64 (m, 5H).

Example 107

N-{1-[(4-Hydroxypiperidin-1-yl)carbonyl]-5-[4-(trifluoromethoxy)phenyl]piperidin-3-yl}benzenecarboxamide [racemic cis isomer]

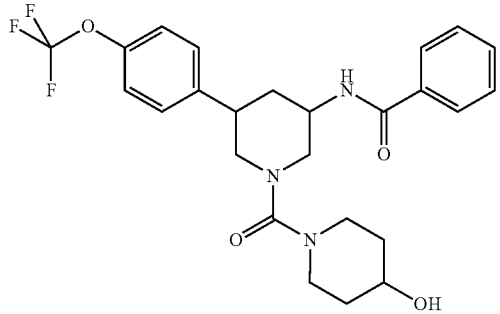 [SMILES: O=C(NC1CC(c2ccc(OC(F)(F)F)cc2)CN(C(=O)N2CCC(O)CC2)C1)c1ccccc1]

550 mg (1.04 mmol) of 4-nitrophenyl 3-[(phenylcarbonyl)amino]-5-[4-(trifluoromethoxy)phenyl]piperidine-1-carboxylate were initially charged in 14 ml of DMF, and 315 mg (3.12 mmol) of piperidin-4-ol and 144 mg (1.04 mmol) of potassium carbonate were added. The mixture was reacted in a microwave (Emrys Optimizer) at 150° C. for 15 min. The crude product was then purified by preparative HPLC (Reprosil C18, water/acetonitrile gradient). Yield: 430 mg (84% of theory)

LC-MS (Method 1B): R$_t$=2.19 min; m/z=492 [M+H]$^+$;

$^1$H-NMR (400 MHz, DMSO-d$_6$): δ=8.38 (d, 1H), 7.86 (d, 2H), 7.52 (d, 1H), 7.47 (d, 2H), 7.44 (d, 2H), 7.34 (d, 2H), 4.68 (d, 1H), 4.09-3.93 (m, 1H), 3.83-3.74 (m, 1H), 3.66-3.57 (m, 2H), 3.49 (d, 2H), 2.90 (d, 3H), 2.76 (d, 1H), 2.65 (s, 1H), 2.15-2.06 (m, 1H), 1.82-1.69 (m, 3H), 1.33 (d, 2H).

Example 108

N-{1-(Morpholin-4-ylcarbonyl)-5-[4-(trifluoromethoxy)phenyl]piperidin-3-yl}benzenecarboxamide [racemic cis isomer]

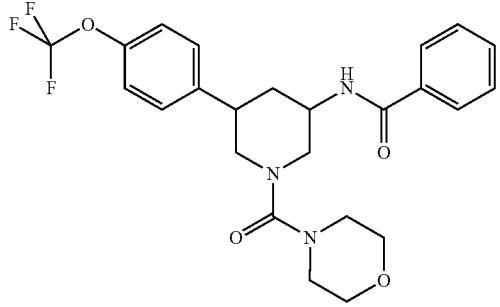 [SMILES: O=C(NC1CC(c2ccc(OC(F)(F)F)cc2)CN(C(=O)N2CCOCC2)C1)c1ccccc1]

At 0° C., 100 mg (0.27 mmol) of N-{5-[4-(trifluoromethoxy)phenyl]piperidin-3-yl}benzamide were initially charged in 1.5 ml of dichloromethane, and 82 mg (0.55 mmol) of morpholine-4-carbonyl chloride and 58 μl (0.412 mmol) of triethylamine were added. The mixture was slowly warmed to RT overnight. Water was added, and the reaction mixture was extracted. The organic phase was dried over magnesium sulphate and concentrated under reduced pressure. The residue was then purified by preparative HPLC (Reprosil C18, water/acetonitrile gradient). Yield: 118 mg (90% of theory)

LC-MS (Method 3B): $R_t$=1.95 min; m/z=478 [M+H]$^+$;

$^1$H-NMR (400 MHz, DMSO-d$_6$): δ=8.39 (d, 1H), 7.86 (d, 2H), 7.52 (d, 1H), 7.50-7.41 (m, 4H), 7.35 (d, 2H), 4.08-3.93 (m, 1H), 3.85 (d, 1H), 3.67 (d, 1H), 3.58 (t, 4H), 3.20 (br. s., 4H), 3.05-2.93 (m, 1H), 2.89 (s, 1H), 2.83-2.63 (m, 2H), 2.11 (d, 1H), 1.86-1.74 (m, 1H).

Example 109

N-{1-(Morpholin-4-ylcarbonyl)-5-[4-(trifluoromethoxy)phenyl]piperidin-3-yl}benzenecarboxamide [enantiomerically pure cis isomer]

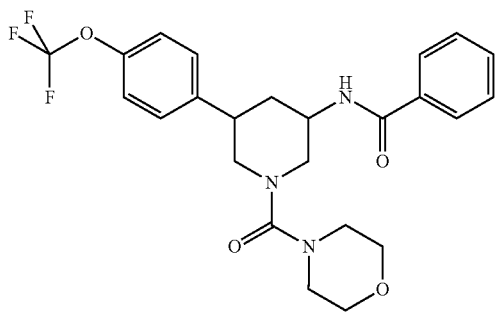 [SMILES: O=C(NC1CC(c2ccc(OC(F)(F)F)cc2)CN(C(=O)N2CCOCC2)C1)c1ccccc1]

The enantiomer separation of 117 mg of the racemic cis isomer mixture (Example 108) according to Method 11D gave 34.8 mg of the compound from Example 109 (enantiomer 1).

LC-MS (Method 2B): $R_t$=1.23 min; m/z=478 [M+H]$^+$.

Example 110

N-{1-(Morpholin-4-ylcarbonyl)-5-[4-(trifluoromethoxy)phenyl]piperidin-3-yl}benzenecarboxamide [enantiomerically pure cis isomer]

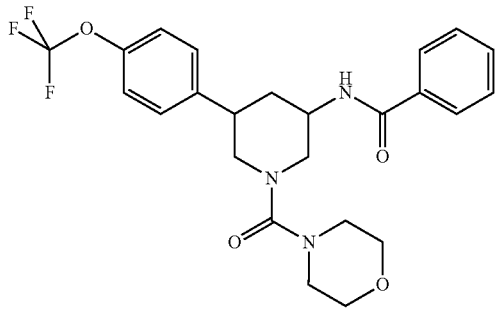 [SMILES: O=C(NC1CC(c2ccc(OC(F)(F)F)cc2)CN(C(=O)N2CCOCC2)C1)c1ccccc1]

The enantiomer separation of 117 mg of the racemic cis isomer mixture (Example 108) according to Method 11D gave 29.7 mg of the compound from Example 110 (enantiomer 2).

LC-MS (Method 2B): $R_t$=1.23 min; m/z=478 [M+H]$^+$.

Example 111

N-(2-Methoxyethyl)-3-[(phenylcarbonyl)amino]-5-[4-(trifluoromethoxy)phenyl]piperidine-1-carboxamide [racemic cis isomer]

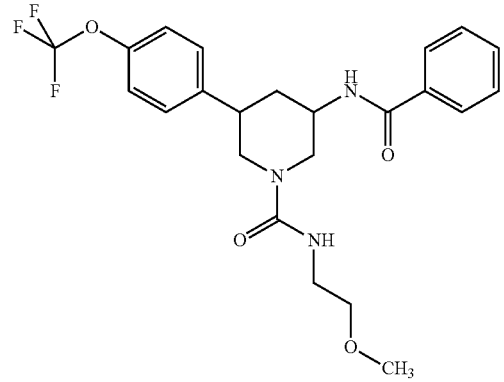 [SMILES: COCCNC(=O)N1CC(NC(=O)c2ccccc2)CC(c2ccc(OC(F)(F)F)cc2)C1]

70 mg (0.19 mmol) of N-{5-[4-(trifluoromethoxy)phenyl]piperidin-3-yl}benzamide were initially charged in 2.5 ml of THF, and 19 mg (0.19 mmol) of 1-isocyanato-2-methoxyethane and 29 μl (0.21 mmol) of triethylamine were added. The mixture was stirred at RT overnight. The reaction mixture was then purified by preparative HPLC (Reprosil C18, water/acetonitrile gradient). Yield: 32 mg (35% of theory)

LC-MS (Method 1B): $R_t$=2.32 min; m/z=466 [M+H]$^+$;

$^1$H-NMR (400 MHz, DMSO-d$_6$): δ=8.38 (d, 1H), 7.85 (d, 2H), 7.52 (d, 1H), 7.49-7.41 (m, 4H), 7.34 (d, 2H), 6.74-6.66 (m, 1H), 4.21 (dd, 1H), 4.05 (d, 1H), 4.00-3.89 (m, 1H), 3.34 (t, 2H), 3.24 (s, 3H), 3.19 (d, 2H), 2.82 (d, 1H), 2.74-2.56 (m, 2H), 2.10 (d, 1H), 1.73 (q, 1H).

Example 112

Methyl N-({3-[(phenylcarbonyl)amino]-5-[4-(trifluoromethoxy)phenyl]piperidin-1-yl}carbonyl)glycinate [racemic cis isomer]

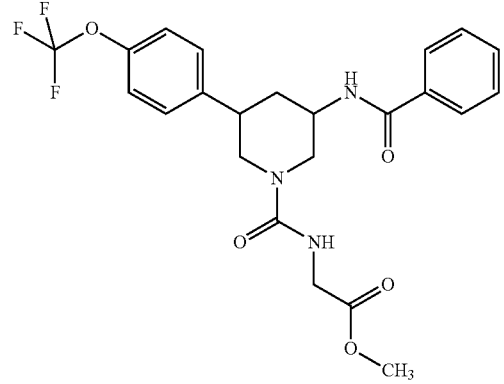 [SMILES: COC(=O)CNC(=O)N1CC(NC(=O)c2ccccc2)CC(c2ccc(OC(F)(F)F)cc2)C1]

70 mg (0.19 mmol) of N-{5-[4-(trifluoromethoxy)phenyl]piperidin-3-yl}benzamide were initially charged in 2.5 ml of THF, and 22 mg (0.19 mmol) of methyl N-(oxomethylidene)

glycinate and 29 μl (0.21 mmol) of triethylamine were added. The mixture was stirred at RT overnight. The reaction mixture was then purified by preparative HPLC (Reprosil C18, water/acetonitrile gradient). Yield: 76 mg (82% of theory)

LC-MS (Method 2B): $R_t$=1.20 min; m/z=480 [M+H]$^+$;
$^1$H-NMR (400 MHz, DMSO-d$_6$): δ=8.39 (d, 1H), 7.85 (d, 2H), 7.53 (d, 1H), 7.49-7.41 (m, 4H), 7.35 (d, 2H), 7.16 (t, 1H), 4.19 (dd, 1H), 4.07 (d, 1H), 4.02-3.91 (m, 1H), 3.75 (d, 2H), 3.63 (s, 3H), 2.93-2.82 (m, 1H), 2.76 (t, 1H), 2.67 (t, 1H), 2.12 (d, 1H), 1.75 (q, 1H).

Example 113

N-{1-[(4-Methylpiperazin-1-yl)carbonyl]-5-[4-(trifluoromethoxy)phenyl]piperidin-3-yl}benzenecarboxamide [racemic cis isomer]

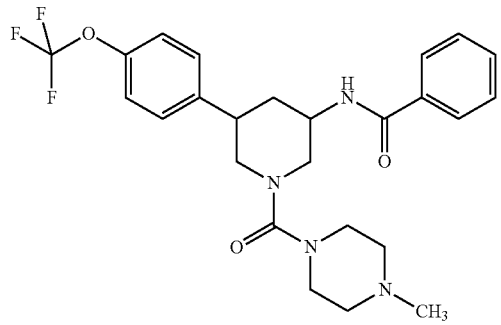 [SMILES: CN1CCN(C(=O)N2CC(NC(=O)c3ccccc3)CC(c3ccc(OC(F)(F)F)cc3)C2)CC1]

At 0° C., 100 mg (0.27 mmol) of N-{5-[4-(trifluoromethoxy)phenyl]piperidin-3-yl}benzamide were initially charged in 1.5 ml of dichloromethane, and 89 mg (0.55 mmol) of 4-methylpiperazine-1-carbonyl chloride and 58 μl (0.412 mmol) of triethylamine were added. The mixture was slowly warmed to RT overnight. Water was added, and the reaction mixture was extracted. The organic phase was dried over magnesium sulphate and concentrated under reduced pressure. The residue was then purified by preparative HPLC (Reprosil C18, water/acetonitrile gradient). Yield: 104 mg (77% of theory)

LC-MS (Method 2B): $R_t$=1.01 min; m/z=491 [M+H]$^+$;
$^1$H-NMR (400 MHz, CD$_3$OD): δ=7.83 (d, 2H), 7.54 (d, 1H), 7.50-7.40 (m, 4H), 7.26 (d, 2H), 4.21-4.08 (m, 1H), 4.02 (br. s., 1H), 3.87 (br. s., 1H), 3.50 (br. s., 4H), 3.05 (br. s., 4H), 2.91-2.76 (m, 2H), 2.72 (s, 3H), 2.25 (br. s., 1H), 2.01-1.84 (m, 2H), 1.35-1.25 (m, 1H).

Example 114

N-{1-(Pyridin-4-ylcarbonyl)-5-[4-(trifluoromethoxy)phenyl]piperidin-3-yl}benzenecarboxamide [racemic cis isomer]

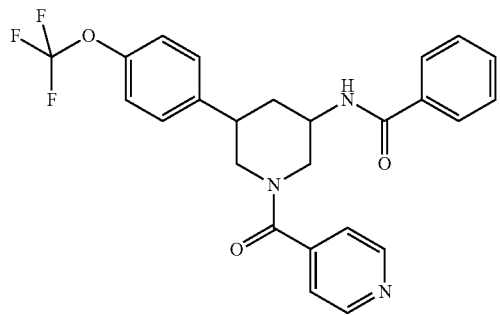 [SMILES: O=C(NC1CC(c2ccc(OC(F)(F)F)cc2)CN(C(=O)c2ccncc2)C1)c1ccccc1]

51 mg (0.41 mmol) of pyridine-4-carboxylic acid together with 157 mg (0.41 mmol) of HATU and 67 mg (0.55 mmol) of 4-dimethylaminopyridine were initially charged in 2 ml of DMF, and 100 mg (0.27 mmol) of N-{5-[4-(trifluoromethoxy)phenyl]piperidin-3-yl}benzamide were added. The reaction mixture was stirred overnight at RT and then purified by preparative HPLC (Reprosil C18, water/acetonitrile gradient). Yield: 112 mg (87% of theory)

LC-MS (Method 2B): $R_t$=1.17 min; m/z=470 [M+H]$^+$;
$^1$H-NMR (400 MHz, DMSO-d$_6$): δ=8.69 (dd, 2H), 8.43 (dd, 1H), 7.83 (dd, 2H), 7.60-7.24 (m, 9H), 4.67 (dd, 1H), 4.10 (d, 1H), 3.58 (dd, 1H), 3.19-2.97 (m, 2H), 2.81 (dt, 1H), 2.27-2.11 (m, 1H), 1.92 (q, 1H).

Example 115

N-{1-(Pyridin-4-ylcarbonyl)-5-[4-(trifluoromethoxy)phenyl]piperidin-3-yl}benzenecarboxamide [enantiomerically pure cis isomer]

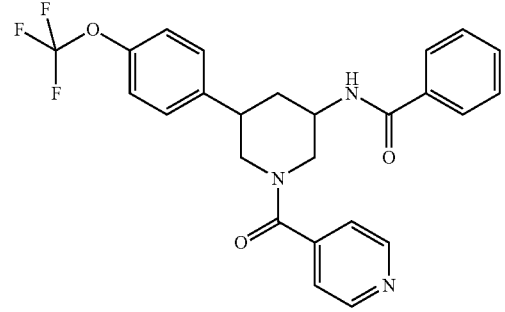 [SMILES: O=C(NC1CC(c2ccc(OC(F)(F)F)cc2)CN(C(=O)c2ccncc2)C1)c1ccccc1]

The enantiomer separation of 112 mg of the racemic cis isomer mixture (Example 114) according to Method 12D gave 37.6 mg of the compound from Example 115 (enantiomer 1).

LC-MS (Method 3B): $R_t$=1.82 min; m/z=470 [M+H]$^+$.

Example 116

N-{1-(Pyridin-4-ylcarbonyl)-5-[4-(trifluoromethoxy)phenyl]piperidin-3-yl}benzenecarboxamide [enantiomerically pure cis isomer]

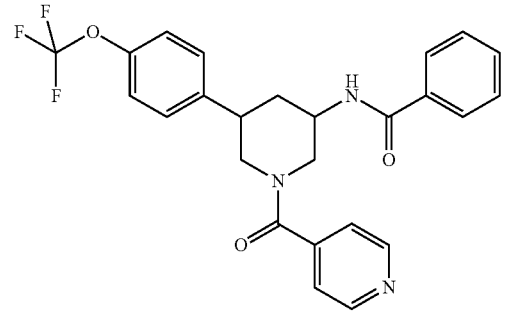 [SMILES: O=C(NC1CC(c2ccc(OC(F)(F)F)cc2)CN(C(=O)c2ccncc2)C1)c1ccccc1]

The enantiomer separation of 112 mg of the racemic cis isomer mixture (Example 114) according to Method 12D gave 33.4 mg of the compound from Example 116 (enantiomer 2).

LC-MS (Method 3B): $R_t$=1.82 min; m/z=470 [M+H]$^+$.

Example 117

N-{1-[(2R)-2-Methoxypropanoyl]-5-[4-(trifluoromethoxy)phenyl]piperidin-3-yl}benzenecarboxamide [racemic cis isomer]

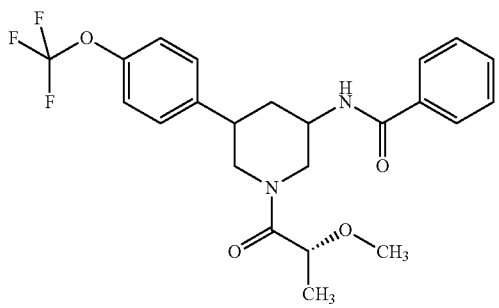 [SMILES: CO[C@H](C)C(=O)N1CC(NC(=O)c2ccccc2)CC(c2ccc(OC(F)(F)F)cc2)C1]

44 mg (0.41 mmol) of (2R)-2-methoxypropanoic acid together with 157 mg (0.41 mmol) of HATU and 67 mg (0.55 mmol) of 4-dimethylaminopyridine were initially charged in 2 ml of DMF, and 100 mg (0.27 mmol) of N-{5-[4-(trifluoromethoxy)phenyl]piperidin-3-yl}benzamide were added. The reaction mixture was stirred overnight at RT and then purified by preparative HPLC (Reprosil C18, water/acetonitrile gradient). Yield: 116 mg (94% of theory)

LC-MS (Method 2B): $R_t$=1.24 min; m/z=451 [M+H]$^+$;
$^1$H-NMR (400 MHz, DMSO-d$_6$): δ=8.63-8.27 (m, 1H), 7.87 (t, 2H), 7.65-7.22 (m, 7H), 4.70-4.43 (m, 1H), 4.40-4.10 (m, 2H), 4.03-3.85 (m, 1H), 3.29-3.20 (m, 3H), 3.12-2.62 (m, 3H), 2.13 (d, 1H), 1.89 (t, 1H), 1.34 (t, 2H), 1.25 (dd, 1H).

Example 118

N-[5-(3,4-Dimethylphenyl)-1-(morpholin-4-ylcarbonyl)piperidin-3-yl]benzenecarboxamide [racemic cis isomer]

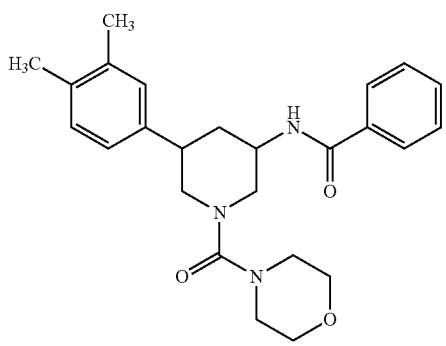 [SMILES: Cc1ccc(C2CC(NC(=O)c3ccccc3)CN(C(=O)N3CCOCC3)C2)cc1C]

At 0° C., 60 mg (0.19 mmol) of N-5-(3,4-dimethylphenyl)piperidin-3-yl}benzamide were initially charged in 1 ml of dichloromethane, and 58 mg (0.39 mmol) of morpholine-4-carbonyl chloride and 41 μl (0.29 mmol) of triethylamine were added. The mixture was slowly warmed to RT overnight. Water was added, and the reaction mixture was extracted. The organic phase was dried over magnesium sulphate and concentrated under reduced pressure. The residue was then purified by preparative HPLC (Reprosil C18, water/acetonitrile gradient). Yield: 58 mg (71% of theory)

LC-MS (Method 3B): $R_t$=1.88 min; m/z=422 [M+H]$^+$;
$^1$H-NMR (400 MHz, DMSO-d$_6$): δ=8.37 (d, 1H), 7.86 (d, 2H), 7.52 (d, 1H), 7.50-7.42 (m, 2H), 7.09 (d, 1H), 7.06 (s, 1H), 6.99 (d, 1H), 4.05-3.90 (m, 1H), 3.85 (d, 1H), 3.63 (d, 1H), 3.58 (s, 4H), 3.19 (br. s., 4H), 2.79 (d, 1H), 2.75-2.61 (m, 2H), 2.20 (d, 6H), 2.06 (d, 1H), 1.80 (d, 1H).

Example 119

N-{1-[(1-Aminocyclobutyl)carbonyl]-5-(3,4-dimethylphenyl)piperidin-3-yl}benzenecarboxamide hydrochloride [racemic cis isomer]

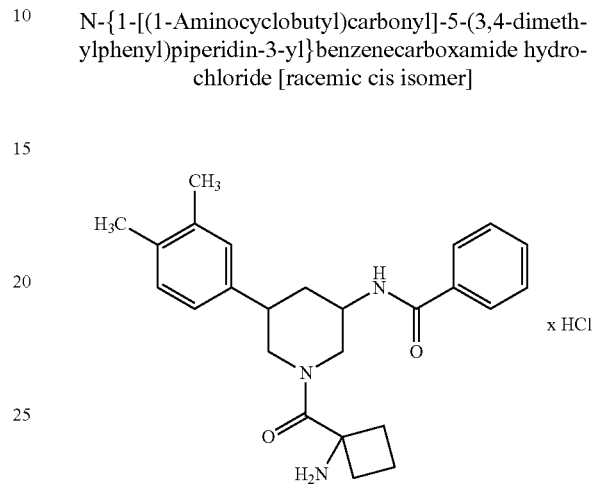

55 mg (0.14 mmol) of tert-butyl [1-({3-(3,4-dimethylphenyl)-5-[(phenylcarbonyl)amino]piperidin-1-yl}carbonyl)cyclobutyl]carbamate were dissolved in 7 ml of dioxane, 1.5 ml of concentrated hydrochloric acid were added and the mixture was immediately concentrated on a rotary evaporator. The residue was then purified by preparative HPLC (Reprosil C18, water/acetonitrile gradient). Yield: 19 mg (39% of theory)

LC-MS (Method 2B): $R_t$=0.98 min; m/z=406 [M+H]$^+$.

Example 120

N-{1-[(4-Aminotetrahydro-2H-pyran-4-yl)carbonyl]-5-(3,4-dimethylphenyl)piperidin-3-yl}benzenecarboxamide hydrochloride [racemic cis isomer]

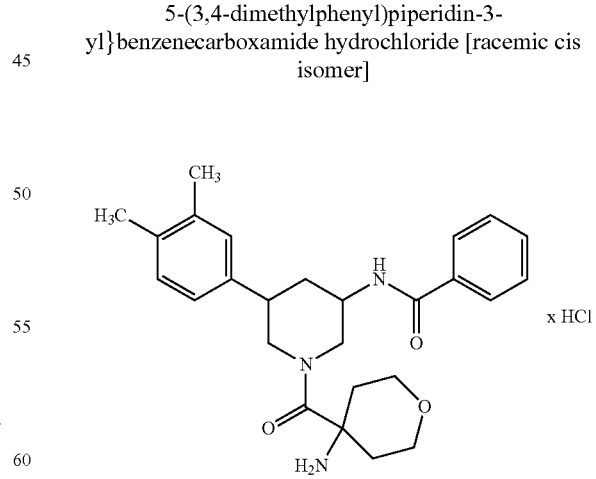

33 mg (0.06 mmol) of tert-butyl [4-({3-(3,4-dimethylphenyl)-5-[(phenylcarbonyl)amino]piperidin-1-yl}carbonyl)tetrahydro-2H-pyran-4-yl]carbamate were dissolved in 4 ml of dioxane, 1 ml of concentrated hydrochloric acid was added and the mixture was immediately concentrated on a rotary evaporator. The residue was then purified by preparative HPLC (Reprosil C18, water/acetonitrile gradient). Yield: 15 mg (57% of theory)

LC-MS (Method 2B): $R_t$=0.97 min; m/z=436 [M+H]$^+$;

$^1$H-NMR (400 MHz, DMSO-$d_6$): δ=8.38 (d, 1H), 7.86 (d, 2H), 7.52 (d, 1H), 7.50-7.43 (m, 2H), 7.09 (d, 1H), 7.05 (s, 1H), 6.99 (d, 1H), 4.02-3.86 (m, 1H), 3.77-3.66 (m, 2H), 3.63-3.46 (m, 2H), 2.81-2.58 (m, 3H), 2.20 (d, 7H), 2.08 (d, 6H), 1.85 (q, 1H), 1.61 (br. s., 1H), 1.46 (d, 1H).

Example 121

N-{1-(Morpholin-4-ylcarbonyl)-5-[3-(propan-2-yl)phenyl]piperidin-3-yl}benzenecarboxamide [racemic cis isomer]

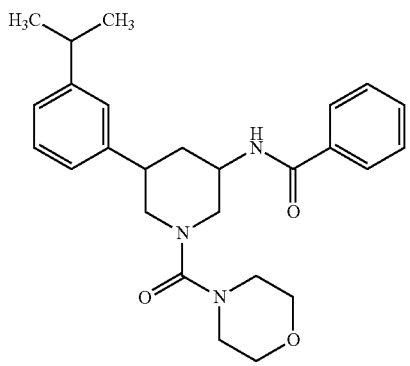 [SMILES: CC(C)c1cccc(C2CC(NC(=O)c3ccccc3)CN(C(=O)N3CCOCC3)C2)c1]

At 0° C., 180 mg (0.54 mmol) of N-{5-[3-(1-methylethyl)phenyl]piperidin-3-yl}benzamide were initially charged in 4 ml of dichloromethane, and 162 mg (1.08 mmol) of morpholine-4-carbonyl chloride and 114 μl (0.81 mmol) of triethylamine were added. The mixture was slowly warmed to RT overnight. Water was added, and the reaction mixture was extracted. The organic phase was dried over magnesium sulphate and concentrated under reduced pressure. The residue was then purified by preparative HPLC (Reprosil C18, water/acetonitrile gradient). Yield: 121 mg (51% of theory)

LC-MS (Method 3B): $R_t$=2.02 min; m/z=436 [M+H]$^+$;

$^1$H-NMR (500 MHz, DMSO-$d_6$): δ=8.36 (d, 1H), 7.87 (d, 2H), 7.52 (d, 1H), 7.49-7.43 (m, 2H), 7.29-7.23 (m, 1H), 7.16 (s, 1H), 7.11 (dd, 2H), 4.06-3.94 (m, 1H), 3.86 (d, 1H), 3.66 (d, 1H), 3.58 (d, 4H), 3.20 (br. s., 4H), 2.92-2.83 (m, 2H), 2.76 (t, 1H), 2.67 (t, 1H), 2.10 (d, 1H), 1.83 (q, 1H), 1.21 (d, 6H).

Example 122

N-[5-(2,3-Dimethylphenyl)-1-(morpholin-4-ylcarbonyl)piperidin-3-yl]benzenecarboxamide [racemic cis isomer]

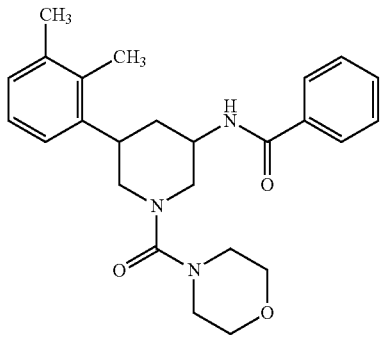 [SMILES: Cc1cccc(C2CC(NC(=O)c3ccccc3)CN(C(=O)N3CCOCC3)C2)c1C]

At 0° C., 80 mg (0.26 mmol) of N-[5-(2,3-dimethylphenyl)piperidin-3-yl]benzamide were initially charged in 1.5 ml of dichloromethane, and 78 mg (0.52 mmol) of morpholine-4-carbonyl chloride and 55 μl (0.39 mmol) of triethylamine were added. The mixture was slowly warmed to RT overnight. Water was added, and the reaction mixture was extracted. The organic phase was dried over magnesium sulphate and concentrated under reduced pressure. The residue was then purified by preparative HPLC (Reprosil C18, water/acetonitrile gradient). Yield: 75 mg (69% of theory)

LC-MS (Method 2B): $R_t$=1.17 min; m/z=422 [M+H]$^+$;

$^1$H-NMR (400 MHz, DMSO-$d_6$): δ=8.38 (d, 1H), 7.87 (d, 2H), 7.55-7.51 (m, 1H), 7.47 (t, 2H), 7.12-6.98 (m, 3H), 4.12-3.96 (m, 1H), 3.85 (dd, 1H), 3.63 (d, 1H), 3.60-3.54 (m, 4H), 3.23-3.16 (m, 4H), 3.17-3.08 (m, 1H), 2.78-2.60 (m, 2H), 2.26 (s, 6H), 2.06-1.95 (m, 1H), 1.88 (q, 1H).

Example 123

Ethyl 4-{1-(morpholin-4-ylcarbonyl)-5-[(phenylcarbonyl)amino]piperidin-3-yl}benzenecarboxylate [racemic cis isomer]

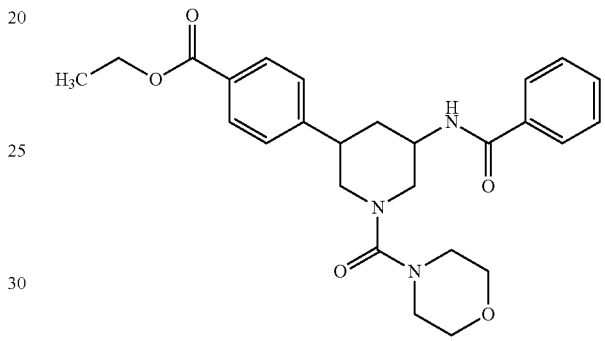

At 0° C., 500 mg (1.42 mmol) of ethyl 4-{5-[(phenylcarbonyl)amino]piperidin-3-yl}benzoate were initially charged in 8 ml of dichloromethane, and 424 mg (2.84 mmol) of morpholine-4-carbonyl chloride and 300 μl (2.13 mmol) of triethylamine were added. The mixture was slowly warmed to RT overnight. Water was added, and the reaction mixture was extracted. The organic phase was dried over magnesium sulphate and concentrated under reduced pressure. The residue was then purified by preparative HPLC (Reprosil C18, water/acetonitrile gradient). Yield: 551 mg (83% of theory)

LC-MS (Method 2B): $R_t$=1.12 min; m/z=466 [M+H]$^+$;

$^1$H-NMR (400 MHz, DMSO-$d_6$): δ=8.41 (d, 1H), 7.94 (d, 2H), 7.86 (d, 2H), 7.57-7.50 (m, 1H), 7.47 (dd, 4H), 4.31 (q, 2H), 4.09-3.96 (m, 1H), 3.86 (d, 1H), 3.68 (d, 1H), 3.58 (d, 4H), 3.21 (br. s., 4H), 3.08-2.96 (m, 1H), 2.86-2.76 (m, 1H), 2.74-2.64 (m, 1H), 2.13 (d, 1H), 1.83 (q, 1H), 1.32 (t, 3H).

Example 124

N-{1-(Morpholin-4-ylcarbonyl)-5-[3-(trifluoromethyl)phenyl]piperidin-3-yl}benzenecarboxamide [racemic cis isomer]

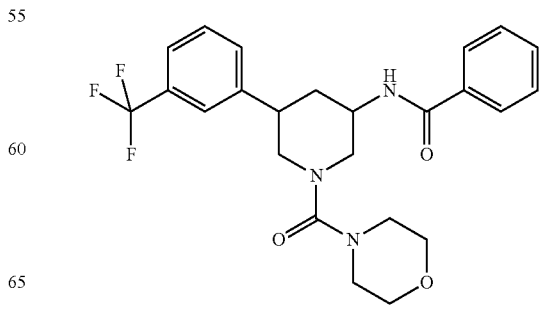

At 0° C., 165 mg (0.47 mmol) of N-{5-[3-(trifluoromethyl)phenyl]piperidin-3-yl}benzamide were initially charged in 17 ml of dichloromethane, and 71 mg (0.47 mmol) of morpholine-4-carbonyl chloride and 132 μl (0.95 mmol) of triethylamine were added. The mixture was slowly warmed to RT overnight. Water was added, and the reaction mixture was extracted. The organic phase was dried over magnesium sulphate and concentrated under reduced pressure. The residue was then purified by preparative HPLC (Reprosil C18, water/acetonitrile gradient). Yield: 202 mg (92% of theory)

LC-MS (Method 5B): $R_t$=2.19 min; m/z=462 [M+H]$^+$;
$^1$H-NMR (400 MHz, DMSO-d$_6$): δ=8.38 (d, 1H), 7.86 (d, 2H), 7.70-7.59 (m, 4H), 7.56-7.50 (m, 1H), 7.50-7.44 (m, 2H), 4.01 (dd, 1H), 3.86 (d, 1H), 3.74-3.52 (m, 5H), 3.21 (br. s., 4H), 3.11-3.02 (m, 1H), 2.84 (t, 1H), 2.75-2.63 (m, 1H), 2.13 (d, 1H), 1.86 (q, 1H).

Example 125

N-{1-(Morpholin-4-ylcarbonyl)-5-[3-(trifluoromethyl)phenyl]piperidin-3-yl}benzenecarboxamide [enantiomerically pure cis isomer]

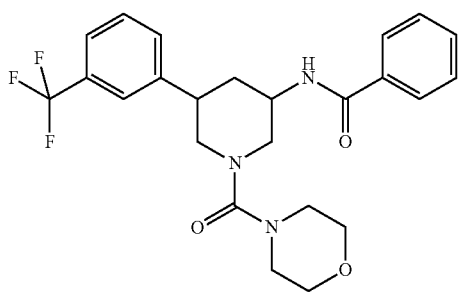 [SMILES: O=C(NC1CC(c2cccc(C(F)(F)F)c2)CN(C(=O)N2CCOCC2)C1)c1ccccc1]

The enantiomer separation of 202 mg of the racemic cis isomer mixture (Example 124) according to Method 13D gave 66 mg of the compound from Example 125 (enantiomer 1).

LC-MS (Method 1B): $R_t$=2.31 min; m/z=462 [M+H]$^+$.

Example 126

N-{1-(Morpholin-4-ylcarbonyl)-5-[4-(trifluoromethyl)phenyl]piperidin-3-yl}benzenecarboxamide [racemic cis isomer]

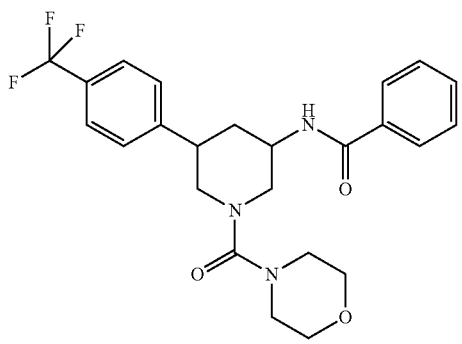 [SMILES: O=C(NC1CC(c2ccc(C(F)(F)F)cc2)CN(C(=O)N2CCOCC2)C1)c1ccccc1]

At 0° C., 705 mg (2.02 mmol) of N-{5-[4-(trifluoromethyl)phenyl]piperidin-3-yl}benzamide were initially charged in 70 ml of dichloromethane, and 321 mg (2.02 mmol) of morpholine-4-carbonyl chloride and 564 μl (4.04 mmol) of triethylamine were added. The mixture was slowly warmed to RT overnight. Water was added, and the reaction mixture was extracted. The organic phase was dried over magnesium sulphate and concentrated under reduced pressure. The residue was then purified by preparative HPLC (Reprosil C18, water/acetonitrile gradient). Yield: 960 mg (100% of theory)

LC-MS (Method 1B): $R_t$=2.32 min; m/z=462 [M+H]$^+$;
$^1$H-NMR (400 MHz, DMSO-d$_6$): δ=8.41 (d, 1H), 7.86 (d, 2H), 7.72 (d, 2H), 7.59-7.50 (m, 3H), 7.47 (t, 2H), 4.10-3.93 (m, 1H), 3.86 (d, 1H), 3.69 (d, 1H), 3.59 (t, 4H), 3.21 (br. s., 4H), 3.10-2.99 (m, 1H), 2.86-2.77 (m, 1H), 2.74-2.65 (m, 1H), 2.13 (d, 1H), 1.83 (q, 1H).

Example 127

N-{1-(Morpholin-4-ylcarbonyl)-5-[4-(trifluoromethyl)phenyl]piperidin-3-yl}benzenecarboxamide [enantiomerically pure cis isomer]

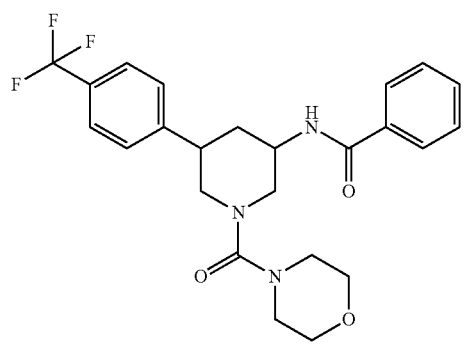 [SMILES: O=C(NC1CC(c2ccc(C(F)(F)F)cc2)CN(C(=O)N2CCOCC2)C1)c1ccccc1]

The enantiomer separation of 900 mg of the racemic cis isomer mixture (Example 126) according to Method 14D gave 388 mg of the compound from Example 127 (enantiomer 1).

Example 128

N-{1-(Morpholin-4-ylcarbonyl)-5-[4-(trifluoromethyl)phenyl]piperidin-3-yl}benzenecarboxamide [enantiomerically pure cis isomer]

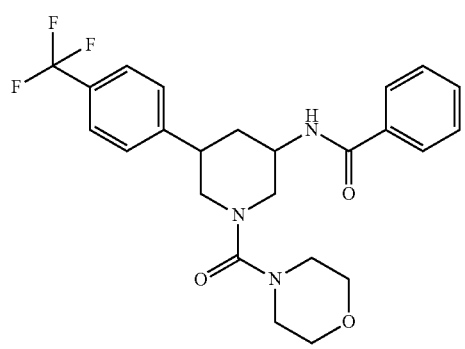 [SMILES: O=C(NC1CC(c2ccc(C(F)(F)F)cc2)CN(C(=O)N2CCOCC2)C1)c1ccccc1]

The enantiomer separation of 900 mg of the racemic cis isomer mixture (Example 126) according to Method 14D gave 361 mg of the compound from Example 128 (enantiomer 2).

LC-MS (Method 1B): $R_t$=2.31 min; m/z=462 [M+H]$^+$.

Example 129

N-{1-[(4-Hydroxypiperidin-1-yl)carbonyl]-5-[4-(trifluoromethyl)phenyl]piperidin-3-yl}benzenecarboxamide [racemic cis isomer]

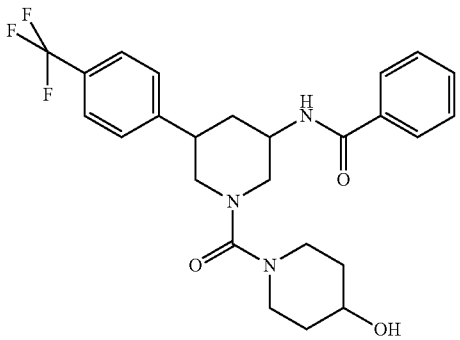 [SMILES: O=C(NC1CC(c2ccc(C(F)(F)F)cc2)CN(C(=O)N2CCC(O)CC2)C1)c1ccccc1]

80 mg (0.16 mmol) of 4-nitrophenyl 3-[(phenylcarbonyl)amino]-5-[4-(trifluoromethyl)phenyl]piperidine-1-carboxylate were initially charged in 1.7 ml of DMF, and 47 mg (0.47 mmol) of piperidin-4-ol and 22 mg (0.16 mmol) of potassium carbonate were added. The mixture was reacted in a microwave (Emrys Optimizer) at 150° C. for 15 min. The crude product was then purified by preparative HPLC (Reprosil C18, water/acetonitrile gradient). Yield: 62 mg (83% of theory)

LC-MS (Method 3B): $R_t$=1.79 min; m/z=476 [M+H]$^+$;

$^1$H-NMR (400 MHz, DMSO-d$_6$): δ=8.39 (d, 1H), 7.86 (d, 2H), 7.72 (d, 2H), 7.58-7.50 (m, 3H), 7.50-7.40 (m, 2H), 4.68 (d, 1H), 4.11-3.95 (m, 1H), 3.79 (d, 1H), 3.63 (d, 2H), 3.49 (d, 2H), 3.05 (t, 1H), 2.97-2.85 (m, 2H), 2.78 (t, 1H), 2.73-2.61 (m, 1H), 2.13 (d, 1H), 1.82 (q, 1H), 1.73 (d, 2H), 1.38-1.27 (m, 2H).

Example 130

N-{1-[(4-Hydroxypiperidin-1-yl)carbonyl]-5-[4-(trifluoromethyl)phenyl]piperidin-3-yl}benzenecarboxamide [enantiomerically pure cis isomer]

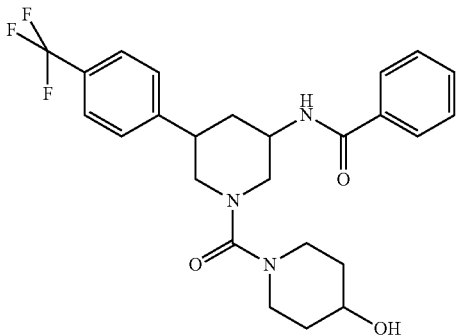 [SMILES: O=C(NC1CC(c2ccc(C(F)(F)F)cc2)CN(C(=O)N2CCC(O)CC2)C1)c1ccccc1]

The enantiomer separation of 52 mg of the racemic cis isomer mixture (Example 129) according to Method 15D gave 19 mg of the compound from Example 130 (enantiomer 1).

$^1$H-NMR (400 MHz, DMSO-d$_6$): δ=8.39 (d, 1H), 7.85 (d, 2H), 7.72 (d, 2H), 7.58-7.50 (m, 3H), 7.49-7.35 (m, 2H), 4.68 (d, 1H), 4.11-3.96 (m, 1H), 3.77 (dd, 1H), 3.68-3.58 (m, 2H), 3.54-3.43 (m, 2H), 3.04 (t, 1H), 2.91 (dt, 2H), 2.78 (t, 1H), 2.72-2.62 (m, 1H), 2.21-2.05 (m, 1H), 1.82 (q, 1H), 1.76-1.67 (m, 2H), 1.39-1.26 (m, 2H).

Example 131

N-{1-[(4-Hydroxypiperidin-1-yl)carbonyl]-5-[4-(trifluoromethyl)phenyl]piperidin-3-yl}benzenecarboxamide [enantiomerically pure cis isomer]

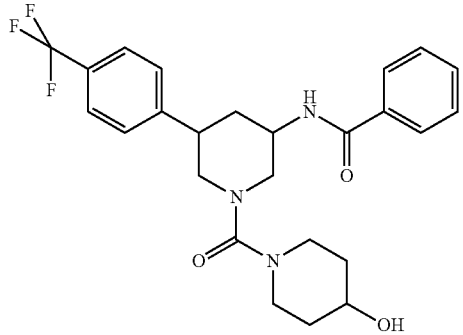 [SMILES: O=C(NC1CC(c2ccc(C(F)(F)F)cc2)CN(C(=O)N2CCC(O)CC2)C1)c1ccccc1]

The enantiomer separation of 52 mg of the racemic cis isomer mixture (Example 129) according to Method 15D gave 20 mg of the compound from Example 131 (enantiomer 2).

$^1$H-NMR (400 MHz, DMSO-d$_6$): δ=8.39 (d, 1H), 7.85 (d, 2H), 7.72 (d, 2H), 7.58-7.50 (m, 3H), 7.49-7.35 (m, 2H), 4.68 (d, 1H), 4.11-3.96 (m, 1H), 3.77 (dd, 1H), 3.68-3.58 (m, 2H), 3.54-3.43 (m, 2H), 3.04 (t, 1H), 2.91 (dt, 2H), 2.78 (t, 1H), 2.72-2.62 (m, 1H), 2.21-2.05 (m, 1H), 1.82 (q, 1H), 1.76-1.67 (m, 2H), 1.39-1.26 (m, 2H).

Example 132

N-{1-(Thiomorpholin-4-ylcarbonyl)-5-[4-(trifluoromethyl)phenyl]piperidin-3-yl}benzenecarboxamide [racemic cis isomer]

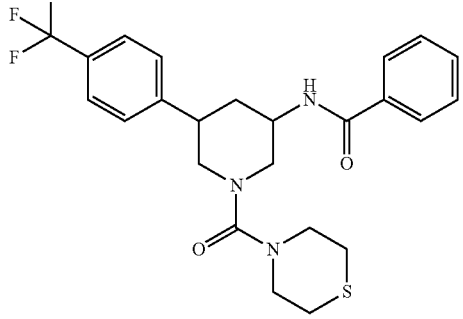

80 mg (0.16 mmol) of 4-nitrophenyl 3-[(phenylcarbonyl)amino]-5-[4-(trifluoromethyl)phenyl]piperidine-1-carboxylate were initially charged in 1.7 ml of DMF, and 48 mg (0.47 mmol) of thiomorpholine and 22 mg (0.16 mmol) of potassium carbonate were added. The mixture was reacted in a microwave (Emrys Optimizer) at 150° C. for 15 min. The crude product was then purified by preparative HPLC (Reprosil C18, water/acetonitrile gradient). Yield: 45 mg (60% of theory)

LC-MS (Method 3B): $R_t$=2.10 min; m/z=478 [M+H]$^+$;
$^1$H-NMR (400 MHz, DMSO-d$_6$): δ=8.40 (d, 1H), 7.86 (d, 2H), 7.72 (d, 2H), 7.59-7.50 (m, 3H), 7.50-7.43 (m, 2H), 4.09-3.95 (m, 1H), 3.79 (d, 1H), 3.64 (d, 1H), 3.46 (dt, 4H), 3.11-3.00 (m, 1H), 2.80 (t, 1H), 2.74-2.65 (m, 1H), 2.64-2.58 (m, 4H), 2.13 (d, 1H), 1.83 (q, 1H).

Example 133

N-(1-{[(2R,5R)-2,5-Dimethylpyrrolidin-1-yl]carbonyl}-5-[4-(trifluoromethyl)phenyl]piperidin-3-yl)benzenecarboxamide [racemic cis isomer]

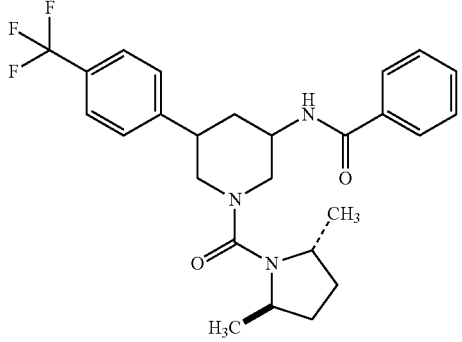 [SMILES: C[C@@H]1CC[C@@H](C)N1C(=O)N1CC(NC(=O)c2ccccc2)CC(c2ccc(C(F)(F)F)cc2)C1]

80 mg (0.16 mmol) of 4-nitrophenyl 3-[(phenylcarbonyl)amino]-5-[4-(trifluoromethyl)phenyl]piperidine-1-carboxylate were initially charged in 1.7 ml of DMF, and 46 mg (0.47 mmol) of (2R,5R)-2,5-dimethylpyrrolidine and 22 mg (0.16 mmol) of potassium carbonate were added. The mixture was reacted in a microwave (Emrys Optimizer) at 150° C. for 15 min. The crude product was then purified by preparative HPLC (Reprosil C18, water/acetonitrile gradient). Yield: 12 mg (15% of theory)

LC-MS (Method 2B): $R_t$=0.73 min; m/z=474 [M+H]$^+$;
$^1$H-NMR (400 MHz, DMSO-d$_6$): δ=8.38 (d, 1H), 7.89-7.81 (m, 2H), 7.71 (d, 2H), 7.59-7.51 (m, 3H), 7.49-7.43 (m, 2H), 4.16-3.93 (m, 3H), 3.92-3.61 (m, 2H), 3.13-2.57 (m, 3H), 2.19-1.99 (m, 2H), 1.92-1.76 (m, 2H), 1.64-1.38 (m, 2H), 1.20 (d, 3H), 1.07 (d, 3H).

Example 134

N-{1-[(1,1-Dioxidothiomorpholin-4-yl)carbonyl]-5-[4-(trifluoromethyl)phenyl]piperidin-3-yl}-benzenecarboxamide [racemic cic isomer]

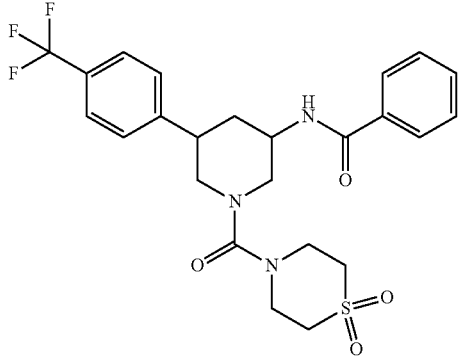 [SMILES: O=C(NC1CC(c2ccc(C(F)(F)F)cc2)CN(C(=O)N2CCS(=O)(=O)CC2)C1)c1ccccc1]

200 mg (0.39 mmol) of 4-nitrophenyl 3-[(phenylcarbonyl)amino]-5-[4-(trifluoromethyl)phenyl]piperidine-1-carboxylate were initially charged in 4.3 ml of DMF, and 158 mg (1.17 mmol) of thiomorpholine 1,1-dioxide and 54 mg (0.39 mmol) of potassium carbonate were added. The mixture was reacted in a microwave (Emrys Optimizer) at 150° C. for 15 min. The crude product was then purified by preparative HPLC (Reprosil C18, water/acetonitrile gradient).

Yield: 27 mg (14% of theory)
LC-MS (Method 2B): $R_t$=1.18 min; m/z=510 [M+H]$^+$;
$^1$H-NMR (400 MHz, DMSO-d$_6$): δ=8.42 (d, 1H), 7.86 (d, 2H), 7.73 (d, 2H), 7.58-7.51 (m, 3H), 7.47 (t, 2H), 4.11-3.98 (m, 1H), 3.88 (d, 1H), 3.72 (d, 1H), 3.64 (br. s., 4H), 3.19 (br. s., 4H), 3.08 (t, 1H), 2.91-2.81 (m, 1H), 2.77-2.68 (m, 1H), 2.15 (d, 1H), 1.84 (q, 1H).

Example 135

N-(2-Hydroxyethyl)-3-[(phenylcarbonyl)amino]-5-[4-(trifluoromethyl)phenyl]piperidine-1-carboxamide [racemic cis isomer]

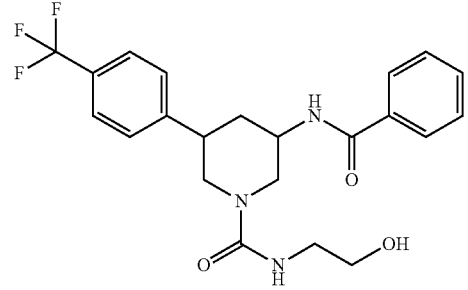 [SMILES: O=C(NC1CC(c2ccc(C(F)(F)F)cc2)CN(C(=O)NCCO)C1)c1ccccc1]

80 mg (0.16 mmol) of 4-nitrophenyl 3-[(phenylcarbonyl)amino]-5-[4-(trifluoromethyl)phenyl]piperidine-1-carboxylate were initially charged in 1.7 ml of DMF, and 29 mg (0.47 mmol) of 2-aminoethanol and 22 mg (0.16 mmol) of potassium carbonate were added. The mixture was reacted in a microwave (Emrys Optimizer) at 150° C. for 15 min. The crude product was then purified by preparative HPLC (Reprosil C18, water/acetonitrile gradient). Yield: 10 mg (15% of theory)

LC-MS (Method 1B): $R_t$=2.12 min; m/z=436 [M+H]$^+$;
$^1$H-NMR (400 MHz, DMSO-d$_6$): δ=8.39 (d, 1H), 7.85 (d, 2H), 7.72 (d, 2H), 7.59-7.50 (m, 3H), 7.47 (t, 2H), 6.64 (t, 1H), 4.60 (t, 1H), 4.20 (d, 1H), 4.08 (d, 1H), 4.03-3.91 (m, 1H), 3.40 (q, 2H), 3.11 (q, 2H), 2.96-2.84 (m, 1H), 2.77-2.68 (m, 1H), 2.68-2.58 (m, 1H), 2.10 (br. s., 1H), 1.76 (q, 1H).

Example 136

N-{1-[(3-Hydroxyazetidin-1-yl)carbonyl]-5-[4-(trifluoromethyl)phenyl]piperidin-3-yl}benzenecarboxamide [racemic cis isomer]

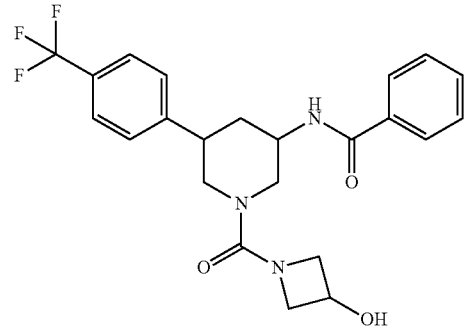 [SMILES: O=C(NC1CC(c2ccc(C(F)(F)F)cc2)CN(C(=O)N2CC(O)C2)C1)c1ccccc1]

80 mg (0.16 mmol) of 4-nitrophenyl 3-[(phenylcarbonyl)amino]-5-[4-(trifluoromethyl)phenyl]piperidine-1-carboxylate were initially charged in 1.7 ml of DMF, and 51 mg (0.47 mmol) of azetidin-3-ol hydrochloride and 22 mg (0.16 mmol) of potassium carbonate were added. The mixture was reacted in a microwave (Emrys Optimizer) at 150° C. for 15 min. The crude product was then purified by preparative HPLC (Reprosil C18, water/acetonitrile gradient).

Yield: 44 mg (62% of theory)

LC-MS (Method 3B): $R_t$=1.74 min; m/z=448 [M+H]$^+$;

$^1$H-NMR (400 MHz, DMSO-d$_6$): δ=8.38 (d, 1H), 7.86 (d, 2H), 7.72 (d, 2H), 7.59-7.50 (m, 3H), 7.47 (t, 2H), 5.58 (d, 1H), 4.45-4.35 (m, 1H), 4.18-4.05 (m, 2H), 3.97 (d, 2H), 3.87 (d, 1H), 3.77-3.62 (m, 2H), 2.93 (t, 1H), 2.83-2.62 (m, 2H), 2.10 (d, 1H), 1.84 (q, 1H).

Example 137

N-{1-[(4-Cyanopiperidin-1-yl)carbonyl]-5-[4-(trifluoromethyl)phenyl]piperidin-3-yl}benzenecarboxamide [racemic cis isomer]

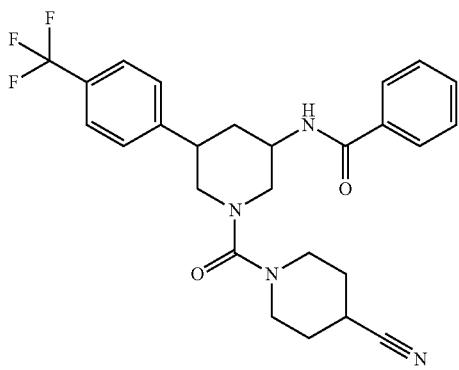 [SMILES: N#CC1CCN(C(=O)N2CC(NC(=O)c3ccccc3)CC(c3ccc(C(F)(F)F)cc3)C2)CC1]

115 mg (0.22 mmol) of 4-nitrophenyl 3-[(phenylcarbonyl)amino]-5-[4-(trifluoromethyl)phenyl]piperidine-1-carboxylate were initially charged in 2.5 ml of DMF, and 74 mg (0.67 mmol) of piperidine-4-carbonitrile and 31 mg (0.22 mmol) of potassium carbonate were added. The mixture was reacted in a microwave (Emrys Optimizer) at 150° C. for 15 min. The crude product was then purified by preparative HPLC (Reprosil C18, water/acetonitrile gradient). Yield: 71 mg (65% of theory)

LC-MS (Method 1B): $R_t$=2.43 min; m/z=485 [M+H]$^+$;

$^1$H-NMR (400 MHz, DMSO-d$_6$): δ=8.40 (d, 1H), 7.86 (d, 2H), 7.72 (d, 2H), 7.57-7.51 (m, 3H), 7.47 (t, 2H), 4.09-3.96 (m, 1H), 3.81 (d, 1H), 3.64 (d, 1H), 3.44-3.35 (m, 2H), 3.07 (m, 4H), 2.80 (t, 1H), 2.74-2.62 (m, 1H), 2.12 (br. s., 1H), 1.95-1.63 (m, 5H).

Example 138

3-[(Phenylcarbonyl)amino]-N-(pyridin-4-yl)-5-[4-(trifluoromethyl)phenyl]piperidine-1-carboxamide [racemic cis isomer]

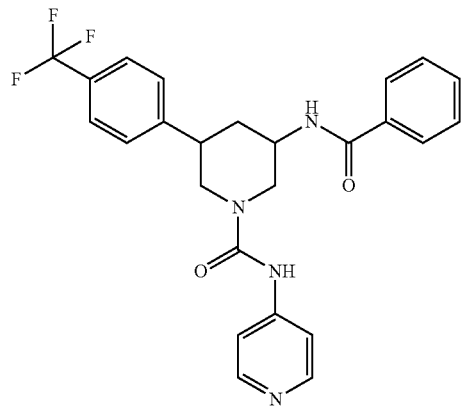 [SMILES: O=C(NC1CC(c2ccc(C(F)(F)F)cc2)CN(C(=O)Nc2ccncc2)C1)c1ccccc1]

80 mg (0.23 mmol) of ethyl-N-{5-[4-(trifluoromethyl)phenyl]piperidin-3-yl}benzamide were initially charged in 2 ml of THF, and 28 mg (0.23 mmol) of 4-isocyanatopyridine and 35 μl (0.25 mmol) of triethylamine were added. The mixture was stirred at RT overnight. The reaction mixture was then purified by preparative HPLC (Reprosil C18, water/acetonitrile gradient). Yield: 75 mg (70% of theory)

LC-MS (Method 1B): $R_t$=1.64 min; m/z=469 [M+H]$^+$;

$^1$H-NMR (400 MHz, DMSO-d$_6$): δ=9.07 (s, 1H), 8.47 (d, 1H), 8.32 (d, 2H), 7.87 (d, 2H), 7.74 (d, 2H), 7.59 (d, 2H), 7.54-7.42 (m, 5H), 4.47-4.22 (m, 2H), 4.16-3.98 (m, 1H), 3.11-2.90 (m, 2H), 2.80 (t, 1H), 2.16 (d, 1H), 1.84 (q, 1H).

Example 139

N-(4-Hydroxycyclohexyl)-3-[(phenylcarbonyl)amino]-5-[4-(trifluoromethyl)phenyl]piperidine-1-carboxamide [racemic cis isomer]

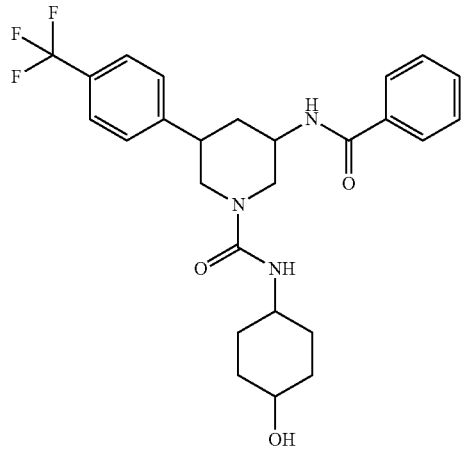 [SMILES: O=C(NC1CC(c2ccc(C(F)(F)F)cc2)CN(C(=O)NC2CCC(O)CC2)C1)c1ccccc1]

80 mg (0.16 mmol) of 4-nitrophenyl 3-[(phenylcarbonyl)amino]-5-[4-(trifluoromethyl)phenyl]piperidine-1-carboxylate were initially charged in 1.7 ml of DMF, and 71 mg (0.47 mmol) of cis-4-aminocyclohexanol hydrochloride and 129 mg (0.94 mmol) of potassium carbonate were added. The mixture was reacted in a microwave (Emrys Optimizer) at 150° C. for 15 min. The crude product was then purified by preparative HPLC (Reprosil C18, water/acetonitrile gradient). Yield: 3 mg (4% of theory)

LC-MS (Method 1B): $R_t$=2.24 min; m/z=490 [M+H]$^+$;

$^1$H-NMR (500 MHz, CD$_3$OD): δ=7.83 (d, 2H), 7.64 (d, 2H), 7.57-7.50 (m, 3H), 7.50-7.44 (m, 2H), 6.39 (d, 1H), 4.25 (dd, 4H), 4.17-4.08 (m, 2H), 3.87 (br. s., 2H), 3.65-3.58 (m, 2H), 3.02-2.94 (m, 2H), 2.84-2.74 (m, 4H), 2.28 (d, 2H), 1.87 (q, 2H).

Example 140

N-{1-[(2,6-Dimethylmorpholin-4-yl)carbonyl]-5-[4-(trifluoromethyl)phenyl]piperidin-3-yl}benzenecarboxamide [racemic cis isomer]

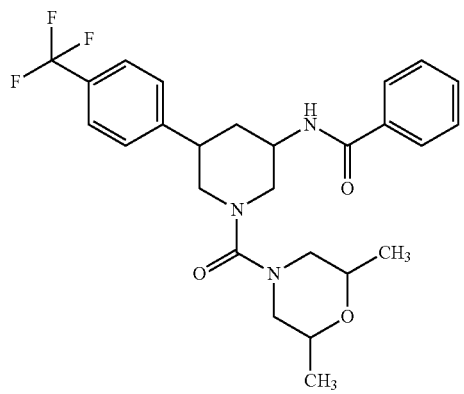 [SMILES: CC1CN(C(=O)N2CC(NC(=O)c3ccccc3)CC(c3ccc(C(F)(F)F)cc3)C2)CC(C)O1]

80 mg (0.16 mmol) of 4-nitrophenyl 3-[(phenylcarbonyl)amino]-5-[4-(trifluoromethyl)phenyl]piperidine-1-carboxylate were initially charged in 1.7 ml of DMF, and 53 mg (0.47 mmol) of (2R,6S)-2,6-dimethylmorpholine and 22 mg (0.16 mmol) of potassium carbonate were added. The mixture was reacted in a microwave (Emrys Optimizer) at 150° C. for 15 min. The crude product was then purified by preparative HPLC (Reprosil C18, water/acetonitrile gradient). Yield: 49 mg (64% of theory)

LC-MS (Method 3B): $R_t$=1.80 min; m/z=490 [M+H]$^+$;

$^1$H-NMR (400 MHz, DMSO-d$_6$): δ=8.41 (d, 1H), 7.86 (d, 2H), 7.72 (d, 2H), 7.58-7.50 (m, 3H), 7.47 (t, 2H), 4.13-3.94 (m, 1H), 3.83 (d, 1H), 3.67 (d, 1H), 3.59-3.44 (m, 4H), 3.11-3.00 (m, 1H), 2.80 (t, 1H), 2.69 (t, 1H), 2.48-2.42 (m, 2H), 2.13 (d, 1H), 1.86 (q, 1H), 1.12 (d, 3H), 1.08 (d, 3H).

Example 141

N-{1-[(3-Oxopiperazin-1-yl)carbonyl]-5-[4-(trifluoromethyl)phenyl]piperidin-3-yl}benzenecarboxamide [racemic cis isomer]

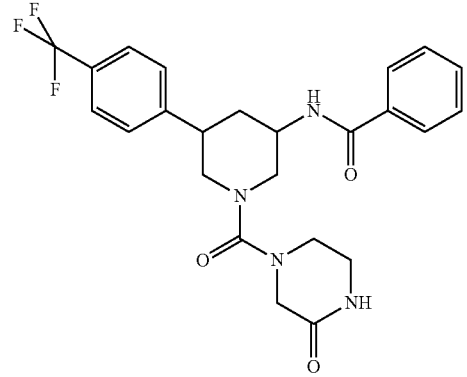 [SMILES: O=C1CN(C(=O)N2CC(NC(=O)c3ccccc3)CC(c3ccc(C(F)(F)F)cc3)C2)CCN1]

80 mg (0.16 mmol) of 4-nitrophenyl 3-[(phenylcarbonyl)amino]-5-[4-(trifluoromethyl)phenyl]piperidine-1-carboxylate were initially charged in 1.7 ml of DMF, and 47 mg (0.47 mmol) of piperazin-2-one and 22 mg (0.16 mmol) of potassium carbonate were added. The mixture was reacted in a microwave (Emrys Optimizer) at 150° C. for 15 min. The crude product was then purified by preparative HPLC (Reprosil C18, water/acetonitrile gradient). Yield: 39 mg (52% of theory)

LC-MS (Method 3B): $R_t$=1.69 min; m/z=475 [M+H]$^+$;

$^1$H-NMR (400 MHz, DMSO-d$_6$): δ=8.41 (d, 1H), 7.96 (br. s., 1H), 7.86 (d, 2H), 7.72 (d, 2H), 7.58-7.42 (m, 5H), 4.11-3.98 (m, 1H), 3.85 (d, 1H), 3.76 (s, 2H), 3.70 (d, 1H), 3.46-3.38 (m, 2H), 3.23 (br. s., 2H), 3.07 (t, 1H), 2.85 (t, 1H), 2.78-2.67 (m, 1H), 2.14 (d, 1H), 1.85 (q, 1H).

Example 142

3-[(Phenylcarbonyl)amino]-N-(tetrahydrofuran-2-ylmethyl)-5-[4-(trifluoromethyl)phenyl]piperidine-1-carboxamide [racemic cis isomer]

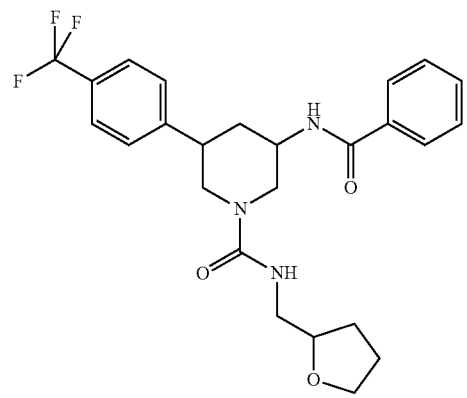 [SMILES: O=C(NC1CC(c2ccc(C(F)(F)F)cc2)CN(C(=O)NCC2CCCO2)C1)c1ccccc1]

80 mg (0.23 mmol) of ethyl-N-{5-[4-(trifluoromethyl)phenyl]piperidin-3-yl}benzamide were initially charged in 2 ml of THF, and 29 mg (0.23 mmol) of 2-(isocyanatomethyl)tetrahydrofuran and 35 µl (0.25 mmol) of triethylamine were added. The mixture was stirred at RT overnight. The reaction mixture was then purified by preparative HPLC (Reprosil C18, water/acetonitrile gradient). Yield: 88 mg (81% of theory)

LC-MS (Method 1B): $R_t$=2.34 min; m/z=476 [M+H]$^+$;

$^1$H-NMR (400 MHz, DMSO-d$_6$): δ=8.39 (d, 1H), 7.85 (d, 2H), 7.72 (d, 2H), 7.59-7.44 (m, 5H), 6.72 (q, 1H), 4.20 (d, 1H), 4.11 (d, 1H), 3.96 (br. s., 1H), 3.90-3.81 (m, 1H), 3.79-3.70 (m, 1H), 3.60 (q, 1H), 3.19-3.00 (m, 2H), 2.93-2.83 (m, 1H), 2.79-2.69 (m, 1H), 2.63 (t, 1H), 2.12 (d, 1H), 1.91-1.69 (m, 4H), 1.62-1.48 (m, 1H).

The following examples were prepared according to the synthesis of Example 141:

| Example | Structure | LC-MS Method | $R_t$ [min] | MS (ESIpos) m/z |
|---|---|---|---|---|
| 143 | 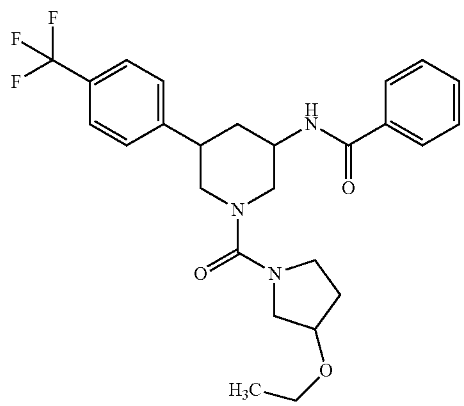 [SMILES: CCOC1CCN(C(=O)N2CC(NC(=O)c3ccccc3)CC(c3ccc(C(F)(F)F)cc3)C2)C1] | 1B | 2.50 | 490 |
| 144 | 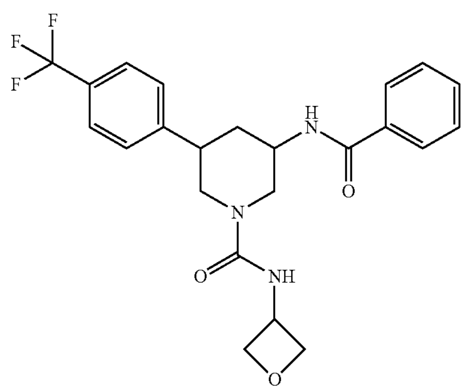 [SMILES: O=C(NC1CC(c2ccc(C(F)(F)F)cc2)CN(C(=O)NC2COC2)C1)c1ccccc1] | 1B | 2.25 | 448 |
| 145 | 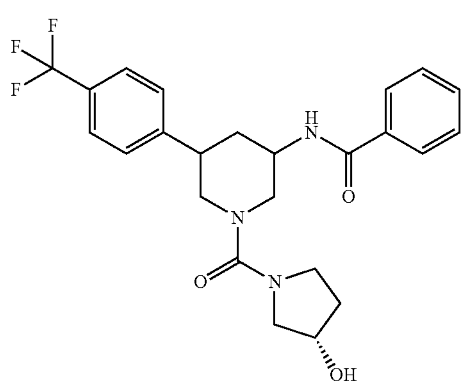 [SMILES: O=C(NC1CC(c2ccc(C(F)(F)F)cc2)CN(C(=O)N2CC[C@H](O)C2)C1)c1ccccc1] | 2B | 1.14 | 462 |

| Example | Structure | LC-MS Method | $R_t$ [min] | MS (ESIpos) m/z |
|---|---|---|---|---|
| 146 | 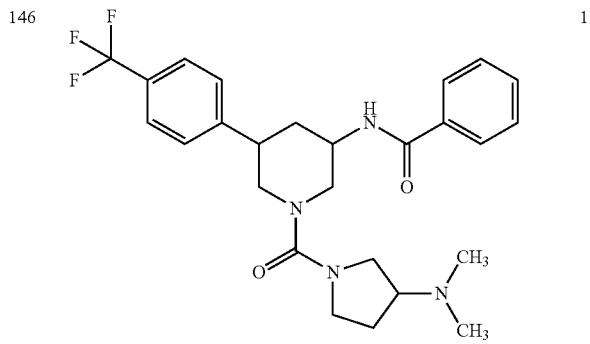 | 1B | 1.57 | 489 |
| 147 | 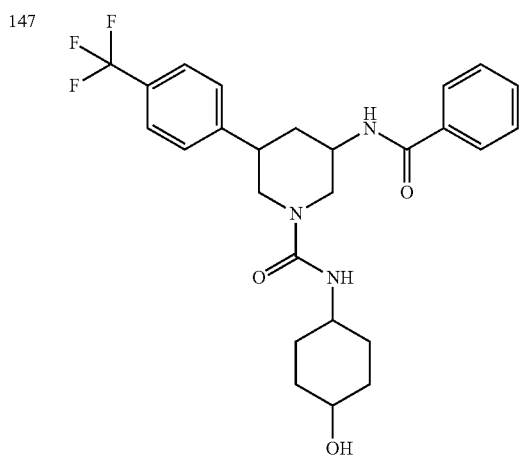 | 3B | 1.79 | 490 |
| 148 | 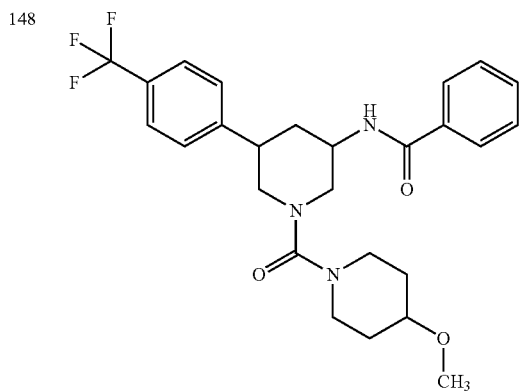 | 2B | 1.27 | 490 |

| Example | Structure | LC-MS Method | $R_t$ [min] | MS (ESIpos) m/z |
|---|---|---|---|---|
| 149 | 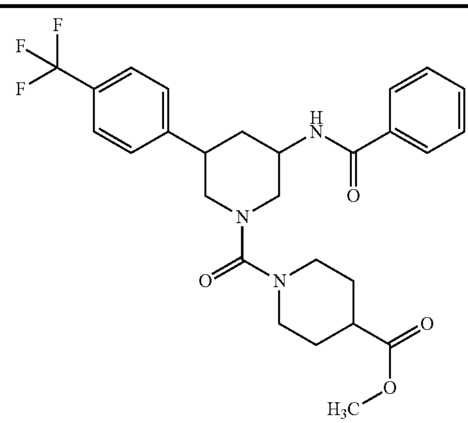 | 1B | 2.51 | 518 |

Example 150

1-({3-[(Phenylcarbonyl)amino]-5-[4-(trifluoromethyl)phenyl]piperidin-1-yl}carbonyl)piperidine-4-carboxylic acid [racemic cis isomer]

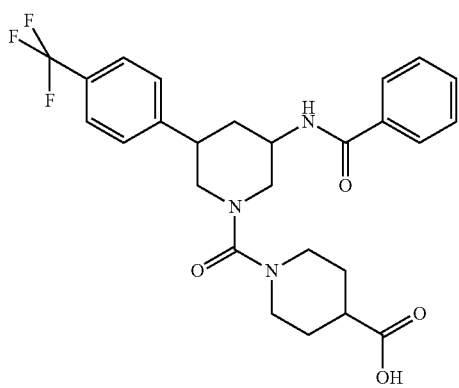 [SMILES: O=C(NC1CC(c2ccc(C(F)(F)F)cc2)CN(C(=O)N2CCC(C(=O)O)CC2)C1)c1ccccc1]

27 mg (0.05 mmol) of methyl 1-({3-[(phenylcarbonyl)amino]-5-[4-(trifluoromethyl)phenyl]piperidin-1-yl}carbonyl)piperidine-4-carboxylate were initially charged in 0.8 ml each of THF and water, and 4 mg (0.15 mmol) of lithium hydroxide were added. The mixture was stirred at RT overnight. The reaction solution was concentrated under reduced pressure and acidified, and the precipitate was filtered off and dried. Yield: 16 mg (62% of theory)

LC-MS (Method 1B): $R_t$=2.29 min; m/z=504 [M+H]$^+$;

$^1$H-NMR (400 MHz, DMSO-$d_6$): δ=12.23 (s, 1H), 8.39 (d, 1H), 7.86 (d, 2H), 7.72 (d, 2H), 7.57-7.50 (m, 3H), 7.49-7.40 (m, 2H), 4.03 (dd, 1H), 3.80 (d, 1H), 3.71-3.52 (m, 3H), 3.10-2.98 (m, 1H), 2.94-2.62 (m, 4H), 2.47-2.35 (m, 1H), 2.11 (br. s., 1H), 1.86-1.77 (m, 3H), 1.49 (d, 2H).

Example 151

1-({3-[(Phenylcarbonyl)amino]-5-[4-(trifluoromethyl)phenyl]piperidin-1-yl}carbonyl)piperidine-4-carboxamide [racemic cis isomer]

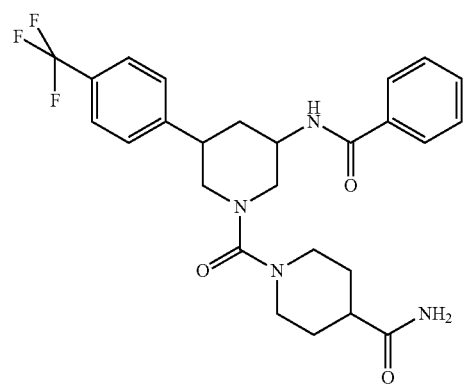 [SMILES: NC(=O)C1CCN(C(=O)N2CC(NC(=O)c3ccccc3)CC(c3ccc(C(F)(F)F)cc3)C2)CC1]

85 mg (0.17 mmol) of 1-({3-[(phenylcarbonyl)amino]-5-[4-(trifluoromethyl)phenyl]piperidin-1-yl}carbonyl)piperidine-4-carboxylic acid together with 80 mg (0.21 mmol) of HATU and 34 mg (0.28 mmol) of 4-dimethylaminopyridine were initially charged in 1.3 ml of DMF, and 11 mg (0.14 mmol) of ammonium acetate were added. The reaction mixture was stirred overnight at RT and then purified by preparative HPLC (Reprosil C18, water/acetonitrile gradient). Yield: 46 mg (53% of theory)

LC-MS (Method 3B): $R_t$=1.72 min; m/z=503 [M+H]$^+$;

$^1$H-NMR (400 MHz, DMSO-$d_6$): δ=8.40 (d, 1H), 7.86 (d, 2H), 7.72 (d, 2H), 7.59-7.51 (m, 3H), 7.51-7.41 (m, 2H), 7.27 (s, 1H), 6.77 (s, 1H), 4.02 (d, 1H), 3.80 (d, 1H), 3.65 (br. s., 3H), 3.11-2.97 (m, 1H), 2.84-2.64 (m, 4H), 2.32-2.21 (m, 1H), 2.12 (br. s., 1H), 1.82 (q, 1H), 1.68 (br. s., 2H), 1.49 (br. s., 2H).

Example 152

N,N-Dimethyl-1-({3-[(phenylcarbonyl)amino]-5-[4-(trifluoromethyl)phenyl]piperidin-1-yl}carbonyl)piperidine-4-carboxamide [racemic cis isomer]

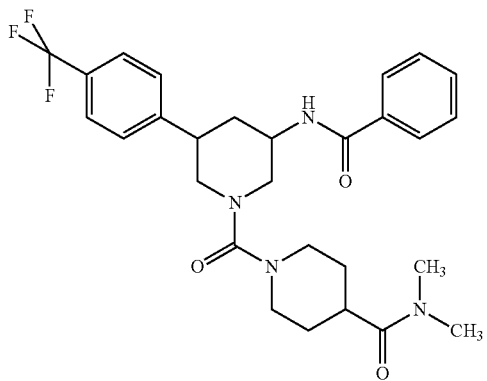 [SMILES: CN(C)C(=O)C1CCN(C(=O)N2CC(NC(=O)c3ccccc3)CC(c3ccc(C(F)(F)F)cc3)C2)CC1]

85 mg (0.17 mmol) of 1-({3-[(phenylcarbonyl)amino]-5-[4-(trifluoromethyl)phenyl]piperidin-1-yl}carbonyl)piperidine-4-carboxylic acid together with 80 mg (0.21 mmol) of HATU and 34 mg (0.28 mmol) of 4-dimethylaminopyridine were initially charged in 1.3 ml of DMF, and 6 mg (0.14 mmol) of N-methylmethanamine were added. The reaction mixture was stirred overnight at RT and then purified by preparative HPLC (Reprosil C18, water/acetonitrile gradient). Yield: 62 mg (69% of theory)

LC-MS (Method 3B): $R_t$=1.86 min; m/z=531 [M+H]$^+$;
$^1$H-NMR (400 MHz, DMSO-$d_6$): δ=8.40 (d, 1H), 7.85 (d, 2H), 7.72 (d, 2H), 7.58-7.42 (m, 5H), 4.10-3.99 (m, 1H), 3.78 (br. s., 1H), 3.72-3.59 (m, 3H), 3.09-2.98 (m, 4H), 2.90-2.75 (m, 7H), 2.73-2.63 (m, 1H), 2.12 (d, 1H), 1.82 (q, 1H), 1.61 (br. s., 2H), 1.48 (d, 2H).

Example 153

N-{1-[(1-Cyanocyclopropyl)carbonyl]-5-[4-(trifluoromethyl)phenyl]piperidin-3-yl}benzenecarboxamide [racemic cis isomer]

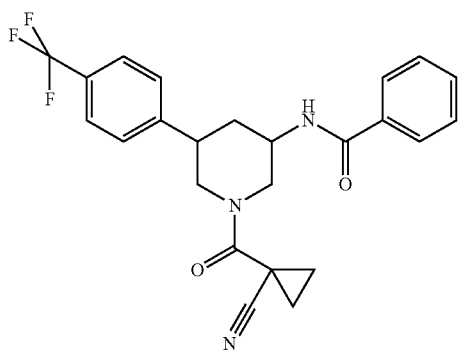 [SMILES: N#CC1(C(=O)N2CC(NC(=O)c3ccccc3)CC(c3ccc(C(F)(F)F)cc3)C2)CC1]

31 mg (0.28 mmol) of 1-cyanocyclopropanecarboxylic acid together with 131 mg (0.34 mmol) of HATU and 56 mg (0.46 mmol) of 4-dimethylaminopyridine were initially charged in 2 ml of DMF, and 80 mg (0.23 mmol) of N-{5-[4-(trifluoromethyl)phenyl]piperidin-3-yl}benzamide were added. The reaction mixture was stirred overnight at RT and then purified by preparative HPLC (Reprosil C18, water/acetonitrile gradient). Yield: 73 mg (72% of theory)

LC-MS (Method 2B): $R_t$=1.25 min; m/z=442 [M+H]$^+$;
$^1$H-NMR (400 MHz, DMSO-$d_6$): δ=8.50 (d, 1H), 7.88 (d, 2H), 7.76 (d, 2H), 7.65-7.43 (m, 5H), 4.53 (d, 1H), 4.31 (d, 1H), 4.05 (br. s., 1H), 3.26-3.09 (m, 2H), 2.18 (d, 1H), 1.97 (q, 1H), 1.64 (d, 5H).

Example 154

N-{1-[(3-Methylpyridin-4-yl)carbonyl]-5-[4-(trifluoromethyl)phenyl]piperidin-3-yl}benzenecarboxamide [racemic cis isomer]

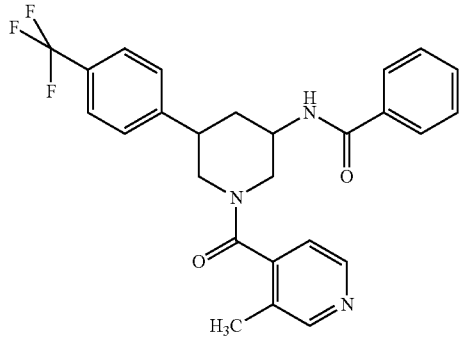 [SMILES: Cc1cnccc1C(=O)N1CC(NC(=O)c2ccccc2)CC(c2ccc(C(F)(F)F)cc2)C1]

38 mg (0.28 mmol) of 3-methylpyridine-4-carboxylic acid together with 131 mg (0.34 mmol) of HATU and 56 mg (0.46 mmol) of 4-dimethylaminopyridine were initially charged in 2 ml of DMF, and 80 mg (0.23 mmol) of N-{5-[4-(trifluoromethyl)phenyl]piperidin-3-yl}benzamide were added. The reaction mixture was stirred overnight at RT and then purified by preparative HPLC (Reprosil C18, water/acetonitrile gradient). Yield: 65 mg (59% of theory)

LC-MS (Method 1B): $R_t$=2.14 min; m/z=468 [M+H]$^+$.

Example 155

N-{1-[(4-Cyanopiperidin-1-yl)carbonyl]-5-(4-ethylphenyl)piperidin-3-yl}pyridine-4-carboxamide [racemic cis isomer]

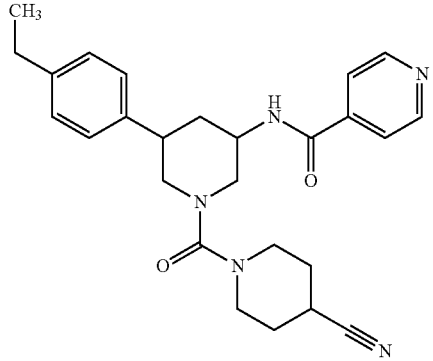 [SMILES: CCc1ccc(C2CC(NC(=O)c3ccncc3)CN(C(=O)N3CCC(C#N)CC3)C2)cc1]

70 mg (0.21 mmol) of the compound from Example 56A were reacted with 28 mg (0.23 mmol) of isonicotinic acid according to General Method 1. In a variation to General Method 1, more isonicotinic acid, HATU and N,N-diisopropylamine were added. After a reaction time of two days in total, the mixture was worked up as described in General Method 1. Yield: 42 mg (46% of theory)

HPLC (Method 2A): R$_t$=3.94 min; m/z=446 [M+H]$^+$;
$^1$H-NMR (400 MHz, DMSO-d$_6$): δ=8.72 (d, 2H), 8.67 (d, 1H), 7.76 (d, 2H), 7.21-7.19 (m, 3H), 4.05-3.95 (m, 1H), 3.80 (br d, 1H), 3.60 (br d, 1H), 3.37 (q, 2H), 3.12-3.02 (m, 3H), 2.90-2.82 (m, 1H), 2.77-2.60 (m, 3H), 2.37 (q, 2H), 2.08 (br d, 1H), 1.92-1.85 (m, 2H), 1.77 (q, 1H), 1.72-1.62 (m, 2H), 1.17 (t, 3H).

Example 156

N-{1-[(4-Cyanopiperidin-1-yl)carbonyl]-5-(4-ethylphenyl)piperidin-3-yl}-3-methoxybenzenecarboxamide [racemic cis isomer]

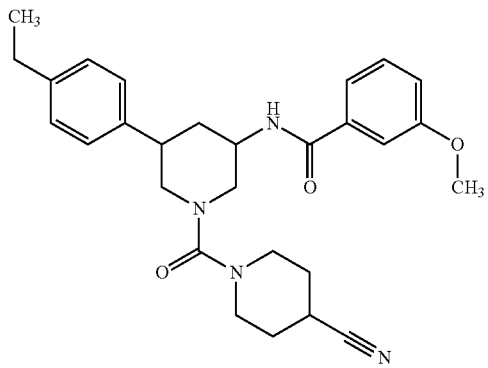 [SMILES: CCc1ccc(C2CC(NC(=O)c3cccc(OC)c3)CN(C(=O)N3CCC(C#N)CC3)C2)cc1]

70 mg (0.21 mmol) of the compound from Example 56A were reacted with 39 mg (0.23 mmol) of 3-methoxybenzoyl chloride in dichloromethane according to General Method 2. Yield: 87 mg (89% of theory)
HPLC (Method 2A): R$_t$=4.48 min; m/z=475 [M+H]$^+$;
$^1$H-NMR (400 MHz, DMSO-d$_6$): δ=8.34 (d, 1H), 7.47-7.42 (m, 1H), 7.42-7.34 (m, 2H), 7.23-7.15 (m, 4H), 7.09 (dd, 1H), 4.05-3.92 (m, 1H), 3.83-3.75 (m, 1H), 3.80 (s, 3H), 3.62 (br d, 1H), 3.38 (br d, 2H), 3.13-3.01 (m, 3H), 2.91-2.81 (m, 1H), 2.71 (s, 2H), 2.58 (q, 2H), 2.07 (br d, 1H), 1.93-1.84 (m, 2H), 1.78 (q, 1H), 1.74-1.63 (m, 2H), 1.17 (t, 3H).

Example 157

N-{1-[(4-Cyanopiperidin-1-yl)carbonyl]-5-(4-ethylphenyl)piperidin-3-yl}-3-fluorobenzenecarboxamide [racemic cis isomer]

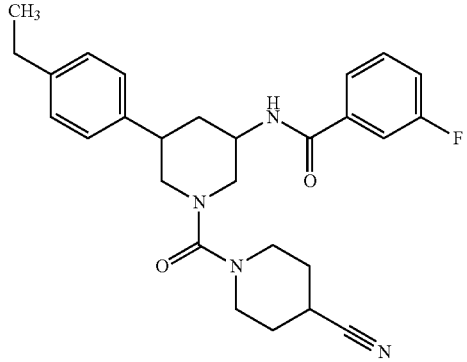 [SMILES: CCc1ccc(C2CC(NC(=O)c3cccc(F)c3)CN(C(=O)N3CCC(C#N)CC3)C2)cc1]

70 mg (0.21 mmol) of the compound from Example 56A were reacted with 36 mg (0.23 mmol) of 3-fluorobenzoyl chloride in dichloromethane according to General Method 2. Yield: 62 mg (66% of theory)
HPLC (Method 2A): R$_t$=4.49 min; m/z=463 [M+H]$^+$;
$^1$H-NMR (400 MHz, DMSO-d$_6$): δ=8.46 (d, 1H), 7.74-7.64 (m, 2H), 7.53 (td, 1H), 7.42-7.36 (m, 1H), 7.22-7.15 (m, 4H), 3.99 (td, 1H), 3.83-3.76 (m, 1H), 3.60 (br d, 1H), 3.42-3.33 (m, 2H), 3.12-3.01 (m, 3H), 2.91-2.82 (m, 1H), 2.72-2.69 (m, 2H), 2.56 (q, 2H), 2.07 (br d, 1H), 1.92-1.63 (m, 5H), 1.17 (t, 3H).

Example 158

N-{1-[(4-Cyanopiperidin-1-yl)carbonyl]-5-(4-ethylphenyl)piperidin-3-yl}-3-methylbenzenecarboxamide [racemic cis isomer]

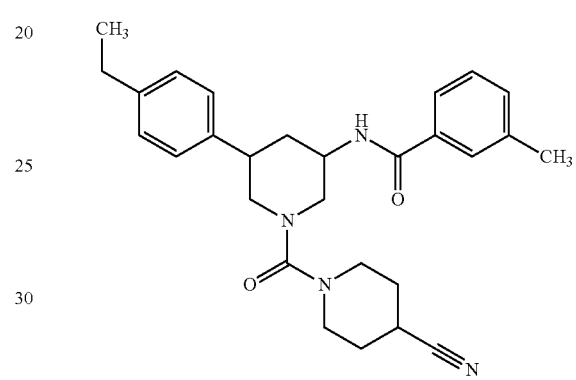

70 mg (0.21 mmol) of the compound from Example 56A were reacted with 35 mg (0.23 mmol) of 3-methylbenzenecarbonyl chloride in dichloromethane according to General Method 2. Yield: 85 mg (91% of theory)
HPLC (Method 2A): R$_t$=4.56 min; m/z=459 [M+H]$^+$;
$^1$H-NMR (400 MHz, DMSO-d$_6$): δ=8.32 (d, 1H), 7.79-7.50 (m, 2H), 7.37-7.32 (m, 2H), 7.23-7.14 (m, 4H), 3.98 (dd, 1H), 3.83-3.76 (m, 1H), 3.61 (br d, 1H), 3.42-3.34 (m, 2H), 3.12-3.01 (m, 3H), 2.90-2.82 (m, 1H), 2.71-2.68 (m, 2H), 2.58 (q, 2H), 2.07 (br d, 1H), 1.92-1.63 (m, 5H), 1.17 (t, 3H).

Example 159

3-Cyano-N-{1-(morpholin-4-ylcarbonyl)-5-[4-(trifluoromethyl)phenyl]piperidin-3-yl}benzenecarboxamide [racemic cis isomer]

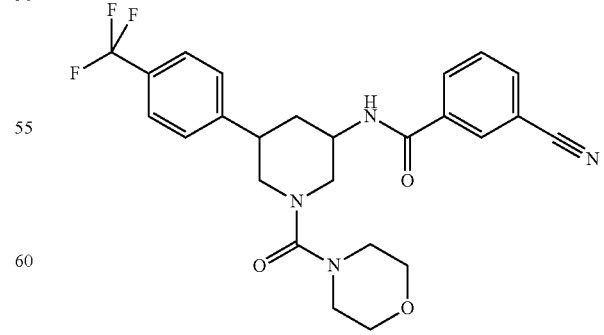

200 mg (0.508 mmol) of the amine from Example 57A [racemic cis isomer] and 112 mg (0.762 mmol) of 3-cyanobenzoic acid were reacted according to General Method 8. Yield: 206 mg (80% of theory)

LC-MS (Method 2B): R$_t$=1.18 min; MS (ESIpos): m/z=487 [M+H]$^+$;

$^1$H NMR (400 MHz, DMSO-d$_6$): δ=8.63 (d, 1H), 8.30 (s, 1H), 8.17 (d, 1H), 8.02 (d, 1H), 7.63-7.79 (m, 3H), 7.55 (d, 2H), 3.94-4.10 (m, 1H), 3.87 (d, 1H), 3.68 (d, 1H), 3.59 (br. s., 4H), 3.21 (br. s., 4H), 3.06 (t, 1H), 2.79-2.89 (m, 1H), 2.70 (t, 1H), 2.16 (d, 1H), 1.81 (q, 1H).

The following compounds [racemic cis isomers] were prepared in an analogous manner

| Example | Structure | LC-MS Method | R$_t$ [min] | MS (ESIpos) m/z |
|---|---|---|---|---|
| 160 | 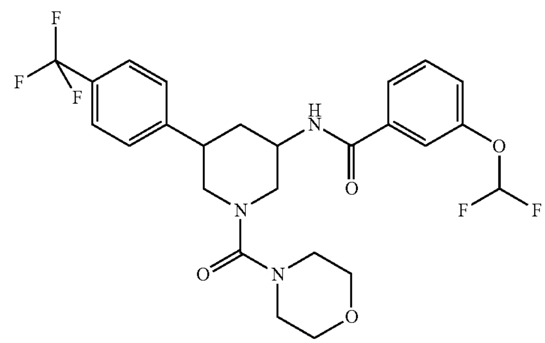 [SMILES: O=C(NC1CC(c2ccc(C(F)(F)F)cc2)CN(C(=O)N2CCOCC2)C1)c1cccc(OC(F)F)c1] | 2B | 1.29 | 528 |
| 161 | 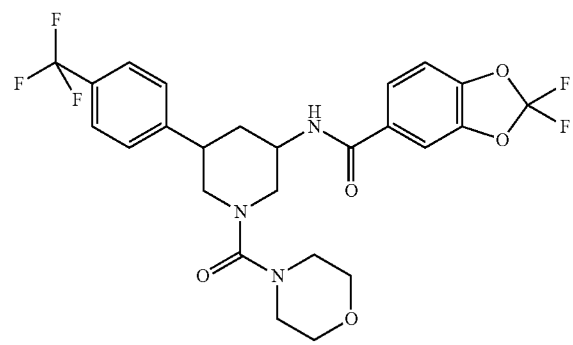 [SMILES: O=C(NC1CC(c2ccc(C(F)(F)F)cc2)CN(C(=O)N2CCOCC2)C1)c1ccc2c(c1)OC(F)(F)O2] | 2B | 1.35 | 542 |
| 162 | 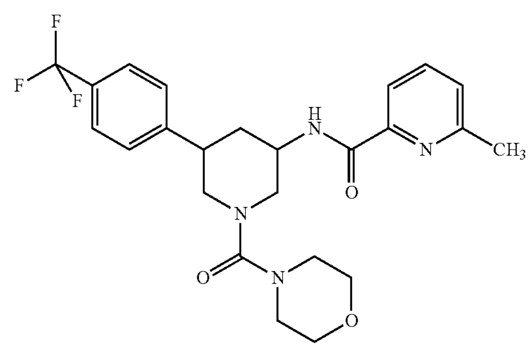 [SMILES: Cc1cccc(C(=O)NC2CC(c3ccc(C(F)(F)F)cc3)CN(C(=O)N3CCOCC3)C2)n1] | 11B | 1.10 | 477 |
| 163 | 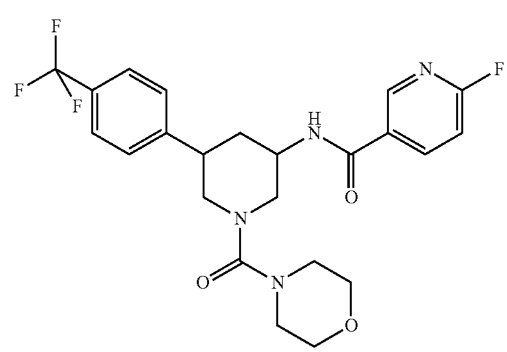 [SMILES: O=C(NC1CC(c2ccc(C(F)(F)F)cc2)CN(C(=O)N2CCOCC2)C1)c1ccc(F)nc1] | 2B | 1.13 | 481 |

| Example | Structure | LC-MS Method | $R_t$ [min] | MS (ESIpos) m/z |
|---|---|---|---|---|
| 164 | 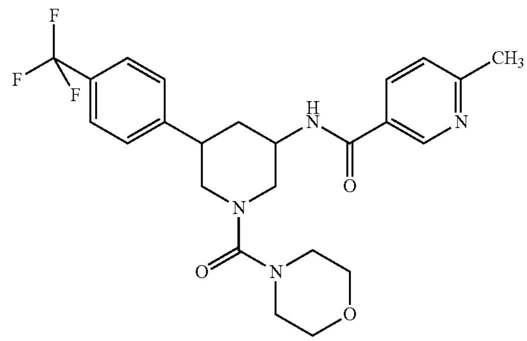 [SMILES: Cc1ccc(C(=O)NC2CC(c3ccc(C(F)(F)F)cc3)CN(C(=O)N3CCOCC3)C2)cn1] | 2B | 1.03 | 477 |
| 165 | 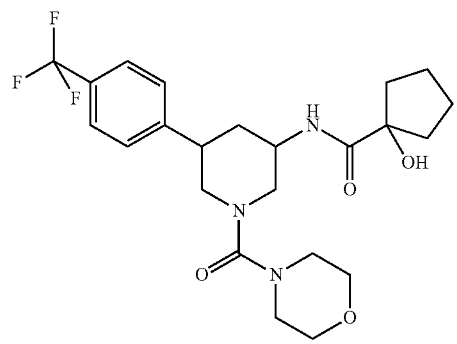 [SMILES: O=C(N1CCOCC1)N1CC(NC(=O)C2(O)CCCC2)CC(c2ccc(C(F)(F)F)cc2)C1] | 2B | 1.11 | 470 |

Example 166

N-{1-(Morpholin-4-ylcarbonyl)-5-[4-(trifluoromethyl)phenyl]piperidin-3-yl}cyclopentanecarboxamide [racemic cis isomer]

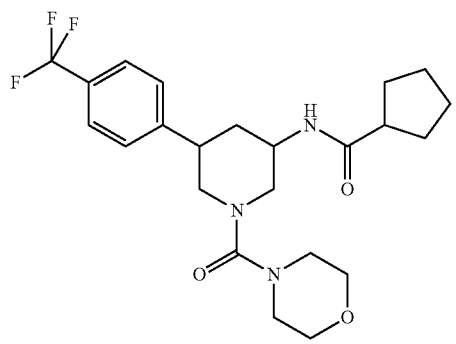 [SMILES: O=C(NC1CC(c2ccc(C(F)(F)F)cc2)CN(C(=O)N2CCOCC2)C1)C1CCCC1]

212 µl of triethylamine (1.52 mmol) and 18.6 mg of DMAP (0.152 mmol) were added to a solution of the compound from Example 57A (200 mg, 0.508 mmol) in dichloromethane (12 ml), and 93 µl of cyclopentanecarbonyl chloride (0.762 mmol) were then added at 0° C. The reaction mixture was warmed to RT and stirred overnight. The reaction solution was washed with aqueous 1 N hydrochloric acid and the organic phase was dried over magnesium sulphate, filtered and concentrated under reduced pressure. The crude product was purified by preparative HPLC(RP18 column; acetonitrile/water gradient). Yield: 133 mg (57% of theory)

LC-MS (Method 5B): $R_t$=2.17 min; MS (ESIpos): m/z=454 [M+H]$^+$;

$^1$H-NMR (400 MHz, DMSO-d$_6$): δ=7.80 (d, 1H), 7.70 (d, 2H), 7.52 (d, 2H), 3.74 (d, 2H), 3.63 (d, 1H), 3.56 (br. s., 4H), 3.17 (br. s., 4H), 2.97 (br. s., 1H), 2.84-2.73 (m, 1H), 2.02 (d, 1H), 1.78-1.66 (m, 2H), 1.54-1.66 (m, 5H), 1.48 (br. s., 2H).

Example 167

2,2-Dimethyl-N-{1-(morpholin-4-ylcarbonyl)-5-[4-(trifluoromethyl)phenyl]piperidin-3-yl}propanamide [racemic cis isomer]

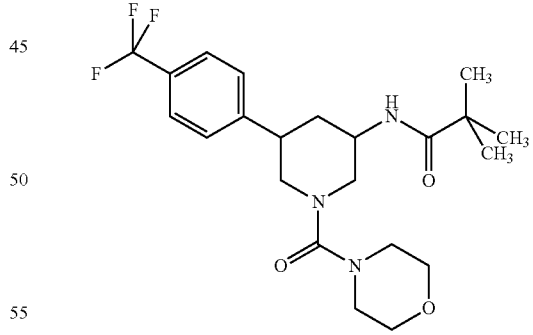

212 µl of triethylamine (1.52 mmol) and 18.6 mg of DMAP (0.152 mmol) were added to a solution of the compound from Example 57A (200 mg, 0.508 mmol) in dichloromethane (12 ml), and 94 µl of pivaloyl chloride (0.76 mmol) were then added at 0° C. The reaction mixture was warmed to RT and stirred overnight. The reaction solution was washed with aqueous 1 N hydrochloric acid and the organic phase was dried over magnesium sulphate, filtered and concentrated under reduced pressure. The crude product was purified by preparative HPLC (RP18 column; acetonitrile/water gradient). Yield: 154 mg (68% of theory)

LC-MS (Method 5B): $R_t$=2.17 min; MS (ESIpos): m/z=442 [M+H]$^+$;

$^1$H-NMR (400 MHz, DMSO-d$_6$): δ=7.70 (d, 2H), 7.52 (d, 2H), 7.31 (d, 1H), 3.85-3.72 (m, 1H), 3.71-3.61 (m, 2H), 3.56 (d, 4H), 3.18 (br. s., 4H), 3.04-2.92 (m, 1H), 2.76 (t, 1H), 1.97 (d, 1H), 1.73 (q, 1H), 1.09 (s, 9H).

Example 168

2-Methyl-N-{1-(morpholin-4-ylcarbonyl)-5-[4-(trifluoromethyl)phenyl]piperidin-3-yl}propanamide [racemic cis isomer]

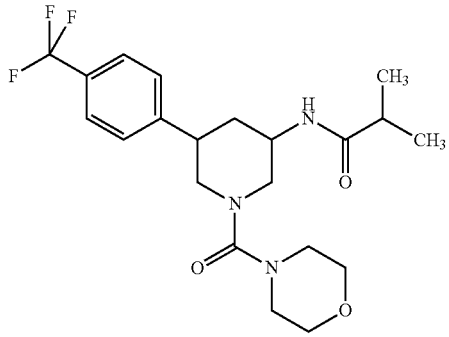 [SMILES: CC(C)C(=O)NC1CC(c2ccc(C(F)(F)F)cc2)CN(C(=O)N2CCOCC2)C1]

212 μl of triethylamine (1.52 mmol) and 18.6 mg of DMAP (0.152 mmol) were added to a solution of the compound from Example 57A (200 mg, 0.508 mmol) in dichloromethane (12 ml), and 80 μl of isobutyryl chloride (0.76 mmol) were then added at 0° C. The reaction mixture was warmed to RT and stirred overnight. The reaction solution was washed with aqueous 1 N hydrochloric acid and the organic phase was dried over magnesium sulphate, filtered and concentrated under reduced pressure. The crude product was purified by preparative HPLC(RP18 column; acetonitrile/water gradient). Yield: 142 mg (65% of theory)

LC-MS (Method 5B): $R_t$=2.03 min; MS (ESIpos): m/z=428 [M+H]$^+$;

$^1$H-NMR (400 MHz, DMSO-d$_6$): δ=7.76 (d, 1H), 7.70 (d, 2H), 7.52 (d, 2H), 3.74 (d, 2H), 3.63 (d, 1H), 3.56 (t, 4H), 3.18 (d, 4H), 2.92-3.03 (m, 1H), 2.74-2.84 (m, 1H), 2.29-2.39 (m, 1H), 2.01 (d, 1H), 1.60 (q, 1H), 1.00 (t, 7H).

Example 169

3-Chloro-N-{1-[(4-hydroxypiperidin-1-yl)carbonyl]-5-[4-(trifluoromethyl)phenyl]piperidin-3-yl}benzenecarboxamide [racemic cis isomer]

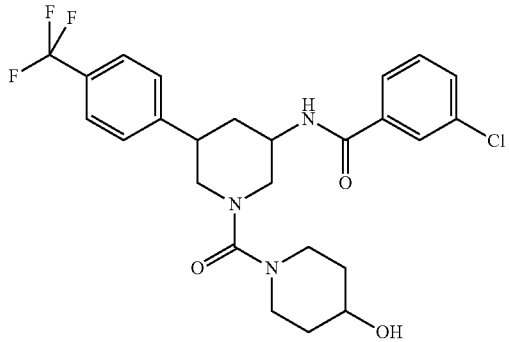 [SMILES: O=C(NC1CC(c2ccc(C(F)(F)F)cc2)CN(C(=O)N2CCC(O)CC2)C1)c1cccc(Cl)c1]

At 0° C., 7.2 mg of sodium borohydride (0.19 mmol) were added to a solution of the ketone from Example 174 (60 mg, 0.118 mmol) in methanol (2.4 ml). The reaction mixture was warmed to RT and stirred for 1 h. The reaction solution was concentrated under reduced pressure, taken up in water and extracted with dichloromethane. The organic phase was dried over magnesium sulphate, filtered and concentrated under reduced pressure. Yield: 52 mg (85% of theory)

LC-MS (Method 2B): $R_t$=1.24 min; MS (ESIpos): m/z=510 [M+H]$^+$;

$^1$H-NMR (400 MHz, DMSO-d$_6$) δ=8.52 (d, 1H), 7.91 (s, 1H), 7.82 (d, 1H), 7.72 (d, 2H), 7.58-7.64 (m, 1H), 7.48-7.57 (m, 3H), 4.68 (d, 1H), 3.96-4.09 (m, 1H), 3.78 (d, 1H), 3.62 (d, 2H), 3.44-3.54 (m, 2H), 2.97-3.09 (m, 1H), 2.86-2.96 (m, 2H), 2.74-2.84 (m, 1H), 2.63-2.73 (m, 1H), 2.13 (d, 1H), 1.66-1.88 (m, 3H), 1.32 (q, 2H).

Example 170

N-{1-[(4-Hydroxypiperidin-1-yl)carbonyl]-5-[4-(trifluoromethyl)phenyl]piperidin-3-yl}cyclopentanecarboxamide [racemic cis isomer]

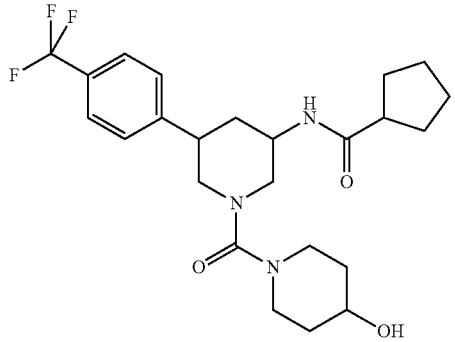 [SMILES: O=C(NC1CC(c2ccc(C(F)(F)F)cc2)CN(C(=O)N2CCC(O)CC2)C1)C1CCCC1]

At 0° C., 6.8 mg of sodium borohydride (0.18 mmol) were added to a solution of the ketone from Example 173 (52.6 mg, 0.113 mmol) in methanol (3.0 ml). The reaction mixture was warmed to RT and stirred for 2.5 h. The reaction solution was concentrated under reduced pressure, taken up in water and extracted with dichloromethane. The organic phase was dried over magnesium sulphate, filtered and concentrated under reduced pressure. Yield: 46.6 mg (91% of theory)

LC-MS (Method 2B): $R_t$=1.16 min; MS (ESIpos): m/z=468 [M+H]$^+$;

$^1$H-NMR (400 MHz, DMSO-d$_6$): δ=7.78 (d, 1H), 7.70 (d, 2H), 7.51 (d, 2H), 4.67 (d, 1H), 3.64-3.81 (m, 2H), 3.53-3.64 (m, 2H), 3.46 (d, 2H), 2.81-3.04 (m, 3H), 2.69-2.79 (m, 1H), 2.01 (d, 1H), 1.71 (d, 4H), 1.55-1.66 (m, 5H), 1.43-1.54 (m, 2H), 1.23-1.35 (m, 2H).

Example 171

1-[1-(Cyclopentylcarbonyl)-5-(4-ethylphenyl)piperidin-3-yl]-3-phenylurea [racemic cis isomer]

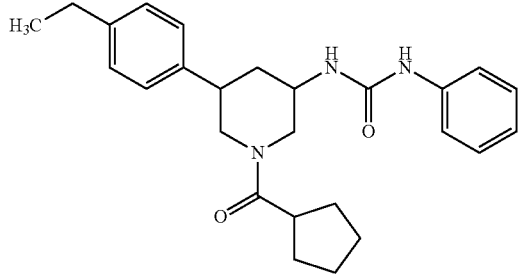 [SMILES: CCc1ccc(C2CC(NC(=O)Nc3ccccc3)CN(C(=O)C3CCCC3)C2)cc1]

108 mg (0.22 mmol) of 1-(cyclopentylcarbonyl)-5-(4-ethylphenyl)piperidine-3-amine trifluoroacetate (Example 8A) and 31 mg (0.26 mmol, 1.2 eq.) of phenyl isocyanate were reacted according to General Method 4. Yield: 72 mg (79% of theory)

HPLC (Method 1): $R_t$=4.79 min; MS (ESIpos): m/z=420 [M+H]$^+$;

$^1$H-NMR (500 MHz, DMSO-d$_6$): δ=8.45 (s, 0.6H), 8.41 (s, 0.4H), 7.38 (d, 2H), 7.28-7.13 (m, 6H), 6.95-6.87 (m, 1H), 6.25 (d, 0.6H), 6.19 (d, 0.4H), 4.66 (br d, 0.4H), 4.45 (br d, 0.6H), 4.22 (br d, 0.6H), 3.93 (br d, 0.4H), 3.66-3.49 (m, 1H), 3.08-2.97 (m, 1.4H), 2.83-2.72 (m, 1H), 2.69-2.61 (m, 0.6H), 2.58 (q, 2H), 2.33 (t, 0.6H), 2.10-2.00 (m, 1.4H), 1.85-1.44 (m, 9H), 1.17 (t, 3H).

Example 172 tert-Butyl {1-(morpholin-4-ylcarbonyl)-5-[4-(trifluoromethyl)phenyl]piperidin-3-yl}carbamate [racemic cis isomer]

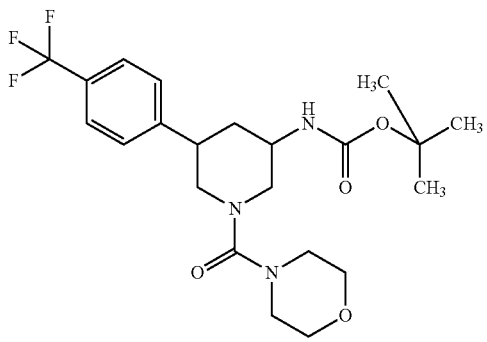 [SMILES: CC(C)(C)OC(=O)NC1CC(c2ccc(C(F)(F)F)cc2)CN(C(=O)N2CCOCC2)C1]

Activated molecular sieves 4 Å (about 10 g), 2.16 ml (15.5 mmol) of triethylamine and 3.92 g (14.2 mmol) of diphenyl phosphorazidate were added to the carboxylic acid from Example 55A (5.00 g, 12.9 mmol) in tert-butanol (235 ml), and the mixture was stirred under reflux overnight. The reaction solution was cooled, and the molecular sieves were then filtered off and washed thoroughly with ethyl acetate. The solvent was removed under reduced pressure and the residue was taken up in ethyl acetate. After washing with 2 N aqueous hydrogen chloride solution, saturated aqueous sodium bicarbonate solution and water, the organic phase was dried over magnesium sulphate, filtered and concentrated under reduced pressure. The crude product was used for the next step without further purification. Yield: 5.53 g (89% of theory)

LC-MS (Method 11B): $R_t$=1.15 min; MS (ESIpos): m/z=458 [M+H]$^+$.

Example 173

N-{1-[(4-Oxopiperidin-1-yl)carbonyl]-5-[4-(trifluoromethyl)phenyl]piperidin-3-yl}cyclopentanecarboxamide [racemic cis isomer]

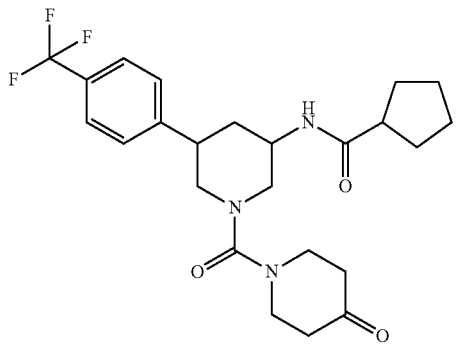 [SMILES: O=C1CCN(C(=O)N2CC(NC(=O)C3CCCC3)CC(c3ccc(C(F)(F)F)cc3)C2)CC1]

14.3 mg of pyridinium p-toluenesulphonate (0.057 mmol) were added to a solution of the acetal from Example 63A (97.2 mg, 0.191 mmol) in 5.5 ml of acetone/water (10:1), and the mixture was stirred under reflux overnight. Another 14.3 mg of pyridinium p-toluenesulphonate (0.057 mmol) were added, and the mixture was stirred under reflux for another night. The mixture was then cooled, and the precipitate formed was filtered off. Yield: 66.2 mg (74% of theory)

LC-MS (Method 11B): $R_t$=1.05 min; MS (ESIpos): m/z=466 [M+H]$^+$.

Example 174

3-Chloro-N-{1-[(4-oxopiperidin-1-yl)carbonyl]-5-[4-(trifluoromethyl)phenyl]piperidin-3-yl}benzenecarboxamide [racemic cis isomer]

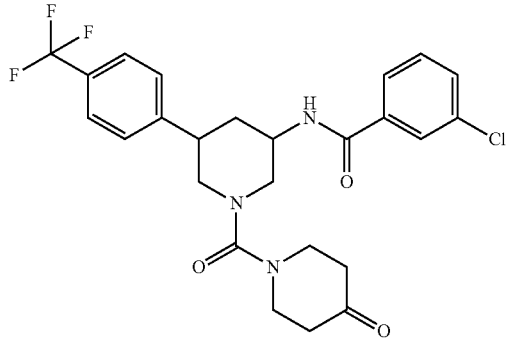 [SMILES: O=C1CCN(C(=O)N2CC(NC(=O)c3cccc(Cl)c3)CC(c3ccc(C(F)(F)F)cc3)C2)CC1]

54.6 mg of pyridinium p-toluenesulphonate (0.217 mmol) were added to a solution of the acetal from Example 64A (400 mg, 0.725 mmol) in 15 ml of acetone/water (10:1) and the mixture was stirred under reflux for 3 d, with another 54.6 mg of pyridinium p-toluenesulphonate (0.217 mmol) being added after 24 h and 48 h. The solvent was then removed under reduced pressure, the residue was taken up in water and the mixture was extracted with dichloromethane. The organic phase was dried over magnesium sulphate, filtered and concentrated under reduced pressure. Yield: 363 mg (92% of theory)

LC-MS (Method 11B): $R_t$=1.12 min; MS (ESIpos): m/z=508 [M+H]$^+$.

Example 175

N-{1-[(4-Cyanopiperidin-1-yl)carbonyl]-5-(4-ethylphenyl)piperidin-3-yl}cyclopentanecarboxamide [racemic cis isomer]

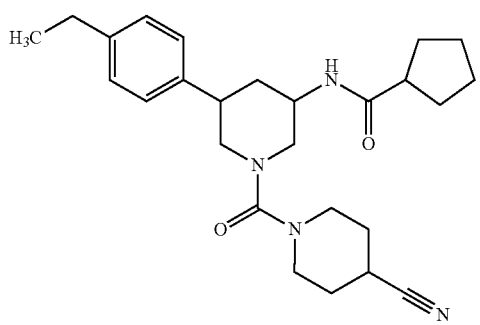 [SMILES: CCc1ccc(C2CC(NC(=O)C3CCCC3)CN(C(=O)N3CCC(C#N)CC3)C2)cc1]

At 0° C., 80 mg (0.24 mmol) of the compound from Example 56A were initially charged in 2.5 ml of dichloromethane, and 49 μl (36 mg, 1.5 eq.) of triethylamine and 58 μl (64 mg, 0.47 mmol) of cyclopentanecarbonyl chloride were added. The reaction mixture was allowed to warm to RT and was stirred at RT for a further 16 h. Then the mixture was twice washed with water and the organic phase was dried over sodium sulphate, filtered and concentrated under reduced pressure. The crude product was taken up in methanol/DMF, the residue was separated off and the filtrate was purified by preparative HPLC(RP18 column; acetonitrile/water gradient). The residue and the product-containing fractions were combined. Yield: 94 mg (91% of theory)

LC-MS (Method 5B): $R_t$=2.31 min; MS (ESIpos): m/z=437 [M+H]$^+$;

$^1$H-NMR (400 MHz, DMSO-d$_6$): δ=7.51 (d, NH), 7.36-6.98 (m, 4H), 3.70 (d, 2H), 3.56 (d, 1H), 3.04 (t, 4H), 2.86-2.72 (m, 1H), 2.72-2.60 (m, 2H), 2.55 (q, 2H), 1.97 (d, 1H), 1.86 (d, 2H), 1.79-1.43 (m, 12H), 1.16 (t, 3H).

Example 176

N-{1-[(4-Hydroxypiperidin-1-yl)carbonyl]-5-[4-(trifluoromethyl)phenyl]piperidin-3-yl}cyclopentanecarboxamide [enantiomerically pure cis isomer]

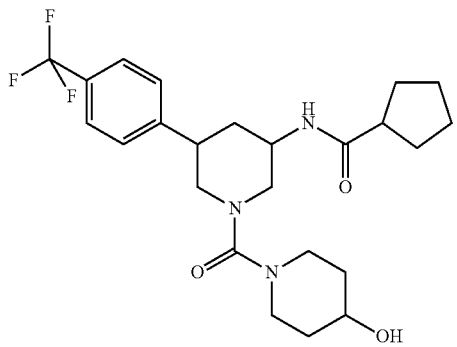 [SMILES: O=C(NC1CC(c2ccc(C(F)(F)F)cc2)CN(C(=O)N2CCC(O)CC2)C1)C1CCCC1]

The enantiomer separation of 48.6 mg of the racemate from Example 170 according to Method 16D gave 14 mg of the compound from Example 176 (enantiomer 1) and 16 mg of the compound from Example 177 (enantiomer 2).

HPLC (Method 8E): $R_t$=4.50 min, >99.0% ee;

LC-MS (Method 11B): $R_t$=1.00 min; MS (ESIpos): m/z=468 [M+H]$^+$;

$^1$H-NMR (400 MHz, DMSO-d$_6$): δ=7.78 (d, 1H), 7.70 (d, 2H), 7.51 (d, 2H), 4.67 (d, 1H), 3.82-3.53 (m, 4H), 3.46 (d, 2H), 3.05-2.81 (m, 3H), 2.80-2.69 (m, 1H), 2.01 (d, 1H), 1.81-1.41 (m, 12H), 1.37-1.19 (m, 2H).

Example 177

N-{1-[(4-Hydroxypiperidin-1-yl)carbonyl]-5-[4-(trifluoromethyl)phenyl]piperidin-3-yl}cyclopentanecarboxamide [enantiomerically pure cis isomer]

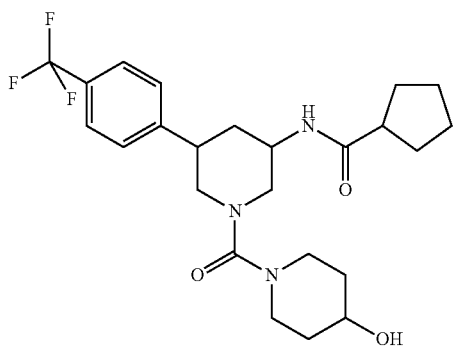 [SMILES: O=C(NC1CC(c2ccc(C(F)(F)F)cc2)CN(C(=O)N2CCC(O)CC2)C1)C1CCCC1]

The enantiomer separation of 48.6 mg of the racemate from Example 170 according to Method 16D gave 14 mg of the compound from Example 176 (enantiomer 1) and 16 mg of the compound from Example 177 (enantiomer 2).

HPLC (Method 8E): $R_t$=5.14 min, >95.0% ee;

LC-MS (Method 11B): $R_t$=1.00 min; MS (ESIpos): m/z=468 [M+H]$^+$;

$^1$H-NMR (400 MHz, DMSO-d$_6$): δ=7.78 (d, 1H), 7.70 (d, 2H), 7.51 (d, 2H), 4.67 (d, 1H), 3.82-3.53 (m, 4H), 3.46 (d, 2H), 3.05-2.81 (m, 3H), 2.80-2.69 (m, 1H), 2.01 (d, 1H), 1.81-1.41 (m, 12H), 1.37-1.19 (m, 2H).

Example 178

N-{1-[(4-Cyanopiperidin-1-yl)carbonyl]-5-[4-(trifluoromethyl)phenyl]piperidin-3-yl}cyclopentanecarboxamide [enantiomerically pure cis isomer]

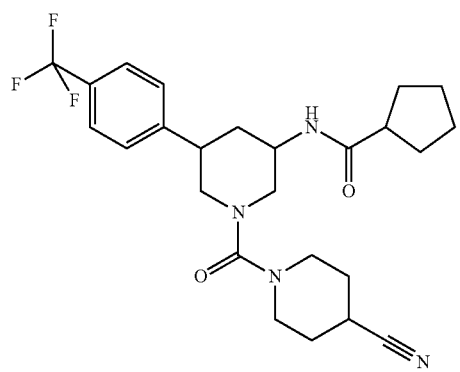 [SMILES: N#CC1CCN(C(=O)N2CC(NC(=O)C3CCCC3)CC(c3ccc(C(F)(F)F)cc3)C2)CC1]

At 0° C., 90 mg (0.21 mmol) of the compound from Example 69A were initially charged in 5.0 ml of dichloromethane, and 86 μl (62 mg, 1.5 eq.) of triethylamine, 37 μl (41 mg, 0.31 mmol) of cyclopentanecarbonyl chloride and 7.5 mg (0.062 mmol) of 4-(dimethylamino)pyridine were added. The reaction mixture was allowed to warm to RT and was stirred at RT for a further 16 h. The mixture was washed with 1N hydrochloric acid and the organic phase was dried over magnesium sulphate, filtered and concentrated under reduced pressure. The crude product was purified by preparative HPLC (RP18 column; acetonitrile/water gradient). Yield: 74.8 mg (77% of theory). The enantiomer separation of 74.8 mg of the racemate according to Method 17D gave 27 mg of the compound from Example 178 (enantiomer 1) and 28 mg of the compound from Example 179 (enantiomer 2).

HPLC (Method 8E): $R_t$=5.96 min, >99.0% ee;

LC-MS (Method 11B): $R_t$=1.11 min; MS (ESIpos): m/z=477 [M+H]$^+$;

$^1$H-NMR (400 MHz, DMSO-d$_6$): δ=7.80 (d, 1H), 7.70 (d, 2H), 7.52 (d, 2H), 3.80-3.65 (m, 2H), 3.60 (d, 1H), 3.14-2.90 (m, 4H), 2.85-2.72 (m, 1H), 2.01 (d, 1H), 1.85 (br. s, 2H), 1.77-1.39 (m, 16H), 4H obscured.

Example 179

N-{1-[(4-Cyanopiperidin-1-yl)carbonyl]-5-[4-(trifluoromethyl)phenyl]piperidin-3-yl}cyclopentanecarboxamide [enantiomerically pure cis isomer]

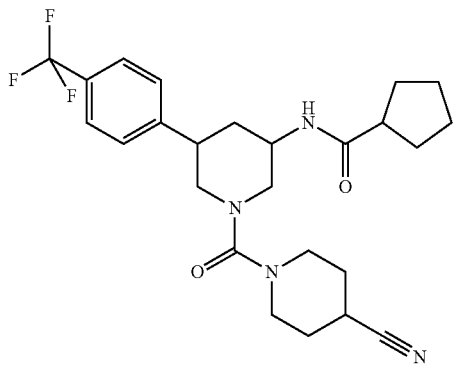 [SMILES: N#CC1CCN(C(=O)N2CC(NC(=O)C3CCCC3)CC(c3ccc(C(F)(F)F)cc3)C2)CC1]

The enantiomer separation of 74.8 mg of the racemate from Example 178 according to Method 17D gave 27 mg of the compound from Example 178 (enantiomer 1) and 28 mg of the compound from Example 179 (enantiomer 2).

HPLC (Method 8E): $R_t$=6.68 min, >98.0% ee;

LC-MS (Method 11B): $R_t$=1.11 min; MS (ESIpos): m/z=477 [M+H]$^+$;

$^1$H-NMR (400 MHz, DMSO-$d_6$): δ=7.80 (d, 1H), 7.70 (d, 2H), 7.52 (d, 2H), 3.80-3.65 (m, 2H), 3.60 (d, 1H), 3.14-2.90 (m, 4H), 2.85-2.72 (m, 1H), 2.01 (d, 1H), 1.85 (br. s, 2H), 1.77-1.39 (m, 16H), 4H obscured.

B) ASSESSMENT OF PHYSIOLOGICAL EFFICACY

Abbreviations

BSA bovine serum albumin
DMEM Dulbecco's Modified Eagle Medium
EGTA ethylene glycol-bis(2-aminoethyl)-N,N,N',N'-tetraacetic acid
FCS fetal calf serum
HEPES 4-(2-hydroxyethyl)-1-piperazineethanesulphonic acid
[3H]haTRAP tritiated high affinity thrombin receptor activating peptide
PRP platelet-rich plasma The suitability of the compounds according to the invention for treating thromboembolic disorders can be demonstrated in the following assay systems:

1.) In Vitro Assays
1.a) Cellular, Functional In Vitro Test

A recombinant cell line is used to identify agonists of the human protease activated receptor 1 (PAR-1) and to quantify the activity of the substances described herein. The cell is originally derived from a human embryonal kidney cell (HEK293; ATCC: American Type Culture Collection, Manassas, Va. 20108, USA). The test cell line constitutively expresses a modified form of the calcium-sensitive photoprotein aequorin which, after reconstitution with the cofactor coelenterazine, emits light when the free calcium concentration in the inner mitochondrial compartment is increased (Rizzuto R, Simpson A W, Brini M, Pozzan T.; *Nature* 1992, 358, 325-327). Additionally, the cell stably expresses the endogenous human PAR-1 receptor and the endogenous purinergic receptor P2Y2. The resulting PAR-1 test cell responds to stimulation of the endogenous PAR-1 or P2Y2 receptor with an intracellular release of calcium ions, which can be quantified through resulting aequorin luminescence with a suitable luminometer (Milligan G, Marshall F, Rees S, *Trends in Pharmacological Sciences* 1996, 17, 235-237).

For the testing of the substance specificity, the effect thereof after activation of the endogenous PAR-1 receptor is compared with the effect after activation of the endogenous purinergic P2Y2 receptor which utilizes the same intracellular signal path.

Assay Procedure:

Two days (48 hours) before the assay, the cells are plated out in culture medium (DMEM F12, supplemented with 10% FCS, 2 mM glutamine, 10 mM HEPES, 1.4 mM pyruvate, 0.1 mg/ml gentamycin, 0.15% Na bicarbonate; BioWhittaker Cat. #BE04-687Q; B-4800 Verviers, Belgium) in 384-well microtitre plates and kept in a cell incubator (96% humidity, 5% v/v $CO_2$, 37° C.). On the day of the test, the culture medium is replaced by a tyrode solution (in mM: 140 sodium chloride, 5 potassium chloride, 1 magnesium chloride, 2 calcium chloride, 20 glucose, 20 HEPES), which additionally contains the cofactor coelenterazine (25 μM) and glutathione (4 mM), and the microtitre plate is then incubated for a further 3-4 hours. The test substances are then pipetted onto the microtitre plate, and 5 minutes after the transfer of the test substances into the wells of the microtitre plate the plate is transferred into the luminometer, a PAR-1 agonist concentration which corresponds to the $EC_{50}$ is added and the resulting light signal is immediately measured in the luminometer. To distinguish an antagonist substance action from a toxic action, the endogenous purinergic receptor is immediately subsequently activated with agonist (ATP, final concentration 10 μM) and the resulting light signal is measured. The results are shown in Table A:

TABLE A

| Example No. | $IC_{50}$ [nM] |
| --- | --- |
| 7 | 29 |
| 8 | 109 |
| 18 | 483 |
| 36 | 98.2 |
| 83 | 19.7 |
| 90 | 359 |
| 91 | 17.4 |
| 95 | 237 |
| 97 | 109 |
| 102 | 165 |
| 104 | 248 |
| 105 | 18.4 |
| 106 | 7.05 |
| 115 | 11.1 |
| 119 | 15.7 |
| 121 | 79.9 |
| 128 | 17.04 |
| 129 | 33.6 |
| 133 | 14.6 |
| 134 | 15.4 |
| 141 | 53.7 |
| 156 | 11.1 |
| 162 | 25 |
| 170 | 21.3 |
| 177 | 81 |
| 178 | 63 |

1.b) PAR-1 Receptor Binding Assay

Platelet membranes are incubated with 12 nM [3H]haTRAP and test substance in different concentrations in a buffer (50 mM Tris pH 7.5, 10 mM magnesium chloride, 1 mM EGTA, 0.1% BSA) at room temperature for 80 min. Then the mixture is transferred to a filter plate and washed twice with buffer. After addition of scintillation liquid, the radioactivity on the filter is measured in a beta counter.

1.c) Platelet Aggregation in Plasma

Platelet aggregation is determined using blood from healthy volunteers of both genders, who had not received any thrombocyte aggregation-influencing medication for the last ten days. The blood is taken up into monovettes (Sarstedt, Nümbrecht, Germany) which contain, as anticoagulant, sodium citrate 3.8% (1 part citrate+9 parts blood). To obtain platelet-rich plasma, the citrated whole blood is centrifuged at 140 g for 20 min.

For the aggregation measurements, aliquots of the platelet-rich plasma with increasing concentrations of test substance are incubated at 37° C. for 10 min. Subsequently, aggregation is triggered by addition of a thrombin receptor agonist (TRAP6, SFLLRN) in an aggregometer and determined at 37° C. by means of the turbidimetry method according to Born (Born, G. V. R., Cross M. J., The Aggregation of Blood Platelets; *J. Physiol.* 1963, 168, 178-195). The SFLLRN concentration leading to maximum aggregation is, if appropriate, determined individually for each donor.

To calculate the inhibitory effect, the maximum increase of light transmission (amplitude of the aggregation curve in %) is determined within 5 minutes of addition of the agonist in the presence and absence of test substance, and the inhibition is calculated. The inhibition curves are used to calculate the concentration which inhibits aggregation by 50%.

1.c) Platelet Aggregation in Buffer

Platelet aggregation is determined using blood from healthy volunteers of both genders, who had not received any thrombocyte aggregation-influencing medication for the last ten days. The blood is taken up into monovettes (Sarstedt, Nümbrecht, Germany) which contain, as anticoagulant, sodium citrate 3.8% (1 part citrate+9 parts blood). To obtain platelet-rich plasma, the citrated whole blood is centrifuged at 140 g for 20 min. One quarter of the volume of ACD buffer (44.8 mM sodium citrate, 20.9 mM citric acid, 74.1 mM glucose and 4 mM potassium chloride) is added to the PRP, and the mixture is centrifuged at 1000 g for 10 minutes. The platelet pellet is resuspended in wash buffer and centrifuged at 1000 g for 10 minutes. The platelets are resuspended in incubation buffer and adjusted to 200 000 cells/μl. Prior to the start of the test, calcium chloride and magnesium chloride, final concentration in each case 2 mM (2M stock solution, dilution 1:1000), are added. Note: in the case of ADP-induced aggregation, only calcium chloride is added. The following agonists can be used: TRAP6 trifluoroacetate salt, collagen, human α-thrombin and U-46619. For each donor, the agonist concentration is determined.

Test Procedure:

96-well microtitre plates are used. The test substance is diluted in DMSO, and 2 μl per well is initially charged. 178 μl of platelet suspension are added, and the mixture is preincubated at room temperature for 10 minutes. 20 μl of agonist are added, and the measurement in the Spectramax, OD 405 nm, is started immediately. Kinetics are determined in 11 measurements of 1 minute each. Between the measurements, the mixture is shaken for 55 seconds.

1.c) Platelet Aggregation in Fibrinogen-Depleted Plasma

Platelet aggregation is determined using blood from healthy volunteers of both genders, who had not received any thrombocyte aggregation-influencing medication for the last ten days. The blood is taken up into monovettes (Sarstedt, Nümbrecht, Germany) which contain, as anticoagulant, sodium citrate 3.8% (1 part citrate+9 parts blood).

Preparation of Fibrinogen-Depleted Plasma:

To obtain low-platelet plasma, the citrated whole blood is centrifuged at 140 g for 20 min. The low-platelet plasma is admixed in a ratio of 1:25 with reptilase (Roche Diagnostic, Germany) and inverted cautiously. This is followed by 10 min of incubation at 37° C. in a water bath, followed directly by 10 min of incubation on ice. The plasma/reptilase mixture is centrifuged at 1300 g for 15 min, and the supernatant (fibrinogen-depleted plasma) is obtained.

Platelet Isolation:

To obtain platelet-rich plasma, the citrated whole blood is centrifuged at 140 g for 20 min. One quarter of the volume of ACD buffer (44.8 mM sodium citrate, 20.9 mM citric acid, 74.1 mM glucose and 4 mM potassium chloride) is added to the PRP, and the mixture is centrifuged at 1300 g for 10 minutes. The platelet pellet is resuspended in wash buffer and centrifuged at 1300 g for 10 minutes. The platelets are resuspended in incubation buffer and adjusted to 400 000 cells/W, and calcium chloride solution is added to a final concentration of 5 mM (dilution 1/200).

For the aggregation measurements, aliquots (98 μl of fibrinogen-depleted plasma and 80 μl of platelet suspension) are incubated with increasing concentrations of test substance at RT for 10 min. Subsequently, aggregation is triggered by addition of human alpha thrombin in an aggregometer and determined at 37° C. by means of the turbidimetry method according to Born (Born, G. V. R., Cross M. J., The Aggregation of Blood Platelets; *J. Physiol.* 1963, 168, 178-195). The alpha thrombin concentration which just leads to the maximum aggregation is determined individually for each donor.

To calculate the inhibitory activity, the increase of the maximum light transmission (amplitude of the aggregation curve in %) is determined within 5 minutes after addition of the agonist in the presence and absence of test substance, and the inhibition is calculated. The inhibition curves are used to calculate the concentration which inhibits aggregation by 50%.

1.f) Stimulation of Washed Platelets and Analysis in Flow Cytometry

Isolation of Washed Platelets:

Human whole blood is obtained by venipuncture from voluntary donors and transferred into monovettes (Sarstedt, Nümbrecht, Germany) containing sodium citrate as anticoagulant (1 part of sodium citrate 3.8%+9 parts of whole blood). At 90° rotations per minute and 4° C., the monovettes are centrifuged for a period of 20 minutes (Heraeus Instruments, Germany; Megafuge 1.0RS). The platelet-rich plasma is carefully removed and transferred into a 50 ml Falcon tube. ACD buffer (44 mM sodium citrate, 20.9 mM citric acid, 74.1 mM glucose) is then added to the plasma. The volume of the ACD buffer corresponds to one quarter of the plasma volume. Centrifuging at 2500 rpm and 4° C. for ten minutes sediments the platelets. Thereafter, the supernatant is cautiously decanted off and discarded. The precipitated platelets are initially carefully resuspended in one milliliter of wash buffer (113 mM sodium chloride, 4 mM disodium hydrogen phosphate, 24 mM sodium dihydrogen phosphate, 4 mM potassium chloride, 0.2 mM ethylene glycol-bis(2-aminoethyl)-N,N,N'N'-tetraacetic acid, 0.1% glucose) and then made up with wash buffer to a volume which corresponds to that of the amount of plasma. The wash procedure is repeated. The platelets are precipitated by another ten-minute centrifugation at 2500 rotations and 4° C. and then carefully resuspended in a milliliter of incubation buffer (134 mM sodium chloride, 12 mM sodium hydrogen carbonate, 2.9 mM potassium chloride, 0.34 mM sodium dihydrogen carbonate, 5 mM HEPES, 5 mM glucose, 2 mM calcium chloride and 2 mM magnesium chloride) and adjusted with incubation buffer to a concentration of 300 000 platelets per µl.

Staining and Stimulation of the Human Platelets with Human α-Thrombin in the Presence or Absence of a PAR-1 Antagonist:

The platelet suspension is preincubated with the substance to be tested or the appropriate solvent at 37° C. for 10 minutes (Eppendorf, Germany; Thermomixer Comfort). Platelet activation is triggered by addition of the agonist (0.5 µM or 1 µM α-thrombin; Kordia, The Netherlands, 3281 NIH units/mg; or 30 µg/ml of thrombin receptor activating peptide (TRAP6); Bachem, Switzerland) at 37° and with shaking at 500 rotations per minute. At the time points 0, 1, 2.5, 5, 10 and 15 minutes, in each case one aliquot of 50 µl is removed and transferred into one milliliter of singly-concentrated Cell-Fix™ solution (Becton Dickinson Immunocytometry Systems, USA). To fix the cells, they are incubated in the dark at 4° C. for 30 minutes. The platelets are precipitated by centrifuging at 600 g and 4° C. for ten minutes. The supernatant is discarded and the platelets are resuspended in 400 µl Cell-Wash™ (Becton Dickinson Immunocytometry Systems, USA). One aliquot of 100 µl is transferred to a new FACS tube. 1 µl of the platelet-identifying antibody and 1 µl of the activation state-detecting antibody are made up with Cell-Wash™ to a volume of 100 µl. This antibody solution is then added to the platelet suspension and incubated in the dark at 4° C. for 20 minutes. After staining, the mixture volume is increased by addition of a further 400 µl of CellWash™

The platelets are identified using a fluorescein isothiocyanate-conjugated antibody directed against human glycoprotein IIb (CD41) (Immunotech Coulter, France; Cat. No. 0649). With the aid of the phycoerythrin-conjugated antibody directed against human glycoprotein P-selectin (Immunotech Coulter, France; Cat. No. 1759), it is possible to determine the activation state of the platelets. P-Selectin (CD62P) is localized in the α-granules of resting platelets. However, following in vitro or in vivo stimulation, it is translocalized to the external plasma membrane.

Flow Cytometry and Data Evaluation:

The samples are measured in the FACSCalibur™ Flow Cytometry System instrument from Becton Dickinson Immunocytometry Systems, USA, and evaluation and graphic representation is carried out with the aid of the CellQuest software, Version 3.3 (Becton Dickinson Immunocytometry Systems, USA). The degree of platelet activation is determined by the percentage of CD62P-positive platelets (CD41-positive events). From each sample, 10 000 CD41-positive events are counted.

The inhibitory effect of the substances to be tested is calculated via the reduction in platelet activation, which relates to the activation by the agonist.

1.g) Platelet Aggregation Measurement Using the Parallel-Plate Flow Chamber

Platelet aggregation is determined using blood from healthy volunteers of both genders, who had not received any thrombocyte aggregation-influencing medication for the last ten days. The blood is taken up into monovettes (Sarstedt, Nümbrecht, Germany) which contain, as anticoagulant, sodium citrate 3.8% (1 part citrate+9 parts blood). To obtain platelet-rich plasma, the citrated whole blood is centrifuged at 140 g for 20 min. One quarter of the volume of ACD buffer (44.8 mM sodium citrate, 20.9 mM citric acid, 74.1 mM glucose and 4 mM potassium chloride) is added to the PRP, and the mixture is centrifuged at 1000 g for 10 minutes. The platelet pellet is resuspended in wash buffer and centrifuged at 1000 g for 10 minutes. For the perfusion study, a mixture of 40% erythrocytes and 60% washed platelets (200 000/µl) is prepared and suspended in HEPES-tyrode buffer. Platelet aggregation under flow conditions is measured using the parallel-plate flow chamber (B. Nieswandt et al., EMBO J. 2001, 20, 2120-2130; C. Weeterings, *Arterioscler Thromb. Vasc. Biol.* 2006, 26, 670-675; J J Sixma, *Thromb. Res.* 1998, 92, 43-46). Glass slides are wetted with 100 µl of a solution of human α-thrombin (dissolved in Tris buffer) at 4° C. overnight α-thrombin in various concentrations, for example 10 to 50 µg/ml) and then blocked using 2% BSA.

Reconstituted blood is passed over the thrombin-wetted glass slides at a constant flow rate (for example a shear rate of 300/second) for 5 minutes and observed and recorded using a microscope video system. The inhibitory effect of the substances to be tested is determined morphometrically via the reduction in platelet aggregate formation. Alternatively, the inhibition of the platelet activation can be determined by flow cytometry, for example via p-selectin expression (CD62p) (see Method 1.f).

2.) Ex Vivo Assay 2.a) Platelet Aggregation (Primates, Guinea Pigs)

Awake or anaesthetized guinea pigs or primates are treated orally, intravenously or intraperitoneally with test substances in suitable formulations. As a control, other guinea pigs or primates are treated in an identical manner with the corresponding vehicle. Depending on the mode of application, blood of the deeply anaesthetized animals is obtained by puncture of the heart or of the aorta for different periods of time. The blood is transferred into monovettes (Sarstedt, Nümbrecht, Germany) which, as anticoagulant, contain sodium citrate 3.8% (1 part citrate solution+9 parts blood). To obtain platelet-rich plasma, the citrated whole blood is centrifuged at 140 g for 20 min.

Aggregation is triggered by addition of a thrombin receptor agonist (TRAP6, SFLLRN, 50 µg/ml; in each experiment, the concentration is determined for each animal species) in an aggregometer and determined at 37° C. using the turbidimetric method according to Born (Born, G. V. R., Cross M. J., The Aggregation of Blood Platelets; *J. Physiol.* 1963, 168, 178-195).

To measure the aggregation, the maximum increase in the light transmission (amplitude of the aggregation curve in %) is determined within 5 minutes of addition of the agonist. The inhibitory effect of the administered test substances in the treated animals is calculated via the reduction in aggregation, based on the mean of the control animals.

3.) In Vivo Assays 3.a) Thrombosis Models

The compounds according to the invention can be studied in thrombosis models in suitable animal species in which thrombin-induced platelet aggregation is mediated via the PAR-1 receptor. Suitable animal species are guinea pigs and, in particular, primates (compare: Lindahl, A. K., Scarborough, R. M., Naughton, M. A., Harker, L. A., Hanson, S. R., *Thromb Haemost* 1993, 69, 1196; Cook J J, Sitko G R, Bednar B, Condra C, Mellott M J, Feng D-M, Nutt R F, Shager J A, Gould R J, Connolly T M, *Circulation* 1995, 91, 2961-2971; Kogushi M, Kobayashi H, Matsuoka T, Suzuki S, Kawahara T, Kajiwara A, Hishinuma I, *Circulation* 2003, 108 Suppl. 17, IV-280; Derian C K, Damiano B P, Addo M F, Darrow A L, D'Andrea M R, Nedelman M, Zhang H—C, Maryanoff B E, Andrade-Gordon P, *J. Pharmacol. Exp. Ther.* 2003, 304, 855-861). Alternatively, it is possible to use guinea pigs which have been pretreated with inhibitors of PAR-3 and/or PAR-4

(Leger A J et al., *Circulation* 2006, 113, 1244-1254), or transgenic PAR-3- and/or PAR-4-knockdown guinea pigs.

3.b) Impaired Coagulation and Organ Dysfunction in Disseminated Intravasal Coagulation (DIC)

The compounds according to the invention can be studied in models of DIC and/or sepsis in suitable animal species. Suitable animal species are guinea pigs and, in particular, primates, and for the study of endothelium-mediated effects also mice and rats (compare: Kogushi M, Kobayashi H, Matsuoka T, Suzuki S, Kawahara T, Kajiwara A, Hishinuma I, *Circulation* 2003, 108 Suppl. 17, IV-280; Derian C K, Damiano B P, Addo M F, Darrow A L, D'Andrea M R, Nedelman M, Zhang H-C, Maryanoff B E, Andrade-Gordon P, *J. Pharmacol. Exp. Ther.* 2003, 304, 855-861; Kaneider N C et al., *Nat Immunol,* 2007, 8, 1303-12; Camerer E et al., *Blood,* 2006, 107, 3912-21; Riewald M et al., *J Biol Chem,* 2005, 280, 19808-14.). Alternatively, it is possible to use guinea pigs which have been pretreated with inhibitors of PAR-3 and/or PAR-4 (Leger A J et al., *Circulation* 2006, 113, 1244-1254), or transgenic PAR-3- and/or PAR-4-knockdown guinea pigs.

3.b.1) Thrombin-Antithrombin Complexes

Thrombin/antithrombin complexes (referred to hereinafter as "TAT") are a measure of the thrombin formed endogenously by coagulation activation. TATs are determined via an ELISA assay (Enzygnost TAT micro, Dade-Behring). Plasma is obtained from citrated blood by centrifugation. 50 µl of TAT sample buffer are added to 50 µl of plasma, shaken briefly and incubated at room temperature for 15 min. The samples are filtered with suction, and the well is washed 3 times with wash buffer (300 Owen). Between the wash steps, the plates are tapped to remove any residual wash buffer. Conjugate solution (100 µl) is added and the mixture is incubated at room temperature for 15 min. The samples are filtered with suction, and the well is washed 3 times with wash buffer (300 µl/well). The chromogenic substrate (100 µl/well) is then added, the mixture is incubated in the dark at room temperature for 30 min, stop solution (100 µl/well) is added, and the formation of colour at 492 nm is measured (Saphire Plate reader).

3.b.2) Parameters for Organ Dysfunction

Various parameters are determined, which allow conclusions to be drawn with respect to the functional restriction of various internal organs owing to the administration of LPS, and the therapeutic effect of test substances can be assessed. Citrated blood or, if appropriate, lithium heparin blood, is centrifuged, and the plasma is used to determine the parameters. Typically, the following parameters are determined: creatinine, urea, aspartate aminotransferase (AST), alanine aminotransferase (ALT), total bilirubin, lactate dehydrogenase (LDH), total protein, total albumin and fibrinogen. The values give indications regarding kidney function, liver function, cardiovascular function and vascular function.

3.b.2) Parameters for Inflammation

The extent of the inflammatory reaction triggered by endotoxin can be demonstrated by the increase of inflammation mediators, for example interleukins (1, 6, 8 and 10), tumour necrosis factor alpha or monocyte chemoattractant protein-1, in the plasma. ELISAs or the Luminex system may be used for this purpose.

3.c) Antitumour Activity

The compounds according to the invention can be tested in models of cancer, for example in the human breast cancer model in immunodeficient mice (compare: S. Even-Ram et. al., *Nature Medicine,* 1988, 4, 909-914).

3.d) Antiangiogenetic Activity

The compounds according to the invention can be tested in in vitro and in vivo models of angiogenesis (compare: Caunt et al., *Journal of Thrombosis and Haemostasis,* 2003, 10, 2097-2102; Haralabopoulos et al., *Am J Physiol*, 1997, C239-C245; Tsopanoglou et al., *JBC,* 1999, 274, 23969-23976; Zania et al., *JPET,* 2006, 318, 246-254).

3.e) Blood Pressure- and Heart Rate-Modulating Activity

The compounds according to the invention can be tested in in vivo models for their action on arterial blood pressure and heart rate. To this end, rats (for example Wistar) are provided with implantable radiotelemetry units, and an electronic data acquisition and storage system (Data Sciences, MN, USA) consisting of a chronically implantable transducer/transmitter unit in combination with a liquid-filled catheter is employed. The transmitter is implanted into the peritoneal cavity, and the sensor catheter is positioned in the descending aorta. The compounds according to the invention can be administered (for example orally or intravenously). Prior to the treatment, the mean arterial blood pressure and the heart rate of the untreated and treated animals are measured, and it is made sure that they are in the range of about 131-142 mmHg and 279-321 beats/minute. PAR-1-activating peptide (SFLLRN; for example doses between 0.1 and 5 mg/kg) is administered intravenously. Blood pressure and heart rate are measured at various time intervals and time spans with and without PAR-1-activating peptide and with and without a compound according to the invention (compare: Cicala C et al., *The FASEB Journal,* 2001, 15, 1433-5; Stasch J P et al., *British Journal of Pharmacology* 2002, 135, 344-355).

4.) Determination of the Solubility

Preparation of the Starting Solution (Original Solution):

At least 1.5 mg of the test substance are weighed out accurately into a wide-mouth 10 mm screw V-vial (from Glastechnik Gräfenroda GmbH, Art. No. 8004-WM-H/V15µ with fitting screw cap and septum, DMSO is added to a concentration of 50 mg/ml and the vial is vortexed for 30 minutes.

Preparation of the Calibration Solutions:

The pipetting steps necessary are effected in 1.2 ml 96-deep well plates (DWP) with the aid of a liquid-handling robot. The solvent used is a mixture of acetonitrile/water 8:2.

Preparation of the starting solution for calibration solutions (stock solution): 833 µl of the solvent mixture are added to 10 µl of the original solution (concentration=600 mg/ml), and the mixture is homogenized. 1:100 dilutions in separate DWPs are prepared from each test substance, and these are homogenized in turn.

Calibration solution 5 (600 ng/ml): 270 µl of the solvent mixture are added to 30 µl of the stock solution, and the mixture is homogenized.

Calibration solution 4 (60 ng/ml): 270 µl of the solvent mixture are added to 30 µl of the calibration solution 5, and the mixture is homogenized.

Calibration solution 3 (12 ng/ml): 400 µl of the solvent mixture are added to 100 µl of the calibration solution 4, and the mixture is homogenized.

Calibration solution 2 (1.2 ng/ml): 270 µl of the solvent mixture are added to 30 µl of the calibration solution 3, and the mixture is homogenized.

Calibration solution 1 (0.6 ng/ml): 150 µl of the solvent mixture are added to 150 µl of the calibration solution 2, and the mixture is homogenized.

Preparation of the Sample Solutions:

The pipetting steps necessary are effected in 1.2 ml 96-well DWPs with the aid of a liquid-handling robot. 1000 µl of PBS buffer pH 6.5 are added to 10.1 µl of the stock solution. (PBS buffer pH 6.5: 61.86 g sodium chloride, 39.54 g sodium dihydrogen phosphate and 83.35 g 1 N aqueous sodium hydroxide solution are weighed out into a 1 liter measuring flask and made up with water, and the mixture is stirred for about 1 hour. 500 ml of this solution are added into a 5 liter measuring flask and made up with water. The pH is adjusted to 6.5 using 1 N aqueous sodium hydroxide solution.)
Procedure:

The pipetting steps necessary are effected in 1.2 ml 96-well DWPs with the aid of a liquid-handling robot. The sample solutions prepared in this manner are shaken at 1400 rpm and at 20° C. using a variable temperature shaker for 24 hours. In each case 180 µl are removed from these solutions and transferred into Beckman Polyallomer centrifuge tubes. These solutions are centrifuged at about 223 000×g for 1 hour. 100 µl of the supernatant are removed from each sample solution, and diluted 1:10 and 1:1000 with PBS buffer 6.5.
Analysis:

The samples are analysed by means of HPLC/MS-MS. The test compound is quantified by means of a five-point calibration curve. The solubility is expressed in mg/l. Analysis sequence: 1) blank (solvent mixture); 2) calibration solution 0.6 ng/ml; 3) calibration solution 1.2 ng/ml; 4) calibration solution 12 ng/ml; 5) calibration solution 60 ng/ml; 6) calibration solution 600 ng/ml; 7) blank (solvent mixture); 8) sample solution 1:1000; 9) sample solution 1:10.
HPLC/MS-MS Method:

HPLC: Agilent 1100, quat. pump (G1311A), autosampler CTC HTS PAL, degasser (G1322A) and column thermostat (G1316A); column: Oasis HLB 20 mm×2.1 mm, 25µ; temperature: 40° C.; eluent A: water+0.5 ml of formic acid/1; eluent B: acetonitrile+0.5 ml of formic acid/1; flow rate: 2.5 ml/min; stop time 1.5 min; gradient: 0 min 95% A, 5% B; ramp: 0-0.5 min 5% A, 95% B; 0.5-0.84 min 5% A, 95% B; ramp: 0.84-0.85 min 95% A, 5% B; 0.85-1.5 min 95% A, 5% B.

MS/MS: WATERS Quattro Micro Tandem MS/MS; Z-Spray API interface; HPLC-MS inlet splitter 1:20; measurement in the ESI mode.

C. WORKING EXAMPLES FOR PHARMACEUTICAL COMPOSITIONS

The substances according to the invention can be converted to pharmaceutical preparations as follows:
Tablet:
Composition:

100 mg of the compound of Example 1, 50 mg of lactose (monohydrate), 50 mg of maize starch, 10 mg of polyvinylpyrrolidone (PVP 25) (from BASF, Germany) and 2 mg of magnesium stearate.

Tablet weight 212 mg, diameter 8 mm, radius of curvature 12 mm.
Preparation:

The mixture of the compound of Example 1, lactose and starch is granulated with a 5% strength solution (m/m) of the PVP in water. After drying, the granules are mixed with the magnesium stearate for 5 min. This mixture is pressed with a conventional tableting press (for tablet dimensions see above).
Oral Suspension:
Composition:

1000 mg of the compound of Example 1, 1000 mg of ethanol (96%), 400 mg of Rhodigel (xanthan gum) (from FMC, USA) and 99 g of water.

A single dose of 100 mg of the compound according to the invention corresponds to 10 ml of oral suspension.

Preparation:

The Rhodigel is suspended in ethanol, and the compound of Example 1 is added to the suspension. The water is added while stirring. The mixture is stirred for approx. 6 h until the Rhodigel has finished swelling.
Intravenously Administrable Solution:
Composition:

1 mg of the compound of Example 1, 15 g of polyethylene glycol 400 and 250 g of water for injection purposes.
Preparation:

The compound of Example 1 is dissolved together with polyethylene glycol 400 by stirring in the water. The solution is sterilized by filtration (pore diameter 0.22 µm) and dispensed under aseptic conditions into heat-sterilized infusion bottles. The latter are closed with infusion stoppers and crimped caps.

The invention claimed is:
1. A compound of formula (I)

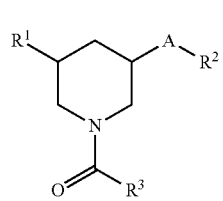

in which
A represents a group of the formula

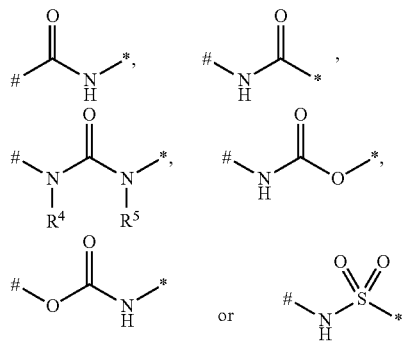

where
# is the point of attachment to the piperidine ring,
* is the point of attachment to $R^2$,
$R^4$ represents hydrogen or $C_1$-$C_3$-alkyl,
and
$R^5$ represents hydrogen or $C_1$-$C_3$-alkyl,
$R^1$ represents phenyl,
where phenyl may be substituted by 1 to 3 substituents independently of one another selected from the group consisting of monofluoromethyl, difluoromethyl, trifluoromethyl, monofluoromethoxy, difluoromethoxy, trifluoromethoxy, monofluoromethylsulphanyl, difluoromethylsulphanyl, trifluoromethylsulphanyl, methylsulphonyl, $C_1$-$C_4$-alkyl, $C_1$-$C_4$-alkoxy and $C_1$-$C_4$-alkoxycarbonyl,
$R^2$ represents phenyl
where phenyl may be substituted by 1 to 3 substituents independently of one another selected from the group consisting of halogen, cyano, hydroxyl, amino, monofluoromethyl, difluoromethyl, trifluoromethyl, monofluoromethoxy, difluoromethoxy, trifluoromethoxy, monofluoromethylsulphanyl, difluoromethylsulphanyl, trifluoromethylsulphanyl, $C_1$-$C_4$-alkyl, $C_1$-$C_4$-alkoxy, $C_1$-$C_6$-alkylamino and phenyl,
where phenyl may be substituted by 1 to 3 substituents independently of one another selected from the group consisting of halogen and trifluoromethyl, $R^3$ represents 4- to 7-membered heterocyclyl,
where heterocyclyl, may be substituted by 1 to 3 substituents independently of one another selected from the group consisting of halogen, cyano, oxo, hydroxyl, amino, monofluoromethyl, difluoromethyl, trifluoromethyl, monofluoromethoxy, difluoromethoxy, trifluoromethoxy, monofluoromethylsulphanyl, difluoromethylsulphanyl, trifluoromethylsulphanyl, hydroxycarbonyl, aminocarbonyl, $C_1$-$C_4$-alkyl, $C_1$-$C_4$-alkoxy, $C_1$-$C_6$-alkylamino, $C_1$-$C_4$-alkoxycarbonyl, $C_1$-$C_4$-alkylaminocarbonyl and cyclopropyl,
where alkyl may be substituted by a hydroxyl substituent,
or a salt thereof.

2. The compound of claim 1, wherein
A represents a group of the formula

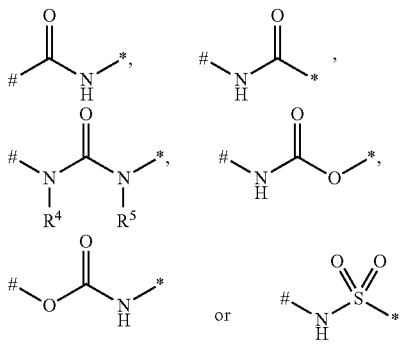

where
# is the point of attachment to the piperidine ring,
* is the point of attachment to $R^2$,
$R^4$ represents hydrogen or methyl,
and
$R^5$ represents hydrogen or methyl, $R^1$ represents phenyl,
where phenyl is substituted by 1 or 2 substituents independently of one another selected from the group consisting of trifluoromethyl, trifluoromethoxy, methyl, ethyl, isopropyl, methoxy and ethoxycarbonyl, $R^2$ represents phenyl,
where phenyl may be substituted by 1 or 2 substituents independently of one another selected from the group consisting of halogen, cyano, hydroxyl, trifluoromethyl, difluoromethoxy, trifluoromethoxy, methyl, ethyl, methoxy, ethoxy and phenyl,
where phenyl may be substituted by 1 or 2 substituents independently of one another selected from the group consisting of halogen and trifluoromethyl, $R^3$ represents tetrahydrofuranyl, tetrahydropyranyl, morpholin-4-yl, thiomorpholin-4-yl, 1,1-dioxidothiomorpholin-4-yl, azetidin-1-yl, pyrrolidin-1-yl, piperidin-1-yl, piperazin-1-yl,
where tetrahydrofuranyl, morpholin-4-yl, azetidin-1-yl, pyrrolidin-1-yl, piperidin-1-yl, piperazin-1-yl, may be substituted by 1 or 2 substituents independently of one another selected from the group consisting of halogen, cyano, oxo, hydroxyl, amino, trifluoromethyl, difluoromethoxy, trifluoromethoxy, hydroxycarbonyl, aminocarbonyl, methyl, ethyl, methoxy, ethoxy, dimethylamino, methoxycarbonyl, ethoxycarbonyl, dimethylaminocarbonyl and cyclopropyl,
in which methyl and ethyl may be substituted by a hydroxyl substituent,
or a salt thereof.

3. The compound of claim 1 wherein
A represents a group of the formula

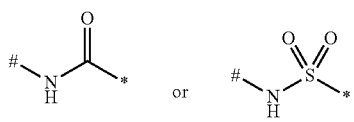

where
# is the point of attachment to the piperidine ring,
* is the point of attachment to $R^2$,
$R^1$ represents phenyl,
where phenyl is substituted by 1 or 2 substituents independently of one another selected from the group consisting of trifluoromethyl, trifluoromethoxy, methyl and ethyl,
$R^2$ represents phenyl,
where phenyl may be substituted by 1 or 2 substituents independently of one another selected from the group consisting of halogen, cyano, trifluoromethyl, trifluoromethoxy, methyl, methoxy and phenyl,
where phenyl may be substituted by 1 or 2 substituents independently of one another selected from the group consisting of chlorine, fluorine and trifluoromethyl,
$R^3$ represents morpholin-4-yl, 1,1-dioxidothiomorpholin-4-yl, 3-hydroxyazetidiny-1-yl, 3-hydroxypyrrolidin-1-yl, 4-cyanopiperidin-1-yl or 4-hydroxypiperidin-1-yl,
or a salt thereof.

4. The compound of claim 1, wherein —$R^1$ and -A-$R^2$ are in a cis-position to one another.

5. A process for preparing a compound of claim 1, comprising
[A] reacting a compound of the formula

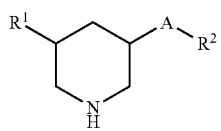

(II)

in which
A, $R^1$ and $R^2$ have the meaning given in claim 1,
with a compound of the formula

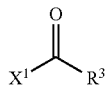

(III)

in which

R³ has the meaning given in claim 1, and

X¹ represents halogen, preferably bromine or chlorine, or hydroxyl, or

[B] reacting a compound of the formula (II) with a compound of the formula

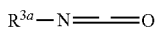

(IV)

in which $R^{3a}$ represents $C_1$-$C_6$-alkyl, $C_3$-$C_7$-cycloalkyl, 4- to 7-membered heterocyclyl, phenyl or 5- or 6-membered heteroaryl, where alkyl may be substituted by a substituent selected from the group consisting of halogen, hydroxyl, amino, cyano, $C_1$-$C_4$-alkoxy, $C_1$-$C_4$-alkoxycarbonyl, $C_3$-$C_7$-cycloalkyl, 4- to 6-membered heterocyclyl, phenyl and 5- or 6-membered heteroaryl, where alkoxy may be substituted by a $C_1$-$C_4$-alkoxy substituent, and where cycloalkyl, heterocyclyl, phenyl and heteroaryl may be substituted by 1 to 3 substituents independently of one another selected from the group consisting of halogen, cyano, oxo, hydroxyl, amino, monofluoromethyl, difluoromethyl, trifluoromethyl, monofluoromethoxy, difluoromethoxy, trifluoromethoxy, monofluoromethylsulphanyl, difluoromethylsulphanyl, trifluoromethylsulphanyl, hydroxycarbonyl, aminocarbonyl, $C_1$-$C_4$-alkyl, $C_1$-$C_4$-alkoxy, $C_1$-$C_6$-alkylamino, $C_1$-$C_4$-alkoxycarbonyl, $C_1$-$C_4$-alkylaminocarbonyl and cyclopropyl, where alkyl may be substituted by a hydroxyl substituent, to give a compound of the formula

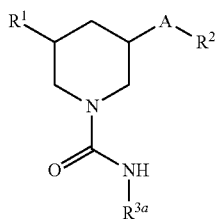

(Ia)

in which

A, R¹, R² and $R^{3a}$ have the meaning given in claim 1, or

[C] reacting a compound of the formula

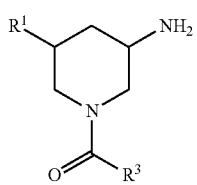

(V)

in which

R¹ and R³ have the meaning given in claim 1, with a compound of the formula

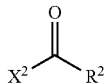

(VI)

in which

R² has the meaning given in claim 1, and

X² represents halogen, preferably bromine or chlorine, or hydroxyl, to give a compound of the formula

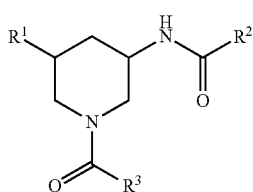

(Ib)

in which

R¹, R² and R³ have the meaning given in claim 1, or

[D] reacting a compound of the formula (V) with a compound of the formula

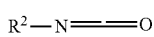

(VII)

in which

R² has the meaning given in claim 1, to give a compound of the formula

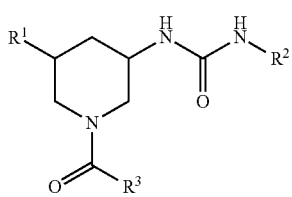

(Ic)

in which

R¹, R² and R³ have the meaning given in claim 1, or

[E] reacting a compound of the formula (V) with a compound of the formula

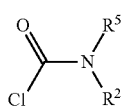

(VIII)

in which
R² and R⁵ have the meaning given in claim 1,
to give a compound of the formula

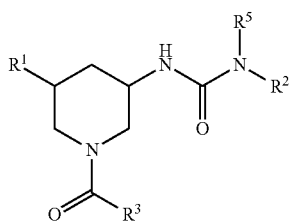 (Id)

in which
R¹, R², R³ and R⁵ have the meaning given in claim 1,
or

[F] reacting a compound of the formula (Id) with a compound of the formula

R⁴—X³  (IX)

in which
R⁴ has the meaning given in claim 1, and
X³ represents halogen, preferably iodine, bromine or chlorine,
to give a compound of the formula

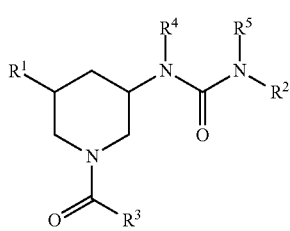 (Ie)

in which
R¹, R², R³, R⁴ and R⁵ have the meaning given in claim 1,
or

[G] reacting a compound of the formula (V) with a compound of the formula

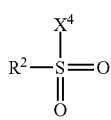 (X)

in which
R² has the meaning given in claim 1, and
X⁴ represents chlorine or hydroxyl, to give a compound of the formula

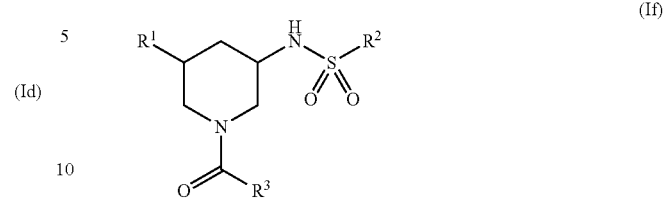 (If)

in which
R¹, R² and R³ have the meaning given in claim 1,
or

[H] reacting a compound of the formula

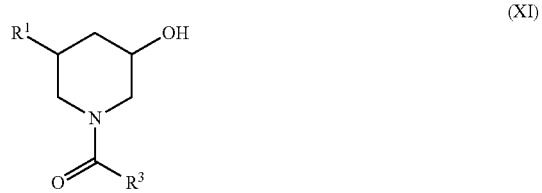 (XI)

in which
R¹ and R³ have the meaning given in claim 1,
initially with disuccinimidyl carbonate and then with a compound of the formula

H₂N—R²  (XII), in which
R² has the meaning given in claim 1,
to give a compound of the formula

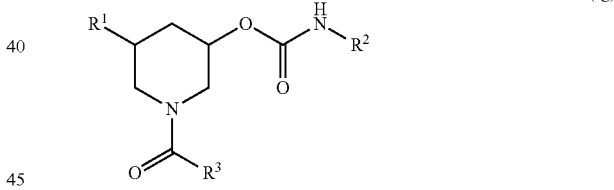 (Ig)

in which
R¹, R² and R³ have the meaning given in claim 1.

6. A pharmaceutical composition comprising a compound of claim 1 and an inert, nontoxic, pharmaceutically suitable excipient.

7. A method of inhibiting platelet aggregation in a thromboembolic disorders in a human or animal comprising administering thereto an anti-platelet aggregation effective amount of at least one compound of claim 1.

8. A method of preventing blood coagulation, comprising adding an anticoagulatory amount of a compound according to claim 1 to an in vitro testing media.

9. A method of inhibiting platelet aggregation in a thromboembolic disorder in a human or animal comprising administering thereto an anti-platelet aggregation effective amount of at least one pharmaceutical composition according to claim 6.

* * * * *